(12) United States Patent
Thorsett et al.

US006900179B2

(10) Patent No.: US 6,900,179 B2
(45) Date of Patent: May 31, 2005

(54) CARBAMYLOXY COMPOUNDS WHICH INHIBIT LEUKOCYTE ADHESION MEDIATED BY VLA-4

(76) Inventors: Eugene D. Thorsett, 571 Buena Vista, Moss Beach, CA (US) 94038; Christopher M. Semko, 2361 Carpenter Ct., Fremont, CA (US) 94539; Dimitrios Sarantakis, 262 Sentinel Ave., Newtown, PA (US) 18940; Michael A. Pleiss, 848 Stella Ct., Sunnyvale, CA (US) 94087; Anthony Kreft, 43 Barley Ct., Langhorne, PA (US) 19047; Andrei W. Konradi, 95 Cervantes #105, San Francisco, CA (US) 94123; Francine S. Grant, 3735 Sacramento St., San Francisco, CA (US) 94118; Darren B. Dressen, 3110 Casa De Campo #2, San Mateo, CA (US) 94403; Susan Ashwell, 1015 Aspen Dr., Plainsboro, NJ (US) 08536; Reinhardt Bernhard Baudy, 5281 Harrington Ct., Doylestown, PA (US) 18901; Louis John Lombardo, 412 S. Woods Rd., Belle Mead, NJ (US) 08502

( * ) Notice: Subject to any disclaimer, the term of this patent is extended or adjusted under 35 U.S.C. 154(b) by 400 days.

(21) Appl. No.: 09/987,619

(22) Filed: Nov. 15, 2001

(65) Prior Publication Data

US 2002/0193312 A1 Dec. 19, 2002

Related U.S. Application Data

(62) Division of application No. 09/126,958, filed on Jul. 31, 1998, now Pat. No. 6,489,300.
(60) Provisional application No. 60/054,453, filed on Aug. 1, 1997, and provisional application No. 60/112,020, filed on Jul. 31, 1997.

(51) Int. Cl.$^7$ .................................................. C07K 5/06
(52) U.S. Cl. ........................ 514/19; 562/445; 562/553
(58) Field of Search ........................... 514/19; 562/445, 562/553

(56) References Cited

U.S. PATENT DOCUMENTS

| | | | | |
|---|---|---|---|---|
| 4,018,912 A | * | 4/1977 | Failli et al. .................... 514/18 |
| 4,018,913 A | * | 4/1977 | Okamoto et al. ............... 514/20 |
| 4,018,915 A | * | 4/1977 | Okamoto et al. ............... 514/20 |
| 4,036,955 A | * | 7/1977 | Okamoto et al. ............... 514/20 |
| 4,041,156 A | * | 8/1977 | Okamoto et al. ............... 514/20 |
| 4,046,876 A | * | 9/1977 | Okamoto et al. ............... 514/20 |
| 4,055,636 A | * | 10/1977 | Okamoto et al. ............... 514/20 |
| 4,055,651 A | * | 10/1977 | Okamoto et al. ............. 514/319 |
| 4,069,318 A | * | 1/1978 | Okamoto et al. ............... 514/20 |
| 4,070,457 A | * | 1/1978 | Okamoto et al. ............. 514/510 |
| 4,071,621 A | * | 1/1978 | Okamoto et al. ............... 514/20 |
| 4,073,914 A | * | 2/1978 | Kikumoto et al. ............ 514/319 |
| 4,074,057 A | * | 2/1978 | Kawamatsu et al. .......... 560/55 |
| 4,096,255 A | * | 6/1978 | Kikumoto et al. ........ 514/227.5 |
| 4,097,591 A | * | 6/1978 | Okamoto et al. ............... 514/20 |
| 4,104,392 A | * | 8/1978 | Okamoto et al. ............. 514/307 |
| 4,977,168 A | * | 12/1990 | Bernat et al. ................... 514/19 |
| 5,338,755 A | * | 8/1994 | Wagnon et al. ............. 514/414 |
| 5,397,801 A | * | 3/1995 | Wagnon et al. ............. 514/418 |
| 5,481,005 A | * | 1/1996 | Wagnon et al. ............. 548/537 |
| 5,578,633 A | * | 11/1996 | Wagnon et al. ............. 514/418 |
| 5,686,628 A | * | 11/1997 | Veale et al. .................. 548/537 |

FOREIGN PATENT DOCUMENTS

| | | |
|---|---|---|
| AU | 6147073 | 4/1995 |
| DE | 2357334 | 6/1974 |
| DE | 2655636 | 6/1977 |
| EP | 0526348 | 2/1993 |
| GB | 9711143.9 | 5/1997 |
| GB | 9714314.3 | 7/1997 |
| GB | 9714316.8 | 7/1997 |
| GB | 9714335.8 | 7/1997 |
| GB | 9722674.0 | 10/1997 |
| GB | 9800680.2 | 1/1998 |
| GB | 9800684.4 | 1/1998 |

(Continued)

OTHER PUBLICATIONS

U.S. Appl. No. 60/022,890, filed Jul. 1996, Lin et al.
U.S. Appl. No. 08/821,825, filed Mar. 1997, He et al.
Simanis et al., *Int. J. Pept. Protein Res.*, (1982), 16:(1), pp. 67–70.
Leibritz, et al., *Tetrahedron* (1982), 38(14), pp. 2165–2181.
El–Naggar, et al., *Acta. Pharm. Jugosl.*, (1985), 35(1), pp. 15–22.
Chemical Abstract No. 126040, vol. 74, No. 23 (Jun. 7, 1971).
Chemical Abstract No. 176262, vol. 99, No. 21 (Nov. 21, 1983).
Chemical Abstract No. 210288, vol. 106, No. 25 (Jun. 22, 1987).
Chemical Abstract No. 167952, vol. 108, No. 19 (May 9, 1988).
Chemical Abstract No. 34164, vol. 125, No. 3 (Jul. 15, 1996).

*Primary Examiner*—Jon Weber
*Assistant Examiner*—David Lukton
(74) *Attorney, Agent, or Firm*—Foley & Lardner LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

13 Claims, No Drawings

FOREIGN PATENT DOCUMENTS

| | | |
|---|---|---|
| GB | 9800686.9 | 1/1998 |
| JP | 04154732 | 5/1992 |
| WO | WO 92/16549 | 10/1992 |
| WO | WO 94/07815 | 4/1994 |
| WO | WO 94/12181 | 6/1994 |
| WO | WO 95/15973 | 6/1995 |
| WO | WO 96/20725 | 7/1996 |
| WO | WO 96/20949 | 7/1996 |
| WO | WO 96/22966 | 8/1996 |
| WO | WO 97/03094 | 1/1997 |
| WO | 97/03094 | 1/1997 |
| WO | WO 98/04247 | 2/1998 |
| WO | WO 98/42656 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | 99/06436 | 2/1999 |
| WO | WO 99/10312 | 3/1999 |
| WO | WO 99/10313 | 3/1999 |

* cited by examiner

CARBAMYLOXY COMPOUNDS WHICH INHIBIT LEUKOCYTE ADHESION MEDIATED BY VLA-4

CROSS-REFERENCE TO RELATED APPLICATIONS

This application is a divisional of application Ser. No. 09/126,958, filed Jul. 31, 1998, now U.S. Pat. No. 6,489,300, which claims the benefit of U.S. Provisional Application No. 60/112,020, which was converted pursuant to 37 C.F.R. § 1.53(c)(2)(i) from U.S. patent application Ser. No. 08/904,424, filed Jul. 31, 1997; and U.S. Provisional Application No. 60/054,453, filed Aug. 1, 1997, which applications are incorporated herein by reference in their entirety.

BACKGROUND OF THE INVENTION

1. Field of the Invention

This invention relates to compounds which inhibit leukocyte adhesion and, in particular, leukocyte adhesion mediated by VLA-4.

References

The following publications, patents and patent applications are cited in this application as superscript numbers:

[1] Hemler and Takada, European Patent Application Publication No. 330,506, published August 30, 1989
[2] Elices, et al., Cell, 60:577–584 (1990)
[3] Springer, Nature, 346:425–434 (1990)
[4] Osborn, Cell, 62:3–6 (1990)
[5] Vedder, et al., Surgery, 106:509 (1989)
[6] Pretolani, et al., J. Exp. Med., 180:795 (1994)
[7] Abraham, et al., J. Clin. Invest., 93:776 (1994)
[8] Mulligan, et al., J. Immunology, 150:2407 (1993)
[9] Cybulsky, et al., Science, 251:788 (1991)
[10] Li, et al., Arterioscler. Thromb., 13:197 (1993)
[11] Sasseville, et al., Am. J. Path., 144:27 (1994)
[12] Yang, et al., Proc. Nat. Acad. Science (USA), 90:10494 (1993)
[13] Burkly, et al., Diabetes, 43:529 (1994)
[14] Baron, et al., J. Clin. Invest., 93:1700 (1994)
[15] Hamann, et al., J. Immunology, 152:3238 (1994)
[16] Yednock, et al., Nature, 356:63 (1992)
[17] Baron, et al., J. Exp. Med., 177:57 (1993)
[18] van Dinther-Janssen, et al., J. Immunology, 147:4207 (1991)
[19] van Dinther-Janssen, et al., Annals. Rheumatic Dis., 52:672 (1993)
[20] Elices, et al., J. Clin. Invest., 93:405 (1994)
[21] Postigo, et al., J. Clin. Invest., 89:1445 (1991)
[22] Paul, et al., Transpl. Proceed., 25:813 (1993)
[23] Okarhara, et al., Can. Res., 54:3233 (1994)
[24] Paavonen, et al., Int. J. Can., 58:298 (1994)
[25] Schadendorf, et al., J. Path., 170:429 (1993)
[26] Bao, et al., Diff., 52:239 (1993)
[27] Lauri, et al., British J. Cancer, 68:862 (1993)
[28] Kawaguchi, et al., Japanese J. Cancer Res., 83:1304 (1992)
[29] Kogan, et al., U.S. Pat. No. 5,510,332, issued April 23, 1996
[30] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

2. State of the Art

VLA-4 (also referred to as α4β1 integrin and CD49d/CD29), first identified by Hemler and Takada[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 is unique among β1 integrins in that it also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory conditions mediated by an adhesion mechanism include, by way of example, asthma[6-8], Alzheimer's disease, atherosclerosis[9-10], AIDS dementia[11], diabetes[12-14] (including acute juvenile onset diabetis), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29,30]. The present invention addresses these and other needs.

SUMMARY OF THE INVENTION

This invention provides compounds which bind to VLA-4. Such compounds can be used, for example, to assay for the presence of VLA-4 in a sample and, in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 μM or less (measured as described in Example A below) which compounds are defined by formula I below:

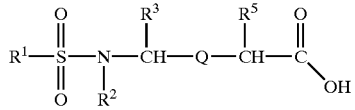

wherein $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O-Z-$NR^8R^{8'}$ and —O-Z-$R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{12}$ is selected from the group consisting of heterocycle and substituted heterocycle, and Z is selected from the group consisting of —C(O)— and —$SO_2$—, Ar is aryl, heteroaryl, substituted aryl or substituted heteroaryl, x is an integer of from 1 to 4;

Q is —C(X)$NR^7$— wherein $R^7$ is selected from the group consisting of hydrogen and alkyl; and X is selected from the group consisting of oxygen and sulfur;

and pharmaceutically acceptable salts thereof.

In another embodiment, the compounds of this invention can also be provided as prodrugs which convert (e.g., hydrolyze, metabolize, etc.) in vivo to a compound of formula I above. In a preferred example of such an embodiment, the carboxylic acid group of the compound of formula I is modified into a group which, in vivo, will convert to a carboxylic acid group (including salts thereof). In a particularly preferred embodiment, such prodrugs are represented by compounds of formula IA:

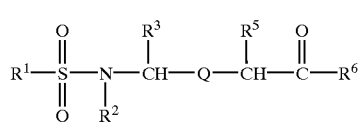

wherein $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, substituted heteroaryl, and $R^1$ and $R^2$ together with the nitrogen atom bound to $R^2$ and the $SO_2$ group bound to $R^1$ can form a heterocyclic or a substituted heterocyclic group;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and, when $R^2$ does not form a heterocyclic group with $R^1$, $R^2$ and $R^3$ together with the nitrogen atom bound to $R^2$ and the carbon atom bound to $R^3$ can form a heterocyclic or a substituted heterocyclic group;

$R^5$ is —$(CH_2)_x$—Ar—$R^{5'}$ where $R^{5'}$ is selected from the group consisting of —O-Z-$NR^8R^{8'}$ and —O-Z-$R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{12}$ is selected from the group consisting of heterocycle and substituted heterocycle, and Z is selected from the group consisting of —C(O)— and —$SO_2$—, Ar is aryl, heteroaryl, substituted aryl or substituted heteroaryl, x is an integer of from 1 to 4;

$R^6$ is selected from the group consisting of 2,4-dioxotetrahydrofuran-3-yl (3,4-enol), amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —NH$(CH_2)_p$COOY where p is an integer of from 1 to 8 and Y is as defined above, —$OCH_2NR^9R^{10}$ where $R^9$ is selected from the group consisting of —C(O)-aryl and —C(O)-substituted aryl and $R^{10}$ is selected from the group consisting of hydrogen and —$CH_2COOR^{11}$ where $R^{11}$ is alkyl, and —$NHSO_2Z'$ where Z' is alkyl, substituted alkyl, cycloalkyl, substituted cycloalkyl, aryl, substituted aryl, heteroaryl, substituted heteroaryl, heterocyclic and substituted heterocyclic;

Q is —C(X)$NR^7$— wherein $R^7$ is selected from the group consisting of hydrogen and alkyl; and X is selected from the group consisting of oxygen and sulfur;

and pharmaceutically acceptable salts thereof with the following provisos (A) when $R^1$ and $R^2$ together with the $SO_2$ group pendent to $R^1$ and the nitrogen pendent to $R^2$ form a saccharin-2-yl group, $R^3$ is —$CH_3$, $R^5$ is p-[$(CH_3)_2$NC(O)O—]benzyl and Q is —C(O)NH— then $R^6$ is not —$OC(CH_3)_3$;

(B) when $R^1$ is p-methylphenyl, $R^2$ and $R^3$ together with the nitrogen atom pendent to $R^2$ and the carbon atom pendent to $R^3$ form a pyrrodinyl ring derived from D-proline; $R^5$ is p-[(4-methylpiperazin-1-yl)NC(O)O—] benzyl derived from D-phenylalanine and Q is —C(O)NH— then $R^6$ is not —$OC(CH_3)_3$;

(C) when $R^1$ is pyrimidin-2-yl, $R^2$ and $R^3$ together with the nitrogen atom bound to $R^2$ and the carbon atom bound to $R^3$ form a pyrrolidinyl ring, $R^5$ is p-[$(CH_3)_2$NC(O)O—] benzyl and Q is —C(O)NH— then $R^6$ is not —$OC(CH_3)_3$.

(D) when $R^1$ is p-methylphenyl, $R^2$ and $R^3$ together with the nitrogen atom pendent to $R^2$ and the carbon atom pendent to $R^3$ form a (2S)-piperazin-2-carbonyl ring; $R^5$ is p-[$(CH_3)_2$NC(O)O—]benzyl and Q is —C(O)NH— then $R^6$ is not —$OC(CH_3)_3$.

Preferably, in the compounds of formula I and IA above, $R^1$ is selected from the group consisting of alkyl, substituted alkyl, aryl, substituted aryl, heterocyclic, substituted heterocylic, heteroaryl and substituted heteroaryl. Even more preferably $R^1$ is selected from the group consisting of methyl, isopropyl, n-butyl, benzyl, phenethyl, phenyl, 4-methylphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl)phenyl, 4-($H_2NC(O)$—)phenyl, 4-($H_2NC(S)$—)phenyl, 4-cyanophenyl, 4-trifluoromethylphenyl, 4-trifluoromethoxyphenyl, 3,5-di-(trifluoromethyl)phenyl, 4-nitrophenyl, 4-aminophenyl, 4-($CH_3C(O)NH$—)phenyl, 4-(PhNHC(O)NH—)phenyl, 4-amidinophenyl, 4-methylamidinophenyl, 4-($CH_3SC$(=NH)—)phenyl, 4-chloro-3-($H_2NS(O)_2$—)phenyl, 1-naphthyl, 2-naphthyl, pyridin-2-yl, pyridin-3-yl, pyrimidin-2-yl, quinolin-8-yl, 2-(trifluoroacetyl)-1,2,3,4-tetrahydroisoquinolin-7-yl, morpholin-4-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

Preferably, in the compounds of formula I and IA above, $R^2$ is hydrogen, methyl, phenyl, benzyl, —$(CH_2)_2$-2-thienyl, and —$(CH_2)_2$-φ.

In one embodiment, $R^1$ and $R^2$ together with the nitrogen atom bound to $R^2$ and the $SO_2$ group bound to $R^1$ are joined to form a heterocyclic group or substituted heterocyclic group. Preferred heterocyclic and substituted heterocyclic groups include those having from 5 to 7 ring atoms having 2 to 3 heteroatoms in the ring selected from the group consisting of nitrogen, oxygen and sulfur which ring is optionally fused to another ring such as a phenyl or cyclohexyl ring to provide for a fused ring heterocycle of from 10 to 14 ring atoms having 2 to 4 heteroatoms in the ring selected from the group consisting of nitrogen, oxygen and sulfur. Specifically preferred $R^1/R^2$ joined groups include, by way of example, benzisothiazolonyl (saccharin-2-yl), N-2,10-camphorsultamyl and 1,1-dioxo-2,3-dihydro-3,3-dimethyl-1,2-benzisothiazol-2-yl.

In one preferred embodiment, $R^2$ and $R^3$ together with the nitrogen atom bound to $R^2$ substituent and the carbon bound to the $R^3$ substituent form a heterocyclic group or a substituted heterocyclic group of 4 to 6 ring atoms having 1 to 2 heteroatoms in the ring selected from the group consisting of nitrogen, oxygen and sulfur which ring is optionally substituted with 1 to 2 substituents selected from the group consisting of fluoro, methyl, hydroxy, oxo (=O), amino, phenyl, thiophenyl, thiobenzyl, (thiomorpholin-4-yl)C(O)O—, $CH_3S(O)_2$— and $CH_3S(O)_2O$—, or can be fused to another ring such as a phenyl or cycloalkyl ring to provide for a fused ring heterocycle of from 10 to 14 ring atoms having 1 to 2 heteroatoms in the ring selected from the group consisting of nitrogen, oxygen and sulfur. Such heterocyclic rings include azetidinyl (e.g., L-azetidinyl), thiazolidinyl (e.g., L-thiazolidinyl), piperidinyl (e.g., L-piperidinyl), piperazinyl (e.g., L-piperazinyl), dihydroindolyl (e.g., L-2,3-dihydroindol-2-yl), tetrahydroquinolinyl (e.g., L-1,2,3,4-tetrahydroquinolin-2-yl), thiomorpholinyl (e.g., L-thiomorpholin-3-yl), pyrrolidinyl (e.g., L-pyrrolidinyl), substituted pyrrolidinyl such as 4-hydroxypyrrolidinyl (e.g., 4-α-(or β-)hydroxy-L-pyrrolidinyl), 4-oxopyrrolidinyl (e.g., 4-oxo-L-pyrolidinyl), 4-fluoropyrrolidinyl (e.g., 4-α-(or β-)fluoro-L-pyrrolidinyl), 4,4-difluoropyrrolidinyl (e.g., 4,4-difluoro-L-pyrrolidinyl), 4-(thiomorpholin-4-ylC(O)O—) pyrrolidinyl (e.g., 4-α-(or β-)-(thiomorpholin-4-ylC(O)O—)-L-pyrrolidinyl, 4-($CH_3S(O)_2O$—)pyrrolidinyl (e.g., 4-α-(or β-)($CH_3S(O)_2O$—)-L-pyrrolidinyl, 3-phenylpyrrolidinyl (e.g., 3-α-(or β-)phenyl-L-pyrrolidinyl), 3-thiophenylpyrrolidinyl (e.g., 3-α-(or β-)-thiophenyl-L-pyrrolidinyl), 4-aminopyrrolidinyl (e.g., 4-α-(or β-)amino-L-pyrrolidinyl), 3-methoxypyrrolidinyl (e.g., 3-α-(or β-)methoxy-L-pyrrolidinyl), 4,4-dimethylpyrrolidinyl, substituted piperazinyl such as 4N-Cbz-piperazinyl and 4-($CH_3S(O)_2$—)piperazinyl, substituted thiazolidinyl such as 5,5-dimethylthiazolindin-4yl, 1,1-dioxo-thiazolidinyl (e.g., L-1,1-dioxo-thiazolidin-2-yl), substituted 1,1-dioxo-thiazolidinyl such as L-1,1-dioxo-5,5-dimethylthiazolidin-2-yl, 1,1-dioxothiomorpholinyl (e.g., L-1,1-dioxo-thiomorpholin-3-yl) and the like.

Preferably, in the compounds of formula I and IA above, $R^3$ includes all of the isomers arising by substitution with methyl, phenyl, benzyl, diphenylmethyl, —$CH_2CH_2$—COOH, —$CH_2$—COOH, 2-amidoethyl, iso-butyl, t-butyl, —$CH_2O$-benzyl and hydroxymethyl. Additionally, in another preferred embodiment, $R^3$ and $R^2$ together with the nitrogen atom bound to $R^2$ can form a heterocyclic group or substituted heterocyclic group.

Q is preferably —C(O)NH— or —C(S)NH—.

Ar is preferably aryl or substituted aryl and, even more preferably, is phenyl or substituted phenyl. Preferably, x is 1.

$R^5$ is preferably selected from all possible isomers arising by substitution with the following groups:

3-[($CH_3)_2NC(O)O$—]benzyl,
4-[($CH_3)_2NC(O)O$—]benzyl,
4-[($CH_3)_2NS(O)_2O$—]benzyl,
4-[(piperidin-1'-yl)C(O)O—]benzyl,
4-[(piperidin-4'-yl)C(O)O—]benzyl,
4-[(1'-methylpiperidin-4'-yl)C(O)O—]benzyl,
4-[(4'-hydroxypiperidin-1'-yl)C(O)O—]benzyl,
4-[(4'-formyloxypiperidin-1'-yl)C(O)O—]benzyl,
4-[(4'-ethoxycarbonylpiperidin-1'-yl)C(O)O—]benzyl,
4-[(4'-carboxylpiperidin-1'-yl)C(O)O—]benzyl,
4-[(3'-hydroxymethylpiperidin-1'-yl)C(O)O—]benzyl,
4-[(4'-hydroxymethylpiperidin-1'-yl)C(O)O—]benzyl,
4-[(4'-phenyl-1'-Boc-piperidin-4'-yl)-C(O)O—]benzyl,
4-[(4'-piperidon-1'-yl ethylene ketal)C(O)O—]benzyl,
4-[(piperazin-4'-yl)-C(O)O—]benzyl,
4-[(1'-Boc-piperazin-4'-yl)-C(O)O—]benzyl,
4-[(4'-methylpiperazin-1'-yl)C(O)O—]benzyl,
4-[(4'-methylhomopiperazin-1'-yl)C(O)O—]benzyl,
4-[(4'-(2-hydroxyethyl)piperazin-1'-yl)C(O)O—]benzyl,
4-[(4'-phenylpiperazin-1'-yl)C(O)O—]benzyl,
4-[(4'-(pyridin-2-yl)piperazin-1'-yl)C(O)O—]benzyl,
4-[(4'-(4-trifluoromethylpyridin-2-yl)piperazin-1'-yl)C(O)O—]benzyl,
4-[(4'-(pyrimidin-2-yl)piperazin-1'-yl)C(O)O—]benzyl,
4-[(4'-acetylpiperazin-1'-yl)C(O)O—]benzyl,
4-[(4'-(phenylC(O)—)piperazin-1'-yl)C(O)O—]benzyl,
4-[(4'-(pyridin-4-ylC(O)—)piperazin-1'-yl)C(O)O—]benzyl,
4-[(4'-(phenylNHC(O)—)piperazin-1'-yl)C(O)O—]benzyl,
4-[(4'-(phenylNHC(S)—)piperazin-1'-yl)C(O)O—]benzyl,
4-[(4'-methanesulfonylpiperazin-1'-yl-C(O)O—)benzyl, 4-[(4'-trifluoromethanesulfonylpiperazin-1'-yl-C(O)O—)benzyl,
4-[(morpholin-4'-yl)C(O)O—]benzyl,
3-nitro-4-[(morpholin-4'-yl)-C(O)O—]benzyl,
4-[(thiomorpholin-4'-yl)C(O)O—]benzyl,
4-[(thiomorpholin-4'-yl sulfone)-C(O)O—]benzyl, (alternative nomenclature 4-[(1,1-dioxothiomorpholin-4yl)-C(O)O—]benzyl),
4-[(pyrrolidin-1'-yl)C(O)O—]benzyl,
4-[(2'-methylpyrrolidin-1'-yl)C(O)O—]benzyl,
4-[(2'-(methoxycarbonyl)pyrrolidin-1'-yl)C(O)O—]benzyl,
4-[(2'-hydroxymethyl)pyrrolidin-1'-yl)C(O)O—]benzyl,
4-[(2'-(N,N-dimethylamino)ethyl)(CH$_3$)NC(O)O—]benzyl,
4-[(2'-(N-methyl-N-toluene-4-sulfonylamino)ethyl)(CH$_3$)N—C(O)O—]benzyl,
4-[(2'-(morpholin-4'-yl)ethyl)(CH$_3$)NC(O)O—]benzyl,
4-[(2'-(hydroxy)ethyl)(CH$_3$)NC(O)O—]benzyl,
4-[bis(2'-(hydroxy)ethyl)NC(O)O—]benzyl,
4-[(2'-(formyloxy)ethyl)(CH$_3$)NC(O)O—]benzyl,
4-[(CH$_3$OC(O)CH$_2$)HNC(O)O—]benzyl,
4-[2'-(phenylNHC(O)O-)ethyl-]HNC(O)O—]benzyl,
3-chloro-4-[(CH$_3$)$_2$NC(O)O—]benzyl,
3-chloro-4-[(4'-methylpiperazin-1'-yl)C(O)O—]benzyl,
3-chloro-4-[(4'-(pyridin-2-yl)piperazin-1'-yl)C(O)O—]benzyl,
3-chloro-4-[thiomorpholin-4'-yl)C(O)O—]benzyl, and
3-fluoro-4-[(CH$_3$)$_2$NC(O)O—]benzyl.

In another embodiment, R$^5$ is selected to form dimeric compounds of the formula:

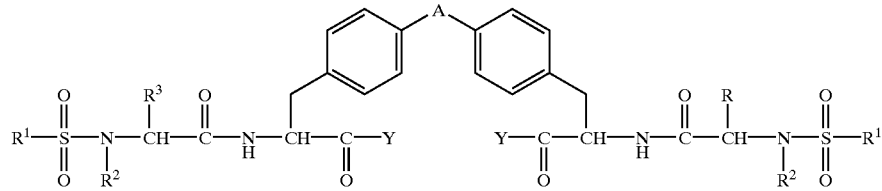

wherein each R$^1$, R$^2$ and R$^3$ is as defined herein; Y is OH or R$^6$, where R$^6$ is as defined herein; and A is a divalent group of the formula:

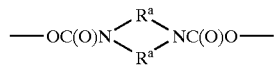

wherein each R$^a$ is independently selected from the group consisting of alkylene and substituted alkylene; each R$^b$ is independently selected from the group consisting of hydrogen, alkyl, substituted alkyl, alkenyl, substituted alkenyl, alkynyl, substituted alkynyl, aryl, substituted aryl, cycloalkyl, substituted cyclalkyl, cycloalkenyl, substituted cycloalkenyl, heteroaryl, substituted heteroaryl, heterocyclic and substituted heterocyclic; and pharmaceutically acceptable salts thereof. Preferably, R$^a$ is ethylene (i.e., —CH$_2$CH$_2$—).

In the compounds of formula IA, R$^6$ is preferably 2,4-dioxo-tetrahydrofuran-3-yl (3,4-enol), methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —O(CH$_2$CH$_2$O)$_2$CH$_3$, 2-(phenoxy)ethoxy, —OCH$_2$C(CH$_3$)$_2$NHBoc, —NH$_2$, benzyloxy, —NHCH$_2$COOH, —NHCH$_2$CH$_2$COOH, —NH-adamantyl, —NHSO$_2$-p-CH$_3$-φ, —NHCH$_2$CH$_2$COOCH$_2$CH$_3$, —NHOY' where Y' is hydrogen, methyl, iso-propyl or benzyl, O—(N-succinimidyl), —O-cholest-5-en-3-β-yl, —OCH$_2$—OC(O)C(CH$_3$)$_3$, —O(CH$_2$)$_z$NHC(O)W where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or CH$_2$C(O)OCH$_2$CH$_3$.

Preferred compounds within the scope of formula I and IA above include by way of example:

N-(toluene-4-sulfonyl)-L-prolyl-L-4-(4-methylpiperazin-1-ylcarbonyloxy)phenylalanine ethyl ester
N-(toluene-4-sulfonyl)-L-prolyl-L-4-(N,N-dimethylcarbamyloxy)phenylalanine ethyl ester
N-(toluene-4-sulfonyl)-L-prolyl-L-4-(4-methylpiperazin-1-ylcarbonyloxy)phenylalanine isopropyl ester
N-(toluene-4-sulfonyl)-L-prolyl-L-4-(4-methylpiperazin-1-ylcarbonyloxy)phenylalanine n-butyl ester
N-(toluene-4-sulfonyl)-L-prolyl-L-4-(4-methylpiperazin-1-ylcarbonyloxy)phenylalanine cyclopentyl ester
N-(toluene-4-sulfonyl)-L-prolyl-L-4-(4-methylpiperazin-1-ylcarbonyloxy)phenylalanine tert-butyl ester
N-(toluene-4-sulfonyl)-L-prolyl-L-4-(4-methylpiperazin-1-ylcarbonyloxy)phenylalanine
N-(toluene-4-sulfonyl)-L-prolyl-L-4-(N,N-dimethylcarbamyloxy)phenylalanine isopropyl ester
N-(toluene-4-sulfonyl)-L-prolyl-L-4-(N,N-dimethylcarbamyloxy)phenylalanine n-butyl ester
N-(toluene-4-sulfonyl)-L-prolyl-L-4-(N,N-dimethylcarbamyloxy)phenylalanine cyclopentyl ester
N-(toluene-4-sulfonyl)-L-prolyl-L-4-(N,N-dimethylcarbamyloxy)phenylalanine tert-butyl ester
N-(toluene-4-sulfonyl)-L-prolyl-L-4-(N,N-dimethylcarbamyloxy)phenylalanine
N-(toluene-4-sulfonyl)-L-prolyl-L-4-(isonipecotoyloxy)phenylalanine ethyl ester
N-(α-toluenesulfonyl)-L-prolyl-L-4-(N-methylisonipecotoyloxy)phenylalanine ethyl ester
N-(α-toluenesulfonyl)-L-prolyl-L-4-(4-methylpiperazin-1-ylcarbonyloxy)phenylalanine
N-(toluene-4-sulfonyl)-L-prolyl-L-3-(N,N-dimethylcarbamyloxy)phenylalanine ethyl ester
N-(toluene-4-sulfonyl)-L-prolyl-L-4-(1-tert-butylcarbonyloxy-4-phenylpiperidin-4-ylcarbonyloxy)phenylalanine ethyl ester
N-(toluene-4-sulfonyl)-L-(5,5-dimethyl)thiaprolyl-L-4-(N,N-dimethylcarbamyloxy)phenylalanine isopropyl ester
N-(toluene-4-sulfonyl)-L-(5,5-dimethyl)thiaprolyl-L-4-(N,N-dimethylcarbamyloxy)phenylalanine tert-butyl ester N-(toluene-4-sulfonyl)-L-(5,5-dimethyl)thiaprolyl-L-4-(N,N-dimethylcarbamyloxy)phenylalanine N-(toluene-4-sulfonyl)-L-[(1,1-dioxo)thiamorpholin-3-carbonyl]-L-4-(N,N-dimethylcarbamyloxy)phenylalanine tert-butyl ester N-(toluene-4-sulfonyl)-L-[(1,1-dioxo)thiamorpholin-3-carbonyl]-L-4-(N,N-dimethylcarbamyloxy)phenylalanine N-(toluene-4-sulfonyl)-L-(5,5-dimethyl)thiaprolyl-L-4-(4-methylpiperazin-1-ylcarbonyloxy)phenylalanine tert-butyl ester N-(toluene-4-sulfonyl)-L-(5,5-dimethyl)thiaprolyl-L-4-(4-methylpiperazin-1-ylcarbonyloxy)phenylalanine N-(toluene-4-sulfonyl)sarcosyl-L-4-(N,N-dimethylcarbamyloxy)phenylalanine isopropyl ester N-(toluene-4-sulfonyl)sarcosyl-L-4-(N,N-dimethylcarbamyloxy)phenylalanine tert-butyl ester N-(toluene-4-sulfonyl)sarcosyl-L-4-(N,N-dimethylcarbamyloxy)phenylalanine N-(toluene-4-sulfonyl)-L-prolyl-L-4-(N,N-dimethylaminosulfonyloxy)phenylalanine tert-butyl ester N-(toluene-4-sulfonyl)-L-prolyl-L-4-(N,N-dimethylaminosulfonyloxy)phenylalanine N-(1-methylimidazole-4-sulfonyl)-L-prolyl-L-4-(N,N-dimethylcarbamyloxy)phenylalanine tert-butyl ester N-(4-aminobenzenesulfonyl)-L-prolyl-L-4-(N,N-dimethylcarbamyloxy)phenylalanine tert-butyl ester N-(toluene-4-sulfonyl)sarcosyl-L-4-(morpholin-4-ylcarbonyloxy)phenylalanine tert-butyl ester N-(toluene-4-sulfonyl)-L-prolyl-L-4-(morpholin-4-ylcarbonyloxy)phenylalanine tert-butyl ester N-(α-toluenesulfonyl)-L-(5,5-dimethyl)thiaprolyl-L-4-(N,N-dimethylcarbamyloxy)phenylalanine N-(toluene-4-sulfonyl)-L-(piperazin-2-carbonyl)-L-4-(N,N-dimethylcarbamyloxy)phenylalanine N-(α-toluene-4-sulfonyl)-L-(5,5-dimethyl)thiaprolyl-L-4-(N,N-dimethylcarbamyloxy)phenylalanine tert-butyl ester N-(toluene-4-sulfonyl)-L-prolyl-L-4-(N,N-dimethylcarbamyloxy)phenylalanine N-adamantyl amide N-(toluene-4-sulfonyl)-L-prolyl-L-4-(N,N-dimethylcarbamyloxy)phenylalanylglycine N-(toluene-4-sulfonyl)-L-prolyl-L-4-(N,N-dimethylaminosulfonyloxy)phenylalanine methyl ester N-(toluene-4-sulfonyl)-L-(piperazin-2-carbonyl)-L-4-(N,N-dimethylcarbamyloxy)phenylalanine tert-butyl ester N-(toluene-4-sulfonyl)-L-(4-benzyloxycarbonylpiperazin-2-carbonyl)-L-4-(N,N-dimethylcarbamyloxy)phenylalanine tert-butyl ester N-(toluene-4-sulfonyl)sarcosyl-L-4-(isonipecotoyloxy)phenylalanine N-(toluene-4-sulfonyl)-L-[(1,1-dioxo)thiamorpholin-3-carbonyl]-L-4-(morpholin-4-ylcarbonyloxy)phenylalanine tert-butyl ester N-(toluene-4-sulfonyl)-L-[(1,1-dioxo)thiamorpholin-3-carbonyl]-L-4-(morpholin-4-ylcarbonyloxy)phenylalanine N-(1-methylpyrazole-4-sulfonyl)-L-prolyl-L-4-(N,N-dimethylcarbamyloxy)phenylalanine tert-butyl ester N-(4-fluorobenzenesulfonyl)-L-prolyl-L-4-(N,N-dimethylcarbamyloxy)phenylalanine tert-butyl ester N-(toluene-4-sulfonyl)sarcosyl-L-4-(4-methylpiperazin-1-ylcarbonyloxy)phenylalanine tert-butyl ester N-(toluene-4-sulfonyl)-L-(1,1dioxo-5,5-dimethyl)thiaprolyl-L-4-(N,N-dimethylcarbamyloxy)phenylalanine tert-butyl ester N-(1-methylimidazole-4-sulfonyl)-L-prolyl-L-4-(N,N-dimethylcarbamyloxy)phenylalanine 2-(saccharin-2-yl)propionoyl-L-4-(N,N-dimethylcarbamyloxy)phenylalanine tert-butyl ester N-(toluene-4-sulfonyl)-L-(1,1-dioxo-5,5-dimethyl)thiaprolyl-L-4-(N,N-dimethylcarbamyloxy)phenylalanine N-(4-fluorobenzenesulfonyl)-L-prolyl-L-4-(N,N-dimethylcarbamyloxy)phenylalanine N-(pyridine-3-sulfonyl)-L-prolyl-L-4-(N,N-dimethylcarbamyloxy)phenylalanine N-(toluene-4-sulfonyl)-D-prolyl-L-4-(4-methylpiperazin-1-ylcarbonyloxy)phenylalanine tert-butyl ester N-(toluene-4-sulfonyl)-L-N-methylalanyl-L-4-(4-methylpiperazin-1-ylcarbonyloxy)phenylalanine tert-butyl ester N-(4-nitrobenzenesulfonyl)-L-prolyl-L-4-(N,N-dimethylcarbamyloxy)phenylalanine tert-butyl ester N-(toluene-4-sulfonyl)-L-[(1,1-dioxo)thiamorpholin-3-carbonyl]-L-4-(N,N-dimethylaminosulfonyloxy)phenylalanine tert-butyl ester N-(toluene-4-sulfonyl)sarcosyl-L-4-(thiomorpholin-4-ylcarbonyloxy)phenylalanine tert-butyl ester N-(toluene-4-sulfonyl)-L-N-methylalanyl-L-4-(4-methylpiperazin-1-ylcarbonyloxy)phenylalanine N-(toluene-4-sulfonyl)-L-prolyl-L-4-(1,1-dioxothiomorpholin-4-ylcarbonyloxy)phenylalanine N-(toluene-4-sulfonyl)-L-prolyl-L-4-(thiomorpholin-4-ylcarbonyloxy)phenylalanine N-(toluene-4-sulfonyl)-L-prolyl-L-4-(isonipecotoyloxy)phenylalanine N-(toluene-4-sulfonyl)-L-prolyl-L-4-(pyrrolidin-1-ylcarbonyloxy)phenylalanine N-(toluene-4-sulfonyl)-L-prolyl-L-4-(morpholin-4-ylcarbonyloxy)phenylalanine N-(toluene-4-sulfonyl)-L-prolyl-L-4-(4-methylpiperazin-1-ylcarbonyloxy)phenylalanine neopentyl ester N-(toluene-4-sulfonyl)-L-prolyl-L-4-(N,N-dimethylcarbamyloxy)phenylalanine neopentyl ester N-(toluene-4-sulfonyl)-L-prolyl-L-4-(4-tert-butyloxycarbonylpiperazin-1-ylcarbonyloxy)phenylalanine ethyl ester N-(toluene-4-sulfonyl)-L-prolyl-L-4-(morpholin-4-ylcarbonyloxy)phenylalanine ethyl ester 2-(saccharin-2-yl)propionoyl-L-4-(4-methylpiperazin-1-ylcarbonyloxy)phenylalanine tert-butyl ester 2-(saccharin-2-yl)propionoyl-L-4-(N,N-dimethylcarbamyloxy)phenylalanine N-(toluene-4-sulfonyl)sarcosyl-L-4-(1,1-dioxothiomorpholin-4-ylcarbonyloxy)phenylalanine tert-butyl ester N-(toluene-4-sulfonyl)sarcosyl-L-4-(thiomorpholin-4-ylcarbonyloxy)phenylalanine N-(toluene-4-sulfonyl)-L-N-methylalanyl-L-4-(N,N-dimethylcarbamyloxy)phenylalanine tert-butyl ester N-(toluene-4-sulfonyl)-L-(thiamorpholin-3-carbonyl)-L-4-(N,N-dimethylcarbamyloxy)phenylalanine tert-butyl ester N-(toluene-4-sulfonyl)sarcosyl-L-4-(1,1-dioxothiomorpholin-4-ylcarbonyloxy)phenylalanine N-(toluene-4-sulfonyl)-L-(1,1-dioxothiamorpholin-3-carbonyl)-L-4-(N,N-dimethylcarbamyloxy)phenylalanine tert-butyl ester N-(toluene-4-sulfonyl)-L-(1,1-dioxothiamorpholin-3-carbonyl)-L-4-(morpholin-4-ylcarbonyloxy)phenylalanine tert-butyl ester N-(toluene-4-sulfonyl)-L-N-methylalanyl-L-4-(N,N-dimethylcarbamyloxy)phenylalanine N-(4-fluorobenzenesulfonyl)-L-(thiamorpholin-3-carbonyl)-L-4-(N,N-dimethylcarbamyloxy)phenylalanine tert-butyl ester N-(4-fluorobenzenesulfonyl)-L-(1,1-dioxothiamorpholin-3-carbonyl)-L-4-(N,N-dimethylcarbamyloxy)phenylalanine tert-butyl ester N-(pyridine-3-sulfonyl)-L-prolyl-L-4-(N,N-dimethylcarbamyloxy)phenylalanine tert-butyl ester N-(pyrimidine-2-sulfonyl)-L-prolyl-L-4-(N,N-dimethylcarbamyloxy)phenylalanine tert-butyl ester N-(4-nitrobenzenesulfonyl)-L-prolyl-L-4-(N,N-dimethylcarbamyloxy)phenylalanine N-(4-cyanobenzenesulfonyl)-L-prolyl-L-4-(N,N-dimethylcarbamyloxy)phenylalanine tert-butyl ester N-(toluene-4-sulfonyl)-L-(1,1-dioxothiamorpholin-3-carbonyl)-L-4-(N,N-dimethylaminosulfonyloxy)phenylalanine N-(toluene-4-sulfonyl)-L-(1,1-dioxothiamorpholin-3-carbonyl)-L-4-(N,N-dimethylcarbamyloxy)phenylalanine N-(toluene-4-sulfonyl)-L-(1,1-dioxo)thiaprolyl-L-4-(N,N-dimethylcarbamyloxy)phenylalanine tert-butyl ester N-(4-fluorobenzenesulfonyl)-L-prolyl-L-4-(N,N-dimethylcarbamyloxy)phenylalanine tert-butyl ester N-(1-methylpyrazole-4-sulfonyl)-L-prolyl-L-4-(N,N-dimethylcarbamyloxy)phenylalanine N-(toluene-4-sulfonyl)-L-(1,1-dioxo)thiaprolyl-L-4-(N,N-dimethylcarbamyloxy)phenylalanine N-(4-fluorobenzenesulfonyl)-L-thiaprolyl-L-4-(N,N-dimethylcarbamyloxy)phenylalanine N-(toluene-4-sulfonyl)-L-prolyl-L-4-(piperazin-1-ylcarbonyloxy)phenylalanine N-(toluene-4-sulfonyl)-L-prolyl-L-4-(1-tert-butyloxycarbonylpiperazin-1-ylcarbonyloxy)phenylalanine tert-butyl ester N-(toluene-4-sulfonyl)-L-prolyl-L-4-(piperazin-1-ylcarbonyloxy)phenylalanine ethyl ester N-(toluene-4-sulfonyl)-L-prolyl-L-4-(4-acetylpiperazin-1-ylcarbonyloxy)phenylalanine ethyl ester N-(toluene-4-sulfonyl)-L-prolyl-L-4-(4-methanesulfonylpiperazin-1-ylcarbonyloxy)phenylalanine ethyl ester N-(toluene-4-sulfonyl)-L-prolyl-L-4-(morpholin-4-ylcarbonyloxy)-3-nitrophenylalanine N-(toluene-4-sulfonyl)-L-prolyl-L-4-(1-tert-butyloxycarbonylpiperazin-1-ylcarbonyloxy)phenylalanine N-(toluene-4-sulfonyl)-L-N-methyl-2-(tert-butyl)glycinyl-L-4-(4-methylpiperazin-1-ylcarbonyloxy)phenylalanine tert-butyl ester N-(4-fluorobenzenesulfonyl)-L-(5,5-dimethyl)thiaprolyl-L-4-(N,N-dimethylcarbamyloxy)phenylalanine tert-butyl ester N-(4-fluorobenzenesulfonyl)-L-(1,1-dioxothiamorpholin-3-carbonyl)-L-4-(1,1-dioxothiomorpholin-4-ylcarbonyloxy)phenylalanine tert-butyl ester N-(toluene-4-sulfonyl)-L-(1,1-dioxothiamorpholin-3-carbonyl)-L-4-(1,1-dioxothiomorpholin-4-ylcarbonyloxy)phenylalanine tert-butyl ester N-(4-fluorobenzenesulfonyl)-L-prolyl-L-4-(1,1-dioxothiomorpholin-4-ylcarbonyloxy)phenylalanine tert-butyl ester N-(4-fluorobenzenesulfonyl)-L-prolyl-L-4-(thiomorpholin-4-ylcarbonyloxy)phenylalanine tert-butyl ester N-(4-fluorobenzenesulfonyl)-L-prolyl-L-4-(morpholin-4-ylcarbonyloxy)phenylalanine tert-butyl ester N-(4-fluorobenzenesulfonyl)-L-(5,5-dimethyl)thiaprolyl-L-4-(N,N-dimethylcarbamyloxy)phenylalanine N-(4-fluorobenzenesulfonyl)-L-(1,1-dioxothiamorpholin-3-carbonyl)-L-4-(morpholin-4-ylcarbonyloxy)phenylalanine tert-butyl ester N-(4-trifluoromethoxybenzenesulfonyl)-L-prolyl-L-4-(N,N-dimethylcarbamyloxy)phenylalanine tert-butyl ester N-(toluene-4-sulfonyl)-L-(1,1-dioxothiamorpholin-3-carbonyl)-L-4-(N,N-dimethylcarbamyloxy)phenylalanine isopropyl ester 3-[N-(toluene-4-sulfonyl)-N-methylamino]-1-[1-tert-butyloxycarbonyl-2-(N,N-dimethylcarbamyloxy)phenylethyl]azetidine N-(4-fluorobenzenesulfonyl)-L-(1,1-dioxo-5,5-dimethyl)thiaprolyl-L-4-(N,N-dimethylcarbamyloxy)phenylalanine tert-butyl ester N-(toluene-4-sulfonyl)-L-(1,1-dioxo-5,5-dimethyl)thiaprolyl-L-4-(N,N-methylcarbamyloxy)phenylalanine isopropyl ester N-(toluene-4-sulfonyl)-L-(1,1-dioxothiamorpholin-3-carbonyl)-L-4-(morpholin-4-ylcarbonyloxy)phenylalanine N-(4-fluorobenzenesulfonyl)-L-(5,5-dimethyl)thiaprolyl-L-4-(N,N-dimethylcarbamyloxy)phenylalanine N-(pyrimidine-2-sulfonyl)-L-prolyl-L-4-(N,N-dimethylcarbamyloxy)phenylalanine N-(toluene-4-sulfonyl)-L-(1,1-dioxothiamorpholin-3-carbonyl)-L-4-(4-methylpiperazin-1-ylcarbonyloxy)phenylalanine tert-butyl ester 3-[N-(toluene-4-sulfonyl)-N-methylamino]-1-[1-carboxy-2-(N,N-dimethylcarbamyloxy)phenylethyl]azetidine N-(1-methylpyrazole-4-sulfonyl)-L-prolyl-L-(4-methylpiperazin-1-ylcarbonyloxy)phenylalanine tert-butyl ester N-(4-fluorobenzenesulfonyl)-L-(1,1-dioxo)thiaprolyl-L-4-(N,N-dimethylcarbamyloxy)phenylalanine N-(toluene-4-sulfonyl)-L-prolyl-L-4-(isonipecotoyloxy)phenylalanine tert-butyl ester N-(toluene-4-sulfonyl)-L-prolyl-L-4-(1,1-dioxothiomorpholin-4-ylcarbonyloxy)phenylalanine tert-butyl ester N-(toluene-4-sulfonyl)-L-prolyl-L-4-(thiomorpholin-4-ylcarbonyloxy)phenylalanine tert-butyl ester N-(toluene-4-sulfonyl)-L-prolyl-L-4-(pyrrolidin-1-ylcarbonyloxy)phenylalanine tert-butyl ester N-(4-fluorobenzenesulfonyl)-L-thiaprolyl-L-4-(N,N-dimethylcarbamyloxy)phenylalanine tert-butyl ester N-(4-fluorobenzenesulfonyl)-L-(1,1-dioxo)thiaprolyl-L-4-(N,N-dimethylcarbamyloxy)phenylalanine tert-butyl ester N-(2,5-dichlorothiophene-3-sulfonyl)-L-prolyl-L-4-(N,N-dimethylcarbamyloxy)phenylalanine tert-butyl ester N-(4-acetamidobenzenesulfonyl)-L-prolyl-L-4-(N,N-dimethylcarbamyloxy)phenylalanine tert-butyl ester N-(4-tert-butylbenzenesulfonyl)-L-(1,1-dioxothiamorpholin-3-carbonyl)-L-4-(N,N-dimethylcarbamyloxy)phenylalanine tert-butyl ester N-(pyridine-2-sulfonyl)-L-prolyl-L-4-(N,N-dimethylcarbamyloxy)phenylalanine N-(2-fluorobenzenesulfonyl)-L-(1,1-dioxothiamorpholin-3-carbonyl)-L-4-(N,N-dimethylcarbamyloxy)phenylalanine tert-butyl ester N-(3-fluorobenzenesulfonyl)-L-(1,1-dioxothiamorpholin-3-carbonyl)-L-4-(N,N-dimethylcarbamyloxy)phenylalanine tert-butyl ester N-(2,4-difluorobenzenesulfonyl)-L-(1,1-dioxothiamorpholin-3-carbonyl)-L-4-(N,N-dimethylcarbamyloxy)phenylalanine tert-butyl ester N-(4-acetamidobenzenesulfonyl)-L-prolyl-L-4-(N,N-dimethylcarbamyloxy)phenylalanine N-(4-trifluoromethoxybenzenesulfonyl)-L-prolyl-L-4-(N,N-dimethylcarbamyloxy)phenylalanine N-(4-fluorobenzenesulfonyl)-L-(5,5-dimethyl)thiaprolyl-L-4-(N,N-dimethylcarbamyloxy)phenylalanine tert-butyl ester N-(4-cyanobenzenesulfonyl)-L-prolyl-L-4-(N,N-dimethylcarbamyloxy)phenylalanine N-(toluene-4-sulfonyl)-L-(3,3-dimethyl)prolyl-L-4-(N,N-dimethylcarbamyloxy)phenylalanine tert-butyl ester N-(toluene-4-sulfonyl)-L-(3,3-dimethyl)prolyl-L-4-(N,N-dimethylcarbamyloxy)phenylalanine isopropyl ester N-(1-methylpyrazole-4-sulfonyl)-L-propyl-L-4-(N,N-dimethylcarbamyloxy)phenylalanine iso-propyl ester N-(1-methylpyrazole-4-sulfonyl)-L-(5,5-dimethyl)thiaprolyl-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine N-(toluene-4-sulfonyl)-L-prolyl-L-4-(N-(1,4-dioxa-8-aza-spiro[4.5]decan-8-yl)carbonyloxy)phenylalanine ethyl ester N-(toluene-4-sulfonyl)-L-prolyl-L-4-(N-(1,4-dioxa-8-aza-spiro[4.5]decan-8-yl)carbonyloxy)phenylalanine N-(toluene-4-sulfonyl)-L-prolyl-L-4-(4'-acetylpiperazin-1-ylcarbonyloxy)phenylalanine N-(toluene-4-sulfonyl)-L-prolyl-L-4-(4'-methanesulfonylpiperazin-1-ylcarbonyloxy)phenylalanine N-(toluene-4-sulfonyl)-L-prolyl-L-4-(4'-phenylpiperazin-1-ylcarbonyloxy)phenylalanine N-(toluene-4-sulfonyl)-L-prolyl-L-4-(piperazin-1-ylcarbonyloxy)phenylalanine tert-butyl ester 2-saccharin-2-yl)propionyl-L-4-(4'-methylpiperazin-1-ylcarbonyloxy)phenylalanine N-(toluene-4-sulfonyl)-L-prolyl-L-4-(4'-methanesulfonylpiperazin-1-ylcarbonyloxy)phenylalanine tert-butyl ester N-(toluene-4-sulfonyl)-L-prolyl-L-4-(N,N-dimethylcarbamyloxy)phenylalanine (N'-tert-butoxycarbonyl-2-amino-2-methylpropyl) ester N-(toluene-4-sulfonyl)-L-prolyl-L-4-(4'-acetylpiperazin-1-ylcarbonyloxy)phenylalanine tert-butyl ester N-(toluene-4-sulfonyl)-L-prolyl-L-4-(4'-hydroxypiperidin-1-ylcarbonyloxy)phenylalanine tert-butyl ester N-(toluene sulfonyl)-L-propyl-L-4-(N-(2'-(morpholin-4'-yl)ethyl)carbamyloxy)phenylalanine tert-butyl ester N-(toluene-4-sulfonyl)-L-prolyl-L-4-(N-(1,4-dioxa-8-aza-spiro[4.5]decan-8-yl)carbonyloxy)phenylalanine tert-butyl ester N-(toluene-4-sulfonyl)-L-prolyl-L-4-(N-(2'-hydroxyethyl)-N-methylcarbamyloxy)phenylalanine tert-butyl ester N-(toluene-4-sulfonyl)-L-prolyl(4'-(2-hydroxyethyl)piperazin-1-ylcarbonyloxy)-L-phenylalanine tert-butyl ester N-(toluene-4-sulfonyl)-L-prolyl-L-4-(N-(2'-formyloxyethyl)-N-methylcarbamyloxy)phenylalanine N-(toluene-4-sulfonyl)-L-prolyl-L-4-(N-(2'-hydroxyethyl)-N-methylcarbamyloxy)phenylalanine isopropyl ester N-(toulene-4-sulfonyl)-L-prolyl-L-4-(N-(methoxycarbonylmethyl)carbamyloxy)phenylalanine tert-butyl ester N-(1-methylpyrazole-4-sulfonyl)-L-(5,5-dimethyl)thiaprolyl-L-(4-N,N-dimethylcarbamyloxy)phenylalanine isopropyl ester N-(toluene-4-sulfonyl)-L-prolyl-L-4-(4'-methoxypiperidin-1-ylcarbonyloxy)phenylalanine isopropyl ester N-(toluene-4-sulfonyl)-L-prolyl-L-4-(4'-methoxypiperidin-1-ylcarbonyloxy)phenylalanine N-(toluene-4-sulfonyl)-L-4-oxoprolyl-L-4-(N,N-dimethylcarbamyloxy)phenylalanine tert-butyl ester N-(toluene-4-sulfonyl)-L-trans-4-hydroxyprolyl-L-4-(N,N-dimethylcarbamyloxy)phenylalanine tert-butyl ester N-(3-fluorobenzenesulfonyl)-L-prolyl-L-4-(N,N-dimethylcarbamyloxy)phenylalanine tert-butyl ester N-(morpholino-sulfonyl)-L-prolyl-L-(4-N,N-dimethylcarbamyloxy)phenylalanine tert-butyl ester N-(morpholino-sulfonyl)-L-prolyl-L-(4-N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine tert-butyl ester N-(2-fluorobenzenesulfonyl)-L-(1,1-dioxothiamorpholin-3-carbonyl)-L-4-(N,N-dimethylcarbamyloxy)phenylalanine N-(2,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine N-(pyridine-3-sulfonyl)-L-(5,5-dimethyl-thiaprolyl-L-4-(N,N-dimethylcarbamyloxy)phenylalanine isopropyl ester N-(3-fluorobenzenesulfonyl)-L-(1,1-dioxothiamorpholin-3-carbonyl)-L-4-(N,N-dimethylcarbamyloxy)phenylalanine N-(1-methylpyrazole-4-sulfonyl)-L-(1,1-dioxothiamorpholin-3-carbonyl)-L-4-(N,N-dimethylcarbamyloxy)phenylalanine N-(4-tert-butylbenzenesulfonyl)-L-(1,1-dioxothiamorpholin-3-carbonyl)-L-4-(N,N-dimethylcarbamyloxy)phenylalanine N-(toluene-4-sulfonyl)-(3,3-dimethyl)prolyl-L-4-(N,N-dimethylcarbamyloxy)phenylalanine N-(2,5-dichlorothiophene-3-sulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine N-(4-methoxybenzenesulfonyl)-L-prolyl-L-4-(N,N-dimethylcarbamyloxy)phenylalanine isopropyl ester N-(toluene-4-sulfonyl)-L-(1-oxo-thiomorpholin-3-carbonyl)-L-4-(N,N-dimethylcarbamyloxy)phenylalanine N-(toluene-4-sulfonyl)-L-(1-oxo-thiomorpholin-3-carbonyl)-L-4-(N,N-dimethylcarbamyloxy)phenylalanine tert-butyl ester N-(3,4-difluorobenzenesulfonyl)-L-prolyl-4-(N,N-dimethylcarbamyloxy)phenylalanine isopropyl ester N-(3,4-difluorobenzenesulfonyl)-L-prolyl-4-(N,N-dimethylcarbamyloxy)phenylalanine N-(3,4-difluorobenzenesulfonyl)-L-(1,1-dioxothiamorpholin-3-carbonyl)-L-4-(N,N-dimethylcarbamyloxy)phenylalanine tert-butyl ester N-(3,4-difluorobenzenesulfonyl)-L-(1,1-dioxothiamorpholin-3-carbonyl)-L-4-(N,N-dimethylcarbamyloxy)phenylalanine N-(toluene-4-sulfonyl)-L-(5,5-dimethyl)thiaprolyl-L-(thiomorpholin-4-ylcarbonyloxy)phenylalanine tert-butyl ester N-(toluene-4-sulfonyl)-L-(5,5-dimethyl)thiaprolyl-L-(thiomorpholin-4-ylcarbonyloxy)phenylalanine N-(1-methylpyrazole-4-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine N-(pyridine-2-sulfonyl)-L-prolyl-L-4-(N,N-dimethylcarbamyloxy)phenylalanine isopropyl ester N-(pyridine-2-sulfonyl)-L-prolyl-L-4-(N,N-dimethylcarbamyloxy)phenylalanine N-(pyridine-2-sulfonyl)-L-(5,5-dimethyl)thiaprolyl-L-4-(N,N-dimethylcarbamyloxy)phenylalanine isopropyl ester N-(pyridine-2-sulfonyl)-L-(5,5-dimethyl)thiaprolyl-L-4-(N,N-dimethylcarbamyloxy)phenylalanine N-(toluene-4-sulfonyl)-L-(thiamorpholin-3-carbonyl)-L-4-(N,N-dimethylcarbamyloxy)phenylalanine isopropyl ester N-(3-fluorobenzenesulfonyl)-L-(5,5-dimethyl)thiaprolyl-L-4-(N,N-dimethylcarbamyloxy)phenylalanine isopropyl ester N-(2-fluorobenzenesulfonyl)-L-(5,5-dimethyl)thiaprolyl-L-4-(N,N-dimethylcarbamyloxy)phenylalanine isopropyl ester N-(3,4-difluorobenzenesulfonyl)-L-(5,5-dimethyl)thiaprolyl-L-4-(N,N-dimethylcarbamyloxy)phenylalanine isopropyl ester N-(3,5-difluorobenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(5,5-dimethyl)thiaprolyl-L-4-(N,N-dimethylcarbamyloxy)phenylalanine isopropyl ester N-(4-chlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(5,5-dimethyl)thiaprolyl-L-4-(N,N-dimethylcarbamyloxy)phenylalanine isopropyl ester N-(2-chlorobenzenesulfonyl)-L-(5,5-dimethyl)thiaprolyl-L-4-(N,N-dimethylcarbamyloxy)phenylalanine isopropyl ester N-(3,4-dichlorobenzenesulfonyl)-L-(5,5-dimethyl)thiaprolyl-L-4-(N,N-dimethylcarbamyloxy)phenylalanine isopropyl ester N-(3,5-dichlorobenzenesulfonyl)-L-(5,5-dimethyl)thiaprolyl-L-4-(N,N-dimethylcarbamyloxy)phenylalanine isopropyl ester N-(3-chlorobenzenesulfonyl)-L-(1,1-dioxothiamorpholin-3-carbonyl)-L-4-(N,N-dimethylcarbamyloxy)phenylalanine tert-butyl ester N-(3,4-dichlorobenzenesulfonyl)-L-(1,1-dioxothiamorpholin-3-carbonyl)-L-4-(N,N-dimethylcarbamyloxy)phenylalanine tert-butyl ester N-(4-methoxybenzenesulfonyl)-L-(5,5-dimethyl)thiaprolyl-L-4-(N,N-dimethylcarbamyloxy)phenylalanine isopropyl ester N-(3-methoxybenzenesulfonyl)-L-(5,5-dimethyl)thiaprolyl-L-4-(N,N-dimethylcarbamyloxy)phenylalanine isopropyl ester N-(2-methoxybenzenesulfonyl)-L-(5,5-dimethyl)thiaprolyl-L-4-(N,N-dimethylcarbamyloxy)phenylalanine isopropyl ester N-(3,4-dimethoxybenzenesulfonyl)-L-(5,5-dimethyl)thiaprolyl-L-4-(N,N-dimethylcarbamyloxy)phenylalanine isopropyl ester N-(2,4-difluorobenzenesulfonyl)-L-(thiamorpholin-3-carbonyl)-L-4-(N,N-dimethylcarbamyloxy)phenylalanine isopropyl ester N-(3,4-dichlorobenzenesulfonyl)-L-(1,1-dioxothiamorpholin-3-carbonyl)-L-4-(N,N-dimethylcarbamyloxy)phenylalanine N-(3-chlorobenzenesulfonyl)-L-(1,1-dioxothiamorpholin-3-carbonyl)-L-4-(N,N-dimethylcarbamyloxy)phenylalanine N-(3-chloro-4-fluorobenzenesulfonyl)-L-(1,1-dioxothiamorpholin-3-carbonyl)-L-4-(N,N-dimethylcarbamyloxy)phenylalanine tert-butyl ester N-(1-methylpyrazole-4-sulfonyl)-L-(thiamorpholin-3-carbonyl)-L-4-(N,N-dimethylcarbamyloxy)phenylalanine tert-butyl ester N-(3,4-difluorobenzenesulfonyl)-L-(thiamorpholin-3-carbonyl)-L-4-(N,N-dimethylcarbamyloxy)phenylalanine tert-butyl ester N-(toluene-4-sulfonyl)-L-(5,5-dimethyl)thioprolyl-L-(thiomorpholin-4-ylcarbonyloxy)phenylalanine isopropyl ester N-(3,4-difluorobenzenesulfonyl)-L-(thiamorpholin-3-carbonyl)-L-4-(N,N-dimethylcarbamyloxy)phenylalanine N-(2,5-dichlorothiophene-3-sulfonyl)-L-(5,5-dimethyl)thiaprolyl-L-4-(N,N-dimethylcarbamyloxy)phenylalanine isopropyl ester N-(1-methylpyrazole-4-sulfonyl)-L-(5,5-dimethyl)thiaprolyl-L-4-(thiomorpholin-4-ylcarbonyloxy)phenylalanine isopropyl ester N-(8-quinolinesulfonyl)-L-prolyl-L-4-(N,N-dimethylcarbamyloxy)phenylalanine isopropyl ester N-(8-quinolinesulfonyl)-L-prolyl-L-4-(N,N-dimethylcarbamyloxy)phenylalanine N-(8-quinolinesulfonyl)-L-(5,5-dimethyl)thiaprolyl-L-4-(N,N-dimethylcarbamyloxy)phenylalanine isoproplyl ester N-(8-quinolinesulfonyl)-L-(5,5-dimethyl)thiaprolyl-L-4-(N,N-dimethylcarbamyloxy)phenylalanine N-(toluene-4-sulfonyl)-L-prolyl-L-4-(4-phenylpiperazin-1-ylcarbonyloxy)phenylalanine tert-butyl ester N-(toluene-4-sulfonyl)-L-prolyl-L-4-(4'-(ethoxycarbonyl)piperidin-1-ylcarbonyloxy)phenylalanine tert-butyl ester N-(pyridine-3-sulfonyl)-L-(5,5-dimethyl)thiaprolyl-L-4-(N,N-dimethylcarbamyloxy)phenylalanine tert-butyl ester N-(3-sulfonamido-4-chloro-benzenesulfonyl)-L-prolyl-L-4-(N,N-dimethylcarbamyloxy)phenylalanine isopropyl ester N-(toluene-4-sulfonyl)-L-(1-oxothiomorpholin-3-carbonyl)-L-4-(N,N-dimethylcarbamyloxy)phenylalanine isopropyl ester N-(2,4-difluorobenzenesulfonyl)-L-(1-oxothiomorpholin-3-carbonyl)-L-4-(N,N-dimethylcarbamyloxy)phenylalanine tert-butyl ester N-(1-methylpyrazole-4-sulfonyl)-L-(5,5-dimethyl)thiaprolyl-L-4-(N,N-dimethylcarbamyloxy)phenylalanine 2,2-dimethylpropyl ester N-(pyridine-3-sulfonyl)-L-(5,5-dimethyl)thiaprolyl-L-4-(N,N-dimethylcarbamyloxy)phenylalanine 2,2-dimethylpropyl ester N-(1-methylpyrazole-4-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine methyl ester N-(pyridine-3-sulfonyl)-L-(5,5-dimethyl)thiaprolyl-L-4-(N,N-dimethylcarbamyloxy)phenylalanine ethyl ester N-(pyridine-3-sulfonyl)-L-(5,5-dimethyl)thiaprolyl-L-4-(N,N-dimethylcarbamyloxy)phenylalanine cyclopropylmethyl ester N-(1-methylpyrazole-4-sulfonyl)-L-(5,5-dimethyl)thiaprolyl-L-4-(N,N-dimethylcarbamyloxy)phenylalanine 2-methoxyphenyl ester N-(1-methylpyrazole-4-sulfonyl)-L-(5,5-dimethyl)thiaprolyl-L-4-(N,N-dimethylcarbamyloxy)phenylalanine n-butyl ester N-(1-methylpyrazole-4-sulfonyl)-L-(5,5-dimethyl)thiaprolyl-L-4-(N,N-dimethylcarbamyloxy)phenylalanine n-propyl ester N-(1-methylpyrazole-4-sulfonyl)-L-(5,5-dimethyl)thiaprolyl-L-4-(N,N-dimethylcarbamyloxy)phenylalanine 2,2-dimethylpropionyloxymethyl ester N-(toluene-4-sulfonyl)-L-prolyl-L-4-(N-(4'-(2'-aminoethyl)morpholino)carbamyloxy)phenylalanine N-(toluene-4-sulfonyl)-L-prolyl-L-4-[4-(carboxy)piperidin-1-ylcarbonyloxy]phenylalanine N-(toluene-4-sulfonyl)-L-prolyl-L-4-(N,N-bis-(2-hydroxyethyl)carbamyloxy)phenylalanine isopropyl ester N-(toluene-4-sulfonyl)-L-prolyl-L-4-[3-(hydroxymethyl)piperidin-1-ylcarbonyloxy]phenylalanine isopropyl ester N-(toluene-4-sulfonyl)-L-prolyl-L-4-(4-trifluoromethanesulfonylpiperazin-1-ylcarbonyloxy)phenylalanine tert-butyl ester N-(4-(N-phenylurea)benzenesulfonyl)-L-prolyl-L-4-(N,N-dimethylcarbamyloxy)phenylalanine tert-butyl ester N-(2-trifluoroacetyl-1,2,3,4-tetrahydroisoquinolin-7-sulfonyl)-L-prolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine N-(pyridine-4-sulfonyl)-L-(5,5-dimethyl)thiaprolyl-L-4-(N,N-dimethylcarbamyloxy)phenylalanine isopropyl ester N-(pyridine-4-sulfonyl)-L-(5,5-dimethyl)thiaprolyl-L-4-(N,N-dimethylcarbamyloxy)phenylalanine N-(toluene-4-sulfonyl)-L-(5,5-methyl)thiaprolyl-L-4-(N-methyl-N-(2-dimethylaminoethyl)carbamyloxy)phenylalanine tert-butyl ester N-(toluene-4-sulfonyl)-L-prolyl-L-4-(N-methyl-N-(2-dimethylaminoethyl)carbamyloxy)phenylalanine tert-butyl ester N-(toluene-4-sulfonyl)-L-(5,5-dimethyl)thiapropyl-L-4-(N-methyl-N-(2-dimethylaminoethyl)carbamyloxy)phenylalanine N-(toluene-4-sulfonyl)-L-prolyl-L-4-(N-methyl-N-(2-dimethylaminoethyl)carbamyloxy)phenylalanine N-(4-fluorobenzenesulfonyl)-L-(5,5-dimethyl)thiaprolyl-L-3-chloro-4-(4-methylpiperazin-1-ylcarbonyloxy)phenylalanine tert-butyl ester N-(4-fluorobenzenesulfonyl)-L-(5,5-dimethyl)thiaprolyl-L-3-chloro-4-(N,N-dimethylcarbamyloxy)phenylalanine N-(4-fluorobenzenesulfonyl)-L-(5,5-dimethyl)thiaprolyl-L-3-chloro-4-(thiomorpholin-4-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine isopropyl ester N-(4-fluorobenzenesulfonyl)-L-(5,5-dimethyl)thiaprolyl-L-3-chloro-4-(N,N-dimethylcarbamyloxy)]phenylalanine isopropyl ester N-(toluene-4-sulfonyl)-L-(5,5-dimethyl)thiaprolyl-L-3-chloro-4-(N,N-dimethylcarbamyloxy)phenylalanine isopropyl ester N-(4-fluorobenzenesulfonyl)-L-(5,5-dimethyl)thiaprolyl-L-3-chloro-4-(4-methylpiperazin-1-ylcarbonyloxy)]phenylalanine isopropyl ester N-(toluene-4-sulfonyl)-L-prolyl-L-3-chloro-4-(N,N-dimethylcarbamyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine isopropyl ester N-(4-fluorobenzenesulfonyl)-L-(5,5-dimethyl)thiaprolyl-L-3-chloro-4-(4-(2'-pyridyl)-piperazin-1-ylcarbonyloxy)]phenylalanine tert-butyl ester N-(4-nitrobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine isopropyl ester N-(toluene-4-sulfonyl)-L-prolyl-L-4-(thiomorpholin-4-ylcarbonyloxy)phenylalanine isopropyl ester N-(toluene-4-sulfonyl)-L-prolyl-L-4-(4-phenylcarbamylpiperazin-1-ylcarbonyloxy)phenylalanine isopropyl ester N-(toluene-4-sulfonyl)-L-prolyl-L-4-(4-phenylcarbamylpiperazin-1-ylcarbonyloxy)phenylalanine N-(1-n-butylpyrazole-4-sulfonyl)-L-(5,5-dimethyl)thiaprolyl-L-4-(N,N-dimethylcarbamyloxy)phenylalanine isopropyl ester N-(toluene-4-sulfonyl)-L-prolyl-L-4-(pyridin-4-ylcarbonyl)piperazin-1-ylcarbonyloxy)phenylalanine isopropyl ester N-(toluene-4-sulfonyl)-L-4-oxoprolyl-L-4-(N,N-dimethylcarbamyloxy)phenylalanine N-(toluene-4-sulfonyl)-L-trans-4-hydroxyprolyl-L-4-(N,N-dimethylcarbamyloxy)phenylalanine N-(4-cyanobenzenesulfonyl)-L-prolyl-L-4-(N,N-dimethylcarbamyloxy)phenylalanine isopropyl ester N-(4-aminobenzenesulfonyl)-L-prolyl-L-4-(N,N-dimethylcarbamyloxy)phenylalanine N-(toluene-4-sulfonyl)-L-4-oxoprolyl-L-4-(4-methylpiperazin-1-ylcarbonyloxy)phenylalanine tert-butyl ester N-(toluene-4-sulfonyl)-L-prolyl-L-4-[3-(hydroxymethyl)piperidin-1-ylcarbonyloxy]phenylalanine N-(toluene-4-sulfonyl)-L-(4,4-difluoro)prolyl-L-4-(N,N-dimethylcarbamyloxy)phenylalanine isopropyl ester N-(toluene-4-sulfonyl)-L-(4,4-difluoro)prolyl-L-4-(N,N-dimethylcarbamyloxy)phenylalanine N-(toluene-4-sulfonyl)-L-prolyl-L-(4-benzoylpiperazin-1-ylcarbonyloxy)phenylalanine isopropyl ester N-(1-methyl-1H-imidazole-4-sulfonyl)-L-prolyl-L-4-(N,N-dimethylcarbamyloxy)phenylalanine isopropyl ester N-(toluene-4-sulfonyl)-L-4-(thiomorpholin-4-ylcarbonyloxy)prolyl-L-4-(thiomorpholin-4-ylcarbonyloxy)phenylalanine N-(4-cyanobenzenesulfonyl)-L-prolyl-L-4-(thiomorpholin-4-ylcarbonyloxy)phenylalanine isopropyl ester N-(4-amidinobenzenesulfonyl)-L-prolyl-L-4-(N,N-dimethylcarbamyloxy)phenylalanine methyl ester N-(toluene-4-sulfonyl)-L-4-oxoprolyl-L-4-(thiomorpholin-4-ylcarbonyloxy)phenylalanine tert-butyl ester N-(toluene-4-sulfonyl)-L-4-hydroxyprolyl-L-4-(thiomorpholin-4-ylcarbonyloxy)phenylalanine N-(toluene-4-sulfonyl)-L-prolyl-L-(4-benzoylpiperazin-1-ylcarbonyloxy)phenylalanine N-(4-amidinobenzenesulfonyl)-L-prolyl-L-4-(thiomorpholin-4-ylcarbonyloxy)phenylalanine methyl ester N-(3-fluorobenzenesulfonyl)-L-prolyl-L-4-(N,N-dimethylcarbamyloxy)phenylalanine N-(toluene-4-sulfonyl)-L-prolyl-L-4-[N-methyl-N-(2-(N'-methyl-N'-toluenesulfonyl-amino)ethyl)carbamyloxy]phenylalanine isopropyl ester N-(toluene-4-sulfonyl)-L-prolyl-L-4-[N-(2-(N'-phenylaminocarbonyloxy)ethyl)carbamyloxy)]phenylalanine isopropyl ester N-(4-fluorobenzenesulfonyl)-L-4-(trans-hydroxy)prolyl-L-4-(N,N-dimethylcarbamyloxy)phenylalanine isopropyl ester N-(4-fluorobenzenesulfonyl)-L-4-(trans-hydroxy)prolyl-L-4-(N,N-dimethylcarbamyloxy)phenylalanine tert-butyl ester N-(4-amidinobenzenesulfonyl)-L-prolyl-L-4-(N,N-dimethylcarbamyloxy)phenylalanine piperazine-1,4-dicarboxylic acid bis-{4-[(2S)-2-tert-butoxycarbonyl-2-((4R)-5,5-dimethyl-3-(toluene-4-sulfonyl)thiazolidine-4-carboxamido)ethyl]phenyl}ester piperazine-1,4-dicarboxylic acid bis-{4-[(2S)-2-carboxy-2-((4R)-5,5-dimethyl-3-(toluene-4-sulfonyl)thiazolidine-4-carboxamido)ethyl]phenyl}ester N-(toluene-4-sulfonyl)-L-(pyrazin-3-carbonyl)-L-4-(N,N-dimethylcarbamyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine tert-butyl ester N-(4-fluorobenzenesulfonyl)-L-(5,5-dimethyl)thiaprolyl-L-4-(2-hydroxymethylpyrrolidin-1-ylcarbonyloxy)phenylalanine N-(toluene-4-sulfonyl)-L-prolyl-L-4-(2-methoxycarbonylpyrrolidin-1-ylcarbonyloxy)phenylalanine tert-butyl ester N-(4-fluorobenzenesulfonyl)-L-(5,5-dimethyl)thiaprolyl-L-3-chloro-4-(thiomorpholin-4-ylcarbonyloxy)phenylalanine N-(4-fluorobenzenesulfonyl)-L-(5,5-dimethyl)thiaprolyl-L-4-(4-(2-pyridyl)piperazin-1-ylcarbonyloxy)]phenylalanine N-(4-fluorobenzenesulfonyl)-L-(5,5-dimethyl)thiaprolyl-L-4-(4-(2-pyridyl)piperazin-1-ylcarbonyloxy)]phenylalanine tert-butyl ester piperazine-1,4-dicarboxylic acid bis-{4-[(2S)-2-isopropoxycarbonyl-2-((2R)-1-(toluene-4-sulfonyl)pyrrolidine-2-carboxamido)ethyl]phenyl}ester N-(toluene-4-sulfonyl)-L-(4-hydroxy)prolyl-L-4-(thiomorpholin-4-ylcarbonyloxy)phenylalanine tert-butyl ester N-(toluene-4-sulfonyl)-L-prolyl-L-4-(N,N-dimethylcarbamyloxy)phenylalanine 2-(2-methoxyethoxy)ethyl ester N-(4-fluorobenzenesulfonyl)-L-(5,5-dimethyl)thiaprolyl-L-4-(4-(2-pyrimidyl)piperazin-1-ylcarbonyloxy)]phenylalanine tert-butyl ester N-(4-fluorobenzenesulfonyl)-L-(5,5-dimethyl)thiaprolyl-L-3-fluoro-4-(N,N-dimethylcarbamyloxy)phenylalanine isopropyl ester N-(toluene-4-sulfonyl)-L-(1-methanesulfonylpyrazin-3-carbonyl)-L-4-(N,N-dimethylcarbamyloxy)phenylalanine tert-butyl ester N-[2-(1,1-dioxo-2,3-dihydro-3,3-dimethyl-1,2-benzisothiazol-2-yl)acetyl]-L-4-(N,N-dimethylcarbamyloxy)phenylalanine N-[2-(N-2,10-camphorsultamyl)acetyl]-L-4-(N,N-dimethylcarbamyloxy)phenylalanine tert-butyl ester N-[2-(N-2,10-camphorsultamyl)acetyl]-L-4-(N,N-dimethylcarbamyloxy)phenylalanine N-[2-(N-2,10-camphorsultamyl)acetyl]-L-3-chloro-4-(N,N-dimethylcarbamyloxy)phenylalanine isopropyl ester N-(4-bromobenzenesulfonyl)-L-(5,5-dimethyl)thiaprolyl-L-4-(N,N-dimethylcarbamyloxy)phenylalanine tert-butyl ester N-(4-bromobenzenesulfonyl)-L-(5,5-dimethyl)thiaprolyl-L-4-(N,N-dimethylcarbamyloxy)phenylalanine N-(toluene-4-sulfonyl)-L-(4-hydroxy)prolyl-L-4-(4-methylpiperazin-1-ylcarbonyloxy)phenylalanine N-(4-fluorobenzenesulfonyl)-L-(5,5-dimethyl)thiaprolyl-L-4-(4-(2-pyrimidyl)piperazin-1-ylcarbonyloxy)]phenylalanine piperazine-1,4-dicarboxylic acid bis-{4-[(2S)-2-tert-butoxycarbonyl-2-((2R)-1-(toluene-4-sulfonyl)pyrrolidine-2-carboxamido)ethyl]phenyl}ester N-(4-fluorobenzenesulfonyl)-L-(5,5-dimethyl)thiaprolyl-L-4-(4-(2-pyridyl)piperazin-1-ylcarbonyloxy)] phenylalanine isopropyl ester N-(4-fluorobenzenesulfonyl)thiazolidinyl-2-carbonyl-L-4-(N,N-dimethylcarbamyloxy)phenylalanine N-(4-fluorobenzenesulfonyl)thiazolidinyl-2-carbonyl-L-4-(N,N-dimethylcarbamyloxy)phenylalanine tert-butyl ester N-(toluene-4-sulfonyl)-L-(4-oxo)prolyl-L-4-(thiomorpholin-4-ylcarbonyloxy)phenylalanine N-(toluene-4-sulfonyl)-L-(4-oxo)prolyl-L-4-(4-methylpiperazin-1-ylcarbonyloxy)phenylalanine N-(4-fluorobenzenesulfonyl)thiazolidinyl-2-carbonyl-L-4-(4-(2-pyridyl)piperazin-1-ylcarbonyloxy)] phenylalanine N-(4-nitrobenzenesulfonyl)-L-prolyl-L-4-(4-(2-pyridyl)piperazin-1-ylcarbonyloxy)]phenylalanine tert-butyl ester N-(4-fluorobenzenesulfonyl)thiazolidinyl-2-carbonyl-L-4-(4-(2-pyridyl)piperazin-1-ylcarbonyloxy)] phenylalanine tert-butyl ester N-(4-bromobenzenesulfonyl)-L-(5,5-dimethyl)thiaprolyl-L-4-(4-(2-pyridyl)piperazin-1-ylcarbonyloxy)]phenylalanine N-(toluene-4-sulfonyl)-L-prolyl-L-4-(4-(N-phenylthiocarbonyl)piperazin-1-ylcarbonyloxy)] phenylalanine isopropyl ester N-(4-fluorobenzenesulfonyl)thiazolidinyl-2-carbonyl-L-4-(4-methylhomopiperazin-1-ylcarbonyloxy) phenylalanine tert-butyl ester piperazine-1,4-dicarboxylic acid bis-{4-[(2S)-2-carboxyl-2-((2R)-1-(toluene-4-sulfonyl)pyrrolidine-2-carboxamido)ethyl]phenyl}ester N-(toluene-4-sulfonyl)-L-4-(methanesulfonyloxy)prolyl-L-4-(N,N-dimethylcarbamyloxy)phenylalanine tert-butyl ester N-(4-aminocarbonylbenzenesulfonyl)-L-prolyl-L-4-(N,N-dimethylcarbamyloxy)phenylalanine N-(4-aminocarbonylbenzenesulfonyl)-L-prolyl-L-4-(thiomorpholin-4-ylcarbonyloxy)phenylalanine N-(4-amidinobenzenesulfonyl)-L-prolyl-L-4-(thiomorpholin-4-ylcarbonyloxy)phenylalanine N-(4-nitrobenzenesulfonyl)-L-prolyl-L-4-(4-(2-pyridyl)piperazin-1-ylcarbonyloxy)]phenylalanine N-(4-fluorobenzenesulfonyl)-L-(5,5-dimethyl)thiaprolyl-L-3-chloro-4-(4-(2-pyridyl)piperazin-1-ylcarbonyloxy)]phenylalanine ethyl ester N-(4-fluorobenzenesulfonyl)-L-(5,5-dimethyl)thiaprolyl-L-3-chloro-4-(4-(2-pyridyl)piperazin-1-ylcarbonyloxy)phenylalanine N-(4-fluorobenzenesulfonyl)thiazolidinyl-2-carbonyl-L-4-(4-methylhomopiperazin-1-ylcarbonyloxy)phenylalanine N-(1-methylpyrazole-3-sulfonyl)-L-(5,5-dimethyl)thiaprolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine isopropyl ester N-(1-methylimidazole-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine N-(toluene-4-sulfonyl)-L-prolyl-L-4-(4-(2-pyridyl)piperazin-1-ylcarbonyloxy)phenylalanine tert-butyl ester N-(toluene-4-sulfonyl)-L-prolyl-L-4-(4-(2-pyridyl)piperazin-1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine isopropyl ester N-(4-fluorobenzenesulfonyl)-L-prolyl-L-4-(4-(2-pyridyl)piperazin-1-ylcarbonyloxy)phenylalanine tert-butyl ester N-(toluene-4-sulfonyl)-L-(1-methanesulfonylpyrazin-3-carbonyl)-L-4-(N,N-dimethylcarbamyloxy)phenylalanine N-(toluene-4-sulfonyl)-L-4-(methanesulfonyloxy)prolyl-L-4-(N,N-dimethylcarbamyloxy)phenylalanine N-(methanesulfonyl)-N-benzylglycinyl-L-4-(N,N-dimethylcarbamyloxy)phenylalanine tert-butyl ester N-(4-bromobenzenesulfonyl)-L-(5,5-dimethyl)thiaprolyl-L-4-(4-(2-pyridyl)piperazin-1-ylcarbonyloxy)phenylalanine tert-butyl ester N-(4-trifluoromethoxybenzenesulfonyl)-L-(5,5-dimethyl)thiaprolyl-L-4-(N,N-dimethylcarbamyloxy)phenylalanine N-(4-trifluoromethoxybenzenesulfonyl)-L-(5,5-dimethyl)thiaprolyl-L-4-(N,N-dimethylcarbamyloxy)phenylalanine tert-butyl ester N-(4-trifluoromethoxybenzenesulfonyl)-L-(5,5-dimethyl)thiaprolyl-L-4-(4-(2-pyridyl)piperazin-1-ylcarbonyloxy)phenylalanine tert-butyl ester N-(4-fluorobenzenesulfonyl)-L-prolyl-L-4-(4-(2-pyridyl)piperazin-1-ylcarbonyloxy)phenylalanine N-(4-fluorobenzenesulfonyl)-L-(4-hydroxy)prolyl-L-4-(4-(2-pyridyl)piperazin-1-ylcarbonyloxy)phenylalanine N-(4-trifluoromethoxybenzenesulfonyl)-L-(5,5-dimethyl)thiaprolyl-L-4-(4-(2-pyridyl)piperazin-1-ylcarbonyloxy)phenylalanine N-(1-methylimidazole-4-sulfonyl)-L-prolyl-L-3-chloro-4-(N,N-dimethylcarbamyloxy)phenylalanine N-(1-methylimidazole-4-sulfonyl)-L-prolyl-L-3-chloro-4-(N,N-dimethylcarbamyloxy)phenylalanine isopropyl ester N-(1-methylimidazole-4-sulfonyl)-L-prolyl-L-4-(4-(2-pyridyl)piperazin-1-ylcarbonyloxy)phenylalanine N-(1-methylimidazole-4-sulfonyl)-L-(5,5-dimethyl)thiaprolyl-L-4-(4-(2-pyridyl)piperazin-1-ylcarbonyloxy)phenylalanine N-(1-methylpyrazole-3-sulfonyl)-L-prolyl-L-4-(4-(2-pyridyl)piperazin-1-ylcarbonyloxy)phenylalanine N-(1-methylpyrazole-3-sulfonyl)-L-prolyl-L-4-(4-(2-pyridyl)piperazin-1-ylcarbonyloxy)phenylalanine isopropyl ester N-(1-methylpyrazole-3-sulfonyl)-L-prolyl-L-4-(4-(2-pyridyl)piperazin-1-ylcarbonyloxy)phenylalanine tert-butyl ester N-(1-methylpyrazole-3-sulfonyl)-L-(5,5-dimethyl)thiaprolyl-L-4-(4-(2-pyridyl)piperazin-1-ylcarbonyloxy)phenylalanine tert-butyl ester N-(1-methylimidazole-4-sulfonyl)-L-prolyl-L-3-chloro-4-(4-(2-pyridyl)piperazin-1-ylcarbonyloxy)phenylalanine isopropyl ester N-(1-methylpyrazole-3-sulfonyl)-L-(5,5-dimethyl)thiaprolyl-L-4-(N,N-dimethylcarbamyloxy)phenylalanine 2-phenoxyethyl ester N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine N-(1-methylpyrazole-3-sulfonyl)-L-(5,5-dimethyl)thiaprolyl-L-3-chloro-4-(4-(2-pyridyl)piperazin-1-ylcarbonyloxy)phenylalanine ethyl ester N-(3-chloro-1,5-dimethylpyrazole-3-sulfonyl)-L-(5,5-dimethyl)thiaprolyl-L-3-chloro-4-(4-(5-trifluoromethyl-2-pyridyl)piperazin-1-ylcarbonyloxy)phenylalanine and pharmaceutically acceptable salts thereof as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester, tert-butyl ester and neopentyl ester.

This invention also provides methods for binding VLA-4 in a biological sample which method comprises contacting the biological sample with a compound of formula I or IA above under conditions wherein said compound binds to VLA-4.

Certain of the compounds of formula I and IA above are also useful in reducing VLA-4 mediated inflammation in vivo.

This invention also provides pharmaceutical compositions comprising a pharmaceutically acceptable carrier and a therapeutically effective amount of one or more of the compounds of formula I or IA above with the exception that $R^3$ and $R^5$ are derived from L-amino acids or other similarly configured starting materials (alternatively racemic mixtures can be used).

The pharmaceutical compositions may be used to treat VLA-4 mediated disease conditions. Such disease conditions include, by way of example, asthma, Alzheimer's disease, atherosclerosis, AIDS dementia, diabetes (including acute juvenile onset diabetis), inflammatory bowel disease (including ulcerative colitis and Crohn'disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in-adult respiratory distress syndrome.

Accordingly, this invention also provides methods for the treatment of an inflammatory disease in a patient mediated by VLA-4 which methods comprise administering to the patient the pharmaceutical compositions described above.

Preferred compounds of formula I and IA above include those set forth in Table I below:

TABLE IA $$R^1-\underset{\underset{O}{\overset{O}{\|}}}{S}-\underset{R^2}{N}-CH-\overset{O}{\overset{\|}{C}}-\underset{H}{N}-\overset{R^5}{CH}-\overset{O}{\overset{\|}{C}}-R^{6'}$$

| $R^1$ | $R^2$ | $R^3$ | $R^5$ | $R^{6'}$ |
|---|---|---|---|---|
| p-CH$_3$-φ | $R^2/R^3$ = cyclic 3 carbon atoms (L-pyrrolidinyl) | | p-[(4-methylpiperazin-1-yl)C(O)O-]benzyl- | —OCH$_2$CH$_3$ |
| p-CH$_3$-φ | $R^2/R^3$ = cyclic 3 carbon atoms (L-pyrrolidinyl) | | p-[(CH$_3$)$_2$NC(O)O-]benzyl- | —OCH$_2$CH$_3$ |
| p-CH$_3$-φ | $R^2/R^3$ = cyclic 3 carbon atoms (L-pyrrolidinyl) | | p-[(4-methylpiperazin-1-yl)C(O)O-]benzyl- | —OCH(CH$_3$)$_2$ |
| p-CH$_3$-φ | $R^2/R^3$ = cyclic 3 carbon atoms (L-pyrrolidinyl) | | p-[(4-methylpiperazin-1-yl)C(O)O-]benzyl- | —O-n-butyl |
| p-CH$_3$-φ | $R^2/R^3$ = cyclic 3 carbon atoms (L-pyrrolidinyl) | | p-[(4-methylpiperazin-1-yl)C(O)O-]benzyl- | —O-cyclopentyl |
| p-CH$_3$-φ | $R^2/R^3$ = cyclic 3 carbon atoms (L-pyrrolidinyl) | | p-[(4-methylpiperazin-1-yl)C(O)O-]benzyl- | —OC(CH$_3$)$_3$ |
| p-CH$_3$-φ | $R^2/R^3$ = cyclic 3 carbon atoms (L-pyrrolidinyl) | | p-[(4-methylpiperazin-1-yl)C(O)O-]benzyl- | —OH |
| p-CH$_3$-φ | $R^2/R^3$ = cyclic 3 carbon atoms (L-pyrrolidinyl) | | p-[(CH$_3$)$_2$NC(O)O-]benzyl- | —OCH(CH$_3$)$_2$ |
| p-CH$_3$-φ | $R^2/R^3$ = cyclic 3 carbon atoms (L-pyrrolidinyl) | | p-[(CH$_3$)$_2$NC(O)O-]benzyl- | —O-n-butyl |
| p-CH$_3$-φ | $R^2/R^3$ = cyclic 3 carbon atoms (L-pyrrolidinyl) | | p-[(CH$_3$)$_2$NC(O)O-]benzyl- | —O-cyclopentyl |
| p-CH$_3$-φ | $R^2/R^3$ = cyclic 3 carbon atoms (L-pyrrolidinyl) | | p-[(CH$_3$)$_2$NC(O)O-]benzyl- | —OC(CH$_3$)$_3$ |

TABLE IA-continued

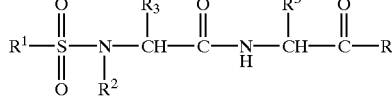

| R¹ | R² | R³ | R⁵ | R⁶' |
|---|---|---|---|---|
| p-CH₃-φ | R²/R³ = cyclic 3 carbon atoms (L-pyrrolidinyl) | | p-[(CH₃)₂NC(O)O-]benzyl- | —OH |
| p-CH₃-φ | R²/R³ = cyclic 3 carbon atoms (L-pyrrolidinyl) | | p-[(piperidin-4-yl)C(O)O-]benzyl- | —OCH₂CH₃ |
| φ-CH₂- | R²/R³ = cyclic 3 carbon atoms (L-pyrrolidinyl) | | p-[(1-methylpiperidin-4-yl)C(O)O-]benzyl- | —OCH₂CH₃ |
| φ-CH₂- | R²/R³ = cyclic 3 carbon atoms (L-pyrrolidinyl) | | p-[(4-methylpiperazin-1-yl)C(O)O-]benzyl- | —OH |
| p-CH₃-φ | R²/R³ = cyclic 3 carbon atoms (L-pyrrolidinyl) | | m-[(CH₃)₂NC(O)O-]benzyl- | —OCH₂CH₃ |
| p-CH₃-φ | R²/R³ = cyclic 3 carbon atoms (L-pyrrolidinyl) | | p-[(1-Boc-4-phenylpiperidin-4-yl)-C(O)O-]benzyl- | —OCH₂CH₃ |
| p-CH₃-φ | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-CH₃-φ | R²/R³ = cyclic —CH₂—S—C(CH₃)₂- (L-5,5-dimethylthiazolidin-4-yl) | | p-[(CH₃)₂NC(O)O-]benzyl- | —OC(CH₃)₃ |
| p-CH₃-φ | R²/R³ = cyclic —CH₂—S—C(CH₃)₂- (L-5,5-dimethylthiazolidin-4-yl) | | p-[(CH₃)₂NC(O)O-]benzyl- | —OH |
| p-CH₃-φ | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| p-CH₃-φ | R²/R³ = cyclic —CH₂CH₂—SO₂—CH₂- (L-1,1-dioxothiomorpholin-3-yl) | | p-[(CH₃)₂NC(O)O-]benzyl- | —OH |
| p-CH₃-φ | R²/R³ = cyclic —CH₂—S—C(CH₃)₂— | | p-[(4-methylpiperazin-1-yl)C(O)O-]benzyl- | —OC(CH₃)₃ |
| p-CH₃-φ | R²/R³ = cyclic —CH₂—S—C(CH₃)₂— | | p-[(4-methylpiperazin-1-yl)C(O)O-]benzyl- | —OH |
| p-CH₃-φ | CH₃— | H | p-[(CH₃)₂NC(O)O-]benzyl- | —OCH(CH₃)₂ |
| p-CH₃-φ | CH₃— | H | p-[(CH₃)₂NC(O)O-]benzyl- | —OC(CH₃)₃ |
| p-CH₃-φ | CH₃— | H | p-[(CH₃)₂NC(O)O-]benzyl- | —OH |
| p-CH₃-φ | R²/R³ = cyclic 3 carbon atoms (L-pyrrolidinyl) | | p-[(CH₃)₂NS(O)₂O-]benzyl- | —OC(CH₃)₃ |
| p-CH₃-φ | R²/R³ = cyclic 3 carbon atoms (L-pyrrolidinyl) | | p-[(CH₃)₂NS(O)₂O-]benzyl- | —OH |
| 1-methylimidazol-4-yl | R²/R³ = cyclic 3 carbon atoms (L-pyrrolidinyl) | | p-[(CH₃)₂NC(O)O-]benzyl- | —OC(CH₃)₃ |
| p-NH₂-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | CH₃— | H | p-[(morpholin-4-yl)C(O)O-]benzyl- | —OC(CH₃)₃ |
| p-CH₃-φ- | R²/R³ = cyclic 3 carbon atoms (L-pyrrolidinyl) | | p-[(morpholin-4-yl)C(O)O-]benzyl- | —OC(CH₃)₃ |
| φ-CH₂- | R²/R³ = cyclic —CH₂—S—C(CH₃)₂- | | p-[(CH₃)₂NC(O)O-]benzyl- | —OH |

TABLE IA-continued

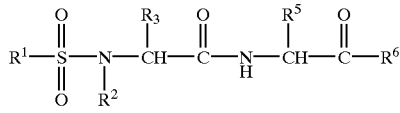

| R¹ | R² | R³ | R⁵ | R⁶' |
|---|---|---|---|---|
| p-CH₃-φ- | R²/R³ = cyclic —CH₂CH₂—NH—CH₂- (L-piperizinyl) | | p-[(CH₃)₂NC(O)O-]benzyl- | —OH |
| φ-CH₂- | R²/R³ = cyclic —CH₂—S—C(CH₃)₂— | | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(CH₃)₂NC(O)O-]benzyl- | —NH-adamantyl |
| p-CH₃-φ- | R²/R³ = cyclic 3 carbon atoms (L-pyrrolidinyl) | | p-[(CH₃)₂NC(O)O-]benzyl- | —NHCH₂C(O)OH |
| p-CH₃-φ- | R²/R³ = cyclic 3 carbon atoms (L-pyrrolidinyl) | | p-[CH₃S(O)₂NH-]benzyl- | —OCH₃ |
| p-CH₃-φ- | R²/R³ = cyclic —CH₂CH₂—NH—CH₂- (L-piperizinyl) | | p-[(CH₃)₂NC(O)O-]benzyl- | —OC(CH₃)₃ |
| p-CH₃-φ- | R²/R³ = cyclic —CH₂CH₂-(Cbz)NHCH₂-[L-4-N-(Cbz)-piperizinyl] | | p-[(CH₃)₂NC(O)O-]benzyl- | —OC(CH₃)₃ |
| p-CH₃-φ- | CH₃— | H | p-[(piperidin-1-yl)C(O)O-]benzyl- | —OH |
| p-CH₃-φ- | R²/R³ = cyclic —CH₂CH₂—SO₂—CH₂-(L-1,1-dioxothiomorpholin-3-yl) | | p-[(morpholin-4-yl)C(O)O-]benzyl- | —OC(CH₃)₃ |
| p-CH₃-φ- | R²/R³ = cyclic —CH₂CH₂—SO₂—CH₂-(L-1,1-dioxothiomorpholin-3-yl) | | p-[(morpholin-4-yl)C(O)O-]benzyl- | —OH |
| 1-methylpyrazol-4-yl- | R²/R³ = cyclic 3 carbon atoms (L-pyrrolidinyl) | | p-[(CH₃)₂NC(O)O-]benzyl- | —OC(CH₃)₃ |
| p-F-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | —CH₃ | H | p-[(4-methylpiperazin-1-yl)C(O)O-]benzyl- | —OC(CH₃)₃ |
| p-CH₃-φ- | R²/R³ = cyclic —CH₂—SO₂—C(CH₃)₂-(L-1,1-dioxo-5,5-dimethylthiazolidin-4-yl) | | p-[(CH₃)₂NC(O)O-]benzyl- | —OC(CH₃)₃ |
| 1-methylpyrazol-4-yl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—SO₂—C(CH₃)₂-(L-1,1-dioxo-5,5-dimethylthiazolidin-4-yl) | | p-[(CH₃)₂NC(O)O-]benzyl- | —OH |
| p-F-φ- | R²/R³ = cyclic 3 carbon atoms (L-pyrrolidinyl) | | p-[(CH₃)₂NC(O)O-]benzyl- | —OH |
| 3-pyridyl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic 3 carbon atoms (D-pyrrolidinyl) | | p-[(4-methylpiperazin-1-yl)C(O)O-]benzyl- | —OC(CH₃)₃ |
| p-CH₃-φ- | —CH₃ | —CH₃ | p-[4-methylpiperazin-1-yl)C(O)O-]benzyl- | —OC(CH₃)₃ |
| p-nitro-φ- | R²/R³ = cyclic 3 carbon atoms (L-pyrrolidinyl) | | p-[(CH₃)₂NC(O)O-]benzyl- | —OC(CH₃)₃ |

TABLE IA-continued

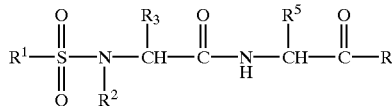

| R¹ | R² | R³ | R⁵ | R⁶' |
|---|---|---|---|---|
| p-CH₃-φ- | R²/R³ = cyclic —CH₂CH₂—SO₂—CH₂- (L-1,1-dioxothiomorpholin-3-yl) | | p-[(CH₃)₂NS(O)₂O-]benzyl- | —OC(CH₃)₃ |
| p-CH₃-φ- | —CH₃ | H | p-[(thiomorpholin-4-yl)C(O)O-]benzyl- | —OC(CH₃)₃ |
| p-CH₃-φ- | —CH₃ | —CH₃ | p-[(4-methylpiperazin-1-yl)C(O)O-]benzyl- | —OH |
| p-CH₃-φ- | R²/R³ = cyclic 3 carbon atoms (L-pyrrolidinyl) | | p-[(thiomorpholin-4-yl sulfone)-C(O)O-]benzyl- | —OH |
| p-CH₃-φ- | R²/R³ = cyclic 3 carbon atoms (L-pyrrolidinyl) | | p-[(thiomorpholin-4-yl)C(O)O-]benzyl- | —OH |
| p-CH₃-φ- | R²/R³ = cyclic 3 carbon atoms (L-pyrrolidinyl) | | p-[(piperidin-1-yl)C(O)O-]benzyl- | —OH |
| p-CH₃-φ- | R²/R³ = cyclic 3 carbon atoms (L-pyrrolidinyl) | | p-[(pyrrolidin-1-yl)C(O)O-]benzyl- | —OH |
| p-CH₃-φ- | R²/R³ = cyclic 3 carbon atoms (L-pyrrolidinyl) | | p-[(morpholin-4-yl)C(O)O-]benzyl- | —OH |
| p-CH₃-φ- | R²/R³ = cyclic 3 carbon atoms (L-pyrrolidinyl) | | p-[(4-methylpiperazin-1-yl)C(O)O-]benzyl- | —OCH₂C(CH₃)₃ |
| p-CH₃-φ- | R²/R³ = cyclic 3 carbon atoms (L-pyrrolidinyl) | | p-[(CH₃)₂NC(O)O-]benzyl- | —OCH₂C(CH₃)₃ |
| p-CH₃-φ- | R²/R³ = cyclic 3 carbon atoms (L-pyrrolidinyl) | | p-[(1-Boc-piperazin-4-yl)C(O)O-]benzyl- | —OCH₂CH₃ |
| p-CH₃-φ- | R²/R³ = cyclic 3 carbon atoms (L-pyrrolidinyl) | | p-[(morpholin-4-yl)C(O)O-]benzyl- | —OCH₂CH₃ |
| R¹/R² = saccharin-2-yl- | | —CH₃ | p-[(4-methylpiperazin-1-yl)C(O)O-]benzyl- | —OC(CH₃)₃ |
| R¹/R² = saccharin-2-yl- | | —CH₃ | p-[(CH₃)₂NC(O)O-]benzyl- | —OH |
| p-CH₃-φ- | —CH₃ | H | p-[(thiomorpholin-4-yl sulfone)-C(O)O-]benzyl- | —OC(CH₃)₃ |
| p-CH₃-φ- | —CH₃ | H | p-[(thiomorpholin-4-yl)C(O)O-]benzyl- | —OH |
| p-CH₃-φ- | —CH₃ | —CH₃ | p-[(CH₃)₂NC(O)O-]benzyl- | —OC(CH₃)₃ |
| p-CH₃-φ- | R²/R³ = cyclic —CH₂—CH₂—S—CH₂- (L-thiomorpholin-3-yl) | | p-[(CH₃)₂NC(O)O-]benzyl- | —OC(CH₃)₃ |
| p-CH₃-φ- | —CH₃ | H | p-[thiomorpholin-4-yl sulfone)-C(O)O-]benzyl- | —OH |
| p-CH₃-φ- | R²/R³ = cyclic —CH₂—CH₂—SO₂—CH₂- (L-1,1-dioxothiomorpholin-3-yl) | | p-[(CH₃)₂NC(O)O-]benzyl- | —OC(CH₃)₃ |
| p-CH₃-φ- | R²/R³ = cyclic —CH₂—CH₂—SO₂—CH₂- (L-1,1-dioxothiomorpholin-3-yl) | | p-[(morpholin-4-yl)C(O)O-]benzyl- | —OC(CH₃)₃ |
| p-CH₃-φ- | —CH₃ | —CH₃ | p-[(CH₃)₂NC(O)O-]benzyl- | —OH |
| p-F-φ- | R²/R³ = cyclic —CH₂—CH₂—S—CH₂- (L-thiomorpholin-3-yl) | | p-[(CH₃)₂NC(O)O-]benzyl- | —OC(CH₃)₃ |
| p-F-φ- | R²/R³ = cyclic —CH₂—CH₂—SO₂—CH₂- (L-1,1-dioxothiomorpholin-3-yl) | | p-[(CH₃)₂NC(O)O-]benzyl- | —OC(CH₃)₃ |
| pyridin-3-yl- | R²/R³ = cyclic 3 carbon atoms | | p-[(CH₃)₂NC(O)O-]benzyl- | —OC(CH₃)₃ |

TABLE IA-continued

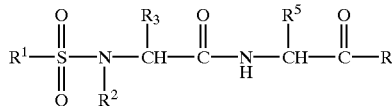

| R¹ | R² | R³ | R⁵ | R⁶' |
|---|---|---|---|---|
| p-nitro-φ- | R²/R³ = cyclic 3 carbon atoms (L-pyrrolidinyl) | | p-[(CH₃)₂NC(O)O-]benzyl- | —OH |
| p-N≡C-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic —CH₂—CH₂—SO₂—CH₂- (L-1,1-dioxothiomorpholin-3-yl) | | p-[(CH₃)₂NS(O)₂O-]benzyl- | —OH |
| p-CH₃-φ- | R²/R³ = cyclic —CH₂—CH₂—SO₂—CH₂- (L-1,1-dioxothiomorpholin-3-yl) | | p-[(CH₃)₂NC(O)O-]benzyl- | —OH |
| p-CH₃-φ- | R²/R³ = cyclic —CH₂—SO₂—CH₂- (L-1,1-dioxothiazolidin-4-yl) | | p-[(CH₃)₂NC(O)O-]benzyl- | —OC(CH₃)₃ |
| p-F₃C-φ- | R²/R³ = cyclic 3 carbon atoms (L-pyrrolidinyl) | | p-[(CH₃)₂NC(O)O-]benzyl- | —OC(CH₃)₃ |
| 1-methylpyrazol-4-yl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—SO₂—CH₂- (L-1,1-dioxothiazolidin-4-yl) | | p-[(CH₃)₂NC(O)O-]benzyl- | —OH |
| p-F-φ- | R²/R³ = cyclic —CH₂—S—CH₂- (L-thiazolidin-4-yl) | | p-[(CH₃)₂NC(O)O-]benzyl- | —OH |
| p-CH₃-φ- | R²/R³ = cyclic 3 carbon atoms (L-pyrrolidinyl) | | p-[(CH₃)₂NC(O)O-]benzyl- | 2,4-dioxo-tetrahydrofuran-3-yl (3,4-enol) |
| p-CH₃-φ- | R²/R³ = cyclic 3 carbon atoms (L-pyrrolidinyl) | | p-[(piperazin-4-yl)C(O)O-]benzyl- | —OH |
| p-CH₃-φ- | R²/R³ = cyclic 3 carbon atoms (L-pyrrolidinyl) | | p-[(1-Boc-piperazin-4-yl)C(O)O-]benzyl- | —OC(CH₃)₃ |
| p-CH₃-φ- | R²/R³ = cyclic 3 carbon atoms (L-pyrrolidinyl) | | p-[(piperazin-4-yl)C(O)O-]benzyl- | —OCH₂CH₃ |
| p-CH₃-φ- | R²/R³ = cyclic 3 carbon atoms (L-pyrrolidinyl) | | p-[(4-acetylpiperazin-1-yl)C(O)O-]benzyl- | —OCH₂CH₃ |
| p-CH₃-φ- | R²/R³ = cyclic 3 carbon atoms (L-pyrrolidinyl) | | p-[(4-methanesulfonylpiperazin-1-yl)-C(O)O-]benzyl- | —OCH₂CH₃ |
| p-CH₃-φ- | R²/R³ = cyclic 3 carbon atoms (L-pyrrolidinyl) | | 3-nitro-4-[(morpholin-4-yl)-C(O)O-]benzyl- | —OH |
| p-CH₃-φ- | R²/R³ = cyclic 3 carbon atoms (L-pyrrolidinyl) | | p-[(1-Boc-piperazin-4-yl)C(O)O-]benzyl- | —OH |
| p-CH₃-φ- | —CH₃ | —C(CH₃)₃ | p-[(4-methylpiperazin-1-yl)C(O)O-]benzyl- | —OC(CH₃)₃ |
| p-F-φ- | R²/R³ = cyclic —CH₂—S—C(CH₃)₂- (L-5,5-dimethylthiazolidin-4-yl) | | p-[(CH₃)₂NC(O)O-]benzyl- | —OC(CH₃)₃ |
| p-F-φ- | R²/R³ = cyclic —CH₂—CH₂—SO₂—CH₂- (L-1,1-dioxothiomorpholin-3-yl) | | p-[(1,1-dioxothiomorpholin-4-yl)-C(O)O-]benzyl- | —OC(CH₃)₃ |
| p-CH₃-φ- | R²/R³ = cyclic | | p-[(1,1-dioxothiomorpholin-4-yl)- | —OC(CH₃)₃ |

TABLE IA-continued

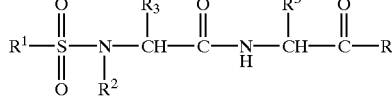

| R¹ | R² | R³ | R⁵ | R⁶' |
|---|---|---|---|---|
| | —CH₂—CH₂—SO₂—CH₂- (L-1,1-dioxothiomorpholin-3-yl) | | C(O)O-]benzyl- | |
| p-F-φ- | R²/R³ = cyclic 3 carbon atoms (L-pyrrolidinyl) | | p-[(1,1-dioxothiomorpholin-4-yl)-C(O)O-]benzyl- | —OC(CH₃)₃ |
| p-F-φ- | R²/R³ = cyclic 3 carbon atoms (L-pyrrolidinyl) | | p-[(thiomorpholin-4-yl)C(O)O-]benzyl- | —OC(CH₃)₃ |
| p-F-φ- | R²/R³ = cyclic 3 carbon atoms (L-pyrrolidinyl) | | p-[(morpholin-4-yl)C(O)O-]benzyl- | —OC(CH₃)₃ |
| p-F-φ- | R²/R³ = cyclic —CH₂—S—C(CH₃)₂- (L-5,5-dimethylthiazolidin-4-yl) | | p-[(CH₃)₂NC(O)O-]benzyl- | —OH |
| p-F-φ- | R²/R³ = cyclic —CH₂—CH₂—SO₂—CH₂- (L-1,1-dioxothiomorpholin-3-yl) | | p-[(morpholin-4-yl)C(O)O-]benzyl- | —OC(CH₃)₃ |
| p-F₃CO-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic —CH₂—CH₂—SO₂—CH₂- (L-1,1-dioxothiomorpholin-3-yl) | | p-[(CH₃)₂NC(O)O-]benzyl- | —OCH(CH₃)₂ |
| p-F-φ- | R²/R³ = cyclic —CH₂—SO₂—C(CH₃)₂- (L-1,1-dioxo-5,5-dimethylthiazolidin-4-yl) | | p-[(CH₃)₂NC(O)O-]benzyl- | —OC(CH₃)₃ |
| p-CH₃-φ- | R²/R³ = cyclic —CH₂—SO₂—C(CH₃)₂- (L-1,1-dioxo-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—CH₂—SO₂—CH₂- (L-1,1-dioxothiomorpholin-3-yl) | | p-[(morpholin-4-yl)C(O)O-]benzyl- | —OH |
| p-F-φ- | R²/R³ = cyclic —CH₂—SO₂—C(CH₃)₂- (L-1,1-dioxo-5,5-dimethylthiazolidin-4-yl) | | p-[(CH₃)₂NC(O)O-]benzyl- | —OH |
| pyrimidin-2-yl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—SO₂—CH₂- (L-1,1-dioxothiomorpholin-3-yl) | | p-[(methylpiperazin-1-yl)C(O)O-]benzyl- | —OC(CH₃)₃ |
| 1-methylpyrazol-4-yl- | R²/R³ = cyclic 3 carbon atoms (L-pyrrolidinyl) | | p-[(4-methylpiperazin-1-yl)C(O)O-]benzyl- | —OC(CH₃)₃ |
| p-F-φ- | R²/R³ = cyclic —CH₂—SO₂—CH₂- (L-1,1-dioxothiazolidin-4-yl) | | p-[(CH₃)₂NC(O)O-]benzyl- | —OH |
| p-CH₃-φ- | R²/R³ = cyclic 3 carbon atoms (L-pyrrolidinyl) | | p-[(piperidin-1-yl)C(O)O-]benzyl- | —OC(CH₃)₃ |
| p-CH₃-φ- | R²/R³ = cyclic | | p-[(1,1-dioxothiomorpholin-4-yl)- | —OC(CH₃)₃ |

TABLE IA-continued $$R^1-\underset{\underset{O}{\overset{O}{\|}}}{S}-\underset{R^2}{N}-\underset{R^3}{CH}-\overset{O}{\overset{\|}{C}}-\underset{H}{N}-\underset{R^5}{CH}-\overset{O}{\overset{\|}{C}}-R^{6'}$$

| R¹ | R² | R³ | R⁵ | R⁶' |
|---|---|---|---|---|
|  |  | 3 carbon atoms (L-pyrrolidinyl) | C(O)O-]benzyl- |  |
| p-CH₃-φ- | R²/R³ = cyclic 3 carbon atoms (L-pyrrolidinyl) |  | p-[(thiomorpholin-4-yl)C(O)O-]benzyl- | —OC(CH₃)₃ |
| p-CH₃-φ- | R²/R³ = cyclic 3 carbon atoms (L-pyrrolidinyl) |  | p-[(pyrrolidin-1-yl)C(O)O-]benzyl- | —OC(CH₃)₃ |
| p-F-φ- | R²/R³ = cyclic —CH₂—S—CH₂- (L-thiazolidin-4-yl) |  | p-[(CH₃)₂NC(O)O-]benzyl- | —OC(CH₃)₃ |
| p-F-φ- | R²/R³ = cyclic —CH₂—SO₂—CH₂- (L-1,1-dioxothiazolidin-4-yl) |  | p-[(CH₃)₂NC(O)O-]benzyl- | —OC(CH₃)₃ |
| 2,5-dichlorothien-3-yl- | R²/R³ = cyclic 3 carbon atoms (L-pyrrolidinyl) |  | p-[(CH₃)₂NC(O)O-]benzyl- | —OC(CH₃)₃ |
| p-CH₃C(O)NH-φ- | R²/R³ = cyclic 3 carbon atoms (L-pyrrolidinyl) |  | p-[(CH₃)₂NC(O)O-]benzyl- | —OC(CH₃)₃ |
| p-C(CH₃)₃-φ- | R²/R³ = cyclic —CH₂—CH₂—SO₂—CH₂- (L-1,1-dioxothiomorpholin-3-yl) |  | p-[(CH₃)₂NC(O)O-]benzyl- | —OC(CH₃)₃ |
| pyridin-2-yl- | R²/R³ = cyclic 3 carbon atoms (L-pyrrolidinyl) |  | p-[(CH₃)₂NC(O)O-]benzyl- | —OH |
| o-F-φ- | R²/R³ = cyclic —CH₂—CH₂—SO₂—CH₂- (L-1,1-dioxothiomorpholin-3-yl) |  | p-[(CH₃)₂NC(O)O-]benzyl- | —OC(CH₃)₃ |
| m-F-φ- | R²/R³ = cyclic —CH₂—CH₂—SO₂—CH₂- (L-1,1-dioxothiomorpholin-3-yl) |  | p-[(CH₃)₂NC(O)O-]benzyl- | —OC(CH₃)₃ |
| 2,4-difluoro-φ- | R²/R³ = cyclic —CH₂—CH₂—SO₂—CH₂- (L-1,1-dioxothiomorpholin-3-yl) |  | p-[(CH₃)₂NC(O)O-]benzyl- | —OC(CH₃)₃ |
| p-CH₃C(O)NH-φ- | R²/R³ = cyclic 3 carbon atoms (L-pyrrolidinyl) |  | p-[(CH₃)₂NC(O)O-]benzyl- | —OH |
| p-C(F)₃O-φ- | R²/R³ = cyclic 3 carbon atoms (L-pyrrolidinyl) |  | p-[(CH₃)₂NC(O)O-]benzyl- | —OH |
| p-F-φ- | R²/R³ = cyclic —CH₂—S—C(CH₃)₂- (L-5,5-dimethylthiazolidin-4-yl) |  | p-[(CH₃)₂NC(O)O-]benzyl- | —OCH(CH₃)₂ |
| p-N≡C-φ- | R²/R³ = cyclic 3 carbon atoms (L-pyrrolidinyl) |  | p-[(CH₃)₂NC(O)O-]benzyl- | —OH |
| morpholin-4-yl- | R²/R³ = cyclic 3 carbon atoms (L-pyrrolidinyl) |  | p-[(CH₃)₂NC(O)O-]benzyl- | —OC(CH₃)₃ |
| p-CH₃-φ- | R²/R³ = cyclic —CH₂—CH₂—C(CH₃)₂- (L-4,4-dimethyl pyrrolidinyl) |  | p-[(CH₃)₂NC(O)O-]benzyl- | —OC(CH₃)₃ |
| p-CH₃-φ- | R²/R³ = cyclic —CH₂—CH₂—C(CH₃)₂- (L-4,4-dimethyl pyrrolidinyl) |  | p-[(CH₃)₂NC(O)O-]benzyl- | —OCH(CH₃)₂ |
| 1-methylpyrazol-4- |  |  | p-[(CH₃)₂NC(O)O-]benzyl- | —OCH(CH₃)₂ |

TABLE IA-continued

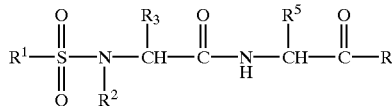

| R¹ | R² | R³ | R⁵ | R⁶' |
|---|---|---|---|---|
| yl | 3 carbon atoms (L-pyrrolidinyl) | | | |
| p-CH₃-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(thiomorpholin-4-yl)C(O)O-]benzyl- | —OC(CH₃)₃ |
| 1-methylimidazol-4-yl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂CH₂—SO₂—CH₂- (L-1,1-dioxothiomorpholin-3-yl) | | p-[(CH₃)₂NC(O)O-]benzyl- | -°C.(CH₃)₃ |
| 1-methylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OC(CH₃)₃ |
| p-CH₃C(O)NH-φ- | R²/R³ = cyclic 3 carbon atoms (L-pyrrolidinyl) | | p-[(CH₃)₂NC(O)O-]benzyl- | —OC(CH₃)₃ |
| p-(CH₃)₃C-φ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| 1-methylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OH |
| pyridin-3-yl- | R²/R³ = cyclic 3 carbon atoms (L-pyrrolidinyl) | | p-[(CH₃)₂NC(O)O-]benzyl- | —OH |
| p-N≡C-φ- | R²/R³ = cyclic 3 carbon atoms (L-pyrrolidinyl) | | p-[(CH₃)₂NC(O)O-]benzyl- | —OH |
| p-F-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OCH₂CH₃ |
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OH |
| p-CH₃-φ- | R²/R³ = cyclic 3 carbon atoms (L-pyrrolidinyl) | | p-[(4-acetylpiperazin-1-yl)C(O)O-]benzyl- | —OH |
| p-CH₃-φ- | R²/R³ = cyclic 3 carbon atoms (L-pyrrolidinyl) | | p-[(4-methanesulfonylpiperazin-1-yl)-C(O)O-]benzyl- | —OH |
| p-CH₃-φ- | R²/R³ = cyclic 3 carbon atoms (L-pyrrolidinyl) | | p-[(4-φ-piperazin-1-yl)C(O)(O)-]benzyl- | —OH |
| p-CH₃-φ- | R²/R³ = cyclic 3 carbon atoms (L-pyrrolidinyl) | | p-[(piperazin-4-yl)C(O)O-]benzyl- | —OC(CH₃)₃ |
| R¹/R² = saccharin-2-yl- | | —CH₃ | p-[(4-methylpiperazin-1-yl)C(O)O-]benzyl- | —OH |
| p-CH₃-φ- | R²/R³ = cyclic —CH₂CH₂—NH—CH₂- (L-piperizinyl) | | p-[(CH₃)₂NC(O)O-]benzyl- | —OC(CH₃)₃ |
| p-F₃CO-φ- | R²/R³ = cyclic | | p-[(CH₃)₂NC(O)O-]benzyl- | —OH |

TABLE IA-continued

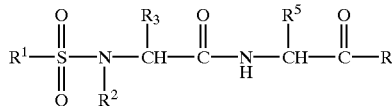

| R¹ | R² | R³ | R⁵ | R⁶' |
|---|---|---|---|---|
| p-CH₃-ϕ- | 3 carbon atoms (L-pyrrolidinyl) R²/R³ = cyclic —CH₂—CH₂—C(CH₃)₂- (4,4-dimethyl pyrrolidinyl) | | p-[(CH₃)₂NC(O)O-]benzyl- | —OC(CH₃)₃ |
| p-CH₃-ϕ- | R²/R³ = cyclic —CH₂—CH₂—C(CH₃)₂- (4,4-dimethyl pyrrolidinyl) | | p-[(CH₃)₂NC(O)O-]benzyl- | —OCH(CH₃)₂ |
| p-CH₃C(O)NH-ϕ- | R²/R³ = cyclic 3 carbon atoms (L-pyrrolidinyl) | | p-[(CH₃)₂NC(O)O-]benzyl- | —OH |
| o-F-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| morpholin-4-yl- | R²/R³ = cyclic 3 carbon atoms (L-pyrrolidinyl) | | p-[(CH₃)₂NC(O)O-]benzyl- | —OC(CH₃)₃ |
| m-F-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| 2,4-difluoro-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| morpholin-4-yl- | R²/R³ = cyclic 3 carbon atoms (L-pyrrolidinyl) | | p-[(CH₃)₂NC(O)O-]benzyl- | —OH |
| 1-methylpyrazol-4-yl- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| o-F-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OH |
| 2,4-difluoro-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OH |
| p-CH₃-ϕ- | R²/R³ = cyclic —CH₂—CH₂—S—CH₂- (L-thiomorpholin-3-yl) | | p-[(CH₃)₂NC(O)O-]benzyl- | —OH |
| pyridin-3-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| m-F-ϕ- | R²/R³ = cyclic —CH₂CH₂—SO₂—CH₂- (L-1,1-dioxothiomorpholin-3-yl) | | p-[(CH₃)₂NC(O)O-]benzyl- | —OH |
| pyridin-2-yl- | R²/R³ = cyclic 3 carbon atoms (L-pyrrolidinyl) | | p-[(CH₃)₂NC(O)O-]benzyl- | —OCH(CH₃)₂ |
| 1-methylpyrazol-4-yl- | R²/R³ = cyclic —CH₂CH₂—SO₂—CH₂- (L-1,1-dioxothiomorpholin- | | p-[(CH₃)₂NC(O)O-]benzyl- | —OH |

TABLE IA-continued

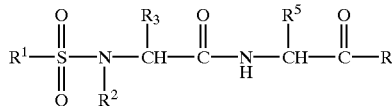

| R¹ | R² | R³ | R⁵ | R⁶' |
|---|---|---|---|---|
| | 3-yl) | | | |
| p-CH₃-φ- | R²/R³ = cyclic 3 carbon atoms (L-pyrrolidinyl) | | p-[(4-methanesulfonylpiperazin-1-yl)-C(O)O-]benzyl- | —OC(CH₃)₃ |
| p-CH₃-φ- | R²/R³ = cyclic 3 carbon atoms (L-pyrrolidinyl) | | p-[(4-φ-piperazin-1-yl)C(O)(O)-]benzyl- | —OC(CH₃)₃ |
| p-CH₃-φ- | R²/R³ = cyclic 3 carbon atoms (L-pyrrolidinyl) | | p-[(CH₃)₂NC(O)O-]benzyl- | —O—CH₂C(CH₃)₂—NHC(O)OC(CH₃)₃ |
| p-CH₃-φ- | R²/R³ = cyclic 3 carbon atoms (L-pyrrolidinyl) | | p-[(CH₃)₂NC(O)O-]benzyl- | —O—CH₂CH₂-(morpholin-4 yl) |
| p-CH₃-φ- | R²/R³ = cyclic 3 carbon atoms (L-pyrrolidinyl) | | p-[(4-acetylpiperazin-1-yl)C(O)O-]benzyl- | —OC(CH₃)₃ |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂-(L-5,5-dimethylthiazolidin-4-yl) | | p-[(CH₃)₂NCH₂CH₂N(CH₃)C(O)O-]benzyl- | —OC(CH₃)₃ |
| p-CH₃-φ- | R²/R³ = cyclic —CH₂—S—C(CH₃)₂-(L-5,5-dimethylthiazolidin-4-yl) | | p-[(CH₃)₂NCH₂CH₂N(CH₃)C(O)O-]benzyl- | —OH |
| p-CH₃-φ- | R²/R³ = cyclic 3 carbon atoms (L-pyrrolidinyl) | | p-[(CH₃)₂NCH₂CH₂N(CH₃)C(O)O-]benzyl- | —OH |
| p-CH₃-φ- | R²/R³ = cyclic 3 carbon atoms (L-pyrrolidinyl) | | p-[(4-hydroxypiperidin-1-yl)C(O)O-]benzyl- | —OC(CH₃)₃ |
| p-(CH₃)₃C-φ- | R²/R³ = cyclic —CH₂CH₂—SO₂—CH₂-(L-1,1-dioxothiomorpholin-3-yl) | | p-[(CH₃)₂NC(O)O-]benzyl- | —OH |
| p-CH₃-φ- | R²/R³ = cyclic —CH₂—S—C(CH₃)₂-(L-5,5-dimethylthiazolidin-4-yl) | | p-[(thiomorpholin-4-yl)C(O)O-]benzyl- | —OC(CH₃)₃ |
| 2,5-dichlorothien-3-yl- | R²/R³ = cyclic 3 carbon atoms (L-pyrrolidinyl) | | p-[(CH₃)₂NC(O)O-]benzyl- | —OH |
| p-CH₃O-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂—CH₂—C(CH₃)₂-(4,4-dimethyl pyrrolidinyl) | | p-[(CH₃)₂NC(O)O-]benzyl- | —OH |
| p-F-φ- | R²/R³ = cyclic —CH₂—S—C(CH₃)₂-(L-5,5-dimethylthiazolidin-4-yl) | | 3-chloro-4-[(4-methylpiperizin-1-yl)C(O)O-]-benzyl- | —OC(CH₃)₃ |
| p-F-φ- | R²/R³ = cyclic —CH₂—S—C(CH₃)₂-(L-5,5-dimethylthiazolidin-4-yl) | | 3-chloro-4-[(CH₃)₂NC(O)O-]-benzyl-benzyl- | —OH |
| p-F-φ- | R²/R³ = cyclic —CH₂—S—C(CH₃)₂-(L-5,5-dimethylthiazolidin-4-yl) | | 3-chloro-4-[(thiomorpholin-4-yl)C(O)O-]-benzyl-benzyl- | —OC(CH₃)₃ |

TABLE IA-continued $$R^1-\underset{\underset{O}{\overset{O}{\|}}}{\overset{\|}{S}}-\underset{R^2}{N}-\underset{\underset{R^3}{\|}}{CH}-\overset{O}{\overset{\|}{C}}-\underset{H}{N}-\underset{\underset{R^5}{\|}}{CH}-\overset{O}{\overset{\|}{C}}-R^{6'}$$

| R¹ | R² | R³ | R⁵ | R⁶' |
|---|---|---|---|---|
| p-CH₃-φ- | R²/R³ = cyclic 3 carbon atoms (L-pyrrolidinyl) | | p-[(morpholin-4-yl)-CH₂CH₂NHC(O)O-]benzyl- | —OC(CH₃)₃ |
| p-CH₃-φ- | R²/R³ = cyclic 3 carbon atoms (L-pyrrolidinyl) | | p-[(1,4-dioxa-8-azaspiro[4.5]decan-8-yl)-C(O)O-]benzyl- | —OC(CH₃)₃ |
| p-F-φ- | R²/R³ = cyclic —CH₂—S—C(CH₃)₂- (L-5,5-dimethylthiazolidin-4-yl) | | 3-chloro-4-[(CH₃)₂NC(O)O-]-benzyl- | —OC(CH₃)₃ |
| p-CH₃-φ- | R²/R³ = cyclic —CH₂—S—C(CH₃)₂- (L-5,5-dimethylthiazolidin-4-yl) | | p-[(thiomorpholin-4-yl)C(O)O-]benzyl- | —OH |
| pyridin-2-yl- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—S(O)—CH₂- (L-1-oxothiomorpholin-4-yl) | | p-[(CH₃)₂NC(O)O-]benzyl- | —OCH(CH₃)₂ |
| 4-Cl-3-(NH₂—SO₂-)-φ- | R²/R³ = cyclic 3 carbon atoms (L-pyrrolidinyl) | | p-[(CH₃)₂NC(O)O-]benzyl- | —OCH(CH₃)₂ |
| p-F-φ- | R²/R³ = cyclic —CH₂—S—C(CH₃)₂- (L-5,5-dimethylthiazolidin-4-yl) | | 3-chloro-4-[(thiomorpholin-4-yl)C(O)O-]-benzyl- | —OCH(CH₃)₂ |
| p-F-φ- | R²/R³ = cyclic —CH₂—S—C(CH₃)₂- (L-5,5-dimethylthiazolidin-4-yl) | | 3-chloro-4-[(CH₃)₂NC(O)O-]-benzyl- | —OCH(CH₃)₂ |
| p-CH₃-φ- | R²/R³ = cyclic 3 carbon atoms (L-pyrrolidinyl) | | p-[HOCH₂CH₂N(CH₃)C(O)O-]benzyl- | —OC(CH₃)₃ |
| p-F-φ- | R²/R³ = cyclic —CH₂—S—C(CH₃)₂- (L-5,5-dimethylthiazolidin-4-yl) | | p-[(2-(hydroxymethyl)pyrrolidin-1-yl)-C(O)O-]-benzyl- | —OC(CH₃)₃ |
| p-F-φ- | R²/R³ = cyclic —CH₂—S—C(CH₃)₂- (L-5,5-dimethylthiazolidin-4-yl) | | p-[(2-(hydroxymethyl)pyrrolidin-1-yl)-C(O)O-]-benzyl- | —OH |
| p-CH₃-φ- | R²/R³ = cyclic 3 carbon atoms (L-pyrrolidinyl) | | p[(2-(CH₃OC(O)-)pyrrolidin-1-yl)-C(O)O-]benzyl- | —OC(CH₃)₃ |
| p-CH₃-φ- | R²/R³ = cyclic 3 carbon atoms (L-pyrrolidinyl) | | p[(4-(HC(O)O-)piperidin-1-yl)-C(O)O-]benzyl- | —OH |
| p-CH₃-φ- | R²/R³ = cyclic 3 carbon atoms (L-pyrrolidinyl) | | p[(4-hydroxypiperidin-1-yl)-C(O)O-]benzyl- | —OCH(CH₃)₂ |
| p-F-φ- | R²/R³ = cyclic —CH₂—S—C(CH₃)₂- (L-5,5-dimethylthiazolidin-4-yl) | | 3-chloro-4-[(thiomorpholin-4-yl)-C(O)O-]benzyl- | —OH |
| p-CH₃-φ- | R²/R³ = cyclic 3 carbon atoms (L-pyrrolidinyl) | | p-[(4-(CH₃CH₂OC(O)-)piperidin-1-yl)C(O)O-]-benzyl- | —OC(CH₃)₃ |
| p-CH₃-φ- | R²/R³ = cyclic 3 carbon atoms (L-pyrrolidinyl) | | p-[(4-(HOCH₂CH₂-)piperazin-1-yl)-C(O)O-]benzyl- | —OC(CH₃)₃ |

TABLE IA-continued

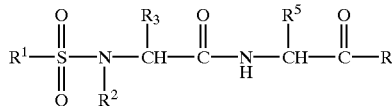

| R¹ | R² | R³ | R⁵ | R⁶' |
|---|---|---|---|---|
| p-F-φ- | R²/R³ = cyclic —CH₂—S—C(CH₃)₂- (L-5,5-dimethylthiazolidin-4-yl) | | p-[(4-pyridin-2-yl)piperazin-1-yl)-C(O)O-]benzyl- | —OH |
| p-F-φ- | R²/R³ = cyclic —CH₂—S—C(CH₃)₂- (L-5,5-dimethylthiazolidin-4-yl) | | p-[(4-pyridin-2-yl)piperazin-1-yl)-C(O)O-]benzyl- | —OC(CH₃)₃ |
| p-CH₃-φ- | R²/R³ = cyclic 3 carbon atoms (L-pyrrolidinyl) | | p-[HC(O)OCH₂CH₂N(CH₃)C(O)O-]benzyl- | —OH |
| p-CH₃-φ- | R²/R³ = cyclic 3 carbon atoms (L-pyrrolidinyl) | | p-[HOCH₂CH₂N(CH₃)C(O)O-]benzyl- | —OCH(CH₃)₂ |
| p-CH₃-φ- | R²/R³ = cyclic 3 carbon atoms (L-pyrrolidinyl) | | p-[CH₃OC(O)CH₂NHC(O)O-]benzyl- | —OC(CH₃)₃ |
| quinolin-8-yl- | R²/R³ = cyclic 3 carbon atoms (L-pyrrolidinyl) | | p-[(CH₃)₂NC(O)O-]benzyl- | —OCH(CH₃)₂ |
| 3,4-difluoro-φ- | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[thiomorpholin-4-yl)-C(O)O-]-benzyl- | —OCH(CH₃)₂ |
| p-CH₃O-φ- | R²/R³ = cyclic 3 carbon atoms (L-pyrrolidinyl) | | p-[(CH₃)₂NC(O)O-]benzyl- | —OH |
| p-CH₃-φ- | R²/R³ = cyclic —CH₂—CH₂—S(O)—CH₂- (L-1-oxothiomorpholin-4-yl) | | p-[(CH₃)₂NC(O)O-]benzyl- | —OH |
| 3,4-difluoro-φ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| p-H₂N-φ- | R²/R³ = cyclic 3 carbon atoms (L-pyrrolidinyl) | | p-[(CH₃)₂NC(O)O-]benzyl- | —OCH(CH₃)₂ |
| 3,4-difluoro-φ- | R²/R³ = cyclic —CH₂CH₂—SO₂—CH₂- (L-1,1-dioxothiomorpholin-3-yl) | | p-[(CH₃)₂NC(O)O-]benzyl- | —OH |
| 3,4-difluoro-φ- | R²/R³ = cyclic 3 carbon atoms (L-pyrrolidinyl) | | p-[(CH₃)₂NC(O)O-]benzyl- | —OH |
| quinolin-8-yl- | R²/R³ = cyclic 3 carbon atoms (L-pyrrolidinyl) | | p-[(CH₃)₂NC(O)O-]benzyl- | —OH |
| 1-methylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-CH₃-φ- | R²/R³ = cyclic —CH₂—CH₂—S(O)—CH₂- (L-1-oxothiomorpholin-4-yl) | | p-[(CH₃)₂NC(O)O-]benzyl- | —OC(CH₃)₃ |
| 1-n-butylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |

TABLE IA-continued

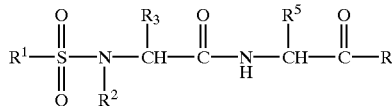

| R¹ | R² | R³ | R⁵ | R⁶' |
|---|---|---|---|---|
| 1-methylpyrazol-3-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 2-(CF₃C(O)-)-1,2,3,4-tetrahydro-isoquinolin-7-yl | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(φNHC(O)-)-piperazin-1-yl)-C(O)O-]benzyl- | —OH |
| p-CH₃-φ- | R²/R³ = cyclic 3 carbon atoms (L-pyrrolidinyl) | | p-[(4-methoxypiperidin-1-yl)C(O)O-]benzyl- | —OH |
| p-CH₃-φ- | R²/R³ = cyclic 3 carbon atoms (L-pyrrolidinyl) | | p-[4-(pyridin-4-ylC(O))piperazin-1-yl)-C(O)O-]benzyl- | —OCH(CH₃)₂ |
| p-CH₃-φ- | R²/R³ = cyclic —CH₂—C(O)—CH₂- (L-4-oxopyrrolidinyl) | | p-[(CH₃)₂NC(O)O-]benzyl- | —OC(CH₃)₃ |
| p-CH₃-φ- | R²/R³ = cyclic —CH₂CH(OH)CH₂- (L-4-hydroxypyrrolidinyl) | | p-[(CH₃)₂NC(O)O-]benzyl- | —OC(CH₃)₃ |
| m-F-φ- | R²/R³ = cyclic 3 carbon atoms (L-pyrrolidinyl) | | p-[(CH₃)₂NC(O)O-]benzyl- | —OC(CH₃)₃ |
| p-CH₃-φ- | R²/R³ = cyclic 3 carbon atoms (L-pyrrolidinyl) | | p-[(4-methoxypiperidin-1-yl)C(O)O-]benzyl- | —OCH(CH₃)₂ |
| p-CH₃-φ- | R²/R³ = cyclic 3 carbon atoms (L-pyrrolidinyl) | | p-[(4-(φNHC(O)-)piperazin-1-yl)-C(O)O-]benzyl- | —OCH(CH₃)₂ |
| p-(φNHC(O)NH)φ- | R²/R³ = cyclic 3 carbon atoms (L-pyrrolidinyl) | | p-[(CH₃)₂NC(O)O-]benzyl- | —OC(CH₃)₃ |
| p-F-φ- | R²/R³ = cyclic —CH₂—S—C(CH₃)₂- (L-5,5-dimethylthiazolidin-4-yl) | | 3-chloro-4-[(4-methylpiperidin-1-yl)-C(O)O-]-benzyl- | —OCH(CH₃)₂ |
| p-CH₃-φ- | R²/R³ = cyclic —CH₂—S—C(CH₃)₂- (L-5,5-dimethylthiazolidin-4-yl) | | 3-chloro-4-[(CH₃)₂NC(O)O-]-benzyl- | —OCH(CH₃)₂ |
| p-CH₃-φ- | R²/R³ = cyclic 3 carbon atoms (L-pyrrolidinyl) | | p-[(4-(CF₃SO₂-)piperazin-1-yl)-C(O)O]benzyl- | —OC(CH₃)₃ |
| p-CH₃-φ- | R²/R³ = cyclic 3 carbon atoms (L-pyrrolidinyl) | | p-[(morpholin-4-yl)CH₂CH₂NHC(O)O-]benzyl- | —OH |
| p-CH₃-φ- | R²/R³ = cyclic 3 carbon atoms (L-pyrrolidinyl) | | p-[(4-(HO(O)C-)piperidin-1-yl)C(O)O-]benzyl- | —OH |
| p-CH₃-φ- | R²/R³ = cyclic 3 carbon atoms (L-pyrrolidinyl) | | p-[(HOCH₂CH₂)₂NC(O)O-]benzyl- | —OCH(CH₃)₂ |
| p-O₂N-φ | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(4-(HOCH₂-)piperidin-1-yl)-C(O)O-]benzyl- | —OCH(CH₃)₂ |
| p-CH₃-φ- | R²/R³ = cyclic 3 carbon atoms (L-pyrrolidinyl) | | 3-chloro-4-[(CH₃)₂NC(O)O)-]-benzyl- | —OCH(CH₃)₂ |
| p-CH₃-φ- | R²/R³ = cyclic —CH₂—CH₂—S—CH₂- (L-thiomorpholin-3- | | p-[(CH₃)₂NC(O)O-]benzyl- | —OCH(CH₃)₂ |

TABLE IA-continued $$R^1-\underset{\underset{O}{\overset{O}{\|}}}{S}-\underset{R^2}{N}-\underset{R_3}{\overset{}{C}H}-\overset{O}{\overset{\|}{C}}-\underset{H}{N}-\underset{R^5}{\overset{}{C}H}-\overset{O}{\overset{\|}{C}}-R^{6'}$$

| R¹ | R² | R³ | R⁵ | R⁶' |
|---|---|---|---|---|
| 1-methylpyrazol-3-yl- | R²/R³ = cyclic —CH₂—S—C(CH₃)₂- (L-5,5-dimethylthiazolidin-4-yl) | | p-[(CH₃)₂NC(O)O-]benzyl- | —OH |
| m-F-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| o-F-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 3,4-difluoro-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 3,5-difluoro-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 2,4-difluoro-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-NH₂-φ- | R²/R³ = cyclic 3 carbon atoms (L-pyrrolidinyl) | | p-[(CH₃)₂NC(O)O-]benzyl- | —OH |
| p-N≡C-φ | R²/R³ = cyclic 3 carbon atoms (L-pyrrolidinyl) | | p-[(CH₃)₂NC(O)O-]benzyl- | —OCH(CH₃)₂ |
| p-CH₃-φ- | R²/R³ = cyclic —CH₂CH(OH)CH₂- (L-4-hydroxypyrrolidinyl) | | p-[(CH₃)₂NC(O)O-]benzyl- | —OH |
| p-CH₃-φ- | R²/R³ = cyclic —CH₂C(O)CH₂- (L-4-oxopyrrolidinyl) | | p-[(CH₃)₂NC(O)O-]benzyl- | —OH |
| pyridin-2-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-Cl-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| m-Cl-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| o-Cl-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 3,4-dichloro-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 3,5-dichloro-φ- | R²/R³ = cyclic | | p-[(CH₃)₂NC(O)O-]benzyl- | —OCH(CH₃)₂ |

TABLE IA-continued

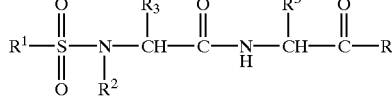

| R¹ | R² | R³ | R⁵ | R⁶' |
|---|---|---|---|---|
| 1-methylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OCH₂CH₃ |
| pyridin-3-yl- | R²/R³ = cyclic —CH₂—S—C(CH₃)₂- (L-5,5-dimethylthiazolidin-4-yl) | | p-[(CH₃)₂NC(O)O-]benzyl- | —OH |
| 1-methylpyrazol-4-yl- | R²/R³ = cyclic —CH₂—S—C(CH₃)₂- (L-5,5-dimethylthiazolidin-4-yl) | | p-[(thiomorpholin-4-yl)-C(O)O-]benzyl- | —OCH(CH₃)₂ |
| quinolin-8-yl | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| m-Cl-φ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| pyridin-2-yl- | R²/R³ = cyclic —CH₂—S—C(CH₃)₂- (L-5,5-dimethylthiazolidin-4-yl) | | p-[(CH₃)₂NC(O)O-]benzyl- | —OH |
| 3,4-dichloro-φ- | R²/R³ = cyclic —CH₂CH₂—SO₂—CH₂- (L-1,1-dioxothiomorpholin-3-yl) | | p-[(CH₃)₂NC(O)O-]benzyl- | —OC(CH₃)₃ |
| 2,5-dichlorothien-3-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-CH₃O-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| m-CH₃O-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| o-CH₃O-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 3,4-dimethoxy-φ- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| 2,4-difluoro-φ- | R²/R³ = cyclic —CH₂—CH₂—S—CH₂- (L-thiomorpholin-3-yl) | | p-[(CH₃)₂NC(O)O-]benzyl- | —OC(CH₃)₃ |
| 3,4-dichloro-φ- | R²/R³ = cyclic —CH₂CH₂—SO₂—CH₂- | | p-[(CH₃)₂NC(O)O-]benzyl- | —OH |

TABLE IA-continued

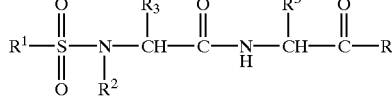

| R¹ | R² | R³ | R⁵ | R⁶' |
|---|---|---|---|---|
| m-Cl-φ- | (L-1,1-dioxothiomorpholin-3-yl) R²/R³ = cyclic —CH₂CH₂—SO₂—CH₂- (L-1,1-dioxothiomorpholin-3-yl) | | p-[(CH₃)₂NC(O)O-]benzyl- | —OH |
| 2,4-difluoro-φ- | R²/R³ = cyclic —CH₂—CH₂—S(O)—CH₂- (L-1-oxothiomorpholin-4-yl) | | p-[(CH₃)₂NC(O)O-]benzyl- | —OC(CH₃)₃ |
| p-CH₃-φ- | R²/R³ = cyclic —CH₂—C(O)—CH₂- (L-4-oxopyrrolidinyl) | | p-[(4-methylpiperazin-1-yl)C(O)O-]benzyl- | —OCH(CH₃)₂ |
| p-CH₃-φ- | R²/R³ = cyclic —CH₂CH(OH)CH₂- (L-4-hydroxypyrrolidinyl) | | p-[(thiomorpholin-4-yl)-C(O)O-]benzyl- | —OC(CH₃)₃ |
| p-CH₃-φ- | R²/R³ = cyclic 3 carbon atoms (L-pyrrolidinyl) | | p-[(3-(HOCH₂-)piperidin-1-yl)-C(O)O-]benzyl- | —OH |
| p-CH₃-φ- | R²/R³ = cyclic —CH₂—CF₂—CH₂- (L-4,4-difluoro-pyrolidinyl) | | p-[(CH₃)₂NC(O)O-]benzyl- | —OCH(CH₃)₂ |
| p-CH₃-φ- | R²/R³ = cyclic 3 carbon atoms (L-pyrrolidinyl) | | p-[(CH₃)₂NC(O)O-]benzyl- | —O(CH₂CH₂O)₂CH₃ |
| p-CH₃-φ- | R²/R³ = cyclic —CH₂CH(—O-C(O)thiomorpholin-4-yl)-CH₂- (L-4-(thiomorpholin-4-ylC(O)O-pyrrolidinyl) | | p-[(thiomorpholin-4-yl)-C(O)O-]benzyl- | —OC(CH₃)₃ |
| p-CH₃-φ- | R²/R³ = cyclic —CH₂—CF₂—CH₂- (L-4,4-difluoro-pyrolidinyl) | | p-[(CH₃)₂NC(O)O-]benzyl- | —OH |
| p-F-φ- | R²/R³ = cyclic —CH₂—S—C(CH₃)₂- (L-5,5-dimethylthiazolidin-4-yl) | | p-[(4-(pyrimidin-2-yl)piperazin-1-yl)-C(O)O-]benzyl- | —OC(CH₃)₃ |
| p-CH₃-φ- | R²/R³ = cyclic 3 carbon atoms (L-pyrrolidinyl) | | p-[(4-(φC(O)-)piperazin-1-yl)-C(O)O-]benzyl- | —OCH(CH₃)₂ |
| p-F-φ- | R²/R³ = cyclic —CH₂—S—C(CH₃)₂- (L-5,5-dimethylthiazolidin-4-yl) | | 3-fluoro-4-[(CH₃)₂NC(O)O-]-benzyl- | —OCH(CH₃)₂ |
| p-F-φ- | R²/R³ = cyclic —CH₂—S—C(CH₃)₂- (L-5,5-dimethylthiazolidin-4-yl) | | 3-chloro-4-[(4-(pyridin-2-yl)piperazin-1-yl)C(O)O-]-benzyl- | —OCH(CH₃)₂ |
| p-F-φ- | R²/R³ = cyclic —CH₂—S—C(CH₃)₂- (L-5,5-dimethylthiazolidin-4-yl) | | 3-chloro-4-[(4-(pyridin-2-yl)piperazin-1-yl)C(O)O-]-benzyl- | —OC(CH₃)₃ |
| p-CH₃-φ- | R²/R³ = cyclic —CH₂CH₂N-(-SO₂CH₃)—CH₂- (L-4-methanesulfonyl-piperizinyl) | | p-[(CH₃)₂NC(O)O-]benzyl- | —OC(CH₃)₂ |

TABLE IA-continued

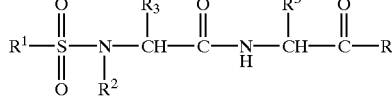

| R¹ | R² | R³ | R⁵ | R⁶' |
|---|---|---|---|---|
| R¹/R² = 1,1-dioxo-2,3-dihydro-3,3-dimethyl-1,2-benzisothiazol-2-yl-1-methylimidazol-4-yl- | | H | p-[(CH₃)₂NC(O)O-]benzyl- | —OH |
| | R²/R³ = cyclic 3 carbon atoms (L-pyrrolidinyl) | | p-[(CH₃)₂NC(O)O-]benzyl- | —OCH(CH₃)₂ |
| R¹/R² = N-2,10-camphorsultamyl- | | H | p-[(CH₃)₂NC(O)O-]benzyl- | —OC(CH₃)₃ |
| R¹/R² = N-2,10-camphorsultamyl- | | H | p-[(CH₃)₂NC(O)O-]benzyl- | —OH |
| R¹/R² = N-2,10-camphorsultamyl- | | H | 3-chloro-4-[(CH₃)₂NC(O)O)-]-benzyl- | —OCH(CH₃)₂ |
| p-Br-φ- | R²/R³ = cyclic —CH₂—S—C(CH₃)₂- (L-5,5-dimethylthiazolidin-4-yl) | | p-[(CH₃)₂NC(O)O-]benzyl- | —OC(CH₃)₃ |
| p-Br-φ- | R²/R³ = cyclic —CH₂—S—C(CH₃)₂- (L-5,5-dimethylthiazolidin-4-yl) | | p-[(CH₃)₂NC(O)O-]benzyl- | —OH |
| p-NH₂C(=N)-φ- | R²/R³ = cyclic 3 carbon atoms (L-pyrrolidinyl) | | p-[(CH₃)₂NC(O)O-]benzyl- | —OCH₃ |
| p-N≡C-φ- | R²/R³ = cyclic 3 carbon atoms (L-pyrrolidinyl) | | p-[(thiomorpholin-4-yl)-C(O)O-]benzyl- | —OCH(CH₃)₂ |
| p-CH₃-φ- | R²/R³ = cyclic —CH₂CH(—O-C(O)thiomorpholin-4-yl)-CH₂- (L-4-(thiomorpholin-4-ylC(O)O-pyrrolidinyl) | | p-[(thiomorpholin-4-yl)-C(O)O-]benzyl- | —OH |
| p-CH₃-φ- | R²/R³ = cyclic —CH₂—C(O)—CH₂- (L-4-oxopyrrolidinyl) | | p-[(thiomorpholin-4-yl-)C(O)O-]benzyl- | —OC(CH₃)₃ |
| p-CH₃-φ- | R²/R³ = cyclic —CH₂—C(O)—CH₂- (L-4-oxopyrrolidinyl) | | p-[(thiomorpholin-4-yl)-C(O)O-]benzyl- | —OH |
| p-CH₃-φ- | R²/R³ = cyclic —CH₂—C(O)—CH₂- (L-4-oxopyrrolidinyl) | | p-[(4-methylpiperazin-1-yl)-C(O)O-]benzyl- | —OH |
| p-F-φ- | R²/R³ = cyclic —CH₂—S—C(CH₃)₂- (L-5,5-dimethylthiazolidin-4-yl) | | p-[(4-(pyrimidin-2-yl)piperazin-1-yl)-C(O)O-]benzyl- | —OH |
| quinolin-8-yl- | R²/R³ = cyclic —CH₂—S—C(CH₃)₂- (L-5,5-dimethylthiazolidin-4-yl) | | p-[(CH₃)₂NC(O)O-]benzyl- | —OH |
| pyridin-4-yl- | R²/R³ = cyclic —CH₂—S—C(CH₃)₂- (L-5,5-dimethylthiazolidin-4-yl) | | p-[(CH₃)₂NC(O)O-]benzyl- | —OCH(CH₃)₂ |
| p-F-φ- | R²/R³ = cyclic —CH₂—S—C(CH₃)₂- (L-5,5-dimethylthiazolidin-4-yl) | | p-[4-(pyridin-2-yl)piperazin-1-yl)C(O)O-]benzyl- | —OCH(CH₃)₂ |
| m-F-φ- | R²/R³ = cyclic | | p-[(CH₃)₂NC(O)O-]benzyl- | —OH |

TABLE IA-continued

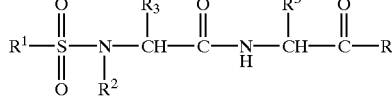

| R¹ | R² | R³ | R⁵ | R⁶' |
|---|---|---|---|---|
| p-F-φ- | R²/R³ = cyclic —CH₂—CH₂—S-(thiazolidin-2-yl) | | p-[(CH₃)₂NC(O)O-]benzyl- | —OH |
| p-F-φ- | R²/R³ = cyclic —CH₂—CH₂—S-(thiazolidin-2-yl) | | p-[(CH₃)₂NC(O)O-]benzyl- | —OC(CH₃)₃ |
| p-CH₃-φ- | R²/R³ = cyclic —CH₂—C(O)—CH₂-(L-4-oxopyrrolidinyl) | | p-[(thiomorpholin-4-yl)C(O)O-]benzyl- | —OH |
| p-NH₂—C(=N)-φ- | R²/R³ = cyclic 3 carbon atoms (L-pyrrolidinyl) | | p-[(thiomorpholin-4-yl)C(O)O-]benzyl- | —OCH₃ |
| p-CH₃-φ- | R²/R³ = cyclic —CH₂—C(O)—CH₂-(L-4-oxopyrrolidinyl) | | p-[(4-methylpiperazin-1-yl)-C(O)O-]benzyl- | —OH |
| p-F-φ- | R²/R³ = cyclic —CH₂—CH₂—S-(thiazolidin-2-yl) | | p-[(4-(pyridin-2-yl)piperazin-1-yl)-C(O)O-]benzyl- | —OH |
| p-NO₂-φ- | R²/R³ = cyclic 3 carbon atoms (L-pyrrolidinyl) | | p-[(4-(pyridin-2-yl)piperazin-1-yl)-C(O)O-]benzyl- | —OC(CH₃)₃ |
| p-F-φ- | R²/R³ = cyclic —CH₂—CH₂—S-(thiazolidin-2-yl) | | p-[(4-(pyridin-2-yl)piperazin-1-yl)-C(O)O-]benzyl- | —OC(CH₃)₃ |
| p-Br-φ- | R²/R³ = cyclic —CH₂—S—C(CH₃)₂-(L-5,5-dimethylthiazolidin-4-yl) | | p-[(4-(pyridin-2-yl)piperazin-1-yl)-C(O)O-]benzyl- | —OH |
| p-CH₃-φ- | R²/R³ = cyclic 3 carbon atoms (L-pyrrolidinyl) | | p-[(4-(φC(O)-)piperazin-1-yl)C(O)O-]benzyl- | —OH |
| p-CH₃-φ- | R²/R³ = cyclic 3 carbon atoms (L-pyrrolidinyl) | | p-[(4-(φNHC(S)-)piperazin-1-yl)-C(O)O-]benzyl- | —OCH(CH₃)₂ |
| p-F-φ- | R²/R³ = cyclic —CH₂—CH₂—S-(thiazolidin-2-yl) | | p-[(4-CH₃-homopiperazin-1-yl)-C(O)O-]benzyl- | —OC(CH₃)₃ |
| p-CH₃-φ- | R²/R³ = cyclic 3 carbon atoms (L-pyrrolidinyl) | | p-[p-CH₃-φ-SO₂N(CH₃)CH₂CH₂N(CH₃)—C(O)O-]benzyl- | —OCH(CH₃)₂ |
| p-CH₃-φ- | R²/R³ = cyclic 3 carbon atoms (L-pyrrolidinyl) | | p-[φNHC(O)O-CH₂CH₂NHC(O)O-]benzyl- | —OCH(CH₃)₂ |
| 3-Cl-4-F-φ- | R²/R³ = cyclic —CH₂CH₂—SO₂—CH₂-(L-1,1-dioxothiomorpholin-3-yl) | | p-[(CH₃)₂NC(O)O-]benzyl- | —OC(CH₃)₃ |
| 1-methylpyrazol-4-yl- | R²/R³ = cyclic —CH₂—CH₂—S—CH₂-(L-thiomorpholin-3-yl) | | p-[(CH₃)₂NC(O)O-]benzyl- | —OC(CH₃)₃ |
| p-CH₃-φ- | R²/R³ = cyclic —CH₂CH(—OSO₂CH₃)—CH₂-(L-4-methanesulfoxy-pyrrolidinyl) | | p-[(CH₃)₂NC(O)O-]benzyl- | —OC(CH₃)₃ |
| p-H₂NC(O)-φ- | R²/R³ = cyclic 3 carbon atoms (L-pyrrolidinyl) | | p-[(CH₃)₂NC(O)O-]benzyl- | —OH |
| p-H₂N—C(=N)-φ | R²/R³ = cyclic 3 carbon atoms (L-pyrrolidinyl) | | p-[(CH₃)₂NC(O)O-]benzyl- | —OH |
| p-H₂NC(O)-φ- | R²/R³ = cyclic 3 carbon atoms (L-pyrrolidinyl) | | p-[(thiomorpholin-4-yl)C(O)O-)benzyl- | —OH |
| p-H₂NC(=N)-φ- | R²/R³ = cyclic | | p-[(thiomorpholin-4-yl)C(O)O-)benzyl- | —OH |

TABLE IA-continued $$R^1-\underset{\underset{O}{\|}}{\overset{\overset{O}{\|}}{S}}-\underset{R^2}{N}-\underset{\underset{H}{|}}{CH}-\overset{\overset{O}{\|}}{C}-\underset{H}{N}-\underset{\underset{H}{|}}{CH}-\overset{\overset{O}{\|}}{C}-R^{6'}$$

| R¹ | R² | R³ | R⁵ | R⁶' |
|---|---|---|---|---|
| p-NO₂-φ- | R²/R³ = cyclic 3 carbon atoms (L-pyrrolidinyl) | | p-[(4-(pyridin-2-yl)piperazin-1-yl)-C(O)O-]benzyl- | —OH |
| p-F-φ- | R²/R³ = cyclic —CH₂—S—C(CH₃)₂- (L-5,5-dimethylthiazolidin-4-yl) | | 3-chloro-4-[(4-(pyridin-2-yl)piperazin-1-yl)C(O)O-]-benzyl- | —OCH₂CH₃ |
| p-F-φ- | R²/R³ = cyclic —CH₂—S—C(CH₃)₂- (L-5,5-dimethylthiazolidin-4-yl) | | 3-chloro-4-[(4-(pyridin-2-yl)piperazin-1-yl)C(O)O-]-benzyl- | —OH |
| p-F-φ- | R²/R³ = cyclic —CH₂—CH₂—S-(thiazolidin-2-yl) | | p-[(4-CH₃-homopiperizin-1-yl)C(O)O-]benzyl- | —OH |
| 1-methylpyrazol-4-yl- | R²/R³ = cyclic —CH₂—S—C(CH₃)₂- (L-5,5-dimethylthiazolidin-4-yl) | | 3-chloro-4-[(CH₃)₂NC(O)O-]benzyl-benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OH |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| p-F-φ- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| p-CH₃-φ- | R²/R³ = cyclic —CH₂CH₂N(—SO₂—CH₃)CH₂- (4-methanesulfonyl-piperizin-2-yl) | | p-[(CH₃)₂NC(O)O-]benzyl- | —OH |
| p-CH₃-φ- | R²/R³ = cyclic —CH₂CH(—OSO₂—CH₃)CH₂- (L-4-methanesulfoxy-pyrrolidinyl) | | p-[(CH₃)₂NC(O)O-]benzyl- | —OH |
| 3,4-difluoro-φ- | R²/R³ = cyclic —CH₂—CH₂—S—CH₂- (L-thiomorpholin-3-yl) | | p-[(CH₃)₂NC(O)O-]benzyl- | —OC(CH₃)₃ |
| pyridin-3-yl- | R²/R³ = cyclic —CH₂—S—C(CH₃)₂- (L-5,5-dimethylthiazolidin-4-yl) | | p-[(thiomorpholin-4-yl)C(O)O-]benzyl- | —OCH(CH₃)₂ |
| CH₃— | —CH₂φ | H | p-[(CH₃)₂NC(O)O-]benzyl- | —OC(CH₃)₃ |
| 3,4-difluoro-φ- | R²/R³ = cyclic —CH₂—CH₂—S—CH₂- (L-thiomorpholin-3-yl) | | p-[(CH₃)₂NC(O)O-]benzyl- | —OH |
| p-F-φ- | R²/R³ = cyclic —CH₂CH(OH)CH₂- | | p-[(CH₃)₂NC(O)O-]benzyl- | —OCH(CH₃)₂ |

TABLE IA-continued

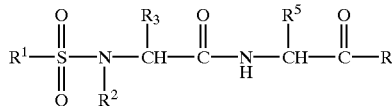

| R¹ | R² | R³ | R⁵ | R⁶' |
|---|---|---|---|---|
| p-Br-φ- | (L-4-hydroxypyrrolidinyl) R²/R³ = cyclic —CH₂—S—C(CH₃)₂- (L-5,5-dimethylthiazolidin-4-yl) | | p-[(4-(pyridin-2-yl)piperazin-1-yl)C(O)O-]benzyl- | —OC(CH₃)₃ |
| p-CF₃O-φ- | R²/R³ = cyclic —CH₂—S—C(CH₃)₂- (L-5,5-dimethylthiazolidin-4-yl) | | p-[(CH₃)₂NC(O)O-]benzyl- | —OH |
| p-CF₃O-φ- | R²/R³ = cyclic —CH₂—S—C(CH₃)₂- (L-5,5-dimethylthiazolidin-4-yl) | | p-[(CH₃)₂NC(O)O-]benzyl- | —OC(CH₃)₃ |
| p-CF₃O-φ | R²/R³ = cyclic —CH₂—S—C(CH₃)₂- (L-5,5-dimethylthiazolidin-4-yl) | | p-[(4-(pyridin-2-yl)piperazin-1-yl)C(O)O-]benzyl- | —OC(CH₃)₃ |
| p-F-φ- | R²/R³ = cyclic 3 carbon atoms (L-pyrrolidinyl) | | p-[(4-pyridin-2-yl)piperazin-1-yl)C(O)O-]benzyl- | —OH |
| p-F-φ- | R²/R³ = cyclic —CH₂CH(OH)CH₂- (L-4-hydroxypyrrolidinyl) | | p-[(4-(pyridin-2-yl)piperazin-1-yl)C(O)O-]benzyl- | —OH |
| p-CF₃O-φ- | R²/R³ = cyclic —CH₂—S—C(CH₃)₂- (L-5,5-dimethylthiazolidin-4-yl) | | p-[(4-(pyridin-2-yl)piperazin-1-yl)C(O)O-]benzyl- | —OH |
| 1-methylimidazol-4-yl- | R²/R³ = cyclic 3 carbon atoms (L-pyrrolidinyl) | | 3-chloro-4-[(CH₃)₂NC(O)O)-]benzyl- | —OH |
| 1-methylimidazol-4-yl- | R²/R³ = cyclic 3 carbon atoms (L-pyrrolidinyl) | | 3-chloro-4-[(CH₃)₂NC(O)O)-]benzyl- | —OCH(CH₃)₂ |
| 1-methylimidazol-4-yl- | R²/R³ = cyclic 3 carbon atoms (L-pyrrolidinyl) | | p-[(4-(pyridin-2-yl)piperazin-1-yl)C(O)O-]benzyl- | —OH |
| 1-methylimidazol-4-yl- | R²/R³ = cyclic —CH₂—S—C(CH₃)₂- (L-5,5-dimethylthiazolidin-4-yl) | | p-[(4-(pyridin-2-yl)piperazin-1-yl)C(O)O-]benzyl- | —OH |
| 1-methypyrazol-4-yl- | R²/R³ = cyclic 3 carbon atoms (L-pyrrolidinyl) | | p[(4-(pyridin-2-yl)piperazin-1-yl)C(O)O-]benzyl- | —OH |
| 1-methylpyrazol-4-yl- | R²/R³ = cyclic 3 carbon atoms (L-pyrrolidinyl) | | p-[(4-(pyridin-2-yl)piperazin-1-yl)C(O)O-]benzyl- | —OCH(CH₃)₂ |
| 1-methylpyrazol-4-yl- | R²/R³ = cyclic 3 carbon atoms (L-pyrrolidinyl) | | p-[(4-(pyridin-2-yl)piperazin-1-yl)C(O)O-]benzyl- | —OC(CH₃)₃ |
| 1-methylpyrazol-4-yl- | R²/R³ = cyclic —CH₂—S—C(CH₃)₂- (L-5,5-dimethylthiazolidin-4-yl) | | p-[(4-(pyridin-2-yl)piperazin-1-yl)C(O)O-]benzyl- | —OC(CH₃)₃ |
| 1-methylimidazol-4-yl- | R²/R³ = cyclic 3 carbon atoms (L-pyrrolidinyl) | | 3-chloro-4-[(4-(pyridin-2-yl)piperazin-1-yl)C(O)O]benzyl- | —OCH(CH₃)₂ |
| 1-methylpyrazol-4-yl- | R²/R³ = cyclic —CH₂—S—C(CH₃)₂- (L-5,5-dimethylthiazolidin-4-yl) | | p-[(CH₃)₂NC(O)O-]benzyl- | —OCH₂CH₂Oφ |

TABLE IA-continued

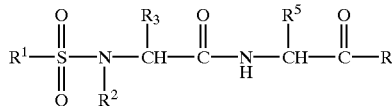

| R¹ | R² | R³ | R⁵ | R⁶' |
|---|---|---|---|---|
| 1-methylpyrazol-4-yl- | R²/R³ = cyclic —CH₂—S—C(CH₃)₂-(L-5,5-dimethylthiazolidin-4-yl) | | 3-chloro-4-[(4-(pyridin-2-yl)piperazin-1-yl)C(O)O-]-benzyl- | —OH |
| 1-methylpyrazol-4-yl- | R²/R³ = cyclic —CH₂—S—C(CH₃)₂-(L-5,5-dimethylthiazolidin-4-yl) | | 3-chloro-4-[(4-(pyridin-2-yl)piperazin-1-yl)C(O)O-]-benzyl- | —OCH₂CH₃ |
| 1,5-dimethyl-3-chloropyrazol-4-yl- | R²/R³ = cyclic —CH₂—S—C(CH₃)₂-(L-5,5-dimethylthiazolidin-4-yl) | | p-[4-[5-CF₃-pyridin-2-yl)piperazin-1 yl)-C(O)O-]benzyl- | —OH |
| p-F-φ- | R²/R³ = cyclic —CH₂CH(OH)CH₂-(L-4-hydroxypyrrolidinyl) | | p-[(CH₃)₂NC(O)O-]benzyl- | —OC(CH₃)₃ |
| pyridin-4-yl- | R²/R³ = cyclic —CH₂—S—C(CH₃)₂-(L-5,5-dimethylthiazolidin-4-yl) | | p-[(CH₃)₂NC(O)O-]benzyl- | —OH |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | —OCH₂C(CH₃)₃ |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | —OCH₂—C(O)C(CH₃)₃ |
| pyridin-3-yl- | R²/R³ = cyclic —CH₂—S—C(CH₃)₂-(L-5,5-dimethylthiazolidin-4-yl) | | p-[(CH₃)₂NC(O)O-]benzyl- | —OCH₂C(CH₃)₃ |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | 2-CH₃O-φ-O- |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | -OCH₂cyclopropyl |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | —OCH₂CH₂CH₃ |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | —OCH₂CH₂CH₂CH₃ |
| 1-methylpyrazol-4-yl- | R²/R³ = cyclic —CH₂—S—C(CH₃)₂-(L-5,5-dimethylthiazolidin-4-yl) | | p-[(CH₃)₂NC(O)O-]benzyl- | —O—CH₃ |
| pyridin-3-yl- | R²/R³ = cyclic —CH₂—S—C(CH₃)₂-(L-5,5-dimethylthiazolidin-4-yl) | | p-[(CH₃)₂NC(O)O-]benzyl- | —OC(CH₃)₃ |
| pyridin-3-yl- | R²/R³ = cyclic | | p-[(CH₃)₂NC(O)O-]benzyl- | —OCH₂CH₃ |

TABLE IA-continued

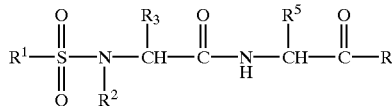

| R¹ | R² | R³ | R⁵ | R⁶' |
|---|---|---|---|---|
| pyridin-3-yl- | —CH₂—S—C(CH₃)₂- (L-5,5-dimethylthiazolidin-4-yl) R²/R³ = cyclic —CH₂—S—C(CH₃)₂- (L-5,5-dimethylthiazolidin-4-yl) | | p-[(CH₃)₂NC(O)O-]benzyl- | -OCH₂cyclopropyl |

TABLE IB

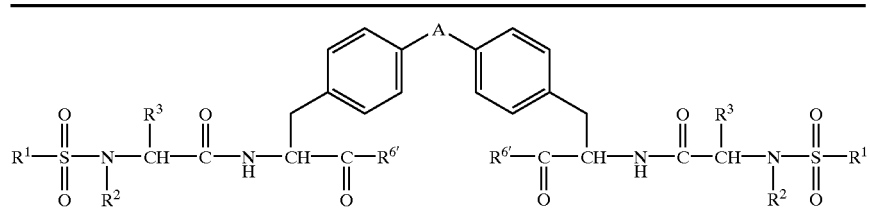

| R¹ | R² | R³ | A | R⁶ |
|---|---|---|---|---|
| p-CH₁-φ- | R²/R³ = cyclic 3 carbon atoms (L-pyrrolidinyl) | | —OC(O)-(pyrizin-1,4-diyl)-C(O))— | —OCH(CH₃)₂ |
| p-CH₁-φ- | R²/R³ = cyclic 3 carbon atoms (L-pyrrolidinyl) | | —OC(O)-(pyrizin-1,4-diyl)-C(O))— | —OC(CH₃)₃ |
| p-CH₁-φ- | R²/R³ = cyclic 3 carbon atoms (L-pyrrolidinyl) | | —OC(O)-(pyrizin-1,4-diyl)-C(O))— | —OH |
| p-CH₁-φ- | R²/R³ = cyclic —CH₂—S—C(CH₃)₂— (L-5,5-dimethylthiazolidin-4-yl) | | —OC(O)-(pyrizin-1,4-diyl)-C(O))— | —OC(CH₃)₃ |
| p-CH₁-φ- | R²/R³ = cyclic —CH₂—S—C(CH₃)₂— (L-5,5-dimethylthiazolidin-4-yl) | | —OC(O)-(pyrizin-1,4-diyl)-C(O))— | —OH |

DETAILED DESCRIPTION OF THE INVENTION

This invention relates to compounds which inhibit leukocyte adhesion and, in particular, leukocyte adhesion mediated by VLA-4. When describing the compounds, compositions and methods of this invention, the following terms have the following meanings, unless otherwise indicated.

Definitions

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂- aryl, —NRS(O)₂-substituted aryl, —NRS(O)₂-heteroaryl, —NRS(O)₂-substituted heteroaryl, —NRS(O)₂- heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent alkylene group preferably having from 1 to 10 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylairino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OS(O)$_2$-NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OS(O)$_2$—NRR where R is hydrogen or alkyl, —NRS(O)$_2$-alkyl, —NRS(O)$_7$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(Q)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of frm 3 to 8 carbon atoms having a single cyclic ring.

"Substituted cycloalkyl" and "substituted cycloalkenyl" refers to an cycloalkyl or cycloalkenyl group, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$- heteroaryl, —SO₂-substituted heteroaryl, —SO₂-heterocyclic, —SO₂-substituted heterocyclic and —SO₂NRR where R is hydrogen or alkyl.

"Cycloalkoxy" refers to —O-cycloalkyl groups.

"Substituted cycloalkoxy" refers to —O-substituted cycloalkyl groups. "Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"N,N-Dimethylcarbamyloxy" refers to the group —OC(O)N(CH₃)₂.

"Guanidinosulfone" refers to the groups —NRC(=NR)NRSO₂-alkyl, —NRC(=NR)NRSO₂-substituted alkyl, —NRC(=NR)NRSO₂-alkenyl, —NRC(=NR)NRSO₂-substituted alkenyl, —NRC(=NR)NRSO₂-alkynyl, —NRC(=NR)NRSO₂-substituted alkynyl, —NRC(=NR)NRSO₂-aryl, —NRC(=NR)NRSO₂-substituted aryl, —NRC(=NR)NRSO₂-cycloalkyl, —NRC(=NR)NRSO₂-substituted cycloalkyl, —NRC(=NR)NRSO₂-heteroaryl, and —NRC(=NR)NRSO₂-substituted heteroaryl, —NRC(=NR)NRSO₂-heterocyclic, and —NRC(=NR)NRSO₂-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)₂-alkyl, —S(O)₂-substituted alkyl, —S(O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S(O)₂-substituted heteroaryl, —S(O)₂-heterocyclic, —S(O)₂-substituted heterocyclic, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO₂NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O-aryl, —C(O)O-substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b] thiophene, thiazole, thiazolidine, thiophene, benzo[b] thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I/IA which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of formula I and IA wherein Q is —C(O)NR$^7$— are prepared by first coupling an amino acid of formula II:

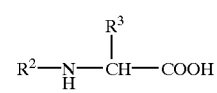

II wherein R$^2$ and R3 are as defined herein (e.g., in formula I and IIA), with a sulfonyl chloride of formula III:

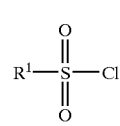

III wherein R$^1$ is as defined herein, to provide an N-sulfonyl amino acid of formula IV:

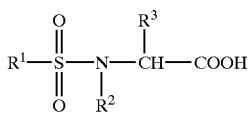

IV wherein $R^1$–$R^3$ are as defined herein.

This reaction is typically conducted by reacting the amino acid of formula II with at least one equivalent, preferably about 1.1 to about 2 equivalents, of sulfonyl chloride III in an inert diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting N-sulfonyl amino acid IV is recovered by conventional methods including neutralization, extraction, precipitation, chromatography, filtration, and the like.

The amino acids of formula II employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-indoline-2-carboxylic acid, L-1,2,3,4-tetrahydroisoquinoline-3-carboxylic acid, L-thiazolidine-4-carboxylic acid, L-(5,5-dimethyl)thiazolidine-4-carboxylic acid, L-thiamorpholine-3-carboxylic acid, glycine, 2-tert-butylglycine, D,L-phenylglycine, L-alanine, α-methylalanine, N-methyl-L-phenylalanine, L-diphenylalanine, sarcosine, D,L-phenylsarcosine, L-aspartic acid β-tert-butyl ester, L-glutamic acid γ-tert-butyl ester, L-(O-benzyl)serine, 1-aminocyclopropanecarboxylic acid, 1-aminocyclobutanecarboxylic acid, 1-aminocyclopentanecarboxylic acid (cycloleucine) 1-aminocyclohexanecarboxylic acid, L-serine and the like. If desired, the corresponding carboxylic acid esters of the amino acids of formula II, such as the methyl esters, ethyl esters and the like, can be employed in the above reaction with the sulfonyl chloride III. Subsequent hydrolysis of the ester group to the carboxylic acid using conventional reagents and conditions, i.e., treatment with an alkali metal hydroxide in an inert diluent such as methanol/water, then provides the N-sulfonyl amino acid IV.

Similarly, the sulfonyl chlorides of formula III employed in the above reaction are either known compounds or compounds that can be prepared from known compounds by conventional synthetic procedures. Such compounds are typically prepared from the corresponding sulfonic acid, i.e., from compounds of the formula $R^1$—$SO_3H$ where $R^1$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides of formula m can be prepared from the corresponding thiol compound, i.e., from compounds of the formula $R^1$—SH where $R^1$ is as defined herein, by treating the thiol with chlorine ($Cl_2$) and water under conventional reaction conditions.

Examples of sulfonyl chlorides suitable for use in this, invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids of formula IV.

The intermediate N-sulfonyl amino acids of formula IV can also be prepared by reacting a sulfonamide of formula V:

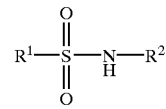

V wherein $R^1$ and $R^2$ are as defined herein, with a carboxylic acid derivative of the formula L($R^3$)CHCOOR where L is a leaving group, such as chloro, bromo, iodo, mesylate, tosylate and the like, $R^3$ is as defined herein and R is hydrogen or an alkyl group. This reaction is typically conducted by contacting the sulfonamide V with at least one equivalent, preferably 1.1 to 2 equivalents, of the carboxylic acid derivative in the presence of a suitable base, such as triethylamine, in an inert diluent, such as DMF, at a temperature ranging from about 24° C. to about 37° C. for about 0.5 to about 4 hours. This reaction is further described in Zuckermann et al., *J. Am. Chem. Soc.*, 1992, 114, 10646–10647. Preferred carboxylic acid derivatives for use in this reaction are α-chloro and α-bromocarboxylic acid esters such as tert-butyl bromoacetate and the like. When a carboxylic acid ester is employed in his reaction, the ester group is subsequently hydrolyzed using conventional procedures to afford an N-sulfonyl amino acid of formula IV.

The compounds of formula I/IA are then prepared by coupling the intermediate N-sulfonyl amino acid of formula IV with an amino acid derivative of formula VI:

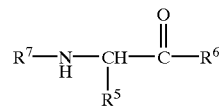

VI wherein $R^5$–$R^7$ are as defined herein. This coupling reaction is typically conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethylamino-propyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid IV with about 1 to about 2 equivalents of the coupling reagent and at least one equivalent, preferably about 1 to about 1.2 equivalents, of amino acid derivative VI in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound of formula I/IA is recovered by conventional methods including neutralization, extraction, precipitation, chromatography, filtration, and the like.

Alternatively, the N-sulfonyl amino acid IV can be converted into an acid halide and the acid halide coupled with amino acid derivative VI to provide compounds of formula I/IA. The acid halide of VI can be prepared by contacting VI with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid IV is then contacted with at least one equivalent, preferably about 1.1 to about 1.5 equivalents, of amino acid derivative VI in an inert diluent, such as dichloromethane, at a temperature ranging from about –70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of formula I/IA is recovered by conventional methods including neutralization, extraction, precipitation, chromatography, filtration, and the like.

Alternatively, the compounds of formula I/IA can be prepared by first forming a diamino acid derivative of formula VII:

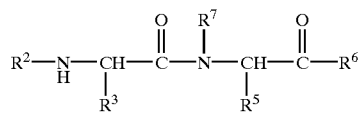

VII wherein $R^2$, $R^3$, $R^5$, $R^6$ and $R^7$ are as defined herein. The diamino acid derivatives of formula VII can be readily prepared by coupling an amino acid of formula II with an amino acid derivative of formula VI using conventional amino acid coupling techniques and reagents, such carbodiimides, BOP reagent and the like, as described above. Diamino acid VII can then be sulfonated using a sulfonyl chloride of formula m and using the synthetic procedures described above to provide a compound of formula I/IA.

The amino acid derivatives of formula VI employed in the above reactions are either known compounds or compounds that can be prepared from known compounds by conventional synthetic procedures. For example, amino acid derivatives of formula VI can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives of formula VI suitable for use in the above reactions include, but are not limited to, L-tyrosine methyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

For ease of synthesis, the compounds of formula I are typically prepared as an ester, i.e., where $R^6$ is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 10 hours. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

As will be apparent to those skilled in the art, other functional groups present on any of the substituents of the compounds of formula I can be readily modified or derivatized either before or after the above-described coupling reactions using well-known synthetic procedures. For example, a nitro group present on a substituent of a compound of formula I/IA or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on, e.g., the $R^3$ substituent, can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid. Compounds having a pyridyl group can be readily prepared by using, for example, β-(2-pyridyl)-, β-(3-pyridyl)- or β-(4-pyridyl)-L-alanine derivatives in the above-described coupling reactions.

Additionally, when a substituent of a compound of formula I/A or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on such a substituent may be prepared, for example, by reduction of the corresponding nitro compound as described above. Alternatively, such compounds can be prepared by using an amino acid derivative of formula VI derived from lysine, 4-aminophenylalanine and the like in the above-described coupling reactions.

By way of illustration, a compound of formula I/IA or an intermediate thereof having a substituent containing a primary or secondary amino group can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)-phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxybenzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I/IA or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoromethylbenzoyl chloride, isonicotinoyl chloride, nicotinoyl chloride, picolinoyl chloride, acetic anhydride, succinic anhydride and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I/IA or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride and the like. Similarly, sulfamoyl chlorides, such as dimethylsulfamoyl chloride, can be used to provide sulfamides (e.g., >N—SO$_2$—N<).

Additionally, a primary and secondary amino group present on a substituent of a compound of formula I/IA or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I), and the like.

Furthermore, when a compound of formula I/IA or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I/IA or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^5$ substituent, for example, can be prepared using an amino acid derivative of formula VI derived from tyrosine and the like in the above-described reactions.

By way of example, a compound of formula I/IA or an intermediate thereof having a substituent containing a hydroxyl group can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino) ethyl chloride, 3-(N,N-ethylamino)propyl chloride, 3-(N-benzyl-N-methylamino)propyl chloride, N-(2-chloroethyl) morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine) ethyl chloride, N-tert-butyloxycarbonyl-3-piperidinemethyl tosylate and the like.

Alternatively, a hydroxyl group present on a substituent of a compound of formula I/IA or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I/IA or an intermediate thereof containing a aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I/IA or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I/IA or an intermediate thereof contains a primary or secondary hydroxyl group, such hydroxyl groups can be readily converted into a leaving group and displaced to form, for example, amines, sulfides and fluorides. For example, derivatives of 4-hydroxy-L-proline can be converted into the corresponding 4-amino, 4-thio or 4-fluoro-L-proline derivatives via nucleophilic displacement of the derivatized hydroxyl group. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino (—$NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I/IA or an intermediate thereof having a substituent containing an iodoaryl group, for example, when $R^5$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra (triphenylphosphine), in an inert diluent, such as tetrahydrofuran, at a temperature ranging from about 24° C. to about 30° C. until the reaction is complete. This reaction is further described, for example, in Rieke, *J. Org. Chem.* 1991, 56, 1445.

In some cases, the compounds of formula MIA or intermediates thereof may contain substituents having one or more sulfur atoms. Such sulfur atoms will be present, for example, when the amino acid of formula II employed in the above reactions is derived from L-thiazolidine-4-carboxylic acid, L-(5,5-dimethyl)thiazolidine-4-carboxylic acid, L-thiamorpholine-3-carboxylic acid and the like. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "*Advanced Organic Chemistry*", 4th Ed., pp. 1202–1202, Wiley Publishers, (1992).

As described above, the compounds of formula I/IA having an $R^2$ substituent other an hydrogen can be prepared using an N-substituted amino acid of formula II, such as sarcosine, N-methyl-L-phenylalanine and the like, in the above-described coupling reactions. Alternatively, such compounds can be prepared by N-alkylation of a, sulfonamide of formula I or IV (where $R^2$ is hydrogen) using conventional synthetic procedures. Typically, this N-alkylation reaction is conducted by contacting the sulfonamide with at least one equivalent, preferably 1.1 to 2 equivalents, of an alkyl or substituted alkyl halide in the presence of a suitable base, such as potassium carbonate, in an inert diluent, such as acetone, 2-butanone and the like, at a temperature ranging from about 25° C. to about 70° C. for about 2 to about 48 hours. Examples of alkyl or substituted alkyl halides suitable for use in this reaction include, but are not limited to, methyl iodide, and the like.

Additionally, the sulfonamides of formula I or IV wherein $R^2$ is hydrogen and $R^1$ is a 2-alkoxycarbonylaryl group can be intramolecularly cyclized to form 1,2-benzisothiazol-3-one derivatives or analogues thereof. This reaction is typically conducted by treating a sulfonamide, such as N-(2-methoxycarbonylphenylsulfonyl)glycine-L-phenylalanine benzyl ester, with about 1.0 to 1.5 equivalents of a suitable base, such as an alkali metal hydride, in a inert diluent, such as tetrahydrofuran, at a temperature ranging from about 0° C. to about 30° C. for about 2 to about 48 hours to afford the cyclized 1,2-benzisothiazol-3-one derivative.

Lastly, the compounds of formula I where Q is —C(S) $NR^7$— are prepared by using an amino thionoacid derivative in place of amino acid II in the above described synthetic procedures. Such amino thionoacid derivatives can be prepared by the procedures described in Shalaky, et al., *J. Org. Chem.*, 61:9045–9048 (1996) and Brain, et al., *J. Org. Chem.*, 62:3808–3809 (1997) and references cited therein.

Pharmaceutical Formulations

When employed as pharmaceuticals, the compounds of formula I and IA are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the-active ingredient, one or more of the compounds of formula I and IA above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound, administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |

-continued

| Ingredient | Quantity (mg/tablet) |
|---|---|
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 mL |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, which is incorporated herein by reference in its entirety. Such patches may be constructed for continuous, pulsatile, or on demand delivery of pharmaceutical agents.

When it is desirable or necessary to introduce the pharmaceutical composition to the brain, either direct or indirect techniques may be employed. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is incorporated herein by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples and, accordingly have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 and, accordingly, can be used in the treatment of diseases mediated by VLA-4. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., $IgG_1$) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds and the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon α4 integrins.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef, et al., Eur. J. Drug Metab. Pharmacokinet., 1990, 15(2):83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic images can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments, the pharmaceutical compositions are used to treat inflammatory brain disorders, such as Alzheimer's disease, AIDS dementia, multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune-response to foreign antigens in the transplant (host-versus-graft disease) leading to destruction of the transplanted tissue. $CD8^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420–425 (1996); Georczynski et al., *Immunology* 87, 573–580 (1996); Georcyznski et al., *Transplant. Immunol.* 3, 55–61 (1995); Yang et al., *Transplantation* 60, 71–76 (1995); Anderson et al., *APMIS* 102, 23–27 (1994).

A related use for compounds of this invention which bind to VLA-4 is in modulating the immune response involved in "graft versus host" disease (GVHD). See e.g., Schlegel et al., *J. Immunol.* 155, 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175–83 (1995); Orosz et al., *Int. J. Cancer* 60,–867–71 (1995); Freedman et al., *Leuk. Lymphoma* 13, 47–52 (1994); Okahara et al., *Cancer Res.* 54, 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals.[16]

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq. = | aqueous |
| AcOH = | acetic acid |
| bd = | broad doublet |
| bm = | broad multiplet |
| bs = | broad singlet |
| Bn = | benzyl |
| Boc = | tert-butoxycarbonyl |
| $Boc_2O$ = | di-tert-butyl dicarbonate |
| BOP = | benzotriazol-1-yloxy-tris(dimethylamino)phosphonium hexafluorophosphate |
| Cbz = | carbobenzyloxy |
| $CHCl_3$ = | chloroform |
| $CH_2Cl_2$ = | dichloromethane |
| $(COCl)_2$ = | oxalyl chloride |
| d = | doublet |
| dd = | doublet of doublets |
| dt = | doublet of triplets |
| DBU = | 1,8-diazabicyclo[5.4.0]undec-7-ene |
| DCC = | 1,3-dicyclohexylcarbodiimide |
| DMAP = | 4-N,N-dimethylaminopyridine |
| DME = | ethylene glycol dimethyl ether |
| DMF = | N,N-dimethylformamide |
| DMSO = | dimethylsulfoxide |
| EDC = | 1-(3-dimethylaminopropyl)-3-ethylcarbodiimide hydrochloride |
| $Et_3N$ = | triethylamine |
| $Et_2O$ = | diethyl ether |
| EtOAc = | ethyl acetate |
| EtOH = | ethanol |
| eq or eq. = | equivalent |
| Fmoc = | N-(9-fluorenylmethoxycarbonyl) |
| FmocONSu = | N-(9-fluorenylmethoxycarbonyl)-succinimide |
| g = | grams |
| h = | hour |
| $H_2O$ = | water |
| HBr = | hydrobromic acid |
| HCl = | hydrochloric acid |
| HOBT = | 1-hydroxybenzotriazole hydrate |
| hr = | hour |
| $K_2CO_3$ = | potassium carbonate |
| L = | liter |
| m = | multiplet |
| MeOH = | methanol |
| mg = | milligram |
| $MgSO_4$ = | magnesium sulfate |
| mL = | milliliter |
| mm = | millimeter |
| mM = | millimolar |
| mmol = | millimol |
| mp = | melting point |
| N = | normal |
| NaCl = | sodium chloride |
| $Na_2CO_3$ = | sodium carbonate |
| $NaHCO_3$ = | sodium bicarbonate |
| NaOEt = | sodium ethoxide |
| NaOH = | sodium hydroxide |
| $NH_4Cl$ = | ammonium chloride |
| NMM = | N-methylmorpholine |
| Phe = | L-phenylalanine |
| Pro = | L-proline |
| psi = | pounds per square inch |
| $PtO_2$ = | platinum oxide |
| q = | quartet |
| quint. = | quintet |
| rt = | room temperature |
| s = | singlet |
| sat = | saturated |
| t = | triplet |
| t-BuOH = | tert-butanol |
| TFA = | trifluoroacetic acid |
| THF = | tetrahydrofuran |

| | |
|---|---|
| TLC or tlc = | thin layer chromatography |
| Ts = | tosyl |
| TsCl = | tosyl chloride |
| TsOH = | tosylate |
| μL = | microliter |

In the examples below, all temperatures are in degrees Celsius (unless otherwise indicated). The following Methods were used to prepare the compounds set forth below as indicated.

Method 1

N-Tosylation Procedure

N-Tosylation of the appropriate amino acid was conducted via the method of Cupps, Boutin and Rapoport *J. Org. Chem.* 1985, 50, 3972.

Method 2

Methyl Ester Preparation Procedure

Amino acid methyl esters were prepared using the method of Brenner and Huber *Helv. Chim. Acta* 1953, 36, 1109.

Method 3

BOP Coupling Procedure

The desired dipeptide ester was prepared by the reaction of a suitable N-protected amino acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method 4

Hydrogenation Procedure I

Hydrogenation was performed using 10% palladium on carbon (10% by weight) in methanol at 30 psi overnight. The mixture was filtered through a pad of Celite and the filtrate concentrated to yield the desired amino compound.

Method 5

Hydrolysis Procedure I

To a chilled (0° C.) THF/$H_2O$ solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method 6

Ester Hydrolysis Procedure II

To a chilled (0° C.) THF/$H_2O$ solution (2:1, 5–10 mL) of the appropriate ester was added LiOH (1.1 equivalents). The temperature was maintained at 0° C. and the reaction was complete in 1–3 hours. The reaction mixture was concentrated and the residue was taken up into $H_2O$ and the pH adjusted to 2–3 with aqueous HCl. The product was extracted with ethyl acetate and the combined organic phase was washed with brine, dried over $MgSO_4$, filtered and concentrated to yield the desired acid.

Method 7

Ester Hydrolysis Procedure III

The appropriate ester was dissolved in dioxane/$H_2O$ (1:1) and 0.9 equivalents of 0.5 N NaOH was added. The reaction was stirred for 3–16 hours and than concentrated. The resulting residue was dissolved in $H_2O$ and extracted with ethyl acetate. The aqueous phase was lyophilized to yield the desired carboxylate sodium salt.

Method 8

Sulfonylation Procedure I

To the appropriately protected aminophenylalanine analog (11.2 mmol), dissolved in methylene chloride (25 ml) and cooled to −78° C. was added the desired sulfonyl chloride (12 mmol) followed by dropwise addition of pyridine (2 mL). The solution was allowed to warm to room temperature and was stirred for 48 hr. The reaction solution was transferred to a 250 mL separatory funnel with methylene chloride (100 mL) and extracted with 1N HCl (50 mL×3), brine (50 mL), and water (100 mL). The organic phase was dried (MgSO4) and the solvent concentrated to yield the desired product.

Method 9

Reductive Amination Procedure

Reductive amination of Tos-Pro-p-$NH_2$-Phe with the appropriate aldehyde was conducted using acetic acid, sodium triacetoxyborohydride, methylene chloride and the combined mixture was stirred at room temperature overnight. The crude product was purified by flash chromatography.

Method 10

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method 11 tert-Butyl Ester Hydrolysis Procedure I

The tert-butyl ester was dissolved in $CH_2Cl_2$ and treated with TFA. The reaction was complete in 1–3 hr at which time the reaction mixture was concentrated and the residue dissolved in $H_2O$ and lyophilized to yield the desired acid.

Method 12

EDC Coupling Procedure I

To a $CH_2Cl_2$ solution (5–20 mL) of N-(toluene-4-sulfonyl)-L-proline (1 equivalent), the appropriate amino acid ester hydrochloride (1 equivalent), N-methylmorpholine (1.1–2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into $H_2O$ and the organic phase was washed with sat. $NaHCO_3$, brine, dried ($MgSO_4$ or $Na_2SO_4$), filtered and concentrated. The crude product was purified by column chromatography.

Method 13

EDC Coupling Procedure II

To a DMF solution (5–20 mL) of the appropriate N-protected amino acid (1 equivalent), the appropriated amino acid ester hydrochloride (1 equivalent), $Et_3N$ (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and $H_2O$ and, the organic phase washed with 0.2 N citric acid, $H_2O$, sat. $NaHCO_3$, brine, dried ($MgSO_4$ or $Na_2SO_4$), filtered and concentrated. The crude product was purified by column chromatography or preparative TLC.

Method 14

Sulfonylation Procedure II

The appropriate sulfonyl chloride was dissolved in $CH_2Cl_2$ and placed in an ice bath. L-Pro-L-Phe-OMe.HCl (1 equivalent) and $Et_3N$ (1.1 equivalent) was added and the reaction allowed to warm to room temperature and stirred overnight under an atmosphere of nitrogen. The reaction mixture was concentrated and the residue partitioned between EtOAc and $H_2O$ and the organic phase washed with sat. $NaHCO_3$, brine, dried ($MgSO_4$ or $Na_2SO_4$), filtered and concentrated. The crude product was purified by column chromatography or preparative TLC.

Method 15

Sulfonylation Procedure III

To a solution of L-Pro-L-4-(3-dimethylaminopropyloxy)-Phe-OMe [prepared using the procedure described in Method 10] (1 equivalent) in $CH_2Cl_2$ was added $Et_3N$ (5 equivalents) followed by the appropriate sulfonyl chloride (1.1 equivalent). The reaction was allowed to warm to room temperature and stirred overnite under an atmosphere of nitrogen. The mixture was concentrated, dissolved in EtOAc, washed with sat. $NaHCO_3$ and 0.2 N citric acid. The aqueous phase was made basic with solid $NaHCO_3$ and the product extracted with EtOAc. The organic phase was washed with brine, dried ($MgSO_4$ or $Na_2SO_4$), filtered and concentrated. The crude methyl ester was purified by preparative TLC. The corresponding acid was prepared using the procedure described in Method 7.

Method 16

Hydrogenation Procedure II

To a methanol (10–15 mL) solution of the azlactone was added NaOAc (1 equivalent) and 10% Pd/C. This mixture was placed on the hydrogenator at 40 psi $H_2$. After 8–16 hours, the reaction mixture was filtered through a pad of Celite and the filtrate concentrated to yield the dehydrodipeptide methyl ester. The ester was dissolved in dioxane/$H_2O$ (5–10 mL), to which was added 0.5 N NaOH (1.05 equivalents). After stirring for 1–3 hours, the reaction mix was concentrated and the residue was redissolved in $H_2O$ and washed with EtOAc. The aqueous phase was made acidic with 0.2 N HCl and the product was extracted with EtOAc. The combined organic phase was washed with brine (1×5 mL), dried ($MgSO_4$ or $Na_2SO_4$), filtered and concentrated to yield the acid as approximately a 1:1 mixture of diastereomers.

Method 17 tert-Butyl Ester Hydrolysis Procedure II

The tert-butyl ester was dissolved in $CH_2Cl_2$ (5 mL) and treated with TFA (5 mL). The reaction was complete in 1–3 hours at which time the reaction mixture was concentrated and the residue dissolved in $H_2O$ and concentrated. The residue was redissolved in $H_2O$ and lyophilized to yield the desired product.

Example 1

Synthesis of N-(Toluene-4-sulfonyl)-L-prolyl-L-4-(4-methylpiperazin-1-ylcarbonyloxy)phenylalanine Ethyl Ester The title compound was prepared following the procedure outlined for the preparation of Example 4 and substitution of appropriate starting materials.

NMR data was as follows:

$^1H$ NMR $(CD_3)_2SO$): δ=8.33 (d, 1H), 7.70 (d, 2H), 7.41 (d, 2H), 7.24 (d, 2H), 7.00 (d, 2H), 4.52–4.44 (m, 1H), 4.09–4.00 (m, 3H), 3.53 (bs, 2H), 3.38–3.31 (m, 3H), 3.11–3.01 (m, 3H), 2.39 (s, 3H), 2.32 (bs, 4H), 2.19 (s, 3H), 1.61–1.50 (m, 3H), 1.43–1.38 (m, 1H), 1.13 (t, 3H).

$^{13}C$ NMR $(CD_3)_2SO$): δ=171.1, 171.1, 153.9, 149.8, 143.6, 134.1, 133.9, 130.0, 129.8, 127.4, 121.5, 61.2, 60.7, 54.2, 54.1, 53.3, 49.0, 45.7, 44.0, 43.4, 35.8, 30.5, 23.8, 21.0, 14.0.

Example 2

Synthesis of N-(Toluene-4-sulfonyl)-L-prolyl-L-4-(N,N-dimethylcarbamyloxy)phenylalanine Ethyl Ester Into a reaction vial were combined 7.00 g (15.2 mmol, 1.0 eq) Ts-Pro-Tyr(H)-OEt and 1.86 g (15.2 mmol, 1.0 eq) DMAP. Methylene chloride (50 mL), triethylamine (2.12 mL—1.54 g, 15.2 mmol, 1.0 eq), and dimethylcarbamyl chloride (1.68 mL—1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The workup of the reaction solution was as follows: add 50 mL EtOAc and 50 mL hexanes to the reaction mixture, and wash with 3×50 mL 0.5 mL hexanes to the reaction mixture, and wash with 3×50 mL 0.5 M citric acid, 2×50 mL water, 2×50 mL 10% $K_2CO_3$, and 1×50 mL sat. NaCl. Dry with $MgSO_4$. Filter. Evaporate to obtain 8.00 g (99%) of the title compound as a clear oil, which solidifies upon standing. Recrystallize from 5:3:2 heptane/EtOAc/$CH_2Cl_2$.

NMR data was as follows:

$^1H$ NMR $(CD_3)_2SO$): δ=8.32 (d, 1H), 7.70 (d, 2H), 7.41 (d, 2H), 7.23 (d, 2H), 7.00 (d, 2H), 4.52–4.44 (m, 1H), 4.09–4.02 (m, 3H), 3.37–3.31 (m, 1H), 3.11–2.96 (m, 3H), 3.00 (s, 3H), 2.87 (s, 3H), 2.39 (s, 3H), 1.61–1.50 (m, 3H), 1.43–1.38 (m, 1H), 1.13 (t, 3H).

$^{13}$C NMR (CD$_3$)$_2$SO): δ=171.1, 171.1, 154.0, 150.0, 143.6, 133.9, 133.9, 130.0, 129.8, 127.4, 121.5, 61.2, 60.6, 53.3, 49.0, 36.3, 36.1, 35.8, 30.5, 23.8, 21.0, 14.0.

Example 3

Synthesis of N-(Toluene-4-sulfonyl)-L-prolyl-L-4-(4-methylpiperazin-1-ylcarbonyloxy)phenylalanine Isopropyl Ester The title compound was prepared following the procedure outlined for the preparation of Example 4 and substitution of appropriate starting materials.

NMR data was as follows:

$^1$H NMR (CDCl$_3$): δ=7.72 (d, 2H), 7.36 (d, 1H), 7.33 (d, 2H), 7.16 (d, 2H), 7.03 (d, 2H), 5.07 (Sept., 1H), 4.78 (dt, 1H), 4.08–4.05 (m, 1H), 3.67 (bs, 2H), 3.57 (bs, 2H), 3.41–3.35 (m, 1H), 3.24 (dd, 1H), 3.15–3.07 (m, 1H), 3.04 (dd, 1H), 3.46–2.43 (m, 7H), 2.34 (s, 3H), 2.05–2.02 (m, 1H).

$^{13}$C NMR (CDCl$_3$): δ=170.9, 170.4, 153.6, 150.5, 144.3, 133.2, 133.1, 130.2, 130.0, 127.9, 121.7, 69.5, 62.2, 54.7, 53.4, 49.6, 46.1, 44.3, 43.7, 37.2, 29.7, 24.1, 21.6, 21.6, 21.4.

Example 4

Synthesis of N-(Toluene-4-sulfonyl)-L-prolyl-L-4-(4-methylpiperazin-1-ylcarbonyloxy)phenylalanine tert-Butyl Ester Combine 41.2 g (84.34 mmol, 1.0 eq) Ts-Pro-Tyr(H)-OtBu and 17.0 g (84.34 mmol, 1.0 eq) 4-nitrophenyl chloroformate. Add 700 mL CH$_2$Cl$_2$. Cap with a septum. Attach a N$_2$ line. Immerse the flask in a 4:1 water/EtOH+dry ice slurry, and stir to cool to −15° C. Add 29.38 mL (21.33 g, 210.81 mmol, 2.5 eq) Et$_3$N over five minutes with stirring. Stir at −10 to −15° C. for 1 h. Add 9.35 mL (8.45 g, 84.34 mmol, 1.0 eq) N-methyl piperazine over 3 minutes with stirring. Stir overnight while warming to room temperature. Dilute with 700 mL hexanes. Wash repeatedly with 10% K$_2$CO$_3$, until no yellow color (4-nitrophenol) is seen in the aqueous layer. Wash with sat. NaCl. Dry over anhydrous MgSO$_4$. Filter. Evaporate. Dissolve in 500 mL EtOH, and evaporate, to remove Et$_3$N. Repeat once. Dissolve in 400 mL EtOH, and add 600 mL water with stirring, to precipitate a solid or oil. If an oil, stir vigorously to solidify. Isolate the solid by filtration. Repeat dissolution, precipitation, and filtration, once. Rinse with water to remove traces of yellow color. High vacuum to constant mass yields the title compound as a white solid.

NMR data was as follows:

$^1$H NMR (CDCl$_3$): δ=7.72 (d, 2H), 7.33 (d, 3H), 7.17 (d, 2H), 7.02 (d, 2H), 4.71 (q, 1H), 4.09–4.06 (m, 1H), 3.67 (bs, 2H), 3.57 (bs, 2H), 3.41–3.34 (m, 1H), 3.22 (dd, 1H), 3.16–3.09 (m, 1H), 3.03 (dd, 1H), 2.46–2.43 (m, 7H), 2.34 (s, 3H), 2.05–2.02 (m, 1H), 1.57–1.43 (m, 3H), 1.47 (s, 9H).

$^{13}$C NMR (CDCl$_3$): δ=171.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

Example 5

Synthesis of N-(Toluene-4-sulfonyl)-L-prolyl-L-4-(4-methylpiperazin-1-ylcarbonyloxy)phenylalanine The title compound was prepared from the product of Example 1 using the procedure described in Method 7.

NMR data was as follows:

$^1$H NMR (CD$_3$OD): δ=7.74 (d, 2H), 7.42 (d, 2H), 7.26 (d, 2H), 7.04 (d, 2H), 4.58–4.54 (m, 1H), 4.16–4.12 (m, 1H), 3.70 (bs, 2H) 3.53 (bs, 2H), 3.43–3.31 (m, 1H), 3.26–3.13 (m, 7H), 2.82 (s, 3H), 2.43 (s, 3H), 1.98–1.94 (m, 1H), 1.76–1.51 (m, 3H).

$^{13}$C NMR (CD$_3$OD): δ=175.7, 173.6, 154.8, 151.6, 146.1, 136.3, 134.8, 131.9, 131.3, 129.1, 122.7, 63.6, 55.9, 53.9, 50.7, 43.5, 37.6, 31.3, 25.5, 21.5.

Example 6

Synthesis of N-(Toluene-4-sulfonyl)-L-prolyl-L-4-(N,N-dimethylcarbamyloxy)phenylalanine n-Butyl Ester The title compound was prepared following the procedure outlined for the preparation of Example 2 and substitution of appropriate starting materials.

NMR data was as follows:

$^1$H NMR (CD$_3$)$_2$SO): δ=8.31 (d, 1H), 7.70 (d, 2H), 7.41 (d, 2H), 7.23 (d, 2H), 6.99 (d, 2H), 4.53–4.46 (m, 1H), 4.10–4.01 (m, 1H), 3.63–3.30 (m, 1H), 3.10–2.96 (m, 3H), 3.00 (s, 3H), 2.88 (s, 3H), 2.39 (s, 3H), 1.59–1.30 (m, 6H), 1.33–1.20 (m, 2H), 0.85 (t, 3H).

$^{13}$C NMR (CD$_3$)$_2$SO): δ=171.4, 171.3, 154.2, 150.2, 143.7, 134.0, 130.1, 130.0, 127.6, 121.7, 64.3, 61.2, 59.2, 53.4, 49.0, 36.2, 36.0, 35.8, 30.0, 23.8, 21.0, 18.5, 13.5.

Example 7

Synthesis of N-(Toluene-4-sulfonyl)-L-prolyl-L-4-(N,N-dimethylcarbamyloxy)phenylalanine Cyclopentyl Ester The title compound was prepared following the procedure outlined for the preparation of Example 2 and substitution of appropriate starting materials.

NMR data was as follows:

$^1$H NMR (CD$_3$)$_2$SO): δ=8.27 (d, 1H), 7.70 (d, 2H), 7.41 (d, 2H), 7.22 (d, 2H), 6.99 (d, 2H), 5.04 (bs, 1H), 4.48–4.40 (m, 1H), 4.08–4.05 (m, 1H), 3.34–3.30 (m, 1H), 3.09–2.95 (m, 3H), 3.00 (s, 3H), 2.88 (s, 3H), 2.39 (s, 3H), 1.76–1.74 (m, 2H), 1.57–1.40 (m, 10H).

$^{13}$C NMR (CD$_3$)$_2$SO): δ=171.3, 171.0, 154.2, 150.2, 432.7, 134.1, 130.1, 130.0, 127.6, 121.6, 77.4, 61.2, 53.4, 49.0, 36.2, 36.1, 35.7, 32.0, 30.5, 23.8, 23.2, 21.0.

Example 8

Synthesis of N-Toluene-4-sulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CD$_3$)$_2$SO): δ=8.18 (d, 1H), 7.71 (d, 2H), 7.41 (d, 2H), 7.23 (d, 2H), 6.99 (d, 2H), 4.42–4.38 (m, 1H), 4.10–4.07 (m, 1H), 3.37–3.30 (m, 1H), 3.09–2.95 (m, 3H), 3.00 (s, 3H), 2.88 (s, 3H), 2.39 (s, 3H), 1.58–1.50 (m, 3H), 1.40–1.30 (m, 1H), 1.36 (s, 9H).

$^{13}$C NMR (CD$_3$)$_2$SO): δ=171.1, 170.3, 154.2, 150.2, 143.8, 134.2, 134.1, 130.2, 130.0, 127.6, 121.6, 81.0, 61.3, 53.8, 49.0, 36.3, 36.0, 35.9, 30.5, 27.5, 23.8, 21.0.

Example 9

Synthesis of N-(Toluene-4-sulfonyl)-L-prolyl-L-4-(N,N-dimethylcarbamyloxy)phenylalanine The tide compound was prepared from the product of Example 2 using the procedure described in Method 7.

NMR data was as follows:

$^1$H NMR (CD$_3$)$_2$SO): δ=8.13 (d, 1H), 7.70 (d, 2H), 7.41 (d, 2H), 7.23 (d, 2H), 6.99 (d, 2H), 4.51–4.44 (m, 1H), 4.11–4.09 (m, 1H), 3.40–3.34 (m, 2H), 3.11–2.94 (m, 3H), 3.00 (s, 3H), 2.87 (s, 3H), 2.39 (s, 3H), 1.59–1.36 (m, 4H).

$^{13}$C NMR (CD$_3$)$_2$SO: δ=172.7, 171.2, 153.6, 150.2, 143.8, 134.3, 134.0, 130.2, 130.0, 127.6, 121.6, 61.3, 53.2, 49.0, 36.3, 36.1, 35.9, 30.4, 23.8, 21.0.

Example 10

Synthesis of N-(Toluene-4-sulfonyl)-L-prolyl-L-3-(N,N-dimethylcarbamyloxy)phenylalanine Ethyl Ester The title compound was prepared following the procedure outlined for the preparation of Example 2 and substitution of appropriate starting materials.

NMR data was as follows:

$^1$H NMR (CDCl$_3$): δ=7.74 (m, 2H), 7.70–7.36 (m, 4H), 7.24–7.14 (m, 3H), 6.93–4.90 (m, 1H), 4.78–4.27 (m, 3H), 4.05–3.55 (m, 0.5H), 3.48–3.43 (m, 0.5H), 3.37–3.30 (m, 3H), 3.02–3.08 (bs, 3H), 2.99 (bs, 3H), 2.45 (s, 1.5H), 2.43 (s, 1.5H), 2.12 (m, 1H), 198, 1.80 (m, 0.5M), 1.62–1.44 (m, 2.5H), 1.29 (t, 1.5H), 1.24 (t, 1.5H).

$^{13}$C NMR (CDCl$_3$): δ=171.1, 171.0, 170.9, 154.9, 154.8, 151.8, 151.6, 144.4, 144.3, 137.6, 137.1, 133.1, 132.9, 130.0, 129.9, 129.5, 129.2, 127.9, 127.9, 126.5, 126.1, 122.9, 122.7, 120.7, 120.5.

Example 11

Synthesis of N-(Toluene-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Example 2 and substitution of appropriate starting materials.

NMR data was as follows:

$^1$H NMR (CDCl$_3$): δ=7.76 (d, 2H), 7.35 (d, 2H), 7.22 (d, 2H), 7.01 (m, 3H), 5.05 (m, 1H), 4.85 (m, 1H), 4.57 (d, 1H), 4.38 (d, 1H), 3.86 (s, 1H), 3.19–3.00 (m, 2H), 3.09 (s, 3H), 3.01 (s, 3H), 2.45 (s, 3H), 1.24 (t, 6H), 1.16 (s, 3H), 1.09 (s, 3H).

$^{13}$C NMR (CDCl$_3$): δ=170.3, 168.4, 154.9, 150.6, 144.8, 132.9, 132.8, 130.3, 130.0, 128.2, 121.7, 73.4, 69.5, 54.5, 53.2, 50.4, 37.7, 36.5, 36.3, 29.0, 23.8, 21.5, 21.4.

Example 12

Synthesis of N-(Toluene-4-sulfonyl)-L-(5,5-dimethyl)thiaprolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): δ=7.75 (d, 2H), 7.34 (d, 2H), 7.23 (d, 2H), 7.05–6.98 (m, 3H), 4.76 (m, 1H), 4.56 (d, 1H), 4.40 (d, 1H), 3.85 (s, 1H), 3.09–3.00 (m, 8H), 2.44 (s, 3H), 1.43 (s, 3H), 1.16 (s, 3H), 1.09 (s, 3H).

$^{13}$C NMR (CDCl$_3$): δ=169.8, 168.3, 154.9, 150.6, 144.8, 133.2, 132.9, 130.4, 130.0, 128.2, 121.6, 82.6, 73.4, 54.6, 53.8, 50.4, 37.8, 36.5, 36.3, 29.0, 27.7, 23.8, 21.5.

Example 13

Synthesis of N-(Toluene-4-sulfonyl)-L-(5,5-dimethyl)thiaprolyl-L-4-(N,N-dimethylcarbamyloxy)phenylalanine The title compound was prepared from the product of Example 11 using the procedure described in Method 7.

NMR data was as follows:

$^1$H NMR (CDCl$_3$): δ=7.76 (d, 2H), 7.35 (d, 2H), 7.25 (d, 2H), 7.14 (d, 1H), 7.02 (d, 2H), 5.17 (br s, 1H), 4.89 (m, 1H), 4.56 (d, 1H), 4.40 (d, 1H), 3.90 (s, 1H), 3.30–3.00 (m, 8H), 2.43 (s, 3H), 1.09 (s, 6H).

$^{13}$C NMR (CDCl$_3$): δ=172.7, 169.3, 155.2, 150.6, 144.9, 133.1, 132.7, 130.5, 130.1, 128.1, 121.9, 73.3, 54.5, 53.3, 50.5, 36.9, 36.6, 36.4, 29.0, 23.7, 21.5.

Example 14

Synthesis of N-(Toluene-4-sulfonyl)-L-[(1,1-dioxo)thiamorpholin-3-carbonyl]-L-4-(N,N-dimethylcarbamyloxy)phenylalanine tert-Butyl Ester L-Thiamorpholine-5-carboxylic acid was prepared by the method of Larsson and Carlson (*Acta Chemica Scan.* 1994, 48, 517–525). N-(Toluene-4-sulfonyl)-L-thiamorpholine-5-carboxylic acid was prepared using the procedure described in Method 1 and was then coupled to t-butyl tyrosine in DMF in the presence of BOP and NMM, to give after aqueous workup and flash chromatography N-(Toluene-4-sulfonyl)-L-[thiamorpholin-3-carbonyl]-L-4-phenylalanine tert-butyl ester.

Formation of the 4-(N,N-dimethylcarbamyloxy) group was per Example 2 above and oxidation of the thiamorpholino group to the 1,1-dioxo-thiamorpholino group was per Larsson and Carlson (*Acta Chemica Scan.* 1994, 48, 522).

NMR data was as follows:

$^1$H NMR (CDCl$_3$): δ=7.68 (d, 2H), 7.37 (d, 2H), 7.08 (m, 4H), 6.73 (d, 1H), 5.11 (m, 1H), 4.62 (m, 1H), 4.23 (m, 1H), 4.00 (m, 1H), 3.82 (m, 1H), 3.14 (s, 3H), 3.03 (s, 3H), 2.80 (m, 5H), 2.44 (s, 3H), 1.48 (s, 9H).

$^{13}$C NMR (CDCl$_3$): δ=171.3, 169.9, 164.4, 145.6, 135.4, 132.6, 130.8, 130.4, 127.3, 121.9, 83.0, 56.1, 53.8, 49.4, 48.7, 44.5, 42.0, 36.9, 36.6, 36.4, 27.8, 21.5.

Example 15

Synthesis of N-(Toluene-4-sulfonyl)-L-[(1,1-dioxo)thiamorpholin-3-carbonyl]-L-4-(N,N-dimethylcarbamyloxy)phenylalanine The title compound was prepared from the product of Example 14 using the procedure described in Method 11.

NMR data was as follows:

$^1$H NMR (CD$_3$OD): δ=7.77 (d, 2H), 7.40 (d, 2H), 7.22 (d, 2H), 7.00 (d, 2H), 5.19 (m, 1H), 4.65 (m, 1H), 4.30 (m, 1H), 3.95 (m, 1H), 3.61 (m, 1H), 3.20 (m, 5H), 3.09 (s, 3H), 2.97 (s, 3H), 2.43 (s, 3H).

$^{13}$C NMR (CD$_3$OD): δ=174.1, 168.0, 157.0, 152.0, 146.4, 137.7, 135.3, 131.7, 131.6, 128.8, 123.0, 57.1, 54.8, 51.1, 50.9, 48.0, 47.7, 43.2, 37.4, 36.8, 36.7, 21.5.

Example 16

Synthesis of N-(Toluene-4-sulfonyl)-L-(5,5-dimethyl)thiaprolyl-L-4-(4-methylpiperazin-1-ylcarbonyloxy)phenylalanine tert-Butyl Ester The title compound was prepared following the procedure outlined for the preparation of Example 4 and substitution of appropriate starting materials.

NMR data was as follows:

$^1$H NMR (CDCl$_3$): δ=7.74 (d, 2H), 7.33 (d, 2H), 7.25 (d, 2H), 7.20–7.00 (m, 3H), 4.74 (m, 1H), 4.55 (d, 1H), 4.38 (d,

1H), 3.83 (s, 1H), 3.66 (br m, 2H), 3.57 (br m, 2H), 3.08–3.05 (m, 2H), 2.45–2.42 (m, 7H), 2.33 (s, 3H), 1.42 (s, 9H), 1.15 (s, 3H), 1.08 (s, 3H).

$^{13}$C NMR (CDCl$_3$): δ=169.7, 168.2, 153.6, 150.3, 144.7, 133.3, 132.7, 130.4, 129.9, 128.1, 121.5, 82.6, 73.4, 54.5, 53.7, 50.4, 46.0, 44.2, 43.6, 37.7, 28.9, 27.7, 23.8, 21.4.

Example 17

Synthesis of N-(Toluene-4-sulfonyl)-L-(5,5-dimethyl)thiaprolyl-L-4-(4-methylpiperazin-1-ylcarbonyloxy)phenylalanine The title compound was prepared from the product Example 16 using the procedure described in Method 11.

NMR data was as follows:

$^1$H NMR (CDCl$_3$): δ=8.31 (d, 1H), 7.72 (d, 2H), 7.42–7.35 (m, 4H), 7.08 (d, 2H), 4.90–4.68 (m, 1H), 4.64–4.61 (m, 1H), 4.47–4.44 (m, 1H), 4.01 (s, 1H), 3.36–3.32 (br m, 4H), 3.27–3.25 (m, 1H), 3.22–3.10 (m, 1H), 2.94 (s, 3H), 2.43 (s, 3H), 1.14 (s, 3H), 1.07 (s, 3H).

Example 18

Synthesis of N-(Toluene-4-sulfonyl)sarcosyl-L-4-(N,N-dimethylcarbamyloxy)phenylalanine Isopropyl Ester The title compound was prepared following the procedure outlined for the preparation of Example 2 and substitution of appropriate starting materials.

NMR data was as follows:

$^1$H NMR (CDCl$_3$): δ=7.66 (d, 2H), 7.34 (d, 2H), 7.18 (d, 2H), 7.07 (d, 2H), 6.98 (d, 1H), 5.03 (m, 1H), 4.81 (m, 1H), 3.69 (d, 1H), 3.49 (d, 1H), 3.08 (m, 2H), 3.04 (s, 3H), 2.99 (s, 3H), 2.63 (s, 3H), 2.43 (s, 3H).

$^{13}$C NMR (CDCl$_3$): δ=167.4, 154.9, 150.8, 144.4, 132.6, 130.2, 130.1, 127.7, 122.0, 110.9, 69.5, 57.3, 53.9, 53.0, 37.1, 36.6, 21.6, 21.4.

Example 19

Synthesis of N-(Toluene-4-sulfonyl)sarcosyl-L-4-(N,N-dimethylcarbamyloxy)phenylalanine tert-Butyl Ester The title compound was prepared following the procedure for the preparation of Example 2 and substitution of appropriate starting materials.

NMR data was as follows:

$^1$H NMR (CDCl$_3$): δ=7.67 (d, 2H), 7.34 (d, 2H), 7.19 (d, 2H), 7.03 (d, 2H), 6.98 (d, 1H), 4.76 (m, 1H), 3.67 (q, 1H), 3.06 (m, 2H), 3.16 (s, 3H), 2.99 (s, 3H), 2.64 (s, 3H), 2.43 (s, 3H), 1.42 (s, 9H).

$^{13}$C NMR (CDCl$_3$): δ=170.0, 137.2, 154.9, 150.7, 144.3, 133.2, 132.9, 130.3, 130.0, 127.7, 121.9, 82.6, 83.9, 53.3, 37.2, 36.6, 36.4, 27.9, 21.4.

Example 20

Synthesis of N-(Toluene-4-sulfonyl)sarcosyl-L-4-(N,N-dimethylcarbamyloxy)phenylalanine The title compound was prepared from the product of Example 18 using the procedure described in Method 7.

NMR data was as follows:

$^1$H NMR (CDCl$_3$): δ=7.41 (d, 2H), 7.10 (d, 2H), 6.98 (d, 2H), 6.75 (d, 2H), 4.42 (m, 1H), 3.43 (m, 2H), 3.04 (m, 2H), 2.80 (s, 3H), 2.69 (s, 3H), 2.33 (s, 3H), 2.14 (s, 3H).

$^{13}$C NMR (CDCl$_3$): δ=174.2, 170.2, 156.9, 151.9, 145.6, 135.5, 135.2, 131.4, 131.1, 128.9, 123.0, 54.6, 54.0, 37.4, 36.8, 36.7, 21.4.

Example 21

Synthesis of N-(Toluene-4-sulfonyl)-L-prolyl-L-4-(N,N-dimethylaminosulfonyloxy)phenylalanine tert-Butyl Ester Substituting dimethysulfamoyl chloride for dimethylcarbamyl chloride, and following the method for the preparation of Example 2, gave the title compound.

NMR data was as follows:

$^1$H NMR (CDCl$_3$): δ=7.72 (d, 2H), 7.34 (d, 2H), 7.21 (s, 4H), 4.69 (m, 1H), 4.04 (m, 1H), 3.4 (m, 1H), 3.24 (m, 3H), 2.96 (s, 6H), 2.42 (s, 3H), 2.02 (m, 1H), 1.45 (m, 3H).

$^{13}$C NMR (CDCl$_3$): δ=166.3, 165.3, 144.8, 140.0, 130.9, 126.4, 125.6, 123.5, 117.3, 95.5, 78.3, 57.8, 49.2, 45.2, 34.2, 32.9, 25.0, 23.4, 19.7, 17.1.

Example 22

Synthesis of N-(Toluene-4-sulfonyl)-L-prolyl-L-4-(N,N-dimethylaminosulfonyloxy)phenylalanine The title compound was prepared from the product of Example 21 using the procedure described in method 11.

NMR data was as follows:

$^1$H NMR (CD$_3$OD): δ=7.73 (d, 2H), 7.41 (d, 2H), 7.38 (d, 2H), 7.22 (d, 2H), 4.69 (m, 1H), 4.11 (m, 1H), 3.41 (m, 2H), 3.19 (m, 2H), 2.94 (s, 6H), 2.41 (s, 3A), 1.78 (m, 1H), 1.61 (m, 3H).

$^{13}$C NMR (CD$_3$OD): δ=174.3, 174.0, 150.8, 145.9, 137.3, 135.1, 132.1, 131.2, 129.1, 123.1, 63.3, 54.6, 50.6, 39.1, 37.5, 31.6, 25.3, 21.5.

Example 23

Synthesis of N-(Toluene-4-sulfonyl)-sarcosyl-L-(4-morpholinecarbamyloxy) phenylalanine t-butyl ester Substituting sacrosine for L-proline in the preparation of Ts-Pro-Tyr(H)—O-t-butyl ester and substitution of 4-morpholinecarbonyl chloride for dimethylcarbamyl chloride, and following the method for the preparation of Example 2, gave the title compound as a white solid.

NMR data was as follows:

$^1$H NMR (CDCl$_3$): δ 7.61 (d, 2H), 7.28 (d, 2H), 7.16 (d, 2H), 7.02 (d, 2H), 4.69 (m, 1H), 3.67 (m, 8H), 3.58 (m, 1H), 3.48 (m, 1H), 3.06 (m, 2H), 2.59 (s, 3H), 2.36 (s, 3H), 1.26 (s, 9H).

$^{13}$C NMR (CDCl$_3$): δ 169.7, 167.1, 153.5, 150.1, 144.1, 133.1, 133.0, 133.0, 130.1, 129.8, 127.4, 121.6, 82.6, 66.3, 53.6, 53.1, 44.5, 43.7, 36.9, 36.4, 27.6, 21.2.

Example 24

Synthesis of N-(Toluene-4-sulfonyl)sarcosyl-L-4-(isonipecotoyloxy)phenylalanine

The title compound was prepared from the product of Example 23 using the procedure described in Method 11.

NMR data was as follows:

$^1$H NMR (CD$_3$OD): δ=7.30 (d, 2H), 7.02 (d, 2H), 6.88 (d, 2H), 6.67 (d, 2H), 4.33 (m, 1H), 3.32 (m, 3H), 3.25 (m, 2H), 3.12 (m, 3H), 2.89 (m, 1H), 2.70 (m, 3H), 2.22 (s, 3H), 2.03 (s, 3H).

$^{13}$C NMR (CD$_3$OD): δ=174.2, 170.3, 155.6, 151.7, 145.6, 135.8, 135.2, 131.5, 131.1, 128.9, 123.0, 67.5, 54.6, 54.0, 37.4, 36.8, 21.5.

Example 25

Synthesis of N-(Toluene-4-sulfonyl)-L-[(1,1-dioxo) thiamorpholin-3-carbonyl]-L-4-(morpholin-4-ylcarbonyloxy)phenylalanine tert-Butyl Ester Substitution of 4-morpholinecarbonyl chloride for dimethylcarbamyl chloride, and following the methods for the preparation of Example 2 and 14, gave the title compound as a white solid.

NMR data was as follows:

$^1$H NMR (CDCl$_3$): δ=7.76 (d, 1H), 7.68 (d, 1H), 7.37 (m, 2H), 7.14 (m, 2H), 7.05 (m, 1H), 6.97 (d, 1H), 6.80 (d, 0.5H), 6.57 (d, 0.5H), 5.09 (m, 0.5H), 4.91 (m, 0.5H), 4.75 (m, 0.5H), 4.62 (m, 0.5H), 4.25 (m, 0.5H), 4.09 (m, 2H), 3.79 (m, 4H), 3.65 (m, 4H), 2.91 (s, 3H), 2.44 (s, 3H), 1.69 (s, 4H), 1.44 (s, 5H).

$^{13}$C NMR (CDCl$_3$): δ=170.0, 169.8, 164.8, 164.4, 153.7, 150.4, 145.6, 145.4, 135.4, 135.3, 132.9, 130.8, 130.7, 130.5, 130.4, 127.5, 127.2, 122.1, 121.8, 83.01, 82.8, 66.4, 56.1, 56.1, 53.7, 53.6, 49.5, 49.3, 48.6, 44.7, 43.9, 42.0, 41.6, 36.9, 36.3, 27.8, 21.5.

Example 26

Synthesis of N-(Toluene-4-sulfonyl)-L-[(1,1-dioxo) thiamorpholin-3-carbonyl]-L-4-(morpholin-4-ylcarbonyloxy)phenylalanine The title compound was prepared from the product of Example 25 using the procedure described in Method 11.

NMR data was as follows:

$^1$H NMR (CD$_3$OD): δ=7.67 (m, 2H), 7.32 (m, 2H), 7.08 (m, 2H), 6.93 (m, 2H), 5.09 (m, 1H), 4.54 (m, 1H), 4.19 (m, 0.5H), 4.02 (m, 0.5H), 3.81 (m, 0.5H), 3.66 (m, 8H), 2.99 (m, 7H), 2.32 (s, 3H).

$^{13}$C NMR (CD$_3$OD): δ 174.0, 168.0, 155.7, 151.9, 151.8, 146.6, 146.4, 137.5, 135.5, 135.3, 131.7, 131.6, 131.6, 128.8, 123.3, 122.9, 67.6, 57.3, 57.1, 54.8, 51.1, 50.9, 50.6, 46.0, 45.3, 45.2, 43.0, 37.4, 37.0, 21.5.

Example 27

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^{13}$C NMR (CDCl$_3$): δ=7.87–7.83 (m, 2H), 7.26–7.13 (m, 5H), 4.74–4.69 (m, 1H), 4.05 (m, 1H), 3.36 (m, 1H), 3.24–3.17 (m, 1H), 3.11–3.01 (m, 4H), 2.97 (s, 3H), 2.05–2.02 (m, 1H), 1.60–1.47 (m, 3H), 1.46 (s, 9H).

$^{13}$C NMR (CDCl$_3$): δ=170.6, 170.0, 165.7, 154.9, 150.6, 133.2, 132.4, 130.7, 130.2, 121.7, 116.7, 82.7, 62.3, 53.7, 49.6, 37.2, 36.6, 36.4, 29.9, 27.9, 24.2.

Example 28

Synthesis of N-(Toluene-4-sulfonyl)sarcosyl-L-4-(4-methylpiperazin-1-ylcarbonyloxy)phenylalanine tert-Butyl Ester The title compound was prepared following the procedure outlined for the preparation of Example 4 and substitution of appropriate starting materials.

NMR data was as follows:

$^1$H NMR (CDCl$_3$): δ=8.17 (d, 1H), 7.59 (d, 2H), 7.26 (d, 2H), 7.13 (d, 2H), 7.00 (d, 2H), 4.66 (m, 1H), 3.60 (m, 6H), 3.04 (m, 2H), 2.56 (s, 3H), 2.40 (m, 7H), 2.34 (s, 3H), 1.41 (s, 9H).

$^{13}$C NMR (CDCl$_3$): δ=169.7, 167.0, 153.4, 150.2, 144.0, 133.0, 132.9, 130.1, 129.8, 127.4, 121.6, 82.2, 54.3, 53.5, 53.1, 45.8, 44.2, 43.5, 36.9, 27.6, 21.2.

Example 29

Synthesis of N-(Toluene-4-sulfonyl)-L-(1,1-dioxo-5,5-dimethyl)-thiaprolyl-L-4-(N,N-dimethylcarbamyloxy)phenylalanine tert-Butyl Ester The product of Example 12 was oxidized by the method of Larsson and Carlson (*Acta Chemica Scan.* 1994, 48, 517–525), yielding the title compound as a white solid.

NMR data was as follows:

$^1$H NMR (CDCl$_3$): δ=7.73 (d, 2H), 7.36 (d, 2H), 7.21 (d, 2H), 7.06–6.95 (m, 3H), 4.79 (m, 1H), 4.38 (dd, 2H), 4.10 (s, 1H), 3.18–2.95 (m, 8H), 2.43 (s, 3H), 1.45 (s, 9H), 1.33 (s, 3H), 1.08 (s, 3H).

$^{13}$C NMR (CDCl$_3$): δ=169.8, 166.2, 154.9, 120.7, 145.8, 133.0, 131.9, 130.2, 128.5, 121.9, 82.9, 68.0, 60.9, 59.3, 53.9, 37.5, 36.6, 36.3, 27.7, 21.6, 19.3, 18.5.

Example 30

Synthesis of N-(1-Methylimidazolyl-4-sulfonyl)-L-prolyl-L-4-(N,N-dimethylcarbamyloxy)phenylalanine The title compound was prepared from the product of Example 106 using the procedure described in Method 11.

NMR data was as follows:

$^1$H NMR (CDCl$_3$): δ=8.07 (d, 1H), 7.75 (s, 1H), 7.71 (s, 1H), 7.25 (d, 2H), 7.01 (d, 2H), 4.71–4.66 (m, 1H), 4.28–4.24 (m, 1H), 3.77 (s, 3H), 3.42–3.05 (m, 3H), 3.09 (s, 3H), 2.96 (s, 3H), 1.84–1.69 (m, 2H), 1.61–1.54 (m, 2H).

$^{13}$C NMR (CDCl$_3$): δ=174.4, 174.1, 156.9, 151.9, 141.8, 137.7, 135.6, 131.6, 127.6, 122.9, 63.7, 54.7, 50.8, 37.4, 36.8, 36.7, 34.3, 31.6, 25.4.

Preparative Example A

Synthesis of 2-(Saccharin-2-yl)propionoyl-L-4-(N,N-dimethylcarbamyloxy)phenylalanine tert-Butyl Ester N-(Benzisothiazolone)-L-alanyl-L-tyrosine t-butyl ester was prepared by first combining sodium hydride (washed free of mineral oil) in THF chilled to 0° C., and a solution of N-(2-methoxycarbonyl)sulfonyl-L-alanine-L-tyrosine t-butyl ester in THF which was added dropwise. The reaction was stirred at 0° C. for one hour and then at room temperature for two hours. The reaction mixture was extracted with EtOAc and 0.2 N HCl, the combined EtOAc layers were washed successively with 0.2 N HCl, satd. NaHCO$_3$, and satd. NaCl. The organic layer was dried over MgSO$_4$, filtered and concentrated. The residue was filtered by silica gel chromatography to afford N-(benzisothiazolone)-L-alanyl-L-tyrosine t-butyl ester.

The title compound was then prepared following the procedure described in Example 2.

NMR data was as follows:

$^1$H NMR (DMSO-d$_6$, 400 MHz) (1:1 mixture of diastereomers) δ=8.15 (m, 2H); 8.5 (m, 3H); 7.20 (m, 2H);

6.95 (m, 2H); 4.75 (m, 1H); 4.30 (m, 1H); 3.05 (s, 3H); 2.95 (m, 2H); 2.90 (s, 3H); 1.75 and 1.65 (two d, 3H); 1.30 and 1.35 (two s, 9H).

Example 31

Synthesis of N-(Toluene-4-sulfonyl)-L-(1,1-dioxo-5,5-dimethyl)-thiaprolyl-L-4-(N,N-dimethylcarbamyloxy)phenylalanine The title compound was prepared from the product of Example 29 using the procedure described in Method 11.

NMR data was as follows:

$^1$H NMR (CDCl$_3$): $\delta$=7.75 (m, 3H), 7.29 (m, 4H), 7.08 (d, 2H), 4.95 (m, 1H), 4.46–4.20 (m, 3H), 3.17 (s, 3H), 3.30–3.10 (m, 2H), 3.02 (s, 3H), 2.43 (s, 3H), 1.15 (s, 3H), 0.88 (s, 3H).

$^{13}$C NMR (CDCl$_3$): $\delta$=127.2, 167.5, 155.8, 150.3, 145.4, 133.6, 132.6, 130.8, 130.2, 128.3, 121.9, 67.9, 65.8, 60.8, 53.9, 36.8, 36.6, 35.8, 21.6, 18.8, 15.0.

Example 32

Synthesis of N-(4-Fluorobenzenesulfonyl)-L-prolyl-L-4-(N,N-dimethylcarbamyloxy)phenylalanine The title compound was prepared from the product of Example 27 using the procedure described in Method 11.

NMR data was as follows:

$^{13}$C NMR (CDCl$_3$): $\delta$=7.88–7.84 (m, 2H), 7.54 (d, 1H), 7.26–7.18 (m, 4H), 7.01 (d, 2H), 6.92 (s, 3H), 4.88–4.83 (m, 1H), 4.14–4.11 (m, 1H), 3.39–3.29 (m, 2H), 3.13 (m, 2H), 3.00 (s, 3H), 2.99 (s, 3H), 1.92–1.89 (m, 1H), 1.59–1.43 (m, 3H).

$^{13}$C NMR (CDCl$_3$): $\delta$=173.1, 172.4, 165.6, 155.5, 150.4, 133.2, 131.9, 130.6, 130.3, 121.8, 116.6, 61.9, 53.1, 49.6, 36.6, 36.3, 30.2, 23.9.

Example 33

Synthesis of N-(Toluene-4-sulfonyl)-D-prolyl-L-4-(4-methylpiperazin-1-yl)phenylalanine t-butyl Ester The title compound was prepared following the procedure outlined for the preparation of Example 4 and substitution of appropriate starting materials.

NMR data was as follows:

$^{13}$C NMR (CDCl$_3$): $\delta$=7.72 (d, 2H), 7.33 (d, 3H), 7.17 (d, 2H), 7.02 (d, 2H), 4.71 (q, 1H), 4.09–4.06 (m, 1H), 3.67 (bs, 2H), 3.57 (bs, 2H), 3.41–3.34 (m, 1H), 3.22 (dd, 1H), 3.16–3.09 (m, 1H), 3.03 (dd, 1H), 2.46–2.43 (m, 7H), 2.05–2.02 (m, 1H), 1.57–1.43 (m, 3H), 1.47 (s, 9H).

$^{13}$C NMR (CDCl$_3$): $\delta$=170.8, 169.9, 153.6, 150.4, 144.3, 133.4, 133.1, 130.3, 130.0, 127.9, 121.6, 82.6, 62.3, 54.5, 53.8, 49.6, 46.1, 44.3, 43.7, 37.3, 29.7, 27.8, 24.1, 21.4.

Example 34

Synthesis of N-(Toluene-4-sulfonyl)-N-methyl-L-alanyl-L-4-(4-methylpiperazin-1-ylcarbonyloxy)phenylalanine t-butyl Ester The title compound was prepared following the procedure outlined for the preparation of Example 4 and substitution of appropriate starting materials.

NMR data was as follows:

$^1$H NMR (CDCl$_3$): $\delta$=7.68 (d, 2H), 7.31 (d, 2H), 7.17 (d, 2H), 7.04 (d, 2H), 6.86 (d, 1H), 4.65 (m, 1H), 4.47 (q, 1H), 3.71–3.53 (m, 4H), 3.24–2.92 (m, 2H), 2.50–2.40 (m, 10H), 2.35 (s, 3H), 1.45 (s, 9H), 0.92 (d, 3H).

$^{13}$C NMR (CDCl$_3$): $\delta$=170.1, 169.9, 153.6, 150.4, 143.9, 135.6, 133.3, 130.2, 129.9, 127.2, 121.8, 82.4, 55.4, 54.6, 53.6, 46.0, 44.2, 43.7, 37.2, 29.6, 27.8, 21.4, 11.5.

Example 35

Synthesis of N-(4-Nitrobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): $\delta$=8.38–8.34 (m, 2H), 8.05–8.00 (m, 2H), 7.16–2.12 (m, 2H), 7.03–6.94 (m, 3H), 4.74–4.68 (m, 1H), 4.15–4.14 (m, 1H), 3.41–3.32 (m, 1H), 3,23–3.14 (m, 2H), 3.08 (s, 3H), 3.03 (m, 1H), 2.98 (s, 3H), 2.05 (m, 1H), 1.66–1.48 (m, 3H), 1.47 (s, 9H).

$^{13}$C NMR (CDCl$_3$): $\delta$=170.0, 169.9, 154.8, 150.6, 150.4, 142.4, 132.9, 130.2, 129.0, 124.5, 121.6, 82.7, 62.2, 53.4, 49.4, 37.0, 36.5, 36.2, 30.1, 27.7, 24.1.

Example 36

Synthesis of N-Troluene-4-sulfonyl)-L-[(1,1-dioxo)-thiamorpholin-3-carbonyl]-L-4-(N,N-dimethylaminosulfonyloxy)phenylalanine tert-Butyl Ester The title compound was prepared using the procedure described for the preparation of Example 21 and substitution of appropriate starting materials.

NMR data was as follows:

$^1$H NMR (CDCl$_3$): $\delta$=7.73 (d, 1H), 7.67 (d, 1H), 7.35 (m, 2H), 7.27 (m, 2H), 6.88 (d, 1H), 6.66 (d, 1H), 5.08 (m, 0.5H), 4.97 (m, 0.5H), 4.71 (m, 0.5H), 4.61 (m, 0.5H), 4.25 (m, 0.5H), 4.03 (m, 1H), 3.21–3.04 (m, 4H), 2.89 (s, 3H), 2.83 (s, 3H), 2.78 (m, 3H), 2.42 (s, 3H), 1.44 (s, 4.5H), 1.38 (s, 4.5H).

$^{13}$C NMR (CDCl$_3$): $\delta$=169.8, 169.6, 164.9, 164.5, 149.3, 149.1, 145.6, 145.4, 135.4, 135.0, 134.6, 130.9, 130.6, 130.5, 127.4, 127.2, 122.0, 121.8, 83.0, 83.0, 56.0, 53.7, 49.2, 49.1, 48.5, 41.9, 41.4, 38.6, 36.8, 36.2, 27.7, 21.5.

Example 37

Synthesis of N-(Toluene-4-sulfonyl)sarcosyl-L-4-(thiomorpholin-4-ylcarbonyloxy)phenylalanine tert-Butyl Ester Substituting thiomorpholine for N-methylpiperazine, and following the method for the preparation of Example 4, gave the title compound.

NMR data was as follows:

$^1$H NMR (CDCl$_3$): $\delta$=7.65 (d, 2H), 7.33 (d, 2H), 7.20 (d, 2H), 7.04 (d, 2H), 4.76 (m, 1H), 3.89 (m, 4H), 3.68 (d, 1H), 3.48 (d, 1H), 3.10 (m, 2H), 2.66 (m, 7H), 2.41 (s, 3H), 1.43 (s, 9H).

$^{13}$C NMR (CDCl$_3$): $\delta$=169.9, 167.2, 153.5, 150.3, 144.3, 133.1, 130.3, 130.0, 127.6, 121.8, 82.5, 53.8, 53.3, 47.0, 36.4, 37.2, 36.6, 27.8, 27.3, 27.0, 21.4.

Example 38

Synthesis of N-(Toluene-4-sulfonyl)-L-N-methylalanyl-L-4-(4-methylpiperazin-1-ylcarbonyloxy)phenylalanine The title compound was prepared from the product of Example 34 using the procedure described in Method 11.

NMR data was as follows:

$^1$H NMR (CDCl$_3$): δ=7.65 (d, 2H), 7.34 (d, 2H), 7.27 (d, 2H), 7.09 (d, 12H), 4.64–4.50 (m, 2H), 4.48–4.23 (m, 2H), 3.60–2.96 (m, 8H) 2.92 (s, 3H), 2.55 (s, 3H), 2.40 (s, 3H), 0.93 (d, 3H).

$^{13}$C NMR (CDCl$_3$): δ=174.3, 173.1, 154.9, 151.6, 145.5, 137.0, 136.1, 131.6, 131.2, 128.5, 123.1, 56.4, 54.8, 54.0, 43.8, 37.3, 30.2, 21.5, 13.2.

Example 39

Synthesis of N-(Toluene-4-sulfonyl)-L-prolyl-L-4-(1,1-dioxothiomorpholin-4-ylcarbonyloxy)phenylalanine The title compound was prepared from the product of Example 81 using the procedure described in Method 11.

NMR data was as follows:

$^1$H NMR (CD$_3$OD): δ=8.03 (m, 1H), 7.73 (d, 2H), 7.41 (d, 2H), 7.28 (d, 2H), 7.08 (d, 2H), 4.70–4.65 (m, 1H), 4.12–4.00 (m, 5H), 3.38–3.36 (m, 1H), 3.31–3.06 (m, 7H), 2.43 (s, 3H), 1.77–1.48 (m, 5H).

$^{13}$C NMR (CD$_3$OD): δ=168.4, 159.1, 130.0, 129.1, 125.6, 125.1, 123.0, 116.9, 57.2, 48.8, 46.3, 44.5, 31.5, 25.6, 19.3, 15.4.

Example 40

Synthesis of N-(Toluene-4-sulfonyl)-L-prolyl-L-4-(thiomorpholin-4-ylcarbonyloxy)phenylalanine The title compound was prepared from the product of Example 82 using the procedure described in Method 11.

NMR data was as follows:

$^1$H NMR (CD$_3$OD): δ=7.73 (d, 2H), 7.41 (d, 2H), 7.27 (d, 2H), 7.04 (d, 2H), 4.68–4.65 (m, 1H), 4.10–4.07 (m, 1H), 3.90 (t, 2H), 3.77 (t, 2H), 3.38–3.11 (m, 4H), 2.66 (m, 4H), 2.43 (s, 3H), 1.80–1.48 (m, 5H).

$^{13}$C NMR (CD$_3$OD): δ=168.4, 168.2, 149.4, 145.7, 139.8, 129.7, 129.0, 125.6, 125.1, 123.1, 116.9, 57.2, 48.8, 44.6, 42.1, 36.0, 31.4, 25.7, 22.1, 21.8, 19.3, 15.4.

Example 41

Synthesis of N-(Toluene-4-sulfonyl)-L-prolyl-L-4-(isonipecotoyloxy)phenylalanine The title compound was prepared from the product of Example 80 using the procedure described in Method 11.

NMR data was as follows:

$^1$H NMR (CD$_3$OD): δ=8.08 (m, 1H), 7.73 (d, 2H), 7.41 (d, 2H), 7.27 (d, 2H), 7.03 (d, 2H), 4.71 (m, 1H), 4.11–4.08 (m, 1H), 3.61 (t, 2H), 3.47–3.38 (m, 3H), 3.31–3.11 (m, 4H), 2.43 (s, 3H), 1.77–1.47 (m, 10H).

$^{13}$C NMR (CD$_3$OD): δ=168.3, 168.1, 158.8, 149.6, 145.9, 139.8, 129.5, 129.0, 125.6, 125.1, 123.1, 116.9, 57.2, 48.6, 44.6, 40.6, 40.1, 36.0, 31.4, 25.7, 20.9, 20.6, 19.3.

Example 42

Synthesis of N-(Toluene-4-sulfonyl)-L-prolyl-L-4-(pyrrolidin-1-ylcarbonyloxy)phenylalanine The title compound was prepared from the product of Example 83 using the procedure described in Method 11.

NMR data was as follows:

$^1$H NMR (CD$_3$OD): δ=8.08 (m, 1H), 7.73 (d, 2H), 7.41 (d, 2H), 7.04 (d, 2H), 7.27 (d, 2H), 4.72–4.68 (m, 1H), 4.11–4.08 (m, 1H), 3.57–3.53 (t, 2H), 3.43–3.28 (m, 3H), 3.25–3.06 (m, 4H), 2.43 (s, 3H), 1.99–1.80 (m, 4H), 1.78–1.49 (m, 5H).

$^{13}$C NMR (CD$_3$OD): δ=168.2, 158.3, 149.2, 145.8, 139.8, 129.4, 129.1, 125.6, 125.1, 123.1, 116.9, 57.2, 48.7, 44.5, 41.5, 31.4, 25.7, 20.6, 19.8, 19.3, 15.4.

Example 43

Synthesis of N-(Toluene-4-sulfonyl)-L-prolyl-L-4-(morpholinyl-4-carbonyloxy)phenylalanine The title compound was prepared from the product of Example 108 using the procedure described in Method 11.

NMR data was as follows:

$^1$H NMR (CD$_3$OD): δ=7.73 (d, 2H), 7.41 (d, 2H), 7.27 (d, 2H), 7.04 (d, 2H), 4.95–4.93 (m, 1H), 4.10–4.07 (m, 1H), 3.71–3.65 (m, 6H), 3.50 (t, 2H), 3.40–3.10 (m, 4H), 2.43 (s, 3H), 1.78–1.48 (m, 4H).

$^{13}$C NMR (CD$_3$OD): δ=168.4, 168.2, 149.6, 145.7, 139.8, 129.1, 125.6, 125.1, 123.1, 116.8, 61.5, 57.2, 44.5, 36.0, 31.4, 25.6, 19.3, 15.4.

Example 44

Synthesis of N-(Toluene-4-sulfonyl)-L-prolyl-L-4-(4-methylpiperazin-1-ylcarbonyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 4.

NMR data was as follows:

$^1$H NMR (DMSO-d$_6$, 400 MHz) δ=8.29 (d, 1H, J=7.91 Hz); 7.68 (d, 2H, J=8.45 Hz); 7.40 (d, 2H, J=8.34 Hz); 7.24 (d, 2H, J=8.57 Hz); 7.00 (d, 2H, J=8.57 Hz); 4.56 (m, 1H); 4.07 (m, 1H); 3.73 (s, 2H); 3.55 (br s, 2H); 3.40 (m, 3H); 3.10 (m, 3H); 2.40 (s, 3H); 2.35 (br s, 4H); 2.20 (s, 3H); 1.55 (m, 3H); 1.37 (m, 1H); 0.85 (s, 9H).

Example 45

Synthesis of N-(Toluene-4-sulfonyl)-L-prolyl-L-4-(N,N-dimethylcarbamyloxy)phenylalanine Neopentyl Ester Titanium isopropoxide (0.3 equivalents) was added to Tos-Pro-Tyr ethyl ester (1 equivalent) and an excess of neopentyl alcohol. The mixture was heated to reflux under an argon atmosphere overnight. Excess neopentyl alcohol was removed under reduced pressure and the residue purified by flash column chromatography (silica, hexane: EtOAc 2:1) to give the neopentyl ester a white solid (0.9 g, 85%). The title compound was prepared following the procedure described in Example 2.

NMR data was as follows:

$^1$H NMR (DMSO-d$_6$, 400 MHz) δ=8.28 (d, 1H, J=8.13 Hz); 7.68 (d, 2H, J=8.4 Hz); 7.40 (d, 2H, J=7.9 Hz); 7.23 (d, 2H, J=8.56 Hz); 6.99 (d, 2H, J=8.35 Hz); 4.57 (m, 3H); 2.40 (s, 3H); 1.55 (m, 3H); 1.38 (m, 1H); 0.85 (s, 9H).

Example 46

Synthesis of 2-(Saccharin-2-yl)propionoyl-L-4-(4-methylpiperazin-1-ylcarbonyloxy)phenylalanine tert-Butyl Ester The title compound was prepared following the procedure described in Preparative Example A and Example 4.

NMR data was as follows:

¹H NMR (DMSO-d$_6$, 400 MHz) (1:1 mixture of diastereomers) δ=8.31 (m, 1H); 8.26 (m, 1H); 8.03 (m, 3H); 7.20 (m, 2H); 7.00 (m, 2H); 4.73 (m, 1H); 4.30 (m, 1H); 3.58 (br s, 2H); 3.40 (br s, 2H); 3.02 (m, 1H); 2.95 (m, 1H); 2.35 (br s, 4H); 2.20 (s, 3H); 2.75 and 2.65 (two d, 3H); 1.35 and 1.32 (two s, 9H).

Example 47

Synthesis of 2-(Saccharin-2-yl)propionoyl-L-4-(N,N-dimethylcarbamyloxy)phenylalanine The title compound was prepared from the product of Preparative Example A using the procedure described in Method 11.

NMR data was as follows:

¹H NMR (DMSO-d$_6$, 400 MHz) (1:1 mixture of diastereomers) δ=12.75 (br s, 1H); 8.28 (m, 2H); 8.05 (m, 3H); 7.20 (m, 2H); 7.00 and 9.95 (two d, 2H); 4.75 (m, 1H); 4.40 (m, 1H); 3.10 (m, 1H); 3.05 (s, 3H); 2.95 (m, 1H); 2.90 (s, 3H); 2.75 and 2.60 (two d, 3H).

Example 48

Synthesis of N-(Toluene-4-sulfonyl)-L-N-methylalanyl-L-4-(N,N-dimethylcarbamyloxy)phenylalanine tert-Butyl Ester The title compound was prepared following the procedure for the synthesis of Example 2 with the substitution of appropriate starting materials.

NMR data was as follows:

¹H NMR (CDCl$_3$): δ=7.68 (d, 2H), 7.31 (d, 2H), 7.17 (d, 2H), 7.04 (d, 2H), 6.87 (d, 2H), 4.67 (m, 1H), 4.48 (q, 1H), 3.09 (s, 3H), 3.00 (s, 3H), 3.14–2.92 (m, 2H), 2.46 (s, 3H), 2.43 (s, 3H), 1.45 (s, 9H), 0.92 (d, 3H).

¹³C NMR (CDCl$_3$): δ=170.2, 169.9, 154.9, 150.6, 143.9, 135.6, 133.2, 130.2, 130.0, 127.3, 121.9, 82.5, 55.5, 53.7, 37.2, 36.6, 36.4, 29.7, 27.8, 21.4, 11.5.

Example 49

Synthesis of N-(Toluene-4-sulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 48, 517–525). N-(Toluene-4-sulfonyl)-L-thiamorpholine-3-carboxylic acid was prepared using the procedure described in Method 1. The title compound was prepared following the procedure for the synthesis of Example 2 with substitution of appropriate starting materials.

NMR data was as follows:

¹H NMR (CDCl$_3$): δ=7.69 (d, 2H), 7.31 (d, 2H), 7.16 (d, 2H), 6.98 (d, 2H), 6.86 (d, 1H), 4.71 (m, 1H), 4.62 (m, 1H), 3.94 (m, 1H), 3.31 (m, 1H), 3.09 (m, 4H), 2.98 (s, 3H), 2.67 (m, 1H), 2.50 (m, 1H), 2.40 (s, 3H), 2.31 (m, 1H), 2.10 (m, 1H), 1.49 (s, 9H).

¹³C NMR (CDCl$_3$): δ=169.9, 167.4, 154.8, 150.6, 144.2, 136.8, 132.8, 130.4, 130.2, 127.3, 121.8, 82.6, 55.2, 54.0, 43.3, 36.5, 36.3, 27.8, 25.2, 24.6, 21.4.

Example 50

Synthesis of N-(Toluene-4-sulfonyl)sarcosyl-L-4-(1,1-dioxothiomorpholin-4-ylcarbonyloxy)phenylalanine The title compound was prepared from the product of Example 121 using the procedure described in Method 11.

NMR data was as follows:

¹H NMR (CD$_3$OD): δ=7.67 (d, 2H), 7.40 (d, 2H), 7.27 (d, 2H), 7.09 (d, 2H), 4.61 (m, 1H), 4.12 (m, 2H), 3.99 (m, 2H), 3.60 (m, 2H), 3.23 (m, 8H), 2.58 (s, 3H), 2.42 (s, 3H).

¹³C NMR (CD$_3$OD): δ=174.2, 170.3, 155.0, 151.6, 145.6, 136.1, 135.2, 131.5, 131.1, 128.9, 123.0, 54.6, 54.0, 52.4, 52.2, 44.4, 44.0, 37.4, 36.8, 21.4.

Example 51

Synthesis of N-(Toluene-4-sulfonyl)-L-(1,1-dioxothiamorpholin-3-carbonyl)-L-4-(N,N-dimethylcarbamyloxy)phenylalanine tert-Butyl Ester The title compound was prepared from the product of Example 49 following the procedure described by Larsson and Carlson (*Acta Chemica Scan.* 1994, 48, 522).

NMR data was as follows:

¹H NMR (CDCl$_3$): δ=7.76 (d, 2H), 7.37 (d, 2H), 7.08 (d, 2H), 6.98 (d, 2H), 6.56 (d, 1H), 4.95 (m, 1H), 4.62 (m, 1H), 3.99 (m, 2H), 3.25 (m, 1H), 3.07 (s, 3H), 2.97 (m, 8H), 2.44 (s, 3H), 1.48 (s, 9H).

¹³C NMR (CDCl$_3$): δ=170.0, 164.8, 154.9, 150.7, 145.4, 135.3, 132.6, 130.7, 130.3, 127.5, 122.3, 82.8, 56.1, 53.6, 49.5, 48.6, 41.6, 36.6, 36.4, 27.9, 21.6.

Example 52

Synthesis of N-(Toluene-4-sulfonyl)-L-(1,1-dioxothiamorpholin-3-carbonyl)-L-4-(morpholin 4-ylcarbonyloxy)phenylalanine tert-Butyl Ester The title compound was prepared following the procedure described for the preparation of Example 71.

NMR data was as follows:

¹H NMR (CDCl$_3$): δ=7.75 (d, 2H), 7.36 (d, 2H), 7.12 (d, 2H), 6.98 (d, 2H), 6.58 (d, 1H), 4.93 (m, 1H), 4.63 (m, 1H), 4.09 (m, 2H), 3.72 (m, 4H), 3.63 (m, 2H), 3.51 (m, 2H), 3.24 (m, 1H), 2.96 (m, 4H), 2.43 (s, 3H), 1.46 (s, 9H).

¹³C NMR (CDCl$_3$): δ=170.0, 164.8, 153.7, 150.4, 145.4, 135.2, 132.9, 130.7, 130.4, 127.5, 122.1, 82.9, 66.4, 56.1, 53.6, 49.4, 48.5, 44.7, 43.9, 41.6, 36.3, 27.8, 21.6.

Example 53

Synthesis of N-(Toluene-4-sulfonyl)-L-N-methylalanyl-L-4-(N,N-dimethylcarbamyloxy)phenylalanine The title compound was prepared from the product of Example 48 using the procedure described in Method 11.

NMR data was as follows:

¹H NMR (CDCl$_3$): δ=7.68 (d, 2H), 7.31 (d, 2H), 7.20 (d, 2H), 7.11–7.04 (m, 3H), 6.35 (br s, 1H), 4.81 (m, 1H), 4.52 (q, 1H), 3.35–2.98 (m, 2H), 3.09 (s, 3H), 3.00 (s, 3H), 2.45 (s, 3H), 2.43 (s, 3H), 0.91 (d, 3H).

¹³C NMR (CDCl$_3$): δ=173.7, 170.8, 155.2, 150.6, 144.0, 135.4, 133.2, 130.2, 130.0, 127.3, 122.1, 55.5, 53.2, 36.6, 36.5, 36.4, 29.8, 21.4, 11.6.

Example 54

Synthesis of N-(4-Fluorobenzenesulfonyl)-L-(thiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan.* 1994, 4, 517–525). N-(Toluene-4-sulfonyl)-L-thiamorpholine-3-carboxylic acid was prepared using the procedure described in Method 1.

The title compound was then prepared following the procedure for the synthesis of Example 2.

NMR data was as follows:

$^1$H NMR (CDCl$_3$): δ=7.87–7.82 (m, 2H), 7.20 (t, 2H), 7.16 (d, 2H), 7.00 (d, 2H), 6.76 (d, 1H), 4.74 (t, 1H), 4.65 (q, 1H), 3.92 (d, 1H), 3.32 (dd, 1H), 3.17–3.00 (m, 2H), 3.09 (s, 3H), 2.99 (s, 3H), 2.76–2.66 (m, 1H), 2.62 (dd, 1H), 2.46 (dt, 1H), 2.22 (d, 1H), 1.49 (s, 9H).

$^{13}$C NMR (CDCl$_3$): δ=170.0, 167.2, 165.5, 154.8, 150.7, 135.8, 132.7, 130.5, 130.1, 121.9, 116.9, 82.8, 55.3, 53.9, 43.4, 36.6, 36.4, 36.3, 27.9, 25.8, 25.0.

Example 55

Synthesis of N-(4-Fluorobenzenesulfonyl)-L-(1,1-dioxothiamorpholin-3-carbonyl)-L-4-(N,N-dimethylcarbamyloxy)phenylalanine tert-Butyl Ester The title compound was prepared from the product of Example 54 following the procedure described by Larsson and Carlson (*Acta Chemica Scan.* 1994, 48, 522).

NMR data was as follows:

$^1$H NMR (CDCl$_3$): δ=7.92–7.88 (m, 2H), 7.24 (t, 2H), 7.09 (d, 2H), 6.97 (d, 2H), 6.41 (d, 1H), 4.96 (d, 1H), 4.62 (d, 1H), 4.03 (d, 1H), 3.26 (dd, 1H), 3.13–2.92 (m, 6H), 3.09 (s, 3H), 2.97 (s, 3H), 1.49 (s, 9H).

$^{13}$C NMR (CDCl$_3$): δ=170.1, 165.9, 164.5, 154.9, 150.7, 134.0, 132.4, 130.5, 130.4, 122.2, 117.3, 83.0, 56.1, 53.4, 50.0, 49.1, 41.7, 36.6, 36.3, 36.1, 27.9.

Example 56

Synthesis of N-(Pyridine-3-sulfonyl)-L-prolyl-L-4-(N,N-dimethylcarbamyloxy)phenylalanine tert-Butyl Ester N-Benzyl-L-prolyl was coupled to L-tyrosine t-butyl ester using the procedure described in Method 12. N-Benzyl-L-prolyl-L-(N,N-dimethylcarbamyloxy)phenylalanine t-butyl ester was prepared following the procedure described for the preparation of Example 2. L-Prolyl-L-(4-N,N-dimethylcarbamyloxy)phenylalanine t-butyl ester was prepared from the product of the previous reaction using the procedure described in Method 4. The title compound was prepared using the procedure described for the preparation of 3-pyridine sulfonyl chloride (see Crowell, et al., *J. Med. Chem.*, 1989, 32, 2436–2442) and the product of the last reaction.

NMR data was as follows:

$^1$H NMR (CDCl$_3$): δ=9.95 (d, 1H), 8.83 (dd, 1H), 8.14–8.10 (m, 1H), 7.51–7.47 (m, 1H), 7.16–7.13 (m, 3H), 7.02–6.99 (m, 2H), 4.72–4.69 (m, 1H), 4.09–4.06 (m, 1H), 3.41–3.39 (m, 1H), 3.23–3.17 (m, 1H), 3.13–2.98 (m, 1H), 3.07 (s, 3H), 2.97 (s, 3H), 2.04 (m, 1H), 1.59–1.47 (m, 3H), 1.45 (s, 9H).

$^{13}$C NMR (CDCl$_3$): δ=170.1, 169.9, 154.8, 153.9, 150.5, 148.4, 135.5, 133.0, 130.1, 123.9, 121.6, 82.6, 52.2, 53.6, 49.5, 37.1, 36.5, 36.3, 29.9, 27.8, 24.0.

Preparative Example B

Synthesis of N-(Primidine-2-sulfonyl)-L-prolyl-L-4-(N,N-dimethylcarbamyloxy)phenylalanine tert-Butyl Ester The title compound was prepared by substituting 2-pyrimidine sulfonyl chloride (see Skulnick, et al.,*J. Med. Chem.*, 1997, 40, 1149–1164) and following the method for the preparation of Example 56.

NMR data was as follows:

$^1$H NMR (CDCl$_3$): δ=8.28 (d, 2H), 7.39 (d, 1H), 7.02 (d, 2H), 6.88 (d, 2H), 6.54 (m, 1H), 4.76–4.69 (m, 1H), 4.57–4.55 (m, 1H), 3.64 (m, 1H), 3.55–3.52 (m, 1H), 3.09–3.03 (m, 1H), 3.08 (s, 3H), 2.99–2.95 (m, 1H), 2.98 (s, 3H), 2.32 (m, 1H), 2.01–1.97 (m, 3H), 1.37 (s, 9H).

$^{13}$C NMR (CDCl$_3$): δ=172.1, 170.4, 160.6, 157.7, 154.8, 150.3, 133.0, 130.1, 121.3, 110.5, 82.0, 60.7, 53.3, 47.5, 37.1, 36.5, 36.3, 28.9, 27.7, 24.1.

Example 57

Synthesis of N-(4-Nitrobenzenesulfonyl)-L-prolyl-L-4-(N,N-dimethylcarbamyloxy)phenylalanine The title compound was prepared from the product of Example 35 using the procedure described in method 11.

NMR data was as follows:

$^1$H NMR (CDCl$_3$): δ=8.36 (d, 2H), 8.02 (d, 2H), 7.42 (d, 1H), 7.20 (d, 2H), 7.01 (d, 2H), 4.86 (m, 1H), 4.18–4.15 (m, 1H), 3.46–3.43 (m, 1H), 3.32–3.26 (m, 1H), 3.19–3.11 (m, 2H), 3.09 (s, 3H), 3.01 (s, 3H), 1.91 (m, 1H), 1.65–1.54 (m, 3H).

$^{13}$C NMR (CDCl$_3$): δ=172.9, 171.7, 155.5, 150.4, 150.4, 142.1, 133.2, 130.5, 129.1, 124.6, 121.8, 61.9, 52.9, 49.6, 36.6, 36.3, 36.3, 30.6, 24.1.

Example 58

Synthesis of N-(4-Cyanobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

$^1$H NMR (CDCl$_3$): δ=7.94 (d, 2H), 7.82 (d, 2H), 7.13 (d, 2H), 7.05–6.99 (m, 3H), 4.71–4.66 (m, 1H), 4.12–4.09 (m, 1H), 3.36–3.35 (m, 1H), 3.22–3.11 (m, 2H), 3.07 (s, 3H), 3.06–3.01 (m, 1H), 2.97 (s, 3H), 2.05 (m, 1H), 1.63–1.37 (m, 3H), 1.46 (s, 9H).

$^{13}$C NMR (CDCl$_3$): δ=170.1, 169.9, 154.8, 150.6, 140.8, 133.1, 132.9, 130.2, 128.4, 121.7, 117.1, 116.9, 82.7, 62.2, 53.4, 49.4, 37.0, 36.5, 36.3, 30.1, 27.8, 24.1.

Example 59

Synthesis of N-(Toluene-4-sulfonyl)-L-(1,1-dioxothiamorpholin-3-carbonyl)-L-4-(N,N-dimethylaminosulfonyloxy)phenylalanine The title compound was prepared from the product of Example 36 using the procedure described in Method 11.

NMR data was as follows:

$^1$H NMR (CD$_3$OD): δ=7.79 (m, 2H), 7.44 (m, 2H), 7.27 (m, 2H), 7.17 (m, 2H), 5.21 (m, 1H), 4.64 (m, 1H), 4.14 (m, 1H), 3.61 (m, 2H), 3.24 (m, 2H), 3.08 (m, 2H), 2.89 (s, 6H), 2.80 (m, 2H), 2.43 (s, 3H).

$^{13}$C NMR (CD$_3$OD): δ=173.9, 168.1, 168.0, 150.8, 150.8, 146.7, 146.5, 137.6, 137.5, 137.1, 136.9, 132.2, 132.1, 131.7, 131.6, 128.8, 123.3, 123.1, 57.3, 54.8, 51.0, 50.8, 50.5, 47.9, 47.8, 43.2, 43.0, 39.0, 39.0, 37.4, 37.0, 21.5.

Example 60

Synthesis of N-(Toluene-4-sulfonyl)-L-(1,1-dioxothiamorpholin-3-carbonyl)-L-4-(N,N-dimethylcarbamyloxy)phenylalanine The title compound was prepared from the product of Example 51 using the procedure described in Method 11.

NMR data was as follows:

$^1$H NMR (CDCl$_3$): δ=7.79 (d, 2H), 7.43 (d, 2H), 7.20 (d, 2H), 7.00 (d, 2H), 5.21 (m, 1H), 4.65 (m, 1H), 4.12 (m, 1H), 3.75 (m, 1H), 3.29 (m, 3H), 3.08 (s, 3H), 3.00 (m, 1H), 3.00 (m, 1H), 2.97 (s, 3H), 2.80 (m, 3H), 2.44 (s, 3H).

$^{13}$C NMR (CDCl$_3$): δ=165.1, 159.0, 147.9, 143.1, 137.6, 128.6, 126.1, 122.7, 122.6, 119.8, 114.3, 48.3, 45.8, 41.6, 34.0, 28.0, 27.8, 27.7, 12.5.

Example 61

Synthesis of N-(Toluene-4-sulfonyl)-L-(1,1-dioxo)thiaprolyl-L-4-(N,N-dimethylcarbamyloxy)phenylalanine tert-Butyl Ester The title compound was prepared from N-(toluene-4-sulfonyl)-L-thiaprolyl-L-4-(N,N-dimethylcarbamyloxy)phenylalanine tert-butyl ester, prepared as per the examples herein, following the procedure described by by Larsson and Carlson (*Acta Chemica Scan.* 1994, 48, 522).

NMR data was as follows:

$^1$H NMR (CDCl$_3$): δ=7.77 (d, 2H), 7.38 (d, 2H), 7.18 (m, 3H), 7.09 (d, 2H), 4.83–4.57 (m, 3H), 3.77–3.60 (m, 2H), 3.36–3.23 (m, 1H), 3.15–3.00 (m, 7H), 2.85–2.73 (m, 1H), 2.46 (s, 3H), 1.50 (s, 9H).

Example 62

Synthesis of N-(4-Fluorobenzenesulfonyl)-L-prolyl-L-4-(N,N-dimethylcarbamyloxy)phenylalanine tert-Butyl Ester The title compound was prepared following the procedure outlined for the preparation of Example 2 and substitution of appropriate starting materials.

NMR data was as follows:

$^1$H NMR (CDCl$_3$): δ=7.96 (d, 2H), 7.80 (d, 2H), 7.26–7.13 (m, 3H), 7.01 (d, 2H), 4.72–4.70 (m, 1H), 4.11–4.08 (m, 1H), 3.40–3.37 (m, 1H), 3.25–3.10 (m, 2H), 3.07 (s, 3H), 3.04–3.02 (m, 1H), 2.98 (s, 3H), 2.06 (m, 1H), 2.06–2.04 (m, 1H), 1.61–1.52 (m, 3H), 1.46 (s, 9H).

$^{13}$C NMR (CDCl$_3$): δ=170.3, 169.9, 154.9, 150.6, 139.9, 134.9, 133.1, 130.2, 128.4, 126.5, 121.7, 82.7, 62.3, 5.35, 49.6, 37.2, 36.6, 36.3, 30.0, 27.8 24.1.

Example 63

Synthesis of N-(1-Methylpyrazolylsulfonyl)-L-prolyl-L-4-(N,N-dimethylcarbamyloxy)phenylalanine The title compound was prepared from the product of Example 117 using the procedure described in Method 11.

NMR data was as follows:

$^1$H NMR (CDCl$_3$): δ=8.84 (br s, 1H), 7.93 (s, 1H), 7.79 (s, 1H), 7.68–7.65 (m, 1H), 7.18 (d, 2H), 6.99 (d, 2H), 4.88–4.81 (m, 1H), 4.08–4.06 (m, 1H), 3.92 (s, 3H), 3.45–3.40 (m, 1H), 3.34–3.27 (m, 1H), 3.11–3.01 (m, 5H), 2.97 (s, 3H), 1.82 (m, 1H), 1.66–1.57 (m, 2H), 1.45 (m, 1H).

$^{13}$C NMR (CDCl$_3$): δ=173.1, 172.9, 159.1, 158.6, 150.4, 138.8, 133.4, 133.2, 130.3, 121.9, 117.3, 62.0, 53.1, 49.7, 39.4, 36.6, 36.5, 36.4, 30.4, 23.9.

Example 64

Synthesis of N-(Toluene-4-sulfonyl)-L-(1,1-dioxo)thiaprolyl-L-4-(N,N-dimethylcarbamyloxy)phenylalanine The title compound was prepared from the product of Example 61 using the procedure described in Method 11.

NMR data was as follows:

$^1$H NMR (CDCl$_3$): δ=8.34 (d, 1H), 7.70 (d, 2H), 7.33 (d, 2H), 7.14 (d, 2H), 7.01 (d, 2H), 5.07 (m, 1H), 4.93 (m, 1H), 4.43 (d, 1H), 4.01 (d, 1H), 3.68 (m, 1H), 3.37 (m, 1H), 3.17 (s, 3H), 3.14 (m, 1H), 3.09 (s, 3H), 2.54 (m, 1H), 2.43 (s, 3H).

$^{13}$C NMR (CDCl$_3$): δ=171.5, 166.4, 156.4, 150.5, 145.5, 134.2, 134.1, 131.4, 130.3, 128.1, 121.8, 64.3, 59.2, 53.7, 50.5, 36.9, 36.5, 35.8, 21.6.

Example 65

Synthesis of N-(4-Fluorobenzenesulfonyl)-L-thiaprolyl-L-4-(N,N-dimethylcarbamyloxy)phenylalanine The title compound was prepared from the product of Example 84 using the procedure described in Method 11.

NMR data was as follows:

$^1$H NMR (CDCl$_3$): δ=7.83 (m, 2H), 7.73 (d, 1H), 7.16 (m, 4H), 6.99 (d, 2H), 5.57 (br s, 1H), 4.87 (m, 1H), 4.76 (m, 1H), 4.53 (d, 1H), 4.10 (d, 1H), 3.34 (m, 1H), 3.22 (d, 2H), 3.12 (s, 3H), 3.04 (s, 3H), 2.43 (m, 1H).

$^{13}$C NMR (CDCl$_3$): δ=172.1, 168.7, 155.7, 150.5, 133.6, 133.1, 130.8, 130.7, 121.7, 116.9, 116.6, 65.3, 53.3, 51.3, 36.8, 36.4, 36.1, 33.4.

Example 66

Synthesis of N-(4-Fluorobenzenesulfonyl)-L-(5,5-dimethyl)-thiaprolyl-L-4-(N,N-dimethylcarbamyloxy)phenylalanine tert-Butyl Ester The title compound was prepared following the procedure described for the preparation of Example 2 with the substitution of appropriate starting materials.

NMR data was as follows:

$^1$H NMR (CDCl$_3$): δ=7.91 (m, 2H), 7.26 (m, 4H), 7.02 (d, 2H), 6.96 (d, 1H), 4.75 (m, 1H), 4.55 (d, 1H), 4.42 (d, 1H), 3.86 (s, 1H), 3.08 (s, 3H), 3.05 (m, 2H), 3.00 (s, 3H), 1.43 (s, 9H), 1.17 (s, 3H), 1.16 (s, 3H).

$^{13}$C NMR (CDCl$_3$): δ=169.9, 168.1, 167.6, 164.2, 154.9, 150.6, 133.1, 132.2, 131.0, 130.9, 130.4, 121.7, 116.9, 116.6, 82.7, 73.5, 54.7, 53.7, 50.5, 37.8, 36.6, 36.4, 29.1, 27.8, 23.8.

Example 67

Synthesis of N-(4-Fluorobenzenesulfonyl)-L-(1,1-dioxothiamorpholin-3-carbonyl)-L-4-(1,1-dioxothiomorpholin-4-ylcarbonyloxy)phenylalanine tert-Butyl Ester The title compound was prepared following the procedure described for the preparation of Example 68.

NMR data was as follows:

$^1$H NMR (CDCl$_3$): δ=7.91–7.87 (m, 2H), 7.27–7.25 (m, 2H), 7.15 (d, 2H), 6.51 (d, 1H), 4.93–4.90 (m, 1H), 4.64–4.58 (m, 1H), 4.14–3.99 (m, 7H), 3.28–2.90 (m, 10H), 1.47 (s, 9H).

$^{13}$C NMR (CDCl$_3$): δ=170.1, 167.6, 164.5, 153.1, 149.8, 133.9, 133.4, 130.7, 130.5, 121.7, 117.4, 117.1, 83.1, 56.1, 53.4, 51.6, 49.9, 48.9, 43.1, 41.6, 36.2, 27.8.

Example 68

Synthesis of N-(Toluene-4-sulfonyl)-L-(1,1-dioxothiamorpholin-3-carbonyl)-L-4-(1,1-dioxothiomorpholin-4-ylcarbonyloxy)phenylalanine tert-Butyl Ester Substituting thiomorpholine for N-methylpiperazine, and following the method for the preparation of Examples 4 and oxidation of the sulfur group in the thiomorpholino ring per by Larsson and Carlson (*Acta Chemica Scan.* 1994, 48, 522) gave the title compound as a white solid.

NMR data was as follows:

$^1$H NMR (CDCl$_3$): δ=7.75 (d, 2H), 7.35 (d, 2H), 7.17 (d, 2H), 6.99 (d, 2H), 6.65 (d, 1H), 4.92–4.90 (m, 1H), 4.63–4.60 (m, 1H), 4.15–3.95 (m, 7H), 3.30–3.23 (m, 1H), 3.14 (t, 4H), 3.07–2.80 (m, 6H), 2.45 (s, 3H), 1.48 (s, 9H).

$^{13}$C NMR (CDCl$_3$): δ=169.9, 164.8, 153.1, 149.8, 145.5, 135.1, 133.6, 130.7, 127.5, 121.8, 82.9, 60.3, 56.1, 53.7, 51.8, 49.3, 48.4, 43.1, 42.7, 41.5, 36.3, 27.8, 21.5.

Example 69

Synthesis of N-(4-Fluorobenzenesulfonyl)-L-prolyl-L-4-(thiomorpholin-4-ylcarbonyloxy)phenylalanine tert-Butyl Ester The title compound was prepared following the procedure described in Example 37 and substitution of appropriate starting materials.

NMR data was as follows:

$^1$H NMR (CDCl$_3$): δ=7.88–7.83 (m, 2H), 7.26–7.15 (m, 5H), 7.01 (d, 2H), 4.74–4.67 (m, 1H), 4.08–4.05 (m, 1H), 3.91–3.80 (m, 4H), 3.41–3.35 (m, 1H), 3.24–3.00 (m, 3H), 2.70–2.65 (t, 4H), 2.06–2.04 (m, 1H). 1.60–1.46 (m, 12H).

$^{13}$C NMR (CDCl$_3$): δ=170.5, 169.8, 153.4, 150.2, 133.5, 130.7, 130.5, 130.3, 121.6, 116.8, 116.5, 82.6, 62.2, 53.6, 49.6, 47.0, 46.4, 37.2, 29.8, 27.8, 27.3, 27.0, 24.1.

Example 70

Synthesis of N-(4-Fluorobenzenesulfonyl)-L-(5,5-dimethyl)-thiaprolyl-L-4-(N,N-dimethylcarbamyloxy)phenylalanine The title compound was prepared from the product of Example 66 using the procedure described in Method 11.

NMR data was as follows:

$^1$H NMR (CDCl$_3$): δ=7.90 (m, 2H), 7.30–7.14 (m, 5H), 7.02 (d, 2H), 5.83 (br s, 1H), 4.90 (m, 1H), 4.57 (d, 1H), 4.40 (d, 1H), 3.96 (s, 1H), 3.09 (s, 3H), 3.28–3.02 (m, 2H), 3.00 (s, 3H), 1.13 (s, 6H).

$^{13}$C NMR (CDCl$_3$): δ=173.2, 169.2, 164.2, 163.9, 155.3, 150.6, 133.1, 132.0, 131.0, 130.9, 130.6, 122.0, 117.0, 116.7, 73.3, 54.6, 53.3, 50.5, 37.0, 36.7, 36.4, 29.0, 23.7.

Example 71

Synthesis of N-(4-Fluorobenzenesulfonyl)-L-(1,1-dioxothiamorpholin-3-carbonyl)-L-4-(morpholin-4-ylcarbonyloxy)phenylalanine tert-Butyl Ester Substituting 4-morpholinecarbamyl chloride for dimethylcarbamyl chloride, and following the methods for the preparation of Example 2, gave the title compound as a white solid.

NMR data was as follows:

$^1$H NMR (CDCl$_3$): δ=7.91–7.87 (m, 2H), 7.26–7.20 (m, 2H), 7.11 (d, 2H), 6.98 (d, 2H), 6.43 (d, 1H), 4.95–4.92 (m, 1H), 4.62–4.60 (m, 1H), 4.05–4.00 (m, 2H), 3.74 (t, 4H), 3.66–3.52 (m, 4H), 3.30–2.92 (m, 6H), 1.48 (s, 9H).

$^{13}$C NMR (CDCl$_3$): δ=170.1, 164.5, 150.4, 134.6, 132.7, 130.5, 122.0, 117.4, 117.1, 83.1, 66.5, 56.1, 53.4, 49.9, 49.0, 44.7, 44.0, 41.6, 36.2, 27.8.

Example 72

Synthesis of N-(4-Trifluoromethoxybenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:

$^1$H NMR (CDCl$_3$): δ=7.89 (d, 2H), 7.35 (d, 2H), 7.25–7.13 (m, 3H), 7.01 (d, 2H), 4.70 (m, 1H), 4.09–4.06 (m, 1H), 3.39–3.36 (m, 1H), 3.24–3.01 (m, 5H), 2.98 (s, 3H), 2.05 (m, 1H), 1.62–1.47 (m, 3H), 1.46 (s, 9H).

$^{13}$C NMR (CDCl$_3$): δ=170.4, 169.9, 154.9, 152.7, 150.6, 134.6, 113.2, 130.2, 130.1, 121.7, 120.2, 82.7, 62.2, 53.6, 49.6, 37.2, 36.6, 36.3, 29.9, 27.8, 24.1.

Example 73

Synthesis of N-(Toluene-4-sulfonyl)-L-(1,1-dioxothiamorpholin-3-carbonyl)-L-4-(N,N-dimethylcarbamyloxy)phenylalanine Isopropyl Ester Following the method for the preparation of Example 2 and oxidation of the sulfur group in the thiomorpholino ring per by Larsson and Carlson (*Acta Chemica Scan.* 1994, 48, 522) gave the title compound.

NMR data was as follows:

$^1$H NMR (CDCl$_3$): δ=7.70 (d, 2H), 7.31 (d, 2H), 7.04 (d, 2H), 6.93 (d, 2H), 6.59 (d, 1H), 5.01 (m, 2H), 4.65 (m, 1H), 4.01 (d, 1H), 3.90 (d, 1H), 3.25 (m, 1H), 3.00 (s, 3H), 2.82 (m, 8H), 2.37 (s, 3H), 1.22 (s, 3H), 1.20 (s, 3H).

$^{13}$C NMR (CDCl$_3$): δ=170.3, 165.0, 154.6, 150.5, 145.1, 135.2, 132.3, 130.4, 130.0, 127.2, 122.1, 69.5, 55.9, 53.1, 49.1, 48.5, 41.4, 36.3, 36.1, 35.9, 21.4.

Example 74

Synthesis of N-(4-Fluorobenzenesulfonyl)-L-(1,1-dioxo-5,5-dimethyl)thiaprolyl-L-4-(N,N-dimethylcarbamyloxy)phenylalanine tert-Butyl Ester The title compound was prepared from the product of Example 66 following the procedure described by Larsson and Carlson (*Acta Chemica Scan.* 1994, 48, 522).

NMR data was as follows:

$^1$H NMR (CDCl$_3$): δ=7.88 (m, 2H), 7.24 (m, 4H), 7.05 (d, 2H), 6.95 (d, 1H), 4.80 (m, 1H), 4.40 (m, 2H), 4.10 (s, 1H), 3.17–3.03 (m, 2H), 3.10 (s, 3H), 3.01 (s, 3H), 1.47 (s, 9H), 1.36 (s, 3H), 1.11 (s, 3H).

$^{13}$C NMR (CDCl$_3$): δ=169.8, 168.6, 166.0, 154.5, 150.8, 139.7, 133.0, 131.5, 131.4, 130.3, 122.0, 117.1, 116.8, 83.0, 68.0, 60.9, 59.3, 53.8, 37.4, 36.6, 36.4, 27.8, 18.9, 18.8.

Example 75

Synthesis of N-(Toluene-4-sulfonyl)-L-(1,1-dioxo-5,5-dimethyl)thiaprolyl-L-4-(N,N-dimethylcarbamyloxy)phenylalanine Isopropyl Ester The title compound was prepared from the product of Example 11 following the procedure described by Larsson and Carlson (*Acta Chemica Scan.* 1994, 48, 522).

NMR data was as follows:

$^1$H NMR (CDCl$_3$): δ=7.75 (d, 2H), 7.38 (d, 2H), 7.21 (d, 2H), 7.03 (m, 3H), 5.08 (m, 1H), 4.89 (m, 1H), 4.38 (m, 2H), 4.10 (s, 1H), 3.22–3.04 (m, 2H), 3.10 (s, 3H), 3.00 (s, 3H), 2.43 (s, 3H), 1.26 (m, 9H), 1.09 (s, 3H).

$^{13}$C NMR (CDCl$_3$): δ=170.3, 166.3, 150.8, 145.9, 132.8, 131.9, 130.3, 128.6, 122.0, 69.8, 68.0, 60.9, 59.4, 53.4, 37.4, 36.6, 36.4, 21.6, 21.5, 19.2, 18.6.

Example 76

Synthesis of N-(Fluorobenzenesulfonyl)-L-(5,5-dimethyl)thiaprolyl-L-4-(N,N-dimethylcarbamyloxy)phenylalanine The title compound was prepared from the product of Example 74 using the procedure described in Method 11.

NMR data was as follows:

$^{13}$C NMR (CDCl$_3$): δ=171.7, 167.9, 137.3, 164.5, 155.9, 150.4, 133.6, 131.8, 131.3, 131.2, 130.8, 121.9, 117.1, 116.8, 67.8, 60.9, 59.9, 53.8, 36.8, 36.6, 36.0, 19.1, 19.0.

Example 77

Synthesis of N-(Pyrimidine-2-sulfonyl)-L-prolyl-L-4-(N,N-dimethylcarbamyloxy)phenylalanine The title compound was prepared from the product of Preparative Example B using the procedure described in Method 11.

NMR data was as follows:

$^1$H NMR (CDCl$_3$): δ=8.45 (br m, 2H), 8.22 (br s, 1H), 7.55 (d, 1H), 7.11 (d, 2H), 6.95 (d, 2H), 6.81 (m, 1H), 4.80–4.74 (m, 2H), 3.70 (m, 1H), 3.55 (m, 1H), 3.20–3.08 (m, 4H), 2.98 (s, 3H), 2.89–2.76 (m, 1H), 2.13–1.96 (m, 3H), 1.60 (m, 1H).

$^{13}$C NMR (CDCl$_3$): δ=190.0, 173.6, 171.0, 155.2, 153.9, 150.6, 133.2, 130.1, 121.9, 110.3, 62.0, 55.1, 48.2, 36.6, 36.6, 36.3, 30.2, 23.4.

Example 78

Synthesis of N-(Toluene-4-sulfonyl)-L-(1,1-dioxothiamorpholin-3-carbonyl)-L-4-(4-methylpiperazin-1-ylcarbonyloxy)phenylalanine tert-Butyl Ester Following the method for the preparation of Example 4 and oxidation of the sulfur group in the thiamorpholino ring per Larsson and Carlson (Acta Chemica Scan. 1994, 48, 522) gave the title compound.

NMR data was as follows:

$^1$H NMR (CDCl$_3$): δ=7.76 (d, 2H), 7.37 (d, 2H), 7.12 (d, 2H), 6.96 (d, 2H), 6.57 (d, 1H), 4.95 (m, 1H), 4.62 (m, 1H), 4.03 (m, 2H), 3.67 (m, 4H), 3.25 (m, 1H), 2,89 (m, 4H), 2.45 (m, 6H), 2.35 (s, 3H), 1.48 (s, 9H).

$^{13}$C NMR (CDCl$_3$): δ=170.0, 164.8, 153.7, 150.5, 145.4, 135.3, 132.8, 130.7, 130.4, 127.5, 122.2, 82.9, 56.2, 54.6, 54.5, 53.6, 49.5, 48.6, 46.0, 44.2, 43.7, 41.6, 36.3, 27.9, 21.6.

Example 79

Synthesis of N-(4-Fluorobenzenesulfonyl)-L-(1,1-dioxo)thiaprolyl-L-4-(N,N-dimethylcarbamyloxy)phenylalanine The title compound was prepared from the product of Example 85 using the procedure described in Method 11.

NMR data was as follows:

$^1$H NMR (CDCl$_3$): δ=4.98, (m, 1H), 4.90 (m, 1H), 4.44 (d, 1H), 4.03 (d, 1H), 3.67 (m, 1H), 3.37 (m, 1H), 3.25–3.02 (m, 1H), 3.20 (s, 3H), 3.11 (s, 3H), 2.68 (m, 1H).

$^{13}$C NMR (CDCl$_3$): δ=171.7, 167.9, 166.3, 164.4, 157.0, 156.4, 150.5, 139.6, 134.0, 133.1, 131.3, 131.1, 130.9, 121.9, 117.2, 116.9, 64.1, 58.8, 53.7, 50.6, 36.9, 36.5, 35.6.

Example 80

Synthesis of N-(Toluene-4-sulfonyl)-L-prolyl-L-4-(isonipecotoyloxy)phenylalanine tert-Butyl Ester Substituting piperazine for N-methylpiperazine, and following the methods for the preparation of Example 4, gave the title compound as a white solid.

NMR data was as follows:

$^{13}$C NMR (CDCl$_3$): δ=7.70 (d, 2H), 7.32–7.26 (m, 2H), 7.14 (d, 2H), 7.01 (d, 2H), 4.72–4.68 (m, 1H), 4.07–4.05 (m, 1H), 3.60–3.49 (m, 4H), 3.37–3.31 (m, 1H), 3.22–2.98 (m, 3H), 2.42 (s, 3H), 2.02 (m, 2H), 1.61–1.55 (m, 6H), 1.50–1.45 (m, 13H).

$^{13}$C NMR (CDCl$_3$): δ=177.3, 170.7, 169.8, 150.6, 144.3, 133.1, 130.1, 129.9, 127.9, 121.6, 110.8, 82.5, 62.2, 57,2, 53.7, 49.5, 44.9, 37.2, 29.7, 27.8, 25.7, 24.1, 21.4.

Example 81

Synthesis of N-(Toluene-4-sulfonyl)-L-prolyl-L-4-(1,1-dioxothiomorpholin-4-ylcarbonyloxy)phenylalanine tert-Butyl Ester The product of Example 82 was oxidized by the method of Larsson and Carlson (Acta Chemica Scan. 1994, 4, 517–525), yielding the tide compound as a white solid.

NMR data was as follows:

$^1$H NMR (CDCl$_3$): δ=7.69 (d, 2H), 7.33–7.29 (m, 3H), 7.20 (d, 2H), 7.00 (d, 2H), 4.71–4.66 (m, 1H), 4.13–4.04 (m, 5H), 3.37–3.32 (m, 1H), 3.21–3.00 (m, 7H), 2.41 (s, 3H), 2.05–2.01 (m, 1H), 1.52–1.44 (m, 12H).

$^{13}$C NMR (CDCl$_3$): δ=170.7, 169.7, 149.8, 144.3, 134.4, 133.3, 130,6, 130.0, 127.9, 121.4, 82.7, 62.4, 54.0, 52.1, 49.7, 43.2, 37.6, 29.7, 28.1, 24.4, 21.7.

Example 82

Synthesis of N-(Toluene-4-sulfonyl)-L-prolyl-L-4-(thiomorpholin-4-ylcarbonyloxy)phenylalanine tert-Butyl Ester Substituting thiomorpholine for N-methylpiperazine, and following the methods for the preparation of Example 4, gave the title compound as a white solid.

NMR data was as follows:

$^{13}$C NMR (CDCl$_3$): δ=7.70 (d, 2H), 7.31–7.26 (m, 2H), 7.16 (d, 2H), 7.00 (d, 2H), 4.72–4.66 (m, 1H), 4.07–4.04 (m, 1H), 3.89–3.79 (m, 4H), 3.37–3.32 (m, 1H), 3.22–2.99 (m, 3H), 2.67 (t, 4H), 2.42 (s, 3H), 2.02 (m, 2H), 1.50–1.45 (m, 12H).

$^{13}$C NMR (CDCl$_3$): δ=177.2, 170.7, 169.8, 153.5, 150.2, 144.3, 133.6, 132.9, 130.3, 129.9, 127.9, 121.5, 82.5, 62.4, 53.7, 49.5, 47.0, 46.4, 37.2, 29.6, 27.8, 27.3, 24.1, 21.4.

Example 83

Synthesis of N-(Toluene-4-sulfonyl)-L-prolyl-L-4-(pyrrolidin-1-ylcarbonyloxy)phenylalanine tert-Butyl Ester Substituting pyrrolidinecarbonyl chloride for dimethylcarbamyl chloride, and following the methods for the preparation of Example 2, gave the title compound as a white solid.

NMR data was as follows:

$^1$H NMR (CDCl$_3$): δ=7.71 (d, 2H), 7.32 (d, 2H), 7.15 (d, 2H), 7.04 (d, 2H), 4.73–4.67 (m, 1H), 4.07–4.04 (m, 1H), 3.53 (t, 2H), 3.45 (t, 2H), 3.36–3.32 (m, 1H), 3.24–2.98 (m, 3H), 2.42 (s, 3H), 2.03–1.88 (m, 5H), 1.75 (s, 1H), 1.52 (1.24 (m, 12H).

$^{13}$C NMR (CDCl$_3$): δ=170.7, 169.8, 153.1, 150.4, 144.3, 133.1, 130.1, 129.9, 127.9, 121.6, 110.8, 99.8, 82.5, 62.2, 53.7, 49.5, 46.3, 37.2, 29.7, 27.8, 25.6, 24.8, 24.0, 21.4.

Example 84

Synthesis of N-(4-Fluorobenzenesulfonyl)-L-thiaprolyl-L-4-(N,N-dimethylcarbamyloxy)phenylalanine tert-Butyl Ester The title compound was prepared following the procedures described for the preparation of Example 2 and substitution of appropriate starting materials.

NMR data was as follows:
¹H NMR (CDCl₃): δ=7.87 (m, 2H), 7.28–7.13 (m, 5H), 7.02 (d, 2H), 4.70–4.60 (m, 2H), 4.58 (d, 1H), 4.06 (d, 1H), 3.38–3.01 (m, 3H), 3.09 (s, 3H), 3.00 (s, 3H), 2.58 (m, 1H), 1.47 (s, 9H).
¹³C NMR (CDCl₃): δ=169.7, 167.8, 154.9, 150.7, 132.7, 130.9, 130.7, 130.4, 121.8, 117.1, 116.8, 82.9, 65.1, 53.9, 51.4, 36.8, 36.6, 36.4, 33.1, 27.9.

Example 85

Synthesis of N-(4-Fluorobenzenesulfonyl)-L-(1,1-dioxo)thiaprolyl-L-4-(N,N-dimethylcarbamyloxy)phenylalanine tert-Butyl Ester The title compound was prepared from the product of Example 84 following the procedure oxidation procedure of Larsson and Carlson (*Acta Chemica Scan*. 1994, 48, 517–525).

NMR data was as follows:
¹H NMR (CDCl₃): δ=7.90 (m, 2H), 7.30–7.04 (m, 7H), 4.83–4.58 (m, 3H), 3.66 (m, 2H), 3.32–3.24 (m, 1H), 3.09–2.85 (m, 2H), 3.10 (s, 3H), 3.01 (s, 3H), 1.50 (s, 9H).
¹³C NMR (CDCl₃): δ=173.1, 169.8, 168.0, 165.6, 154.9, 150.9, 132.6, 131.1, 131.0, 130.3, 122.3, 117.3, 117.0, 83.2, 62.8, 57.8, 53.9, 49.0, 36.8, 36.6, 36.4, 27.9.

Example 86

Synthesis of N-(2,5-Dichlorothiophene-3-sulfonyl)-L-prolyl-L-4-(N,N-dimethylcarbamyloxy)phenylalanine tert-Butyl Ester The title compound was prepared following the procedure described for the preparation of Example 2 and substitution of appropriate stating materials.

NMR data was as follows:
¹H NMR (CDCl₃): δ=7.14 (d, 2H), 7.09 (s, 1H), 7.07 (d, 1H), 7.01 (d, 2H), 4.73–4.66 (m, 1H), 4.32–4.28 (m, 1H), 3.42–3.17 (m, 3H), 3.08 (s, 3H), 3.06–3.01 (m, 1H), 2.98 (s, 3H), 2.17–2.04 (m, 1H), 1.84–1.60 (m, 2H), 1.60–1.46 (m, 1H), 1.45 (s, 9H).
¹³C NMR (CDCl₃): δ=170.2, 169.9, 154.9, 150.6, 133.4, 133.1, 131.2, 130.2, 127.9, 127.0, 121.7, 82.7, 62.2, 53.6, 49.3, 37.2, 36.6, 36.4, 30.1, 27.8, 24.2.

Example 87

Synthesis of N-(4-Acetamidobenzenesulfonyl)-L-prolyl-L-4-(N,N-dimethylcarbamyloxy)phenylalanine tert-Butyl Ester The title compound was prepared following the procedure described for the preparation of Example 2 and substitution of appropriate starting materials.

NMR data was as follows:
¹H NMR (CDCl₃): δ=8.58 (s, 1H), 7.70–7.67 (m, 4H), 7.32 (d, 1H), 7.14 (d, 2H), 7.01 (d, 2H), 4.68 (m, 1H), 3.99 (m, 1H), 3.37–3.34 (m, 1H), 3.23–3.16 (m, 1H), 3.11–3.01 (m, 1H), 3.08 (s, 3H), 2.98 (s, 3H), 2.13 (s, 3H), 1.97–1.94 (m, 1H), 1.55–1.47 (m, 3H), 1.44 (s, 9H).
¹³C NMR (CDCl₃): δ=171.1, 169.9, 169.4, 155.0, 150.6, 143.3, 133.3, 130.2, 130.0, 128.9, 121.7, 119.4, 82.7, 62.2, 53.8, 49.6, 37.2, 36.6, 36.4, 29.9, 27.8, 24.4, 24.1.

Example 88

Synthesis of N-(4-tert-Butylbenzenesulfonyl)-L-(1,1-dioxothiamorpholin-3-carbonyl)-L-4-(N,N-dimethylcarbamyloxy)phenylalanine tert-Butyl Ester The title compound was prepared following the procedure outlined for the preparation of Example 73 and substitution of appropriate starting materials.

NMR data was as follows:
¹H NMR (CDCl₃): δ=7.81 (d, 2H), 7.59 (d, 2H), 7.07 (d, 2H), 6.97 (d, 2H), 6.46 (d, 1H), 4.95 (m, 1H), 4.62 (m, 1H), 4.06 (m, 2H), 3.23 (m, 1H), 3.07 (m, 4H), 2.97 (m, 4H), 2.81 (m, 4H), 1.55 (s, 9H), 1.37 (s, 9H).
¹³C NMR (CDCl₃): δ=170.0, 164.9, 158.2, 154.8, 150.6, 135.0, 132.6, 130.2, 127.4, 126.9, 122.2, 82.7, 56.1, 53.5, 49.7, 48.8, 41.5, 36.5, 36.3, 36.1, 35.2, 30.8, 27.8.

Example 89

Synthesis of N-(Pyridine-3-sulfonyl)-L-prolyl-L-4-(N,N-dimethylcarbamyloxy)phenylalanine The title compound was prepared from the product of Example 56 using the procedure described in Method 11.

NMR data was as follows:
¹H NMR (CD₃OD): δ=8.95 (s, 1H), 8.83 (d, 1H), 8.28–8.24 (m, 1H), 7.73–7.69 (m, 1H), 7.30 (d, 2H), 7.05 (d, 2H), 4.68–4.63 (m, 1H), 4.29–4.25 (m, 1H), 3.47–3.41 (m, 1H), 3.38–3.22 (m, 2H), 3.09 (s, 3H), 3.06–3.02 (m, 1H), 2.96 (s, 3H), 1.92–1.66 (m, 4H).
¹³C NMR (CD₃OD): δ=174.2, 173.9, 160.6, 160.0, 156.9, 152.9, 152.0, 147.9, 139.1, 136.9, 135.7, 131.6, 126.5, 123.1, 63.1, 54.8, 50.4, 37.5, 36.8, 36.7, 32.2, 25.5.

Example 90

Synthesis of N-(2-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-3-carboxylic acid was prepared by the method of Larsson and Carlson (*Acta Chemica Scan*. 1994, 48, 517–525). N-(2-fluorobenzene-4-sulfonyl)-L-thiamorpholine-3-carboxylic acid was prepared using the procedure described in Method 1. The title compound was prepared according to the procedures set forth above using suitable starting materials.

NMR data was as follows:
¹H NMR (CDCl₃): δ=7.92 (m, 1H), 7.69 (m, 1H), 7.34 (m, 2H), 7.16 (m, 2H), 6.99 (m, 2H), 6.60 (d, 1H), 5.01 (m, 1H), 4.64 (m, 1H), 4.03 (m, 2H), 3.29 (m, 1H), 3.06 (m, 6H), 2.90 (m, 7H), 1.49 (d, 9H).
¹³C NMR (CDCl₃): δ=169.9, 164.8, 160.3, 156.9, 154.9, 150.7, 136.6, 136.4, 132.7, 131.0, 130.3, 128.8, 126.4, 126.2, 125.1, 122.2, 118.1, 117.8, 82.7, 56.3, 56.7, 50.2, 49.5, 41.8, 36.5, 36.3, 27.8.

Example 91

Synthesis of N-(3-Fluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan*. 1994, 48, 517–525). N-(3-fluorobenzene-4-sulfonyl)-L-thiamorpholine-5-carboxylic acid was prepared using the procedure described in Method 1. The title compound was prepared according to the procedures set forth above using suitable starting materials.

NMR data was as follows:
¹H NMR (CDCl₃): δ=7.66 (m, 1H), 7.58 (m, 2H), 7.34 (m, 1H), 7.07 (d, 1H), 6.92 (d, 1H), 6.42 (d, 1H), 5.00 (m, 1H), 4.58 (m, 1H), 4.02 (m, 2H), 3.22 (m, 1H), 3.05 (s, 3H), 2.98 (m, 6H), 1.45 (s, 9H).

¹³C NMR (CDCl₃): δ=170.0, 164.5, 164.4, 161.0, 154.9, 150.6, 140.3, 140.2, 132.5, 131.9, 131.8, 130.2, 123.2, 123.1, 122.2, 121.4, 121.2, 115.0, 114.7, 82.9, 56.1, 53.4, 49.9, 49.1, 41.7, 36.5, 36.3, 36.0, 27.8.

Example 92

Synthesis of N-(2,4-Difluorobenzenesulfonyl)-L-(1,1-dioxothiamorpholin-3-carbonyl)-L-4-(N,N-dimethylcarbamyloxy)phenylalanine tert-Butyl Ester L-Thiamorpholine-5-carboxylic acid was prepared by the method of Larsson and Carlson (*Acta Chemica Scan*. 1994, 48, 517–525). N-(2,4-difluorobenzene-4-sulfonyl)-L-thiamorpholine-5-carboxylic acid was prepared using the procedure described in Method 1. The title compound was prepared according to the procedures set forth above using suitable starting materials.

NMR data was as follows:

¹H NMR (CDCl₃): δ=7.93 (m, 1H), 7.15 (m, 2H), 7.04 (m, 4H), 6.53 (d, 1H), 4.97 (m, 1H), 4.64 (m, 1H), 4.05 (m, 2H), 3.21 (m, 3H), 3.17 (s, 3H), 2.97 (m, 5H), 1.43 (s, 9H).

¹³C NMR (CDCl₃): δ=170.0, 164.6, 154.9, 150.7, 132.6, 132.6, 130.3, 122.6, 122.1, 112.6, 112.3, 107.0, 106.7, 106.3, 82.8, 56.3, 53.5, 50.5, 49.8, 42.0, 36.5, 36.3, 27.8.

Example 93

Synthesis of N-(4-Acetamidobenzenesulfonyl)-L-prolyl-L-4-(N,N-dimethylcarbamyloxy)phenylalanine The title compound was prepared from the product of Example 87 using the procedure described in Method 11.

NMR data was as follows:

¹H NMR (CD₃OD): δ=8.05 (d, 1H), 7.78 (m, 4H), 7.26 (d, 2H), 7.02 (d, 2H), 4.94 (m, 1H), 4.72–4.67 (m, 1H), 4.13–4.09 (m, 1H), 3.40–3.36 (m, 1H), 3.30–3.05 (m, 3H), 3.08 (s, 3H), 2.97 (s, 3H), 2.15 (s, 3H), 1.81–1.51 (m, 4H).

¹³C NMR (CD₃OD): δ=174.3, 174.2, 172.3, 156.9, 152.0, 144.9, 135.5, 132.4, 131.6, 130.2, 122.9, 120.7, 63.2, 54.7, 50.6, 37.5, 36.8, 36.7, 31.7, 25.4, 24.0.

Example 94

Synthesis of N-(4-Trifluoromethoxybenzenesulfonyl)-L-prolyl-L-4-(N,N-dimethylcarbamyloxy)phenylalanine The title compound was prepared from the product of Example 72 using the procedure described in Method 11.

NMR data was as follows:

¹H NMR (CD₃OD): δ=7.93 (d, 2H), 7.48 (d, 2H), 7.28 (d, 2H), 7.03 (d, 2H), 4.72–4.68 (m, 1H), 4.17–4.13 (m, 1H), 3.45–3.42 (m, 1H), 3.28–3.11 (m, 2H), 3.14–3.07 (m, 1H), 3.09 (s, 3H), 2.97 (s, 3H), 1.85–1.69 (m, 3H), 1.59 (m, 1H).

¹³C NMR (CD₃OD): δ=174.2, 174.1, 157.0, 153.9, 152.0, 137.3, 135.6, 131.7, 131.5, 123.0, 122.5, 121.8, 63.1, 54.7, 50.6, 37.4, 36.8, 36.6, 31.9, 25.4.

Example 95

Synthesis of N-(4-Fluorobenzenesulfonyl)-L-(5,5-dimethyl)thiaprolyl-L-4-(N,N-dimethylcarbamyloxy)phenylalanine tert-Butyl Ester The title compound was prepared using the procedure described in Example 2 and substitution of appropriate starting materials.

NMR data was as follows:

¹H NMR (CDCl₃): δ=7.90 (m, 2H), 7.22 (m, 4H), 7.00 (m, 3H), 5.08 (m, 1H), 4.84 (m, 1H), 4.56 (d, 1H), 4.42 (d, 1H), 3.88 (s, 1H), 3.15–2.99 (m, 2H), 3.09 (s, 3H), 3.00 (s, 3H), 1.26–1.16 (m, 12H).

¹³C NMR (CDCl₃): δ=170.4, 168.2, 167.5, 164.1, 154.9, 150.7, 132.8, 132.2, 132.1, 131.0, 130.8, 130.3, 121.8, 116.9, 116.6, 73.5, 69.6, 54.6, 53.2, 50.5, 37.6, 36.6, 36.3, 29.1, 23.8, 21.6, 21.5.

Example 96

Synthesis of N-(4-Cyanobenzenesulfonyl)-L-prolyl-L-4-(N,N-dimethylcarbamyloxy)phenylalanine The title compound was prepared from the product of Example 58 using the procedure described in Method 11.

NMR data was as follows:

¹H NMR (CD₃OD): δ=8.14 (d, 1H), 7.94–7.89 (m, 4H), 7.29 (d, 2H), 7.03 (d, 2H), 4.70–4.66 (m, 1H), 4.21–4.17 (m, 1H), 3.47–3.40 (m, 1H), 3.31–3.21 (m, 2H), 3.11–3.04 (m, 1H), 3.09 (s, 3H), 2.97 (s, 3H), 1.87–1.72 (m, 3H), 1.70–1.61 (m, 1H).

¹³C NMR (CD₃OD): δ=174.2, 173.9, 157.0, 152.0, 142.9, 135.7, 134.5, 131.7, 129.7, 123.0, 118.6, 111.8, 63.0, 54.7, 50.5, 37.4, 36.8, 36.7, 32.0, 25.4.

Example 97

Synthesis of N-(Toluene-4-sulfonyl)-L-(3,3-dimethyl)prolyl-L-4-(N,N-dimethylcarbamyloxy)phenylalanine tert-Butyl Ester The title compound was prepared using the procedure described for the preparation of Example 98.

NMR data was as follows:

¹H NMR (CDCl₃): δ=7.76 (d, 1H), 7.75 (d, 1H), 7.35 (d, 1H), 7.34 (d, 1H), 7.33 (d, 1H), 7.20 (d, 1H), 7.10 (d, 1H), 7.03 (d, 1H), 6.91 (d, 0.5H), 6.08 (d, 0.5H), 4.86 (ddd, 0.5H), 4.77 (q, 0.5H), 3.61–3.47 (m, 2H), 3.27–3.02 (m, 3H), 3.09 (s, 3H), 3.00 (s, 3H), 2.45 (s, 1.5H), 2.43 (s, 1.5H), 1.75–1.68 (m, 0.5H), 1.61–1.51 (m, 0.5H), 1.45 (s, 4.5H), 1.40 (s, 4.5H), 1.48–1.25 (m, 3H); 0.95 (s, 1.5H), 0.80 (s, 1.5H); 0.61 (s, 1.5H).

¹³C NMR (CDCl₃): δ=170.4, 170.1, 170.0, 169.6, 155.0, 154.9, 150.7, 150.6, 144.3, 144.2, 133.4, 133.1, 132.8, 132.6, 130.7, 130.2, 129.9, 129.8, 128.0, 121.8, 121.7, 82.6, 82.2, 71.5, 71.2, 53.6, 52.7, 47.3, 47.2, 42.7, 42.5, 38.2, 38.1, 37.7, 37.5, 36.6, 36.3, 27.8, 27.8, 27.2, 23.4, 23.2, 21.5.

Example 98

Synthesis of N-(Toluene-4-sulfonyl)-L-(3,3-dimethyl)prolyl-L-4-(N,N-dimethylcarbamyloxy)phenylalanine Isopropyl Ester 3,3-Dimethyl proline (see Sharma and Lubell, *J. Org. Chem*. 1996, 61, 202–209) was N-tosylated using the procedure described in Method 1. The title compound was then prepared following the procedure described for the preparation of Example 2.

NMR data was as follows:

¹H NMR (CDCl₃): δ=7.76 (d, 1H), 7.74 (d, 1H), 7.36 (d, 1H), 7.33 (d, 2H), 7.19 (d, 1H), 7.10 (d, 1H), 7.03 (d, 1H), 6.91 (d, 0.5H), 6.89 (d, 0.5H), 5.06 (sept., 0.5H), 4.96 (sept., 0.5H), 4.98–4.83 (m, 1H), 3.59–3.48 (m, 2H), 3.31–3.03 (m, 3H), 3.09 (s, 3H), 3.00 (s, 3H), 2.45 (s, 1.5H), 2.43 (s, 1.5H), 1.75–1.66 (m, 0.5), 1.62–1.52 (m, 0.5H), 1.34–1.22 (m, 3H), 1.27 (s, 1.5H), 1.25 (s, 1.5H), 1.22 (s, 1.5H), 1.20 (s, 1.5H), 0.95 (s, 1.5H), 0.78 (s, 1.5H), 0.60 (s, 1.5H), 0.57 (s, 1.5H).

$^{13}$C NMR (CDCl$_3$): δ=170.8, 170.6, 170.0, 169.7, 154.9, 150.8, 150.6, 144.4, 144.2, 133.2, 132.5, 132.5, 130.7, 130.2, 129.9, 129.8, 128.0, 122.0, 121.8, 71.5, 17.2, 69.5, 69.3, 53.0, 52.2, 47.3, 47.2, 42.8, 42.5, 38.2, 38.1, 37.6, 37.2, 36.6, 36.3, 27.1, 23.4, 23.2, 21.6, 21.6, 21.5, 21.5.

Other compounds prepared by the methods described above include those set forth in Examples 99–137 in Table II below. In addition, Examples 101, 109, 111, 117, 132 and 137 found in Table II are exemplified as follows:

Example 101

Synthesis of N-(Toluene-4-sulfonyl)-L-prolyl-4-(N, N-dimethylcarbamyloxy)-L-phenylalanine Isopropyl Ester The title compound was prepared following the procedure outlined for the preparation of Example 2.

NMR data was as follows:

$^1$H NMR (CD$_3$)$_2$SO: δ=8.28 (d, 1H), 7.70 (d, 2H), 7.41 (d, 2H), 7.23 (d, 2H), 6.99 (d, 2H), 4.86 (sept, 1H), 4.47 (m, 1H), 4.40 (m, 1H), 4.10 (m, 1H), 4.07 (m, 1H), 3.38 (m, 1H), 3.30 (m, 1H), 3.09 (m, 3H), 2.95 (s, 3H), 3.00 (s, 3H), 2.88 (s, 3H), 2.39 (s, 3H), 1.63 (m, 3H), 1.51 (m, 3H), 1.44 (m, 1H), 1.39 (m, 1H), 1.16 (d, 3H), 1.11 (d, 3H).

$^{13}$C NMR (CD$_3$)$_2$SO: δ=171.3, 170.8, 154.2, 150.2, 143.7, 134.1, 130.2, 130, 127.6, 121.6, 68.2, 61.2, 53.5, 49, 36.3, 36.1, 35.7, 30.5, 23.8, 21.4, 21.4, 21.

Example 109

Synthesis of N-(Benzylsulfonyl)-L-(5,5-dimethyl)thiaprolyl-L-(4-N,N-dimethylcarbamyloxy)phenylalanine The title compound was prepared from the product of Example 111 using the procedure described in Method 11.

Physical data was as follows:

MS (FAB) (M+H)$^+$ 550.

Calcd. for: C$_{25}$H$_{31}$N$_3$O$_7$S$_2$; C, 54.62; H, 5.68; N, 7.64.

Found: C, 54.51; H, 5.60; N, 7.63.

Example 111

Synthesis of N-(Benzylsulfonyl)-L-(5,5-dimethyl)thiaprolyl-L-(4-N,N-dimethylcarbamyloxy)phenylalanine tert-Butyl Ester The title compound was prepared following the procedure outlined for the preparation of Example 2 and by substituting the appropriate starting materials.

Physical data was as follows:

MS [M+H]$^+$ 550.

Calcd. for: C$_{29}$H$_{39}$N$_3$O$_7$S$_2$; C, 57.52; H, 6.45; N, 6.94.

Found: C, 57.32; H, 6.52; N, 6.81.

Example 117

Synthesis of N-(Methyl-pyrazole-sulfonyl)-L-prolyl-L-(4-N,N-dimethylcarbamyloxy)phenylalanine tert-Butyl Ester Substituting N-methyl-pyrazole sulfonyl chloride (see Dickson, U.S. Pat. No. 3,665,009 (May 23, 1972) and following the method for the preparation of Example 56, gave the title compound.

NMR data was as follows:

$^1$H NMR (CDCl$_3$): δ=7.83 (s, 1H), 7.76 (s, 1H), 7.26 (m, 1H), 7.15 (m, 2H), 7.00 (m, 2H), 4.69 (m, 1H), 3.95 (m, 1H), 3.93 (s, 3H), 3.38 (m, 1H), 3.23–3.11 (m, 1H), 3.10–2.99 (m, 4H), 2.99 (s, 3H), 2.05 (m, 1H), 1.66–1.46 (m, 3H), 1.44 (s, 9H).

$^{13}$C NMR (CDCl$_3$): δ 170.7, 169.9, 154.9, 150.6, 138.9, 133.2, 132.5, 130.2, 121.7, 117.9, 82.6, 62.4, 53.7, 49.7, 39.6, 37.7, 36.6, 36.4, 29.9, 27.9, 24.2.

Example 132

Synthesis of N-(4-Fluorobenzenesulfonyl)-L-prolyl-L-4-(1,1-dioxothiomorpholin-4-ylcarbonyloxy)-phenylalanine tert-Butyl Ester Substituting thiamorpholine for N-methylpiperazine, and following the method for the preparation of Example 4 and 14, gave the title compound.

NMR data was as follows:

$^1$H NMR (CDCl$_3$): δ=7.87–7.82 (m, 2H), 7.28–7.17 (m, 5H), 7.01 (d, 2H), 4.71–4.69 (m, 1H), 4.14–4.05 (m, 5H), 3.39–3.36 (m, 1H), 3.23–3.01 (m, 7H), 2.05–2.03 (m, 1H), 1.58–1.44 (m, 12H).

$^{13}$C NMR (CDCl$_3$): δ=170.4, 169.8, 153.0, 149.7, 134.2, 130.6, 130.5, 121.3, 116.8, 116.5, 82.6, 62.1, 53.6, 51.8, 49.5, 43.1, 42.7, 37.2, 29.7, 27.8, 24.2.

Example 137

Synthesis of N-(Methyl-pyrazole-4-sulfonyl)-L-prolyl-L-(4-N,N-dimethylcarbamyloxy)-phenylalanine Isopropyl Ester The title compound was prepared following the procedure described for the preparation of Example 117.

NMR data was as follows:

$^1$H NMR (CDCl$_3$): δ 7.83 (s, 1H), 7.76 (s, 1H), 7.27 (d, 1H), 7.13 (d, 2H), 7.01 (d, 2H), 5.06–5.02 (m, 1H), 4.80–4.73 (m, 1H), 3.97–3.94 (m, 1H), 3.93 (s, 3H), 3.44–3.37 (m, 1H), 3.25–3.19 (m, 1H), 3.09–3.00 (m, 5H), 2.97 (s, 3H), 2.06–2.02 (m, 1H), 1.66–1.48 (m, 3H), 1.23 (d, 6H).

$^{13}$C NMR (CDCl$_3$): δ 170.8, 170.5, 154.9, 150.6, 138.9, 132.9, 32.5, 130.2, 121.7, 117.8, 69.5, 62.3, 53.2, 49.7, 39.6, 37.1, 36.6, 36.3, 29.9, 24.1, 21.6, 21.5.

TABLE II $$R^1-\underset{\underset{O}{\|}}{\overset{\overset{O}{\|}}{S}}-\underset{R^2}{N}-\underset{\underset{R^3}{|}}{CH}-\overset{\overset{O}{\|}}{C}-\underset{H}{N}-\underset{\underset{R^5}{|}}{CH}-\overset{\overset{O}{\|}}{C}-R^{6'}$$

| R¹ | R² | R³ | R₅ | R₆' | Ex. No. |
|---|---|---|---|---|---|
| p-CH₃-ϕ- | R²R³ cyclic 3 carbon atoms (L-pyrrolidinyl) | | p-[(4-methylpiperazine-1-yl)C(O)O—]benzyl- | —O-n-butyl | 99 |
| p-CH₃-ϕ- | R²R³ cyclic 3 carbon atoms (L-pyrrolidinyl) | | p-[(4-methylpiperazine-1-yl)C(O)O—]benzyl- | —O-cyclopentyl | 100 |
| p-CH₃-ϕ- | R²R³ cyclic 3 carbon atoms (L-pyrrolidinyl) | | p-[(CH₃)₂NC(O)O—]benzyl- | —OCH(CH₃)₂ | 101 |
| p-CH₃-ϕ- | R²R³ cyclic 3 carbon atoms (L-pyrrolidinyl) | | p-[(piperdidin-4-yl)C(O)O—]benzyl- | —OCH₂CH₃ | 102 |
| ϕ-CH₂— | R²R³ cyclic 3 carbon atoms (L-pyrrolidinyl) | | p-[(1-methylpiperidine-4-yl)C(O)O—]benzyl- | —OCH₂CH₃ | 103 |
| ϕ-CH₂— | R²R³ cyclic 3 carbon atoms (L-pyrrolidinyl) | | p-[(4-methylpiperazine-1-yl)C(O)O—]benzyl- | —OH | 104 |
| p-CH₃-ϕ- | R²R³ cyclic 3 carbon atoms (L-pyrrolidinyl) | | p-[(1-Boc-4-phenylpiperidin-4-yl)-C(O)O—]benzyl- | —OCH₂CH₃ | 105 |
| 1-methylimidazol-4-yl | R²R³ cyclic 3 carbon atoms (L-pyrrolidinyl) | | p-[(CH₃)₂NC(O)O—]benzyl- | —OC(CH₃)₃ | 106 |
| p-NH₂-ϕ- | R²R³ cyclic 3 carbon atoms (L-pyrrolidinyl) | | p-[(CH₃)₂NC(O)O—]benzyl- | —OC(CH₃)₃ | 107 |
| p-CH₃-ϕ- | R²R³ cyclic 3 carbon atoms (L-pyrrolidinyl) | | p-[(morpholin-4-yl)C(O)O—]benzyl- | —OC(CH₃)₃ | 108 |
| ϕ-CH₂— | R²R³ cyclic —CH₂—S—C(CH₃)₂— | | p-[(CH₃)₂NC(O)O—]benzyl- | —OH | 109 |
| p-CH₃-ϕ- | R²R³ cyclic —CH₂CH₂—NH—CH₂— (L-piperizinyl) | | p-[(CH₃)₂NC(O)O—]benzyl- | —OH | 110 |
| ϕ-CH₂— | R²R³ cyclic —CH₂—S—C(CH₃)₂— | | p-[(CH₃)₂NC(O)O—]benzyl- | —OC(CH₃)₃ | 111 |
| p-CH₃-ϕ- | R²R³ cyclic 3 carbon atoms (L-pyrrolidinyl) | | p-[(CH₃)₂NC(O)O—]benzyl- | —NH-adamantyl | 112 |
| p-CH₃-ϕ- | R²R³ cyclic 3 carbon atoms (L-pyrrolidinyl) | | p-[(CH₃)₂NC(O)O—]benzyl- | —NHCH₂C(O)OH | 113 |
| p-CH₃-ϕ- | R²R³ cyclic 3 carbon atoms (L-pyrrolidinyl) | | p-[(CH₃)₂NS(O)₂O—]benzyl- | —OCH₃ | 114 |
| p-CH₃-ϕ- | R²R³ cyclic —CH₂CH₂—NH—CH₂— (L-piperizinyl) | | p-[(CH₃)₂NC(O)O—]benzyl- | —OC(CH₃)₃ | 115 |
| p-CH₃-ϕ- | R²R³ cyclic —CH₂CH₂— (Cbz)NHCH₂— (L-4-N-(Cbz)-piperizinyl] | | p-[(CH₃)₂NC(O)O—]benzyl- | —OC(CH₃)₃ | 116 |
| 1-methylpyrazol-4-yl | R²R³ cyclic 3 carbons atoms (L-pyrrolidinyl) | | p-[(CH₃(₂NC(O)O—]benzyl- | —OC(CH₃)₃ | 117 |
| 3-pyridyl | R²R³ cyclic 3 carbon atoms (L-pyrrolidinyl) | | p-[(CH₃(₂NC(O)O—]benzyl- | —OH | 118 |
| p-CH₃-ϕ | R²R³ cyclic 3 carbon atoms (L-pyrrolidinyl) | | p-[(1-Boc-piperazin-4-yl)C(O)O—]benzyl- | —OCH₂CH₃ | 119 |
| p-CH₃-ϕ | R²R³ cyclic 3 carbon atoms (L-pyrrolidinyl) | | p-[(morpholin-4-yl)C(O)O—]benzyl- | —OCH₂CH₃ | 120 |
| p-CH₃-ϕ | —CH₁₃ | H | p-[(thiomorpholin-4-yl sulfone)-C(O)O—]benzyl- | —OC(CH₁₃)₃ | 121 |
| p-CH₃-ϕ | —CH₁₃ | H | p-[(thiomorpholin-4-yl sulfone)-C(O)O—]benzyl- | —OH | 122 |
| p-CH₃-ϕ | R²R³ cyclic 3 carbon atoms | | p-[(CH₃)₂NC(O)O—]benzyl- | 2,4-dioxo-tetrahydrofuran- | 123 |

TABLE II-continued $$R^1-\underset{\underset{O}{\|}}{\overset{\overset{O}{\|}}{S}}-\underset{R^2}{N}-\underset{}{CH}-\overset{\overset{O}{\|}}{C}-\underset{H}{N}-\underset{}{CH}-\overset{\overset{O}{\|}}{C}-R^{6'}$$

| R¹ | R² | R³ | R₅ | R₆' | Ex. No. |
|---|---|---|---|---|---|
| p-CH₃-φ | (L-pyrrolidinyl) R²R³ cyclic 3 carbon atoms | | p-[(piperazin-4-yl)C(O)O—]benzyl- | 3-yl(3,4-enol) —OH | 124 |
| p-CH₃-φ | (L-pyrrolidinyl) R²R³ cyclic 3 carbon atoms | | p-[(1-Bpc-piperazin-4-yl)C(O)O—]benzyl- | —OC(CH₃)₃ | 125 |
| p-CH₃-φ | (L-pyrrolidinyl) R²R³ cyclic 3 carbon atoms | | p-[(piperazin-4-yl)C(O)O—]benzyl- | —OCH₂CH₃ | 126 |
| p-CH₃-φ | (L-pyrrolidinyl) R²R³ cyclic 3 carbon atoms | | p-[(4-acetylpiperazin-1-yl)C(O)O—]benzyl— | —OCH₂CH₃ | 127 |
| p-CH₃-φ | (L-pyrrolidinyl) R²R³ cyclic 3 carbon atoms | | p-[(4-methanesulfonylpiperazin-1-yl)C(O)O—]benzyl— | —OCH₂CH₃ | 128 |
| p-CH₃-φ | (L-pyrrolidinyl) R²R³ cyclic 3 carbon atoms | | 3-nitro-4-[(morpholin-4-yl)-C(O)O—]benzyl- | —OH | 129 |
| p-CH₃-φ | (L-pyrrolidinyl) R²R³ cyclic 3 carbon atoms | | p-[(1-Boc-piperazin-4-yl)C(O)O—]benzyl- | —OH | 130 |
| p-CH₃-φ | —CH₃ | —C(CH₃)₃ | p-[(4-methylpiperazine-1-yl)C(O)O—]benzyl- | —OC(CH₃)₃ | 131 |
| p-F-φ | (L-pyrrolidinyl) R²R³ cyclic 3 carbon atoms | | p-[(1,1-dioxothiomorpholin-4-yl)-C(O)O—]benzyl- | —OC(CH₃)₃ | 132 |
| p-F-φ | (L-pyrrolidinyl) R²R³ cyclic 3 carbon atoms | | p-[(morpholin-4-yl)C(O)O—]benzyl- | —OC(CH₃)₃ | 133 |
| p-CH₃-φ | (L-pyrrolidinyl) R²R³ cyclic —CH₂CH₂SO₂CH₂— (L-1,1-dioxothiomorpholin-3-yl) | | p-[(morpholin-4-yl)C(O)O—]benzyl- | —OH | 134 |
| 1-methylpyrazol-4-yl | R³ cyclic 3 carbon atoms (L-pyrrolidinyl) | | p-[(methylpiperazin-1-yl)C(O)O—]benzyl- | —OC(CH₃)₃ | 135 |
| morpholin-4-yl | R³ cyclic 3 carbon atoms (L-pyrrolidinyl) | | p-[(CH₃)₂NC(O)O—]benzyl- | —OC(CH₃)₃ | 136 |
| 1-methylpyrazol-4-yl | R³ cyclic 3 carbon atoms (L-pyrrolidinyl) | | p-[(CH₃)₂NC(O)O—]benzyl- | —OC(CH₃)₃ | 137 |

Additional compounds prepared by the methods described above include the following:

Example 138
Synthesis of N-(1-Methylpyrazole-4-sulfonyl)-L-(5,5-dimethyl)thiaprolyl-L-4-(N,N-dimethylcarbamyloxy)phenylalanine tert-Butyl Ester The N-methylpyrazole sulfonyl chloride was prepared by adding N-methylpyrazole to chilled (0° C.) chlorosulfonic acid. The reaction mixture was allowed to warm to room temperature and then heated to 100° C. overnight under a stream of N₂. The reaction mixture was then cooled to room temperature and chilled to 0° C. To this solution was added thionyl chloride (2.5 eq.) and the reaction was stirred at room temperature for 30 min., then warmed to 70° C. for two hours. The reaction was cooled to room temperature and then chilled in an ice bath. Water and ice were slowly added to the reaction mixture to precipitate a white solid which was collected by filtration. The desired sulfonyl chloride was washed with cold water and hexane.

The title compound was then prepared following the procedure outlined for the preparation of Example 2 by substitution of the appropriate starting materials, mp: 169–170° C.

Example 139
Synthesis of N-(1-Methylpyrazole-4-sulfonyl)-L-(5,5-dimethyl)thiaprolyl-L-4-(N,N-dimethylcarbamyloxy)phenylalanine The title compound was prepared from the product of Example 138 using the procedure described in Method 11. NMR data was as follows:

$^1$H NMR (CDCl₃): δ=7.94 (s, 1H); 7.79 (s, 1H); 7.25 (d, 2H, J=8.8 Hz); 7.0 (d, 2H, J=8.8 Hz); 5.15 (br s, 1H); 4.80 (m, 1H); 4.54 (d, 1H, J=9.9 Hz); 4.39 (d, 1H, J=9.3 Hz); 3.93 (s, 3H); 3.88 (s, 1H); 3.23–3.02 (m, 2H); 3.07 (s, 3H); 2.98 (s, 3H); 1.27 (s, 3H); 1.14 (s, 3H).

$^{13}$C NMR (CDCl₃): 173.86, 169.05, 155.23, 150.47, 139.21, 133.59, 133.15, 130.53, 121.84, 117.57, 73,58, 54,71, 53.75, 50.42, 39.60, 37.18, 36.60, 36.36, 35.11, 28.97, 23.95.

Example 140
Synthesis of N-(Toluene-4-sulfonyl)-L-prolyl-L-4-(N-(1,4-dioxa-8-aza-spiro[4.5]decan-8-yl)carbonyloxy)phenylalanine Ethyl Ester The title compound was prepared following the procedure outlined for Example 4 by substitution of the appropriate starting materials.

Physical data was as follows:

MS (+ESI): 630 [M+H]+.

Anal. Calcd. for $C_{31}H_{39}N_3O_9S.0.2\ CH_2Cl_2$: C, 57.94; H, 6.14; N, 6.50.

Found: C, 57.73; H, 5.90; N, 6.47.

Example 141

Synthesis of N-(Toluene-4-sulfonyl)-L-prolyl-L-4N-(1,4-dioxa-8-aza-spiro[4.5]decan-8-yl)carbonyloxy)phenylalanine The product of Example 140 was hydrolyzed using the procedure described in Method 5 but employing methanol as the solvent and running the reaction at 25° C. for 24 h. The solvent was then evaporated, the residue taken up in $H_2O$, washed with methylene chloride and lyophilized to afford the title compound.

Physical data was as follows:

MS (+ESI): 619 [M+H]+.

Anal. Calcd. for $C_{29}H_{35}N_3O_9SLi.1.5\ H_2O$: C, 53.37; H, 6.02; N, 6.44.

Found: C, 53.40; H, 5.58; N, 6.48.

Example 142

Synthesis of N-(Toluene-4-sulfonyl)-L-prolyl-L-4-(4'-acetylpiperazin-1-ylcarbonyloxy)phenylalanine The product of Example 127 was hydrolyzed using the procedure described in Method 5 but employing methanol as the solvent and running the reaction at 25° C. for 24 h. The solvent was then evaporated, the residue taken up in $H_2O$, washed with methylene chloride and lyophilized to afford the title compound.

Physical data was as follows:

MS (+ESI): 587 [M+H]+.

Anal. Calcd. for $C_{28}H_{33}N_4O_8SLi.3H_2O$: C, 52.01; H, 6.08; N, 8.66.

Found: C, 52.03; H, 5.36; N, 8.04.

Example 143

Synthesis of N-(Toluene-4-sulfonyl)-L-prolyl-L-4-(4'-methanesulfonylpiperazin-1-ylcarbonyloxy)phenylalanine The product of Example 128 was hydrolyzed using the procedure described in Example 142.

Physical data was as follows:

MS (+ESI): 623 [M+H]+.

Anal. Calcd. for $C_{27}H_{33}N_4O_9S_2Li.2\ H_2O$: C, 48.79; H, 5.61; N, 8.43.

Found: C, 48.66; H, 5.14; N, 8.04.

Example 144

Synthesis of N-(Toluene-4-sulfonyl)-L-prolyl-L-4-(4'-phenylpiperazin-1-ylcarbonyloxy)phenylalanine The ethyl ester of the title compound was prepared following the procedure outlined for Example 4 by substitution of the appropriate starting materials. The ethyl ester was then hydrolyzed using the procedure described in Example 142.

Physical data was as follows:

MS (−ESI): 619 [M−H]−.

Anal. Calcd. for $C_{32}H_{36}N_4O_7SLi.2H_2O$: C, 58.00; H, 5.93; N, 8.45.

Found: C, 57.65; H, 5.49; N, 8.13.

Example 145

Synthesis of N-(Toluene-4-sulfonyl)-L-prolyl-L-4-(piperazin-1-ylcarbonyloxy)phenylalanine tert-Butyl Ester The product of Example 125 (0.7 g, 1 mmol) was dissolved in methylene chloride (9 mL). The solution was cooled to 0° C. and trifluoroacetic acid (1.0 mL) was added and the resulting clear solution was stirred for 4 h. The reaction solution was then diluted with additional methylene chloride (50 mL), washed with saturated sodium bicarbonate solution (3×50 mL), dried ($K_2CO_3$) and the solvent stripped off to give a white solid (0.465 g). Flash chromatography (9:1 $CH_2Cl_2$:EtOH) of this material gave a clear oil which was washed several times with hexane to give a white solid (0.289 g, 48%).

Physical data was as follows:

MS (+ESI): 601.7 [M+1]+.

Anal. Calcd. for $C_{30}H_{40}N_4O_7S.0.25\ CH_2Cl_2$: C, 58.42; H, 6.56; N, 9.01.

Found: C, 58.79; H, 6.51; N, 8.74.

Example 146

Synthesis of 2-(Saccharin-2-yl)propionyl-L-4-(4'-methylpiperazin-1-ylcarbonyloxy)phenylalanine The title compound was prepared from the product of Example 46 using the procedure described in Method 11, mp=117–122° C. (with foaming).

Physical data was as follows:

Anal. Calcd. for $C_{25}H_{28}N_4O_8S.1.5H_2O$: C, 52.53; H, 5.47; N, 9.80.

Found: C, 52.26; H, 5.36; N, 9.23.

Example 147

Synthesis of N-(Toluene-4-sulfonyl)-L-prolyl-L-4-(4'-methanesulfonyl piperazin-1-ylcarbonyloxy)phenylalanine tert-Butyl Ester The title compound was prepared following the procedure outlined for Example 128 by substitution of the appropriate starting materials.

Physical data was as follows:

MS (+ESI): 696 [M+NH$_4$]+.

Anal. Calcd. for $C_{31}H_{42}N_4O_9S_2.0.5\ CH_2Cl_2$: C, 51.62; H, 6.00; N, 7.76.

Found: C, 51.55; H, 6.21; N, 7.60.

Example 148

Synthesis of N-(Toluene-4-sulfonyl)-L-prolyl-L-4-(N,N-dimethylcarbamyloxy)phenylalanine (N'-tert-butoxycarbonyl-2-amino-2-methylpropyl) Ester (BOC)$_2$O (96 mg, 0.44 mmol) was added to a solution of the product from Example 9 (200 mg, 0.4 mmol.), N-Boc-2-amino-2-methyl-1-propanol (965 mg, 0.5 mmol) and a catalytic amount of DMAP in THF (92 mL) containing pyridine (50 μl). The mixture was sted at room temperature under argon for 48 h. The mixture was poured into 1N HCl and extracted with ethyl acetate. The organic phase was washed (1N HCl), dried (MgSO$_4$) and the solvent was removed under reduced pressure. The residue was purified by flash chromatography (EtOAc:hexanes 2:1) to give the desired compound as an amorphous white foam (150 mg., 55%).

Physical data was as follows:

MS: [M+H]$^+$ at 675.

MS (+ESI): [M+NH$_4$]$^+$ at 692 (100%).

Example 149

Synthesis of N-(Toluene-4-sulfonyl)-L-prolyl-L-4-(N,N-dimethylcarbamyloxy)phenylalanine 2-(Morpholin-4-yl)ethyl Ester The title compound was prepared following the procedure outlined for Example 148 by substituting 2-morpholinoethanol for N-Boc-2-amino-2-methyl-1-propanol.

Physical data was as follows:

Anal. Calcd. for C$_{30}$H$_{40}$N$_4$O$_8$S.0.5 H$_2$O: C, 57.58; H, 6.60; N, 8.95.

Found: C, 57.26; H, 6.29; N, 8.82.

Example 150

Synthesis of N-(Toluene-4-sulfonyl)-L-prolyl-L-4-(4'-acetylpiperazin-1-ylcarbonyloxy)phenylalanine tert-Butyl Ester The title compound was prepared following the procedure outlined for Example 127 by substitution of the appropriate starting materials.

Physical data was as follows:

MS (+ESI): 660.4 [M+NH$_4$]$^+$.

Anal. Calcd. for C$_{32}$N$_{42}$N$_4$O$_8$S.0.15 CH$_2$Cl$_2$: C, 58.91; H, 6.50; N, 8.55.

Found: C, 58.64; H, 6.36; N, 8.40.

Example 151

Synthesis of N-(Toluene-4-sulfonyl)-L-prolyl-L-4-(4'-hydroxypiperidin-1-ylcarbonyloxy)phenylalanine tert-Butyl Ester The title compound was prepared following the procedure outlined for Example 4 by substituting 4-piperidinol for N-methyl piperazine.

Physical data was as follows:

Anal. Calcd. for C$_{31}$H$_{41}$N$_3$O$_8$S.0.6 H$_2$O.0.22 EtOAc: C, 59.28; H, 6.86; N, 6.51.

Found: C, 58.92; H, 6.37; N, 6.47.

Example 152

Synthesis of N-(Toluene-4-sulfonyl)-L-prolyl-L-4-(N-(2'-(morpholin-4'-yl)ethyl)carbamyloxy)phenylalanine tert-Butyl Ester The title compound was prepared following the procedure outlined for Example 4 by substituting 4-(2-aminoethyl)morpholine for N-methyl piperazine.

Physical data was as follows:

Anal. Calcd. for C$_{32}$H$_{44}$N$_4$O$_8$S.0.25 H$_2$O: C, 59.20; H, 6.91; N, 8.63.

Found: C, 59.01; H, 6.54; N, 8.38.

Example 153

Synthesis of N-(Toluene-4-sulfonyl)-L-prolyl-L-4-(N-(1,4-dioxa-8-aza-spiro[4.5]decan-8-yl)carbonyloxy)phenylalanine tert-Butyl Ester The title compound was prepared following the procedure outlined for Example 4 by substitution of the appropriate starting materials.

Physical data was as follows:

MS (−ESI): 656 [M−H]$^-$.

Anal. Calcd. for C$_{33}$H$_{43}$N$_3$O$_9$S.0.1 CH$_2$Cl$_2$: C, 59.67; H, 6.54; N, 6.31.

Found: C, 59.83; H, 6.63; N, 6.66.

Example 154

Synthesis of N-(Toluene-4-sulfonyl)-L-prolyl-L-4-(N-(2'-hydroxyethyl)-N-methylcarbamyloxy)phenylalanine tert-Butyl Ester The title compound was prepared following the procedure outlined for Example 4 by substituting 2-(methylamino)ethanol for N-methyl piperazine.

Physical data was as follows:

Anal. Calcd. for C$_{29}$H$_{39}$N$_3$O$_8$S.0.5 H$_2$O: C, 58.18; H, 6.73; N, 7.02.

Found: C, 57.95; H, 6.5; N, 6.9.

Example 155

Synthesis of N-(Toluene-4-sulfonyl)-L-prolyl-L-4-(4'-formyloxypiperidin-1-ylcarbonyloxy)phenylalanine The title compound was prepared by treating the product of Example 151 with formic acid overnight with stirring. The title compound was obtained as a white foam (130 mg., 94%), following removal of excess formic acid.

NMR data was as follows:

$^1$H NMR (DMSO-d$_6$, 400 MHZ) δ 12.8 (s, 1H); 8.23 (s, 1H); 8.09 (d, 1H); 7.69 (d, 2H), 7.4 (d, 2H); 7.23 (d, 2H); 7.02 (d, 2H); 5.00 (m, 1H); 4.45 (m, 1H); 4.10 (m, 1H); 3.6–3.8 (br, 2H); 3.4 (br s, 1H); 3.25 (m, 2H); 3.10 (m, 2H); 2.95 (m, 1H); 2.35 (s, 3H); 1.95 (m, 2H); 1.56–1.75 (m, 5H); 1.4 (m, 1H).

IR (KBr, cm$^{-1}$) 3400, 2950, 1720, 1680, 1510, 1430, 1325, 1250, 1150, 1010, 650, 75, 540.

MS ((+)ESI, m/z (%)) 605 (100 [M+NH, 1$^+$).

Anal. Calcd. for C$_{28}$H$_{33}$N$_3$O$_9$S.0.66H$_2$O: C, 56.09; H, 5.77; N, 7.01.

Found: C, 56.14; H, 5.83; N, 6.78.

Example 156

Synthesis of N-(Toluene-4-sulfonyl)-L-prolyl-L-4-(4'-hydroxypiperidin-1-ylcarbonyloxy)phenylalanine Isopropyl Ester The title compound was prepared following the procedure outlined for Example 4 by substitution of the appropriate starting materials, mp. 64–67° C. (with foaming).

Physical data was as follows:

Anal. Calcd. for C$_{30}$H$_{39}$N$_3$O$_8$S.0.75 H$_2$O.0.1 EtOAc: C, 58.51; H, 6.67; N, 6.73.

Found: C, 58.55; H, 6.09; N, 6.78.

Example 157

Synthesis of N-(Toluene-4-sulfonyl)-L-prolyl-L-4-(4'-(2-hydroxyethyl)piperazin-1-ylcarbonyloxy)phenylalanine tert-Butyl Ester The carbonate was prepared by treatment of Tos-Pro-Tyr-t-butyl ester with 4-nitrophenyl chloroformate, followed by addition of N-(2-hydroxyl ethyl)piperazine (triethylamine, methylene chloride, chilled to 0° C., then stirred at room temperature overnight). The crude product was purified by flash chromatography (silica, 95:5 EtOAc:EtOH) to afford a white solid, mp. 158–160° C. (0.387 g, 58%).

NMR data was as follows:

$^1$H NMR (DMSO-d$_6$, 400 MHz) δ=8.15 (d, 1H, J=7.90 Hz); 7.70 (d, 2H, J=6.59 Hz); 7.40 (d, 2H, J=7.90 Hz); 7.23 (d, 2H, J=8.56 Hz); 7.00 (d, 2H, J=8.56 Hz); 4.42 (m, 1H); 4.38 (m, 1H); 4.08 (m, 1H); 3.51 (m, 4H); 3.34 (m, 3H); 3.09 (m, 1H); 2.99 (m, 2H); 2.43 (m, 6H); 2.39 (s, 3H); 1.59 (m, 3H); 1.39 (m, 1H); 1.35 (s, 9H).

IR (KBr,cm$^{-1}$) 3505, 3400, 2990, 2930, 2890, 1730, 1700, 1670, 1510, 1430, 1350, 1220, 1200, 1160, 670, 590, 545.

MS ((−)ESI, m/z (%)) 643 (98 [M−NH$_4$]).

Anal. Calcd. for C$_{32}$H$_{44}$N$_4$O$_8$S: C, 59.61; H, 6.88; N, 8.69.

Found: C, 59.06; H, 6.95; N, 8.43.

Example 158

Synthesis of N-(Toluene-4-sulfonyl)-L-prolyl-L-4-(N-(2'-formyloxyethyl)-N-methylcarbamyloxy) phenylalanine The title compound was prepared by treating the product of Example 154 with formic acid overnight with stirring. The title compound was obtained as a white foam (110 mg., 77%), following removal of excess formic acid.

NMR data was as follows:

$^1$H NMR (DMSO-d$_6$, 400 MHz) δ 12.8 (s, 1H); 8.25 (d, 1H); 8.08 (d, 1H); 7.69 (d, 2H), 7.40 (d, 2H); 7.22 (d, 2H); 6.98 (dd, 2H); 4.47 (m, 1H); 4.35 (m, 1H); 4.27 (m, 1H); 4.10 (m, 1H); 3.65 (m, 1H); 3.55 (m, 1H); 2.85–3.15 (overlapping m, 7H); 2.40 (s, 3H); 1.55 (m, 3H); 1.40 (m, 1H).

IR (KBr,cm$^{-1}$) 3420, 2910, 1725, 1510, 1400, 1340, 1270, 1150, 675, 590, 550.

MS ((+)ESI, m/z (%)) 579 (100 [M+NH,1$^+$).

Anal. Calcd. for C$_{26}$H$_{31}$N$_3$O$_9$S.0.66H$_2$O: C, 54.45; H, 5.68; N, 7.33

Found: C, 54.41; H, 5.60; N, 7.24.

Example 159

Synthesis of N-(Toluene-4-sulfonyl)-L-prolyl-L-4-(N-(2'-hydroxyethyl)-N-methylcarbamyloxy) phenylalanine Isopropyl Ester The title compound was prepared following the procedure outlined for Example 4 by substitution of the appropriate starting materials, mp. 49–52° C.

Physical data was as follows:

Anal Calcd. for C$_{28}$H$_{37}$N$_3$O$_8$S.0.5 H$_2$O: C, 57.52; H, 6.55; N, 7.19.

Found: C, 57.56; H, 6.38; N, 7.14.

Example 160

Synthesis of N-(Toluene-4-sulfonyl)-L-prolyl-4-(N-(methoxycarbonylmethyl)carbamyloxy) phenylalanine tert-Butyl Ester The carbonate was prepared by treatment of Tos-Pro-Tyr-t-butyl ester with 4-nitrophenyl chloroformate, followed by addition of glycine methyl ester (triethylamine, methylene chloride, chilled to 0°, then stirred at room temperature overnight). The crude product was purified by flash chromatography (silica, 3:2 EtOAc:hexane) to afford a white foam (0.640 g, 35%).

NMR data was as follows:

$^1$H NMR (DMSO-d$_6$, 400 MHz) δ 8.15 (d, 1H, J=8.12 Hz); 8.12 (d, 2H, J=6.15 Hz); 7.73 (d, 2H, J=8.34 Hz); 7.40 (d, 2H, J=7.90 Hz); 7.24 (d, 2H, J=8.56 Hz); 6.98 (d, 2H, J=8.34 Hz); 4.25 (m, 1H); 4.07 (m, 1H); 3.83 (d, 2H, J=6.15 Hz); 3.64 (s, 3H); 3.32 (m, 1H); 3.02 (m, 3H); 2.39 (s, 3H); 1.56 (m, 3H); 1.41 (m, 1H); 1.35 (s, 9H).

IR (KBr,CM$^{-1}$) 3400, 2990, 1745, 1680, 1500, 1370, 1350, 1200, 1160, 670, 600.

MS ((+)ESI, m/z (%)) 621 (100[M+NH$_4$]$^+$).

Anal. Calcd. for C29H$_{37}$N$_3$O$_9$S: c, 57.70; H, 6.18; N, 6.96.

Found: C, 57.63; H, 6.11; N, 6.74.

Example 161

Synthesis of N-(1-Methylpyrazole-4-sulfonyl)-L-(5,5-dimethyl) thiaprolyl-L-4-(N,N-dimethylcarbamyloxy)phenylalanine Isopropyl Ester The title compound was prepared following the procedure outlined for Example 138 by substitution of the appropriate starting materials.

NMR data was as follows:

$^1$H NMR (CDCl$_3$): δ 7.91 (s, 1H), 7.81 (s, 1H), 7.21 (d, 2H, J=8.2 Hz), 7.03 (m, 3H); 5.03 (m, 1H), 4.84 (m, 1H), 4.55 (d, 1H), 4.42 (d, 1H), 3.96 (s, 3H), 3.83 (s, 1H), 3.18–3.01 (m, 2H), 3.10 (s, 3H), 3.01 (s, 3H), 1.28 (s, 3H), 1.24 (m, 6H), 1.17 (s, 3H).

$^{13}$C NMR (CDCl$_3$): δ 170.43, 166.31, 154.92, 150.68, 132.91, 132.88, 130.34, 121.78, 117.69, 73.76, 69.61, 54,79, 53.2, 50.52, 39.61, 37.62, 36.58, 36.35, 28.96, 24.02, 21.57, 21.49.

Example 162

Synthesis of N-(Toluene-4-sulfonyl)-L-prolyl-L-4-(4'-methoxypiperidin-1-ylcarbonyloxy) phenylalanine Isopropyl Ester The title compound was prepared following the procedure outlined for Example 156 by substitution of the appropriate starting materials.

NMR data was as follows:

$^1$H NMR (DSMO-d$_6$, 400 MHz) δ 8.10 (d, 1H); 7.72 (d, 2H); 7.41 (d, 2H); 7.24 (d, 2H); 7.02 (d, 2H); 4.92 (m, 1H); 4.45 (m, 1H); 4.10 (m, 1H); 3.8 (br s, 1H); 3.65 (br s, 1H); 3.40 (M, 2H); 3.25 (s, 3H); 2.95–3.15 (overlapping m, 5H); 2.40 (s, 3H); 1.85 (br, 2H); 1.4–1.6 (m, 6H); 1.18 (d, 3H); 1.12 (d, 3H).

IR (KBr,cm$^{-1}$) 3400, 2950, 1720, 1520, 1425, 1340, 1210, 1160, 1100, 625, 590, 540.

MS ((+) ESI, m/z (%)) 633 [M+NH]$^+$).

Example 163

Synthesis of N-(Toluene-4-sulfonyl)-L-prolyl-L-4-(4'-methoxypiperidin-1-ylcarbonyloxy) phenylalanine The title compound was prepared from the product of Example 162 using the procedure described in Method 5.

NMR data was as follows:

¹H NMR (DMSO-d₆, 400 MHz) δ 12.8 (s, 1H); 8.10 (d, 1H); 7.72 (d, 2H); 7.41 (d, 2H); 7.24 (d, 2H); 7.02 (d, 2H); 4.45 (m, 1H); 4.10 (m, 1H); 3.8 (br s, 1H); 3.65 (br s, 1H); 3.40 (m, 2H); 3.25 (s, 3H); 2.95–3.15 (overlapping m, 5H); 2.40 (s, 3H); 1.85 (br, 2H); 1.4–1.6 (m, 6H).

IR (KBr, cm⁻¹) 3400, 2950, 1720, 1520, 1425, 1340, 1210, 1160, 1100, 625, 590, 540.

MS ((−)ESI, m/z (%)) 572 (100 [M−H]⁻.

Anal. Calcd. for $C_{28}H_{35}N_3O_8S \cdot 0.33EtOAc \cdot 1H_2O$: C, 56.73; H, 6.44; N, 6.77.

Found: C, 56.96; H, 6.01; N, 6.76.

Example 164

Synthesis of N-(Toluene-4-sulfonyl)-L-4-oxoprolyl-L-4-(N,N-dimethylcarbamyloxy)phenylalanine tert-Butyl Ester Dichloromethane (7 mL) was cooled to −60° C. (chloroform/dry ice bath). Oxalyl chloride (0.15 mL) was added. The product from Example 165 (870 mg) and dry DMSO (0.26 mL) were dissolved in dichloromethane (8 mL) and added slowly to the above solution. The reaction was stirred at −60° C. for 30 minutes under dry conditions. Triethylamine (1.05 mL) was added. After 5 minutes, the dry ice bath was removed. The reaction was stirred at room temperature for 1 hour. The solvent was evaporated in vacuo. Ethyl acetate (30 mL) was added to the residue. The mixture was washed with citric acid solution (5%, 2×30 mL) and saturated NaHCO solution (2×30 mL); and finally with brine. The solution was dried over MgSO₄. The solvent was evaporated in vacuo, and the residue was flushed on a silica gel column to give 440 mg of the desired product, mp: 78–80° C.

Example 165

Synthesis of N-(Toluene-4-sulfonyl)-L-trans-4-hydroxyprolyl-L-4-(N,N-dimethylcarbamyloxy)phenylalanine tert-Butyl Ester N-(Toluene-4-sulfonyl)-L-trans-4-hydroxyprolyl-L-4-(hydroxy)phenylalanine tert-butyl ester (1.60 g) and dimethylcarbamyl chloride (0.30 mL) were dissolved in DMF at 0° C. in an ice bath. Potassium carbonate powder (2.03 g) was added to the solution. The ice bath was removed after 5 minutes. The reaction was stirred at room temperature for 6 hours. The solid was filtered. Ethyl acetate (40 mL) was added to the solution. The solution was washed with citric acid solution (5%, 40 mL) 2 times, and saturated NaHCO₃ solution (40 mL) 1 time. The solution was then washed with brine and dried with MgSO₄. The solvent was evaporated in vacuo to give 1.07 g of the title compound, mp: 170–172° C.

Example 166

Synthesis of N-(3-Fluorobenzenesulfonyl)-L-prolyl-L-4-(N,N-dimethylcarbamyloxy)phenylalanine tert-Butyl Ester N-(3-Fluorobenzenesulfonyl)-L-prolyl-L-4-(hydroxy)phenylalanine tert-butyl ester (700 mg) and dimethylcarbamyl chloride (0.2 mL) were dissolved in DMF (15 mL) at 0° C. in an ice bath. Potassium carbonate powder (1.375 g) was added to the solution. The ice bath was removed after 5 minutes. The reaction was stirred at room temperature for 6 hours. The solid was filtered. Ethyl acetate (20 mL) was added to the solution. The solution was washed with citric acid solution (5%, 30 mL, 2×), and saturated NaHCO3 solution. The solution was then washed with brine and dried with MgSO₄. The solvent was evaporated in vacuo to give 890 mg of the title compound, mp: 107–109° C.

Example 167

Synthesis of N-(Morpholino-sulfonyl)-L-prolyl-L-(4-N,N-dimethylcarbamyloxy)phenylalanine tert-Butyl Ester N-(Morpholino-sulfonyl)-L-proline was prepared using the procedure described by Cheeseright, et al., *J. Chem. Soc. Perkin Trans. 1* 1994, 12, 1595–1600. The title compound was prepared following the procedure described for the preparation of Example 2.

NMR data was as follows:

¹H NMR (CDCl₃): δ 7.13 (d, 2H), 7.03 (d, 2H), 6.92 (d, 1H), 4.71 (q, 1H), 4.25 (t, 1H), 3.67 (t, 4H), 3.39 (dt, 1H), 3.28–3.19 (m, 1H), 3.23 (t, 4H), 3.18 (dd, 1H), 3.08 (dd, 1H), 3.09 (s, 3H), 3.00 (s, 3H), 2.16–2.08 (m, 2H), 1.98–1.86 (m, 1H), 1.78–1.66 (m, 1H), 1.45 (s, 9H).

¹³C NMR (CDCl₃): δ 171.2, 170.4, 154.8, 150.7, 132.9, 130.3, 121.7, 82.7, 66.3, 62.6, 53.3, 49.6, 46.2, 37.0, 36.6, 36.3, 30.5, 27.8, 24.7.

Example 168

Synthesis of N-(Morpholino-sulfonyl)-L-prolyl-L-(4-N,N-dimethylcarbamyloxy)phenylalanine The title compound was prepared from the product of Example 167 using the procedure described in Method 11.

NMR data was as follows:

¹H NMR (CD₃OD): δ 8.04 (d, 1H), 7.25 (d, 2H), 7.01 (d, 2H), 4.71–4.64 (m, 1H), 4.22 (dd, 1H), 3.62–3.50 (m, 4H), 3.43–3.31 (m, 2H), 3.24 (dd, 1H), 3.11 (t, 4H), 3.09 (s, 3H), 3.03 (dd, 1H), 2.97 (s, 3H), 2.22–2.11 (m, 1H), 1.98–1.80 (m, 3H).

¹³C NMR (CD₃OD): δ 174.65, 174.58, 174.00, 156.60, 151.70, 135.30, 131.20, 122.70, 67.10, 63.10, 54.59, 54.50, 50.6, 47.10, 37.10, 36.50, 36.40, 32.0, 25.60.

Example 169

Synthesis of N-(1-Methylpyrazole-4-sulfonyl)-L-(1,1-dioxothiamorpholin-3-carbonyl)-L-4-(N,N-dimethylcarbamyloxy)phenylalanine tert-Butyl Ester The title compound was prepared following the procedures described for the preparation of Examples 14 and 117.

NMR data was as follows:

¹H NMR (CDCl₃): δ 7.93 (s, 1H), 7.80 (s, 1H), 7.12 (d, 2H), 6.98 (d, 2H), 6.44 (d, 1H0HH), 4.95 (m, 1H), 4.66 (m, 1H), 4.04 (m, 2H), 3.98 (s, 3H), 3.19 (m, 2H), 3.06 (m, 6H), 2.98 (m, 4H), 1.42 (m, 9H).

¹³C NMR (CDCl₃): δ 170.58, 164.75, 154.91, 150.75, 139.33, 132.73, 132.43, 130.43, 122.18, 119.66, 83.07, 56.02, 53.23, 50.03, 49.03, 41.49, 39.63, 36.56, 36.31, 36.16, 27.87.

Example 170

Synthesis of N-(2-Fluorobenzenesulfonyl)-L-(1,1-dioxothiamorpholin-3-carbonyl)-L-4-(N,N-dimethylcarbamyloxy)phenylalanine The title compound was prepared from the product of Example 90 using the procedure described in Method 11.

NMR data was as follows:

$^1$H NMR (CD$_3$OD): δ 7.90 (m, 1H), 7.72 (m, 1H), 7.56 (d, 1H), 7.37 (m, 2H), 7.20 (d, 2H), 7.07 (d, 2H), 5.18 (m, 1H), 4.59 (m, 1H), 4.26 (m, 1H), 3.76 (m, 2H), 3.36 (m, 1H), 3.21 (m, 2H), 3.08 (m, 6H), 2.96 (s, 3H).

$^{13}$C NMR (CD$_3$OD): δ 173.85, 168.04, 162.06, 158.69, 156.92, 152.06, 137.69, 135.05, 131.83, 131.59, 129.77, 128.44, 128.26, 126.21, 123.17, 119.04, 118.75, 57.04, 54.99, 52.08, 51.66, 43.36, 37.24, 36.83, 36.66.

Example 171

Synthesis of N-(2,4-Difluorobenzenesulfonyl)-L-(1,1-dioxothiamorpholin-3-carbonyl)-L-4-(N,N-dimethylcarbamyloxy)phenylalanine The title compound was prepared from the product of Example 92 using the procedure described in Method 11.

NMR data was as follows:

$^1$H NMR (CD$_3$OD): δ 8.88 (m, ½H), 8.14 (m, ½H), 7.90 (m, 1H), (m, 1H), 7.20 (m, 2H), 7.10 (m, 1H), 7.03 (m, 2H), 5.16 (m, 1H), 4,63 (m, 1H), 4.28 (m, 1H), 3.75 (m, 2H), 3.41 (m, 1H), 3.15 (m, 5H), 3.02 (m, 4H).

$^{13}$C NMR (CD$_3$OD): δ 173.91, 168.04, 156.93, 152.05, 135.15, 133.81, 133.67, 131.60, 123.13, 113.48, 113.18, 107.38, 107.02, 57.02, 55.02, 52.29, 51.84, 43.45, 37.34, 36.83, 36.66.

Example 172

Synthesis of N-(Toluene-4-sulfonyl)-L-(thiamorpholin-3-carbonyl)-L-4-(N,N-dimethylcarbamyloxy)phenylalanine The title compound was prepared from the product of Example 49 using the procedure described in Method 11.

NMR data was as follows:

$^1$H NMR (CDCl$_3$): δ 7.67 (d, 2H), 7.32 (d, 2H), 7.21 (d, 2H), 7.10 (d, 1H), 7.00 (d, 2H), 5.40 (bs, >1H), 4.85 (m, 2H), 3.95 (m, 1H), 3.41 (m, 1H), 3.07 (m, 6H), 2.98 (m, 4H), 2.62 (m, 1H), 2.41 (m, 5H), 2.13 (m, 1H).

$^{13}$C NMR (CDCl$_3$): δ 173.40, 168.49, 155.26, 144.44, 136.88, 132.95, 130.51, 130.30, 127.28, 122.08, 55.34, 53.45, 43.43, 36.62, 36.38, 35.85, 25.25, 24.54, 21.43.

Example 173

Synthesis of N-(Pyridine-3-sulfonyl)-L-(5,5-dimethyl-thiaprolyl-L-4-(N,N-dimethylcarbamyloxy)phenylalanine Isopropyl Ester The title compound was prepared following the procedure outlined for the preparation of Example 56 by substitution of the appropriate starting materials.

NMR data was as follows:

$^1$H NMR (CDCl$_3$): δ 9.13 (m, 1H), 8.90 (m, 1H), 8.19 (m, 1H), 7.56 (m, 1H), 7.23 (d, 2H), 7.04 (d, 2H), 6.93 (d, 1H), 5.07 (m, 1H), 4.85 (m, 1H), 4.62 (d, 1H), 4.48 (d, 1H), 3.92 (s, 1H), 3.20–3.05 (m, 2H), 3.12 (s, 3H), 3.03 (s, 3H), 1.32–1.16 (m, 12H).

$^{13}$C NMR (CDCl$_3$): δ 170.30, 167.75, 154.19, 150.67, 148.59, 135.72, 132.94, 132.72, 130.27, 123.91, 121.78, 73.62, 69.64, 54.69, 53.12, 50.48, 37.50, 36.53, 36.29, 29.05, 23.73, 21.54, 21.46.

Example 174

Synthesis of N-(3-Fluorobenzenesulfonyl)-L-(1,1-dioxothiamorpholin-3-carbonyl)-L-4-(N,N-dimethylcarbamyloxy)phenylalanine The title compound was prepared from the product of Example 91 using the procedure described in Method 11.

NMR data was as follows:

$^1$H NMR (CD$_3$OD): δ 7.68 (m, 3H), 7.44 (m, 1H), 7.20 (m, 2H), 7.01 (m, 2H), 5.21 (m, 1H), 4.60 (m, 1H), 4.20 (m, 1H), 3.75 (m, 1H), 3.43 (m, 1H), 3.21 (m, 3H), 3.02 (m, 4H), 2.96 (m, 4H).

$^{13}$C NMR (CD$_3$OD): δ 173.98, 167.98, 165.89, 162.56, 156.94, 152.06, 142.70, 142.61, 135.11, 133.30, 133.19, 131.57, 124.71, 123.25, 122.21, 121.93, 116.05, 115.71, 57.27, 54.87, 54.79, 51.29, 51.06, 43.24, 37.11, 36.83.

Example 175

Synthesis of N-(1-Methylpyrazole-4-sulfonyl)-L-(1,1-dioxothiamorpholin-3-carbonyl)-L-4-(N,N-dimethylcarbamyloxy)phenylalanine The title compound was prepared from the product of Example 169 using the procedure described in Method 11.

NMR data was as follows:

$^1$H NMR (CD$_3$OD): δ 8.11 (s, 1H), 7.83 (s, 1H), 7.36 (d, 1H), 7.24 (d, 2H), 7.02 (d, 2H), 5.16 (m, 1H), 4.69 (m, 1H), 4.19 (m, 1H), 3.90 (s, 3H), 3.81 (m, 2H), 3.33 (m, 3H), 3.10 (s, 3H), 3.02 (m, 4H).

$^{13}$C NMR (CD$_3$OD): δ 174.07, 168.11, 156.93, 152.08, 140.12, 135.05, 134.90, 131.67, 123.28, 121.82, 57.33, 54.77, 50.83, 50.64, 42.94, 39.80, 37.02, 36.84, 36.76.

Example 176

Synthesis of N-(4-tert-Butylbenzenesulfonyl)-L-(1,1-dioxothiamorpholin-3-carbonyl)-L-4-(N,N-dimethylcarbamyloxy)phenylalanine The title compound was prepared from the product of Example 88 using the procedure described in Method 11.

NMR data was as follows:

$^1$H NMR (CD$_3$OD): δ 7.70 (d, 2H), 7.53 (d, 2H), 7.04 (d, 2H), 6.87 (d, 2H), 5.09 (m, 1H), 4.48 (m, 1H), 3.99 (m, 1H), 3.60 (m, 1H), 2.90 (m, 5H), 2.80 (m, 5H), 1.15 (s, 9H).

$^{13}$C NMR (CD$_3$OD): δ 173.95, 168.09, 159.33, 156.88, 152.09, 137.52, 135.03, 131.54,128.68, 128.15, 123.32, 57.27, 54.81, 50.75, 43.04, 36.97, 36.82, 36.65, 36.16, 31.35.

Example 177

Synthesis of N-(Toluene-4-sulfonyl)-(3,3-dimethyl)prolyl-L-4-(N,N-dimethylcarbamyloxy)phenylalanine The title compound was prepared from the product of Example 97 using the procedure described in Method 11.

NMR data was as follows:

$^1$H NMR (CDCl$_3$): δ 7.77 (d, 1H), 7.75 (d, 1H), 7.42–7.33 (m, 3.5H), 7.27 (d, 1H), 7.19 (d, 0.5H), 7.10 (d, 1H), 7.03 (d, 1H), 5.07–5.00 (m, 0.5H) 4.94–4.87 (m, 0.5), 3.67 (d, 1H), 3.58–3.52 (m, 1H), 3.35–3.25 (m, 1H), 3.19–3.08 (m, 2H), 3.11 (s, 3H), 3.02 (s, 3H), 2.45 (s, 1.5H), 2.43 (s, 1.5H) 1.70–1.57 (m, 1H), 1.34–1.27 (m, 1H), 0.94 (s, 1.5H), 0.75 (s, 1.5H), 0.54 (s 6H).

$^{13}$C NMR (CDCl$_3$): δ 174.6, 174.4, 171.8, 171.4, 155.7, 150.5, 150.4, 144.5, 144.4, 133.5, 132.6, 130.9, 130.6, 130.0, 129.9, 128.0, 127.9, 122.2, 122.0, 71.2, 70.9, 53.3, 52.2, 47.3, 47.1, 43.0, 42.7, 38.1, 37.9, 36.6, 36.4, 27.0, 26.8, 23.3, 23.0.

Example 178

Synthesis of N-(2,5-Dichlorothiophene-3-sulfonyl)-L-prolyl-L-4-(N,N-dimethylcarbamyloxy)phenylalanine The title compound was prepared from the product of Example 86 using the procedure described in Method 11.

NMR data was as follows:

¹H NMR (CD₃OD): δ 8.10 (d, 1H), 7.25 (d, 2H), 7.20 (s, 1H), 7.0 (d, 2H), 4.65 (m, 1H), 4.35 (m, 1H), 3.55–3.35 (m, 2H), 3.30–3.20 (m, 2H), 3.15–3.00 (m, 4H), 2.95 (s, 3H), 2.05–1.80 (m, 2H), 1.80–1.65 (m, 2H).

¹³C NMR (CD₃OD): δ 174.2, 173.9, 156.9, 151.9, 135.9, 135.5, 132.3, 131.6, 128.9, 128.6, 122.9, 63.1, 54.8, 54.7, 50.3, 37.4, 36.8, 36.7, 32.1, 25.5.

Example 179

Synthesis of N-(4-Methoxybenzenesulfonyl)-L-prolyl-L-4-(N,N-dimethylcarbamyloxy)phenylalanine The title compound was prepared from the product of Example 180 using the procedure described in Method 7.

NMR data was as follows:

¹H NMR (CD₃OD): δ 7.78 (d, 2H), 7.27 (d, 2H), 7.09 (d, 2H), 7.02 (d, 2H), 4.71–4.67 (m, 1H), 4.10–4.06 (m, 1H), 3.88 (s, 3H), 3.41–3.31 (m, 1H), 3.28–3.07 (m, 6H), 2.97 (s, 3H), 1.81–1.50 (m, 4H).

¹³C NMR (CD₃OD): δ 168.3, 168.2, 159.2, 150.9, 145.9, 129.5, 125.6, 125.3, 123.5, 116.9, 109.6, 57.2, 50.2, 48.7, 44.6, 31.4, 30.8, 30.6, 25.7, 19.3.

Example 180

Synthesis of N-(4-Methoxybenzenesulfonyl)-L-prolyl-L-4-(N,N-dimethylcarbamyloxy)phenylalanine Isopropyl Ester The title compound was prepared using the procedure described in Example 2 by substitution of the appropriate starting materials.

NMR data was as follows:

¹H NMR (CDCl₃): δ 7.76 (d, 2H), 7.34 (d, 1H), 7.14 (d, 2H), 7.03–6.97 (m, 4H), 5.08–5.04 (m, 1H), 4.77 (m, 1H), 4.05–4.03 (m, 1H), 3.86 (s, 3H), 3.37–3.34 (m, 1H), 3.26–3.19 (m, 1H), 3.10–3.01 (m, 4H), 2.98 (s, 3H), 2.02 (m, 1H), 1.56–1.46 (m, 3H), 1.25 (d, 6H).

¹³C NMR (CDCl₃): δ 170.8, 170.3, 163.4, 154.8, 150.5, 132.9, 130.1, 129.9, 127.6, 121.6, 114.3, 69.4, 62.1, 55.4, 53.2, 49.5, 37.1, 36.5, 36.2, 29.7, 24.0, 21.5, 21.4.

Example 181

Synthesis of N-(Toluene-4-sulfonyl)-L-(1-oxo-thiomorpholin-3-carbonyl)thiaprolyl-L-4-(N,N-dimethylcarbamyloxy)phenylalanine The title compound was prepared from the product of Example 182 using the procedure described in Method 11.

NMR data was as follows:

¹H NMR (CD₃OD): δ 7.90 (m, 1H), 7.78 (m, 2H), 7.40 (m, 2H), 7.26 (m, 2H), 7.03 (m, 2H), 5.14 (m, 1H), 4.64 (m, 2H), 3.81 (m, 1H), 3.71 (m, 2H), 3.19 (m, 1H), 3.14 (m, 3H), 3.02 (m, 4H), 2.84 (m, 1H), 2.60 (m, 1H), 2.42 (m, 4H), 2.21 (m, 1H).

¹³C NMR (CD₃OD): δ 174.22, 173.93, 169.59, 156.88, 152.08, 152.05, 146.44, 146.26, 137.75, 137.63, 135.61, 134.96, 131.79, 131.64, 131.55, 131.39, 128.75, 128.66, 123.35, 123.06, 57.03, 54.88, 54.66, 51.64, 42.69, 42.51, 40.34, 37.12, 36.83, 36.66, 32.76, 21.51.

Example 182

Synthesis of N-(Toluene-4-sulfonyl)-L-(1-oxo-thiomorpholin-3-carbonyl)-L-4-(N,N-dimethylcarbamyloxy)phenylalanine tert-Butyl Ester The title compound was prepared following the procedure described for the preparation of Example 49. The oxidation of the thiomorpholine group to the 1-oxo-thiomorpholine group was per Larsson and Carison (*Acta Chemica Scan.* 1994, 48, 517–525).

NMR data was as follows:

¹H NMR (CDCl₃): δ 7.72 (m, 2H), 7.69 (m, 2H), 7.31 (m, 2H), 7.11 (m, 2H), 7.07 (m, 2H), 6.96 (m, 2H), 4.79 (m, 1H), 4.54 (m, 1H), 3.80 (m, 4H), 3.04 (4H), 2.92 (m, 3H), 2.64 (m, 1H), 2.43 (m, 4H), 1.44 (s, 3H), 1.36 (s, 6H).

¹³C NMR (CDCl₃): δ 169.8, 166.5, 166.,3 154.6, 150.5, 150.4, 144.9, 144.4, 135.7, 135.3, 132.8, 130.5, 130.1, 29.9, 127.4, 126.9, 122.1, 121.4, 82.6, 82.2, 55.6, 53.9, 53.1, 50.6, 48.1, 47.8, 41.7, 40.5, 38.3, 36.4, 36.1, 31.1, 27.5, 21.2.

Example 183

Synthesis of N-(3,4-Difluorobenzenesulfonyl)-L-prolyl-4-(N,N-dimethylcarbamyloxy)phenylalanine Isopropyl Ester The title compound was prepared following the procedure described for the preparation of Example 2 by substitution of the appropriate starting materials.

NMR data was as follows:

¹H NMR (CDCl₃): δ 7.72–7.60 (m, 2H), 7.87–7.37 (m, 1H), 7.13–7.11 (m, 3H), 7.01 (d, 2H), 5.08–5.04 (m, 1H), 4.81–4.74 (m, 1H), 4.09–4.06 (m, 1H), 3.39–3.35 (m, 1H), 3.26–3.19 (m, 1H), 3.12–2.97 (m, 8H), 2.06–2.03 (m, 1H), 1.66–1.57 (m, 3H), 1.26 (d, 6H).

¹³C NMR (CDCl₃): δ 170.50, 170.40, 154.90, 153.60, 150.70, 150.30, 133.30, 132.90, 130.10, 125.00, 121.80, 121.80, 118.50, 112.80, 69.60, 62.20, 53.20, 49.60, 37.10, 36.60, 36.30, 30.10, 24.20, 21.59, 21.56.

Example 184

Synthesis of N-(3,4-Difluorobenzenesulfonyl)-L-prolyl-4-(N,N-dimethylcarbamyloxy)phenylalanine The title compound was prepared from the product of Example 183 using the procedure described in Method 7.

NMR data was as follows:

¹H NMR (CD₃OD): δ 8.10 (d, 1H), 7.84–7.77 (m, 1H), 7.69–7.65 (m, 1H), 7.53–7.45 (m, 1H), 7.28 (d, 2H), 7.02 (d, 2H), 4.72–4.68 (m, 1H), 4.19–4.16 (m, 1H), 3.43–3.39 (m, 1H), 3.31–3.21 (m, 2H), 3.13–3.05 (m, 4H), 2.97 (s, 3H), 1.86–1.61 (m, 4H).

¹³C NMR (CD₃OD): δ 174.2; 174.1, 164.7, 156.9, 154.9, 152.0, 151.6, 135.8, 135.6, 131.6, 129.7, 122.9, 119.7, 118.8, 63.1, 54.7, 50.5, 37.4, 36.8, 36.6, 31.9, 25.5.

Example 185

Synthesis of N-(3,4-Difluorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

¹H NMR (CDCl₃): δ 7.71 (m, 2H), 7.33 (m, 1H), 7.07 (d, 2H), 6.91 (d, 2H), 6.36 (d, 1H), 4.95 (m, 1H), 4.61 (m, 1H), 4.03 (m, 2H), 3.16 (m, 2H), 3.13 (m, 4H), 3.07 (m, 1H), 2.93 (s, 9H), 1.43 (s, 9H).

¹³C NMR (CDCl₃): δ 170.07, 169.45, 164.42, 155.06, 155.44, 154.81, 152.21, 152.17, 150.58, 148.81, 148.64, 134.90, 134.85, 132.41, 130.29, 124.82, 124.71, 124.66, 121.97, 119.07, 118.76, 117.52, 117.23, 82.92, 55.98, 53.20, 50.10, 49.40, 41.76, 36.41, 36.16, 35.99, 27.64.

Example 186

Synthesis of N-(3,4-Difluorobenzenesulfonyl)-L-(1,1-dioxothiamorpholin-3-carbonyl)-L-4-(N,N-dimethylcarbamyloxy)phenylalanine The title compound was prepared from the product of Example 185 using the procedure described in Method 11.

NMR data was as follows:

$^1$H NMR (CD$_3$OD): δ 6.22 (m, 1H), 6.03 (m, 1H), 5.84 (m, 1H), 5.58 (m, 2H), 5.38 (m, 2H), 3.33 (m, 1H), 3.01 (m, 1H), 2.57 (m, 1H), 2.14 (m, 1H), 1.91 (m, 1H), 1.66 (m, 3H), 1.44 (s, 3H), 1.35 (m, 3H), 1.32 (s, 3H).

$^{13}$C NMR (CD$_3$OD): δ 173.97, 167.89, 156.94, 153.53, 152.07, 150.00, 137.48, 135.17, 131.63, 126.54, 126.43, 123.20, 120.21, 119.96, 118.84, 118.57, 57.25, 54.82, 51.29, 49.86, 43.29, 37.21, 36.85, 36.67.

Example 187

Synthesis of N-(Toluene-4-sulfonyl)-L-(5,5-dimethyl)thiaprolyl-L-(thiomorpholin-4-ylcarbonyloxy)phenylalanine tert-Butyl Ester The title compound was prepared using the procedure described in Example 82 by substitution of the appropriate starting materials.

NMR data was as follows:

$^1$H NMR (CDCl$_3$): δ 7.64 (d, 2H), 7.33 (d, 2H), 7.25 (d, 2H), 7.08–6.97 (m, 3H), 4.76 (m, 1H), 4.57 (d, 1H), 4.38 (d, 1H), 3.83 (s, 1H), 3.95–3.78 (m, 4H), 3.09 (m, 2H), 2.69 (m, 4H), 2.43 (s, 3H), 1.44 (s, 9H), 1.16 (s, 3H), 1.08 (s, 3H).

$^{13}$C NMR (CDCl$_3$): δ 169.78, 168.36, 153.53, 150.28, 144.84, 133.53, 132.76, 130.51, 130.03, 128.19, 121.58, 82.69, 73.42, 54.56, 53.78, 50.46, 47.05, 46.40, 37.80, 29.06, 27.76, 27.37, 27.04, 23.86, 21.52.

Example 188

Synthesis of N-(Toluene-4-sulfonyl)-L-(5,5-dimethyl)thiaprolyl-L-(thiomorpholin-4-ylcarbonyloxy)phenylalanine The title compound was prepared from the product of Examples 187 using the procedures described in Method 11.

NMR data was as follows:

$^1$H NMR (CDCl$_3$): δ 7.77 (d, 2H), 7.37 (d, 2H), 7.28 (d, 2H), 7.22 (d, 1H), 7.03 (d, 2H), 5.35 (brs, 1H), 4.91 (m, 1H), 4.60 (d, 1H), 4.39 (d, 1H), 3.91 (s, 1H), 3.96–3.28 (m, 4H), 3.30–3.07 (m, 2H), 2.67 (m, 4H), 2.45 (s, 3H), 1.10 (s, 3H), 1.08 (s, 3H).

$^{13}$C NMR (CDCl$_3$): δ 173.09, 169.45, 153.81, 150.28, 145.02, 133.42, 132.61, 130.60, 130.12, 128.13, 121.86, 73.28, 54.51, 53.31, 50.48, 47.08, 46.47, 36.97, 28.97, 27.35, 27.03, 23.70, 21.52.

Example 189

Synthesis of N-(1-Methylpyrazole-4-sulfonyl)-L-(5,5-dimethyl)thiaprolyl-L-4-(N,N-dimethylcarbamyloxy)phenylalanine Ethyl Ester The title compound was prepared following the procedure described for the preparation of Example 117 by substitution of the appropriate starting materials.

NMR data was as follows:

$^1$H NMR (CDCl$_3$): δ 7.89 (s, 1H), 7.81 (s, 1H), 7.19 (d, 2H), 7.00 (m, 3H), 4.87 (m, 1H), 4.54 (d, 1H), 4.42 (d, 1H), 4.18 (q, 2H), 3.95 (s, 3H), 3.81 (s, 1H), 3.11 (m, 2H), 3.08 (s, 3H), 2.99 (s, 3H), 1.30 (s, 3H), 1.25 (t, 3H), 1.16 (s, 3H).

$^{13}$C NMR (CDCl$_3$): δ 170.98, 168.34, 154.91, 150.71, 139.62, 132.88, 130.28, 121.85, 117.71, 73.77, 61.66, 54.80, 53.16, 50.53, 39.64, 37.63, 36.60, 36.36, 28.98, 24.00, 13.92.

Example 190

Synthesis of N-(Pyridine-3-sulfonyl)-L-(5,5-dimethyl)thiaprolyl-L-4-(N,N-dimethylcarbamyloxy)phenylalanine The title compound was prepared from the product of Example 191 using the procedure described in Method 11.

NMR data was as follows:

$^1$H NMR (CDCl$_3$): δ 9.09 (s, 1H), 8.82 (m, 1H), 8.20 (m, 1H), 7.56 (m, 1H), 7.23 (d, 2H), 7.07 (d, 1H), 5.58 (brs, 1H), 4.83 (m, 1H), 4.56 (m, 2H), 4.07 (s, 1H), 3.14 (m, 2H), 3.07 (s, 3H), 2.99 (s, 3H), 1.26 (s, 3H), 1.18 (s, 3H).

$^{13}$C NMR (CDCl$_3$): δ 173.04, 168.29, 155.16, 153.39, 150.60, 147.96, 136.43, 133.91, 133.06, 130.66, 130.50, 124.65, 122.14, 121.91, 73.43, 54.58, 53.21, 50.38, 37.18, 36.64, 36.38, 29.25, 23.64.

Example 191

Synthesis of N-(Pyridine-3-sulfonyl)-L-(5,5-dimethyl)thiaprolyl-L-4-(N,N-dimethylcarbamyloxy)phenylalanine tert-Butyl Ester The title compound was prepared following the procedure described for the preparation of Example 56 and substitution of appropriate starting materials.

Physical data was as follows:

MS: [M+H]$^+$ 593

Anal. Calcd. for C$_{27}$H$_{36}$N$_4$O$_7$S$_2$.0.5 H$_2$O: C, 53.88; H, 6.07; N, 9.27.

Found: C, 53.98; H, 6.07; N, 9.27.

Example 192

Synthesis of N-(Pyridine-2-sulfonyl)-L-prolyl-L-4-(N,N-dimethylcarbamyloxy)phenylalanine Isopropyl Ester Substituting 2-pyridinesulfonyl chloride (see Corey, et al. *J. Org. Chem.* 1989, 54, 389–393) and following the method for the preparation of Example 56, gave the title compound.

NMR data was as follows:

$^1$H NMR (CDCl$_3$): δ 8.59 (d, 1H), 8.00–7.89 (m, 2H), 7.78 (d, 1H), 7.53–7.49 (m, 1H), 7.16 (d, 2H), 7.01 (d, 2H), 5.05–4.99 (m, 1H), 4.85–4.78 (m, 1H), 4.60–4.57 (m, 1H), 3.44–3.35 (m, 2H), 3.25–3.19 (m, 1H), 3.07 (s, 3H), 3.06–3.01 (m, 1H), 2.97 (s, 3H), 2.19–2.13 (m, 1H), 1.88–1.71 (m, 2H), 1.55 (m, 1H), 1.22–1.19 (m, 6H).

$^{13}$C NMR (CDCl$_3$): δ 170.90, 170.30, 156.20, 154.80, 150.50, 150.00, 138.00, 133.10, 130.10, 127.00, 123.40, 121.60, 69.20, 62.80, 53.30, 49.60, 37.20, 36.40, 36.20, 29.80, 24.30, 21.42, 21.40.

Example 193

Synthesis of N-(Pyridine-2-sulfonyl)-L-prolyl-L-4-(N,N-dimethylcarbamyloxy)phenylalanine The title compound was prepared from the product of Example 192 using the procedure described in Method 7.

NMR data was as follows:

$^1$H NMR (CD$_3$OD): δ 8.67 (d, 1H), 8.27 (d, 1H), 8.07–8.02 (m, 1H), 7.96–7.91 (m, 1H), 7.65–7.61 (m, 1H), 7.27 (d, 2H), 7.01 (d, 2H), 4.72–4.69 (m, 1H), 4.58–4.54 (m, 1H), 3.44–3.37 (m, 2H), 3.28–3.24 (m, 1H), 3.13–3.05 (m, 4H), 2.96 (s, 3H), 1.94–1.89 (m, 2H), 1.70–1.63 (m, 2H).

$^{13}$C NMR (CD$_3$OD): δ 174.5, 174.4, 174.2, 157.7, 156.9, 151.9, 139.9, 135.6, 131.6, 128.8, 124.7, 122.9, 64.1, 54.8, 54.7, 50.9, 37.5, 36.8, 36.7, 31.9, 25.6.

Example 194

Synthesis of N-(Pyridine-2-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 192 by substitution of the appropriate starting materials.

NMR data was as follows:

$^1$H NMR (CDCl$_3$): δ 8.64–8.62 (m, 1H), 7.98–7.92 (m, 2H), 7.56–7.51 (m, 1H), 7.28–7.21 (m, 3H), 7.01 (d, 2H), 5.01–4.97 (m, 1H), 4.88–4.85 (m, 2H), 4.80 (d, 1H), 4.63 (d, 1H), 4.19 (s, 1H), 3.11–3.07 (m, 5H), 2.98 (s, 3H), 1.28 (s, 3H), 1.26–1.18 (m, 9H).

$^{13}$C NMR (CDCl$_3$): δ 170.3, 168.4, 155.5, 154.9, 150.7, 150.4, 138.2, 133.0, 130.4, 127.5, 123.5, 121.8, 73.5, 69.5, 54.7, 53.3, 51.0, 37.6, 36.6, 36.4, 29.3, 23.9, 21.52, 21.50.

Example 195

Synthesis of N-(Pyridine-2-sulfonyl)-L-(5,5-dimethyl)thiaprolyl-L-4-(N,N-dimethylcarbamyloxy)phenylalanine The title compound was prepared from the product of Example 194 using the procedure described in Method 7.

NMR data was as follows:

$^1$H NMR (CD$_3$OD): δ 8.70–8.69 (m, 1H), 8.07–8.01 (m, 1H), 7.92–7.89 (m, 1H), 7.67–7.63 (m, 1H), 4.77–4.67 (m, 3H), 4.30 (s, 1H), 3.23–3.06 (m, 5H), 2.97 (s, 3H), 1.27–1.18 (m, 6H).

$^{13}$C NMR(CD$_3$OD): δ 174.1, 171.2, 157.0, 151.9, 151.6, 139.9, 135.7, 131.8, 131.7, 129.0, 124.6, 122.9, 74.3, 61.6, 55.7, 54.9, 51.9, 37.6, 36.8, 36.7, 30.1, 24.9.

Example 196

Synthesis of N-(Toluene-4-sulfonyl)-L-(thiamorpholin-3-carbonyl)-L-4-(N,N-dimethylcarbamyloxy)phenylalanine Isopropyl Ester The title compound was prepared following the procedure described for the preparation of Example 49 by substitution of the appropriate starting materials.

NMR data was as follows:

$^1$H NMR (CDCl$_3$): δ 7.67 (d, 2H), 7.30 (d, 2H), 7.12 (d, 2H), 6.97 (d, 2H), 6.86 (d, 1H), 5.05 (m, 1H), 4.70 (m, 2H), 3.90 (m, 1H), 3.31 (m, 1H), 3.06 (m, 4H), 2.97 (s, 3H), 2.68 (m, 1H), 2.50 (m, 1H), 2.44 (s, 3H), 2.29 (m, 1H), 2.13 (m, 1H), 1.24 (s, 3H), 1.22 (s, 3H).

$^{13}$C NMR (CDCl$_3$): δ 170.35, 167.55, 155.00, 150.61, 144.20, 136.80, 132.51, 130.24, 130.14, 127.20, 121.82, 69.48, 55.14, 53.55, 43.26, 36.43, 36.16, 25.21, 24.56, 21.48, 21.31.

Example 197

Synthesis of N-(3-Fluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.68 (d, 1H), 7.61–7.52 (m, 2H), 7.36 (dt, 1H), 7.21 (d, 2H), 7.02 (d, 2H), 6.94 (d, 1H), 5.05 (sept, 1H), 4.85 (q, 1H), 4.59 (d, 1H), 4.41 (d, 1H), 3.88 (s, 1H), 3.17–3.03 (m, 2H), 3.09 (s, 3H), 3.00 (s, 3H), 1.25 (d, 3H), 1.23 (d, 3H), 1.16 (s, 3H), 1.12 (s, 3H).

$^{13}$C NMR (CDCl$_3$): δ 170;3, 168.1, 162.6, 154.9, 150.7, 137.9, 132.8, 131.3, 130.4, 123.9, 121.8, 121.0, 115.4, 73.5, 69.6, 54.5, 53.2, 50.5, 37.6, 36.6, 36.3, 29.0, 23.7, 21.6, 21.5.

Example 198

Synthesis of N-(2-Fluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.92–7.87 (m, 1H), 7.67–7.59 (m, 1H), 7.33–7.24 (m, 2H), 7.21 (d, 2H), 7.03 (d, 2H), 6.93 (d, 1H), 5.03 (Sept, 1H), 4.83 (q, 1H), 4.67 (d, 1H), 4.63 (d, 1H), 4.03 (s, 1H), 3.16–3.03 (m, 2H), 3.09 (s, 3H), 3.00 (s, 3H), 1.31 (s, 3H), 1.24 (d, 3H), 1.22 (d, 3H), 1.19 (s, 3H).

$^{13}$C NMR (CDCl$_3$): δ 170.3, 168.1, 159.2, 154.9, 150.7, 136.0, 132.9, 132.0, 130.3, 124.6, 121.8, 117.6, 73.3, 69.6, 54.8, 53.2, 50.3, 37.6, 36.6, 36.3, 29.1, 23.9, 21.6, 21.5.

Example 199

Synthesis of N-(3,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.77–7.71 (m, 1H), 7.70–7.65 (m, 1H), 7.40–7.31 (m, 1H), 7.20 (d, 2H), 7.02 (d, 2H), 6.87 (d, 1H), 5.05 (Sept, 1H), 4.88–4.82 (m, 1H), 4.55 (d, 1H), 4.44 (d, 1H), 3.91 (s, 1H), 3.17–3.03 (m, 2H), 3.09 (s 3H), 3.00 (s, 3H), 1.25 (d, 3H), 1.23 (d, 3H), 1.23 (s, 3H), 1.18 (s, 3H).

$^{13}$C NMR (CDCl$_3$): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

Example 200

Synthesis of N-(3,5-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

$^1$H NMR (CDCl$_3$): δ 7.77–7.71 (m, 1H), 7.70–7.65 (m, 1H), 7.40–7.31 (m, 1H), 7.20 (d, 2H), 7.02 (d, 2H), 6.87 (d, 1H), 5.05 (Sept, 1H), 4.88–4.82 (m, 1H), 4.55 (d, 1H), 4.44 (d, 1H), 3.91 (s, 1H), 3.17–3.03 (m, 2H), 3.09 (s, 3H), 3.00 (s, 3H), 1.25 (d, 3H), 1.23 (d, 3H), 1.23 (s, 3H), 1.18 (s, 3H).

$^{13}$C NMR (CDCl$_3$): δ 170.4, 167.9, 154.9, 150.7, 133.1, 132.7, 130.4, 124.4, 121.8, 118.5, 118.0, 73.6, 69.7, 54.6, 53.1, 50.5, 37.6, 36.6, 36.3, 29.2, 23.7, 21.6, 21.5.

Example 201

Synthesis of N-(2,4-Difluorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

¹H NMR (CDCl₃): δ 7.94–7.86 (m, 1H), 7.20 (d, 2H), 7.03 (d, 2H), 7.02–6.95 (m, 2H), 6.88 (d, 1H), 5.03 (Sept, 1H), 4.82 (q, 1H), 4.67 (d, 1H), 4.61 (d, 1H), 4.01 (s, 1H), 3.16–3.03 (m, 2H), 3.09 (s, 3H), 3.00 (s, 3H), 1.36 (s, 3H), 1.23 (d, 3H), 1.21 (d, 3H), 1.20 (s, 3H).

¹³C NMR (CDCl₃): δ 170.3, 167.9, 154.9, 150.7, 133.7, 132.8, 130.3, 121.8, 112.1, 106.1, 73.4, 69.6, 54.9, 53.2, 50.4, 37.6, 36.6, 36.3, 29.1, 23.9, 21.6, 21.5.

Example 202

Synthesis of N-(4-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

¹H NMR (CDCl₃): δ 7.82 (d, 2H), 7.53 (d, 2H), 7.21 (d, 2H), 7.02 (d, 2H), 6.93 (d, 1H), 5.05 (Sept, 1H), 4.89–4.82 (m, 1H), 4.55 (d, 1H), 4.41 (d, 1H), 3.87 (s, 1H), 3.17–3.03 (m, 2H), 3.09 (s, 3H), 3.00 (s, 3H), 1.25 (d, 3H), 1.23 (d, 3H), 1.16 (s, 6H).

¹³C NMR (CDCl₃): δ 170.3, 168.1, 154.9, 150.7, 140.4, 134.5, 132.8, 130.4, 129.7, 129.5, 121.8, 73.5, 69.6, 54.6, 53.1, 50.5, 37.6, 36.6, 36.3, 29.1, 23.8, 21.6, 21.0.

Example 203

Synthesis of N-(3-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

¹H NMR (CDCl₃): δ 7.88 (t, 1H), 7.78–7.75 (m, 1H), 7.64–7.61 (m, 1H), 7.51 (t, 1H), 7.21 (d, 2H), 7.02 (d, 2H), 6.92 (d, 1H), 5.05 (sept, 1H), 4.89–4.82 (m, 1H), 4.58 (d, 1H), 4.40 (d, 1H), 3.88 (s, 1H), 3.18–3.03 (m, 2H), 3.09 (s, 3H), 3.00 (s, 3H), 1.25 (d, 3H), 1.23 (d, 3H), 1.16 (s, 3H), 1.14 (s ¹³C NMR (CDCl₃): δ 170.3, 168.0, 154.9, 150.7, 137.7, 135.7, 133.9, 132.8, 130.7, 130.3, 127.9, 126.2, 121.8, 73.6, 69.96, 54.5, 53.2, 50.5, 37.6, 36.6, 36.3, 29.1, 23.7, 21.6, 21.5.

Example 204

Synthesis of N-(2-Chlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

¹H NMR (CDCl₃): δ 8.08 (dd, 1H), 7.54–7.52 (m, 2H), 7.45–7.39 (m, 1H), 7.19 (d, 2H), 7.02 (d, 2H), 6.79 (d, 1H), 5.00 (sept, 1H), 4.78 (d, 1H), 4.75–4.68 (m, 1H), 4.69 (d, 1H), 4.19 (s, 1H), 3.09 (s, 3H), 3.06 (d, 2H), 3.00 (s, 3H), 1.38 (s, 3H), 1.23 (s, 3H), 1.23 (d, 3H), 1.19 (d, 3H).

¹³C NMR (CDCl₃): δ 170.3, 168.1, 154.9, 150.7, 135.6, 134.4, 132.8, 132.7, 132.4, 130.3, 127.3, 121.8, 73.3, 69.5, 54.7, 53.3, 50.4, 37.6, 36.6, 36.3, 29.6, 23.7, 21.6, 21.5.

Example 205

Synthesis of N-(3,4-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate staring material.

NMR data was as follows:

¹H NMR (CDCl₃): δ 7.97 (d, 1H), 7.70 (dd, 1H), 7.63 (d, 1H), 7.20 (d, 2H), 7.02 (d, 2H), 6.86 (d, 1H), 5.05 (sept, 1H), 4.89–4.82 (m, 1H), 4.55 (d, 1H), 4.43 (d, 1H), 3.92 (s, 1H), 3.17–3.03 (m, 2H), 3.09 (s, 3H), 3.00 (s, 3H), 1.26 (d, 3H), 1.22 (d, 3H), 1.23 (s, 3H), 1.18 (s, 3H).

¹³ C NMR (CDCl₃): δ 170.3, 167.9, 154.9, 150.7, 138.7, 136.1, 134.2, 132.7, 131.4, 130.3, 129.8, 127.1, 121.8, 73.6, 69.7, 54.6, 53.1, 50.5, 37.5, 36.6, 36.3, 29.2, 23.7, 21.6, 21.5.

Example 206

Synthesis of N-(3,5-Dichlorobenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting material.

NMR data was as follows:

¹H NMR (CDCl₃): δ 7.76 (d, 2H), 7.62 (t, 1H), 7.20 (d, 2H), 7.03 (d, 2H), 6.85 (d, 1H), 5.05 (sept, 1H), 4.89–4.82 (m, 1H), 4.57 (d, 1H), 4.42 (d, 1H), 3.92 (s, 1H), 3.18–3.04 (m, 2H), 3.09 (s, 3H), 3.00 (s, 3H), 1.25 (d, 3H), 1.23 (d, 3H), 1.27 (s, 3H), 1.18 (s, 3H).

¹³C NMR (CDCl₃): δ 170.3, 167.8, 154.9, 150.7, 139.1, 136.5, 133.7, 132.7, 130.3, 126.2, 121.8, 73.7, 69.7, 54.6, 53.1, 50.5, 37.5, 36.6, 36.3, 29.2, 23.7, 21.6, 21.5.

Example 207

Synthesis of N-(3-Chlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

¹H NMR (CDCl₃): δ 7.85 (m, 1H), 7.76 (m, 1H), 7.63 (m, 1H), 7.53 (m, 1H), 7.06 (d, 2H), 6.96 (d, 2H), 6.37 (m, 1H), 5.01 (m, 1H), 4.62 (m, 1H), 4.01 (m, 2H), 3.26 (m, 1H), 3.06 (s, 3H), 2.96 (m, 7H), 1.49 (s, 9H).

¹³C NMR (CDCl₃): δ 170.0, 164.5, 154.9, 150.6, 140.0, 136.1, 134.2, 132.5, 131.3, 130.2, 127.4, 125.5, 122.2, 82.8, 56.0, 53.3, 49.9, 49.2, 41.7, 36.5, 36.3, 36.0, 27.8.

Example 208

Synthesis of N-(3,4-Dichlorobenzenesulfonyl)-L-(1,1-dioxothiamorpholin-3-carbonyl)-L-4-(N,N-dimethylcarbamyloxy)phenylalanine tert-Butyl Ester The title compound was prepared using the procedure described in Example 92 by substitution of the appropriate starting materials.

NMR data was as follows:

¹H NMR (CDCl₃): δ 7.91 (m, 1H), 7.66 (m, 2H), 7.06 (d, 2H), 6.94 (d, 2H), 6.33 (m, 1H), 4.98 (m, 1H), 4.60 (m, 1H), 3.49 (m, 3H), 3.12 (m, 2H), 3.04 (s, 3H), 3.00 (m, 2H), 2.94 (s, 3H), 1.44 (s, 9H).

$^{13}$C NMR (CDCl$_3$): δ 170.0, 164.3, 154.8, 150.6, 138.8, 137.9, 134.3, 132.4 132.0, 130.3, 129.2, 126.4, 122.1, 83.0, 55.5, 53.1, 50.2, 49.5, 41.8, 36.5, 36.2, 36.0, 27.7.

Example 209

Synthesis of N-(4-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:
$^1$H NMR (CDCl$_3$): δ 7.81 (d, 2H), 7.22 (d, 2H), 7.06–6.99 (m, 5H), 5.04 (sept, 1H), 4.89–4.82 (m, 1H), 4.56 (d, 1H), 4.39 (d), 3.88 (s, 3H), 3.83 (s, 1H), 3.17–3.03 (m, 2H), 3.09 (s, 3H), 3.00 (s, 3H), 1.25 (d, 3H), 1.22 (d, 3H), 1.15 (s, 3H), 1.12 (s, 3H).

$^{13}$C NMR (CDCl$_3$): δ 170.3, 168.5, 163.8, 154.9, 150.7, 132.9, 130.4, 130.3, 127.4, 121.7, 114.5, 73.5, 69.5, 55.6, 54.6, 53.2, 50.5, 37.7, 36.6, 36.3, 29.1, 23.9, 21.6, 21.5.

Example 210

Synthesis of N-(3-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:
$^1$H NMR (CDCl$_3$): δ 7.47–7.45 (m, 2H), 7.37–7.36 (m, 1H), 7.21 (d, 2H), 7.19–7.15 (m, 1H), 7.04–6.98 (m, 3H), 5.04 (sept, 1H), 4.88–4.82 (m, 1H), 4.58 (d, 1H), 4.40 (d, 1H), 3.89 (s, 1H), 3.87 (s, 3H), 3.17–3.03 (m, 2H), 3.09 (s, 3H), 3.00 (s, 3H), 1.25 (d, 3H), 1.23 (d, 3H), 1.15 (s, 3H), 1.08 (s, 3H).

$^{13}$C NMR (CDCl$_3$): δ 170.3, 168.3, 160.2, 154.9, 150.7, 136.9, 132.9, 130.5, 130.4, 121.7, 120.2, 120.0, 112.6, 73.4, 69.6, 55.7, 54.5, 53.2, 50.4, 37.7, 36.6, 36.3, 29.1, 23.7, 21.6, 21.5.

Example 211

Synthesis of N-(2-Methoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:
$^1$H NMR (CDCl$_3$): δ 7.92 (dd, 1H), 7.54 (dd, 1H), 7.21 (d, 2H), 7.07–7.00 (m, 4H), 6.96 (d, 1H), 5.01 (sept, 1H), 4.83–4.76 (m, 1H), 4.73 (d, 1H) 4.61 (d, 1H), 4.17 (s, 1H), 3.93 (s, 3H), 3.14–3.03 (m, 2H), 3.09 (s, 3H), 3.00 (s, 3H), 1.36 (s, 3H), 1.22 (d, 3H), 1.21 (s, 3H), 1.19 (d, 3H).

$^{13}$C NMR (CDCl$_3$): δ 170.3, 168.7, 157.7, 154.9, 150.6, 135.4, 133.0, 132.5, 130.3, 125.2, 121.7, 120.5, 112.6, 73.3, 69.5, 56.0, 54.8, 53.3, 50.4, 37.7, 36.6, 36.3, 29.2, 24.1, 21.6, 21.5.

Example 212

Synthesis of N-(3,4-Dimethoxybenzenesulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:
$^1$H NMR (CDCl$_3$): δ 7.50 (dd, 1H), 7.31 (d, 1H), 7.21 (d, 2H), 7.05–7.01 (m, 3H), 6.97 (d, 1H), 5.04 (sept, 1H), 4.89–4.82 (m, 1H), 4.56 (d, 1H), 4.40 (d, 1H), 3.95 (s, 3H), 3.94 (s, 3H), 3.89 (s, 1H), 3.17–3.03 (m, 2H), 3.09 (s 3H), 3.00 (s, 3H), 1.25 (d, 3H), 1.22 (d, 3H), 1.16 (s, 3H), 1.14 (s, 3H).

$^{13}$C NMR (CDCl$_3$): δ 170.3, 168.5, 154.9, 153.5, 150.7, 149.4, 132.9, 130.4, 127.6, 122.3, 121.7, 110.6, 110.3, 73.5, 69.6, 56.3, 56.1, 54.6, 53.2, 50.5, 37.7, 36.6, 36.3, 29.2, 23.8, 21.6, 21.5.

Example 213

Synthesis of N-(2,4-Difluorobenzenesulfonyl)-L-(thiamorpholin-3-carbonyl)-L-4-(N,N-dimethylcarbamyloxy)phenylalanine Isopropyl Ester The title compound was prepared following the procedure described for the preparation of Example 49 by substitution of the appropriate starting material.

NMR data was as follows:
$^1$H NMR (CDCl$_3$): δ 7.89 (m, 1H), 7.16 (m, 2H), 6.97 (m, 4H), 6.77 (d, 1H), 4.72 (m, 1H), 4.60 (m, 1H), 3.92 (m, 1H), 3.29 (m, 1H), 3.09 (m, 5H), 2.93 (s, 3H), 2.70 (m, 2H), 2.55 (m, 1H), 2.10 (m, 1H), 1.42 (s, 9H).

$^{13}$C NMR (CDCl$_3$): δ 170.0, 168.0, 167.7, 137.1, 164.4, 164.3, 161.1, 160.9, 157.7, 157.5, 154.8, 150.5, 132.7, 132.6, 132.4, 130.4, 124.0, 123.8, 121.7, 112.2, 111.9, 106.5, 106.1, 105.8, 82.6, 55.4, 53.9, 43.5, 36.4, 36.2, 27.7, 26.8, 25.5.

Example 214

Synthesis of N-(3,4-Dichlorobenzenesulfonyl)-L-(1,1-dioxothiamorpholin-3-carbonyl)-L-4-(N,N-dimethylcarbamyloxy)phenylalanine The title compound was prepared from the product of Example 208 using the procedure described in Method 11.

NMR data was as follows:
$^1$H NMR (CD$_3$OD): δ 8.04 (m, 1H), 7.68 (m, 2H), 7.52 (m, 1H), 7.21 (d, 2H), 7.02 (d, 2H), 5.22 (m, 1H), 4.63 (m, 1H), 4.22 (m, 1H), 3.71 (m, 1H), 3.57 (m, 1H), 3.30 (m, 3H), 3.08 (s, 3H), 3.02 (m, 3H), 2.97 (s, 3H).

$^{13}$C NMR (CD$_3$OD): δ 174.0, 168.0, 156.9, 152.1, 140.7, 139.3, 135.2, 133.2, 131.6, 130.7, 128.3, 123.2, 57.2, 54.9, 54.6, 51.7, 51.4, 43.3, 37.3, 36.9, 36.7.

Example 215

Synthesis of N-(3-Chlorobenzenesulfonyl)-L-(1,1-dioxothiamorpholin-3-carbonyl)-L-4-(N,N-dimethylcarbamyloxy)phenylalanine The title compound was prepared from the product of Example 207 using the procedure described in Method 11.

NMR data was as follows:
$^1$H NMR (CD$_3$OD): δ 7.94 (m, 1H), 7.77 (m, 2H), 7.58 (m, 1H), 7.46 (d, 1H), 7.19 (d, 2H), 7.07 (d, 2H), 5.23 (m, 1H), 4.63 (m, 1H), 4.20 (m, 1H), 3.71 (m, 1H), 3.43 (m, 1H), 3.26 (m, 4H), 3.17 (s, 3H), 2.95 (m, 5H).

$^{13}$C NMR (CD$_3$OD): δ 168.0, 152.1, 142.5, 136.8, 135.0, 132.7, 131.6, 128.6, 127.1, 123.3, 57.2, 54.9, 51.4, 51.2, 43.2, 37.2, 36.8, 36.7.

Example 216

Synthesis of N-(3-Chloro-4-fluorobenzenesulfonyl)-L-(1,1-dioxothiamorpholin-3-carbonyl)-L-4-(N,N-dimethylcarbamytoxy)phenylalanine tert-Butyl Ester The title compound was prepared using the procedure described in Example 92 by substitution of the appropriate starting materials.

NMR data was as follows:

$^1$H NMR (CD$_3$OD): δ 7.93 (d), 7.90 (m), 7.29 (s), 7.27 (d), 7.04 (d), 4.60 (m), 4.46 (d), 3.90–3.40 (m), 3.10 (s), 2.98 (s), 1.43 (s).

$^{13}$C NMR (CD$_3$OD): δ 171.5, 166.5, 156.9, 151.9, 135.2, 131.3, 129.9, 127.9, 127.8, 123.1, 117.8, 117.5, 101.4, 83.7, 57.9, 56.0, 42.9, 37.3, 36.9, 36.7, 28.1.

Example 217

Synthesis of N-(1-Methylpyrazole-4-sulfonyl)-L-(thiamorpholin-3-carbonyl)-L-4-(N,N-dimethylcarbamyloxy)phenylalanine tert-Butyl Ester The title compound was prepared following the procedures described for the preparation of Examples 49 and 117.

NMR data was as follows:

$^1$H NMR (CDCl$_3$): δ 7.77 (s), 7.63 (s), 7.08 (d), 6.93 (d), 6.76 (d), 6.71 (d), 5.50 (d), 5.22 (s), 4.82 (t), 4.61 (q), 3.83 (s), 3.25 (dt), 3.04 (m), 2.90 (s), 2.05 (dd), 1.34 (s).

$^{13}$C NMR (CDCl$_3$): δ 169.3, 166.8, 154.7, 150.4, 138.4, 132.4, 132.2, 130.2, 121.4, 118.3, 105.4, 82.5, 55.2, 53.6, 53.3, 39.5, 38.3, 36.6, 36.3, 36.1, 27.6, 23.5.

Example 218

Synthesis of N-(3,4-Difluorobenzenesulfonyl)-L-(thiamorpholin-3-carbonyl)-L-4-(N,N-dimethylcarbamyloxy)phenylalanine tert-Butyl Ester The title compound was prepared following the procedure described for the preparation of Examples 49 by substitution of the appropriate starting materials.

NMR data was as follows:

$^1$H NMR (CD$_3$OD): δ 7.88 (m, 1H), 7.70 (m, 1H), 7.57 (m, 1H), 7.23 (d, 2H), 7.03 (d, 2H), 6.83 (d, 1H), 5.63 (dd, 1H), 5.07 (t, 1H), 4.58 (m, 1H), 3.22–3.00 (m, 3H), 3.09 (s, 3H), 2.98 (s, 3H), 2.07 (dd, 1H), 1.44 (s, 9H).

$^{13}$C NMR (CD$_3$OD): δ 171.3, 169.3, 156.9, 152.0, 135.0, 131.6, 126.5, 122.9, 120.2, 119.9, 119.4, 118.7, 118.4, 106.4, 83.6, 56.5, 55.6, 37.1, 36.8, 36.6, 28.1, 25.2.

Example 219

Synthesis of N-(Toluene-4-sulfonyl)-L-4-(5,5-dimethyl)thioprolyl-L-(thiomorpholin-4-ylcarbonyloxy)phenylalanine Isopropyl Ester The title compound was prepared using the procedure described in Example 82 by substitution of the appropriate starting materials.

NMR data was as follows:

$^1$H NMR (CDCl$_3$): δ 9.09 (s, 1H), 8.88 (m, 1H), 8.16 (m, 1H), 7.50 (m, 1H), 7.22 (d, 2H), 7.01 (d, 2H), 6.91 (d, 1H), 5.05 (m, 1H), 4.85 (m, 1H), 4.60 (d, 1H), 4.46 (d, 1H), 3.89 (s, 1H), 3.93–3.83 (m, 4H), 3.11 (m, 2H), 2.69 (m, 4H), 1.29–1.16 (m, 12H).

$^{13}$C NMR (CDCl$_3$): δ 170.3, 167.8, 154.3, 153.5, 150.4, 148.7, 135.8, 133.1, 132.9, 130.4, 124.0, 121.8, 73.7, 69.7, 54.7, 53.2, 50.5, 47.1, 46.4, 37.6, 29.1, 27.4, 27.0, 23.8, 21.6, 21.5.

Example 220

Synthesis of N-(3,4-Difluorobenzenesulfonyl)-L-(thiamorpholin-3-carbonyl)-L-4-(N,N-dimethylcarbamyloxy)phenylalanine The title compound was prepared from the product of Example 218 using the procedure described in Method 11.

NMR data was as follows:

$^1$H NMR (CDCl$_3$): δ 7.89 (s, 1H), 7.57–7.46 (m, 2H), 7.35 (d, 1H), 7.32–7.22 (m, 1H), 7.09 (d, 2H), 6.91 (d, 2H), 6.64 (d, 1H), 5.50 (d, 1H), 4.89 (s, 1H), 4.88–4.79 (m, 1H), 3.17–3.02 (m, 3H), 3.02 (s, 3H), 2.93 (s, 3H), 1.75 (dd, 1H).

$^{13}$C NMR (CDCl$_3$): δ 173.6, 167.7, 155.5, 152.0, 151.8, 150.1, 148.4, 132.8, 130.4, 124.6, 121.5, 118.7, 118.5, 117.5, 117.3, 117.1, 106.9, 54.9, 53.0, 36.4, 36.2, 36.0, 23.4.

Example 221

Synthesis of N-(2,5-Dichlorothiophene-3-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 7.18 (d, 2H), 7.11 (s, 1H), 7.00 (d, 2H), 6.87 (d, 1H), 5.03–4.99 (m, 1H), 4.84–4.81 (m, 1H), 4.65–4.56 (m, 2H), 4.07 (s, 1H), 3.10–3.01 (m, 5H), 2.98 (s, 3H), 1.37 (s, 3H), 1.22 (s, 3H), 1.21 (s, 3H), 1.18 (s, 3H).

$^{13}$C NMR (CDCl$_3$): δ 170.3, 167.7, 154.9, 150.7, 132.9, 132.8, 131.9, 130.3, 128.0, 127.0, 121.8, 73.4, 69.6, 54.8, 53.2, 50.5, 37.5, 36.6, 36.3, 29.1, 23.8, 21.6, 21.5.

Example 222

Synthesis of N-(1-Methylpyrazole-4-sulfonyl)-L-(5,5-dimethyl)thiaprolyl-L-4-(thiomorpholin-4-ylcarbonyloxy)phenylalanine Isopropyl Ester The title compound was prepared using the procedure described in Example 82 by substitution of the appropriate starting materials.

NMR data was as follows:

$^1$H NMR(CDCl$_3$): δ 7.89 (s, 1H), 7.80 (s, 1H), 7.21 (d, 2H), 7.01 (m, 3H), 5.03 (m, 1H), 4.83 (m, 1H), 4.54 (d, 1H), 4.40 (d, 1H), 3.95 (s, 3H), 3.86 (m, 4H), 3.80 (s, 1H), 3.09 (m, 2H), 2.68 (m, 4H), 1.28 (s, 3H), 1.22 (m, 6H), 1.16 (s, 3H).

$^{13}$C NMR (CDCl$_3$): δ 170.4, 168.3, 153.5, 150.4, 139.3, 133.3, 132.9, 130.4, 121.7, 117.6, 73.8, 69.7, 54.8, 53.2, 50.5, 47.1, 46.4 39.6, 37.6, 29.0, 27.4, 27.1, 24.0, 21.6, 21.5.

Example 223

Synthesis of N-(8-Quinolinesulfonyl)-L-prolyl-L-4-(N,N-dimethylcarbamyloxy)phenylalanine Isopropyl Ester The title compound was prepared following the procedure described for the preparation of Example 2 by substitution of the appropriate starting materials.

NMR data was as follows:

$^1$H NMR (CDCl$_3$): δ 9.01–8.99 (m, 1H), 8.56–8.53 (m, 1H), 8.27–8.23 (m, 1H), 8.07–8.04 (m, 1H), 7.66–7.61 (m, 2H), 7.55–7.51 (m, 1H), 7.17 (d, 2H), 7.01 (d, 2H), 5.27–5.23 (m, 1H), 5.07–4.98 (m, 1H), 4.84–4.76 (m, 1H), 3.34–3.20 (m, 3H), 3.06–2.98 (m, 4H), 2.97 (s, 3H), 2.15–2.09 (m, 1H), 1.64–1.51 (m, 3H), 1.23 (d, 6H).

$^{13}$C NMR (CDCl$_3$): δ 172.0, 170.5, 154.9, 151.5, 150.6, 143.9, 136.8, 135.6, 134.9, 134.1, 133.3, 130.2, 129.2, 125.6, 122.3, 121.7, 69.3, 62.8, 53.5, 48.7, 37.3, 36.5, 36.3, 29.7, 24.3, 21.6, 21.6.

Example 224

Synthesis of N-(8-Quinolinesulfonyl)-L-prolyl-L-4-(N,N-dimethylcarbamyloxy)phenylalanine The title compound was prepared from the product of Example 223 using the procedure described in Method 7.

NMR data was as follows:

¹H NMR (CD₃OD): δ 9.03–9.01 (m, 1H), 8.49–8.42 (m, 2H), 8.23–8.20 (m, 1H), 8.09–8.07 (m, 1H), 7.73–7.61 (m, 2H), 7.25 (d, 2H), 7.00 (d, 2H), 5.30–5.27 (m, 1H), 4.73–4.69 (m, 1H), 3.38–3.21 (m, 3H), 3.09–3.02 (m, 4H), 2.95 (s, 3H), 1.86 (m, 1H), 1.78–1.73 (m, 1H), 1.58–1.50 (m, 2H).

¹³C NMR (CD₃OD): δ 175.3, 174.2, 164.7, 156.9, 152.9, 145.2, 138.5, 136.9, 135.8, 135.6, 131.6, 130.9, 126.9, 123.8, 122.9, 63.9, 54.7, 50.0, 37.5, 36.8, 36.7, 31.6, 25.5.

Example 225

Synthesis of N-(8-Quinolinesulfonyl)-L-(5,5-dimethyl)thiaprolyl-L-4-(N-dimethylcarbamyloxy)phenylalanine Isoproplyl Ester The title compound was prepared following the procedure described for the preparation of Example 2 by substitution of the appropriate starting materials.

NMR data was as follows:

¹H NMR (CDCl₃): δ 9.05–9.03 (m, 1H), 8.53–8.49 (m, 1H), 8.26–8.22 (m, 1H), 8.08–8.05 (m, 1H), 7.65–7.60 (m, 1H), 7.56–7.52 (m, 1H), 7.19 (d, 2H), 7.06 (d, 1H), 7.00 (d, 2H), 5.17 (d, 1H), 4.94 (m, 1H), 7.74–4.78 (m, 2H), 4.66 (s, 1H), 3.08–2.99 (m, 8H), 1.20–1.16 (m, 12H).

¹³C NMR (CDCl₃): δ 170.2, 168.9, 154.9, 151.5, 150.6, 144.2, 136.7, 134.4, 134.4, 133.1, 130.3, 129.2, 125.5, 122.3, 121.7, 73.2, 69.3, 54.8, 53.3, 50.6, 37.6, 36.6, 36.3, 29.2, 24.1, 21.5, 21.4.

Example 226

Synthesis of N-(8-Quinolinesulfonyl)-L-(5,5-dimethyl)thiaprolyl-L-4-(N,N-dimethylcarbamyloxy)phenylalanine The title compound was prepared from the product of Example 225 using the procedure described in Method 7.

NMR data was as follows:

¹H NMR (CD₃OD): δ 9.06–9.04 (m, 1H), 8.45–8.39 (m, 2H), 8.23–8.14 (m, 1H), 7.72–7.61 (m, 2H), 7.32 (d, 2H), 7.03 (d, 2H), 5.12 (d, 1H), 4.87 (d, 1H), 4.69–4.64 (m, 2H), 3.28–3.02 (m, 5H), 2.98 (s, 2H), 1.18 (s, 3H), 1.08 (s, 3H).

¹³C NMR (CD₃OD): δ 174.1, 171.8, 157.1, 152.9, 152.0, 145.5, 138.4, 137.3, 135.8, 135.6, 135.1, 131.8, 130.9, 126.8, 123.8, 122.9, 73.7, 55.9, 54.8, 51.7, 37.6, 36.8, 36.7, 30.2, 25.0.

Example 227

Synthesis of N-(3-Sulfonamido-4-chloro-benzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

¹H NMR (CDCl₃): δ 8.45 (d, 1H), 7.91 (d, 1H), 7.67 (d, 1H), 7.13 (d, 2H), 7.06 (d, 1H), 7.01 (d, 2H), 5.90 (brs, 2H), 5.06–5.02 (m, 1H), 4.79–4.72 (m, 1H), 4.14–4.10 (m, 1H), 3.42–3.39 (m, 1H), 3.25–3.14 (m, 2H), 3.07 (s, 3H), 3.04–2.97 (m, 1H), 2.96 (s, 3H), 1.98–1.96 (m, 1H), 1.72–1.62 (m, 3H), 1.28–1.25 (m, 6H).

¹³C NMR (CDCl₃): δ 170.8, 170.7, 155.1, 150.6, 141.4, 136.9, 136.1, 132.9, 132.8, 131.9, 130.3, 128.7, 121.9, 69.8, 62.1, 53.3, 49.6, 36.9, 36.6, 36.4, 30.4, 24.3, 21.6, 21.6.

Example 228

Synthesis of N-(Toluene-4-sulfonyl)-L-(1-oxothiomorpholin-3-carbonyl)-L-4-(N,N-dimethylcarbamyloxy)phenylalanine Isopropyl Ester The title compound was prepared following the procedure described for the preparation of Example 182 and substitution of appropriate starting materials.

NMR data was as follows:

¹H NMR (CDCl₃): δ 7.77 (d, 2H), 7.72 (d, 2H, 7.33 (m, 2H), 7.20 (m, 2H), 7.12 (d, 2H), 7.01 (m, 2H), 5.10 (m, 1H), 5.01 (m, 1H), 4.84 (m, 1H), 4.75 (m, 1H), 3.80 (m, 3H), 3.05 (m, 4H), 2.96 (m, 3H), 2.74 (m, 1H), 2.42 (m, 4H), 1.30–1.20 (m, 6H).

¹³C NMR (CDCl₃): δ 170.6, 170.4, 166.8, 166.7, 154.9, 150.7, 150.6, 145.1, 144.8, 135.8, 135.5, 132.7, 130.6, 130.4, 130.3, 130.0, 127.7, 127.1, 122.4, 121.8, 69.8, 69.4, 55.8, 53.7, 52.9, 50.8, 48.2, 47.9, 42.0, 41.2, 38.4, 36.6, 36.5, 36.3, 31.2, 21.5, 21.5.

Example 229

Synthesis of N-(2,4-Difluorobenzenesulfonyl)-L-(1-oxothiomorpholin-3-carbonyl)-L-4-(N,N-dimethylcarbamyloxy)phenylalanine tert-Butyl Ester The title compound was prepared following the procedure described for the preparation of Example 182 and substitution of appropriate starting materials.

NMR data was as follows:

¹H NMR (CDCl₃): δ 7.91 (m, 1H), 7.30 (m, 2H), 6.97 (m, 4H), 4.71 (m, 1H), 4.55 (m, 1H), 3.90 (m, 2H), 3.77 (m, 1H), 3.11 (m, 4H), 2.85 (m, 3H), 2.80 (m, 1H), 2.60 (m, 2H), 1.46 (s, 9H), 1.39 (s, 9H).

¹³C NMR (CDCl₃): δ 170.0, 168.0, 167.9, 166.4, 166.2, 164.6, 164.4, 162.7, 161.4, 161.2, 157.9, 157.8, 154.8, 150.6, 150.4, 132.8, 132.5, 132.4, 130.9, 130.4, 130.1, 123.3, 123.1, 122.2, 121.6, 121.1, 122.6, 122.2, 111.9, 106.6, 106.3, 105.9, 82.8, 82.3, 55.8, 54.1, 53.2, 51.6, 49.2, 48.7, 43.1, 42.3, 38.7, 36.5, 36.2, 31.8, 27.7.

Example 230

Synthesis of N-(1-Methylpyrazole-4-sulfonyl)-L-(5,5-dimethyl)thiaprolyl-L-4-(N,N-dimethylcarbamyloxy)phenylalanine 2,2-Dimethylpropyl Ester The product from Example 161 (1 g., 0.72 mmol) was dissolved in neopentyl alcohol (5 mL). Titanium (IV) isopropoxide (260 mg., 0.9 mmol) was added and the mixture heated at 100° C. under an inert atmosphere for 48 h. Excess neopentyl alcohol was removed under reduced pressure and the residue purified by flash column chromatography (silica, 1% MeOH in CHCl₃) to give the title compound as a white solid (1.02 g, 97%).

Physical data was as follows:

MS (+) ESI [M+H]⁺ 610; [M+NH4]⁺ 627 (100%).

Anal. Calcd. For C₂₉H₃₉N₅O₇S: C, 53.18; H, 6.45; N, 11.49.

Found: C, 53.46; H, 6.38; N, 11.06.

Example 231

Synthesis of N-(Pryridine-3-sulfonyl)-L-(5,5-dimethyl)thiaprolyl-L-4-(N,N-dimethylcarbamyloxy)phenylalanine 2,2-Dimethylpropyl Ester The product from Example 173 was subjected to the transesterification procedure described for the preparation of Example 230. The compound was purified by flash column chromatography (silica, 1% MeOH in CHCl$_3$) followed by recrystallization from ethyl acetate to give the title compound as a white solid (720 mg, 47%).

Physical data was as follows:

Anal. Calcd. For C$_{28}$H$_{38}$N$_4$O$_7$S$_2$: C, 55.43; H, 6.31; N, 9.23.

Found: C, 55.37; H, 6.32; N, 9.22.

Example 232

Synthesis of N-(1-Methylpyrazole-4-sulfonyl)-L-(5,5-dimethyl)thiaprolyl-L-4-(N,N-dimethylcarbamyloxy)phenylalanine Cyclopropylmethyl Ester The product from Example 161 was subjected to the transesterification procedure described for the preparation of Example 230. The title compound was obtained as a white solid following flash column chromatography (silica, 1% MeOH in CHCl$_3$) (860 mg, 70%).

Physical data was as follows:

Anal. Calcd. For C$_{26}$H$_{35}$N$_5$O$_7$S$_2$: C, 52.6; H, 5.94; N, 11.8.

Found: C, 52.49; H, 5.93; N, 11.62.

Example 233

Synthesis of N-(1-Methylpyrazole-4-sulfonyl)-L-(5,5-dimethyl)thiaprolyl-L-4-(N,N-dimethylcarbamyloxy)phenylalanine Methyl Ester The title compound was prepared following the procedure described for the preparation of Example 161 and substitution of appropriate starting materials.

Physical data was as follows:

MS (+) ESI [M+H]$^+$ 554; [M+NH$_4$]$^+$ 571 (100%).

Anal. Calcd. For C$_{23}$H$_{31}$N$_5$O$_7$S$_2$.0.2 EtOAc: C, 50.04; H, 5.75; N, 12.26.

Found: C, 50.12; H, 5.69; N, 12.19.

Example 234

Synthesis of N-(Pyridine-3-sulfonyl)-L-(5,5-dimethyl)thiaprolyl-L-4-(N,N-dimethylcarbamyloxy)phenylalanine Ethyl Ester The product from Example 173 was subjected to the transesterification procedure described for the preparation of Example 230. The compound was purified by flash column chromatography (silica, 2% MeOH in CHCl$_3$), followed by recrystallization from ethyl acetate to give the title compound as a white solid (1.2 g, 61%).

Physical data was as follows:

Anal. Calcd. For C$_{25}$H$_{32}$N$_4$O$_7$S$_2$: C, 53.18; H, 5.71; N, 9.92.

Found: C, 53.14; H, 5.72; N, 9.57.

Example 235

Synthesis of N-(Pyridine-3-sulfonyl)-L-(5,5-dimethyl)thiaprolyl-L-4-(N,N-dimethylcarbamyloxy)phenylalanine Cyclopropylmethyl Ester The product from Example 173 was subjected to the transesterification procedure described for the preparation of Example 230. The compound was isolated as a white solid following flash column chromatography (silica, 2% MeOH in CHCl$_3$) and recrystallization from EtOAc:hexanes (1 g, 65%).

Physical data was as follows:

Anal. Calcd. For C$_{27}$H$_{34}$N$_4$O$_4$S$_2$: C, 54.9; H, 5.8; N, 9.48.

Found: C, 54.77; H, 5.65; N, 9.46.

Example 236

Synthesis of N-(1-Methylpyrazole-4-sulfonyl)-L-(5,5-dimethyl)thiaprolyl-L-4-(N,N-dimethylcarbamyloxy)phenylalanine 2-Methoxyphenyl Ester To a solution of the compound from Example 139 (1.79 g, 3.31 mmol), 2-methoxy-phenol (0.45 g, 3.64 mmol) and BOP (1.61 g, 3.64 mmol) in methylene chloride (25 mL) at 0° C. was added triethylamine (0.7 mL, 4.97 mmol). The reaction mixture was then slowly warmed to 25° C. where it was stirred, under nitrogen, for 24 h. The reaction was quenched by addition, of 100 mL saturated brine and extracted with EtOAc. The organic extract was washed sequentially with 2N HCl (3 times), saturated sodium bicarbonate (3×) and saturated brine (2×), dried over MgSO$_4$, and evaporated to 2.1 g of crude product. Flash chromatography (eluant: 96–4 methylene chloride:EtOAc) afforded 1.85 g of a white solid which upon trituration with hexane gave 1.68 g (79%) of white crystals, mp 72–75° C.

Physical data was as follows:

Anal. Calcd. For C$_{29}$H$_{35}$N$_5$O$_8$S$_2$: C, 59.94; H, 5.46; N, 10.85.

Found: C, 53.45; H, 5.62; N, 10.31.

Example 237

Synthesis of N-(1-Methylpyrazole-4-sulfonyl)-L-(5,5-dimethyl)thiaprolyl-L-4-(N,N-dimethylcarbamyloxy)phenylalanine n-Butyl Ester A solution of the compound of Example 139 (2 g) in n-butanol (50 mL) was saturated upon ice-cooling with HCl gas. The mixture was stirred at ambient temperature for 36 h, evaporated in vacuo to almost dryness, then partitioned between 5% NaHCO$_3$ and chloroform. The organic layer was dried and evaporated in vacuo to furnish 900 mg of the title compound.

Physical data was as follows:

MS: [(+)ESI], [M+H]$^+$ 596.

Example 238

Synthesis of N-(1-Methylpyrazole-4-sulfonyl)-L-(5,5-dimethyl)thiaprolyl-L-4-(N,N-dimethylcarbamyloxy)phenylalanine n-Propyl Ester A solution of N-(1-methylpyrazole-4-sulfonyl)-L-(5,5-dimethyl)thiaprolyl-L-4-(N,N-dimethylcarbamyloxy) phenylalanine (2 g) in n-propanol (50 mL) was saturated upon ice-cooling with HCl gas. The mixture was stirred at ambient temperature for 36 hours, evaporated in vacuo to almost dryness, then partioned between 5% NaHCO$_3$ and chloroform. The organic layer was dried and evaporated in vacuo to provide 1500 mg of the title compound.

Physical data was as follows:

MS: [(+)ESI], [M+H]$^+$ 582.

Example 239

Synthesis of N-(1-Methylpyrazole-4-sulfonyl)-L-(5,5-dimethyl)thiaprolyl-L-4-(N,N-dimethylcarbamyloxy)phenylalanine 2,2-Dimethylpropionyloxymethyl Ester Potassium iodide (324 mg) was added at once to a mixture of the compound of Example 139 (1.08 g), chloromethylpivalate (294 mg) and powdered K$_2$CO$_3$ (222 mg) in DMF (5 mL). The reaction mixture was stirred at ambient temperature overnight, partitioned between water (12 mL) and ethyl acetate (60 mL). The separated organic layer was washed with ice cold 0.1 N sodium thiosulfate, water and brine, then dried over MgSO$_4$, filtered and evaporated in vacuo to yield 750 mg of the title compound.

Physical data was as follows:

MS: [(+)ESI], [M+H]$^+$ 654.

Example 240

Synthesis of N-(Toluene-4-sulfonyl)-L-prolyl-L-4-(4-phenylpiperazin-1-ylcarbonyloxy)phenylalanine tert-Butyl Ester The title compound was prepared following the procedure outlined for Example 4 by substitution of the appropriate starting materials. A white solid was obtained, mp. 60–65° C.

Physical data was as follows:

MS (+ESI) 694.3 [M+NH$_4$]$^+$.

Anal. Calcd for C$_{36}$H$_{44}$N$_4$O$_7$S.0.5C$_4$H$_8$O$_2$: C, 63,31; H, 6.71; N, 7.77.

Found: C, 63.12; H, 6.58; N, 7.69.

Example 241

Synthesis of N-(Toluene-4-sulfonyl)-L-prolyl-L-4-(4'-(ethoxycarbonyl)piperidin-1-ylcarbonyloxy)phenylalanine tert-Butyl Ester The carbamate was prepared by treatment of Tos-Pro-Tyr-t-butyl ester with 4-nitrophenylchloroformate, followed by addition of ethylisonipecotate (triethylamine, methylene chloride, chilled to 0° C., then stirred at room temperature overnight). The crude product was purified by flash chromatography (silica, 95:5 EtOAc:Et$_3$N) to afford a white solid. (0.78 g, 39%).

NMR data was as follows:

$^1$H NMR (DMSO-d$_6$, 400 MHz): δ 8.15 (d, 1H, J=7.68 Hz); 7.70 (d, 2H, J=8.34 Hz); 7.40 (d, 2H, J=7.90 Hz); 7.22 (d, 2H, J=8.56 Hz); 7.00 (d, 2H, J=8.56 Hz); 4.37 (m, 1H), 4.07 (q, 2H, J=7.14, 14.08 Hz); 4.03 (m, 2H); 3.90 (m, 1H); 3.34 (m, 1H); 3.09 (m, 2H); 3.00 (m, 3H); 2.59 (m, 1H); 2.39 (s, 3H); 1.87 (m, 2H); 1.58 (m, 5H); 1.41 (m, 1H); 1.35 (s, 9H); 1.18 (t, 3H, 7.14 Hz)

IR (KBr, cm$^{-1}$): 3410, 2990, 2950, 1725, 1680, 1510, 1430, 1355, 1220, 1200, 1170, 1000, 675, 595.

MS ((+)ESI, m/z (%)) 689 (100[M+NH$_4$]$^+$); 691 (37[M+NH$_4$]$^+$).

Anal. Calc'd for C$_{34}$H$_{45}$N$_3$O$_9$S: C, 60.79; H, 6.75; N, 6.25.

Found: C, 60.59; H, 6.67; N, 6.22.

Example 242

Synthesis of N-(Toluene-4-sulfonyl)-L-prolyl-L-4-(N-(4'-(2'-aminoethyl)morpholino)carbamyloxy)phenylalanine The title compound was prepared from the product of Example 152 using the procedure described in Method 11.

NMR data was as follows:

$^1$H NMR (DMSO-d$_6$, 400 MHz): δ 12.75 (s, 1H); 8.08 (d, 1H); 7.68 (d, 2H); 7.60 (t, 1H); 7.39 (d, 2H); 7.21 (d, 2H); 6.97 (d, 2H); 4.46 (m, 1H); 4.08 (m, 1H); 3.56 (m, 4H); 3.26 (m, 3H); 3.09 (m, 2H); 2.94 (m, 1H); 2.49 (s, 6H); 2.48 (s, 3H); 1.5 (m, 3H); 1.38 (m, 1H).

IR (KBr, cm$^{-1}$) 3400, 2975, 1725, 1650, 1500, 1350, 1150, 650, 575, 550.

MS ((-)ESI, m/z (%)) 587 (100[M–H]$^+$).

Anal. Calc'd for C$_{28}$H$_{36}$N$_4$O$_8$S.HCOOH.0.5H$_2$O: C, 54.11; H, 6.11; N, 8.70.

Found: C, 53.96; H, 6.02; N, 8.68.

Example 243

Synthesis of N-(Toluene-4-sulfonyl)-L-prolyl-L-4-[4-(carboxy)piperidin-1-ylcarbonyloxy]phenylalanine The title compound was prepared from the product of Example 241 using the procedures described in Methods 6 and 11.

NMR data was as follows:

$^1$H NMR (DMSO-d$_6$, 400 MHz): δ 12.50 (bs, 2H); 8.08 (d, 1H, J=7.90 Hz); 7.69 (d, 2H, J=8.34 Hz); 7.39 (d, 2H, J=7.90 Hz); 7.22 (D, 2H, J=8.56 Hz); 6.99 (d, 2H, J=8.56 Hz); 4.46 (m, 1H); 4.09 (m, 1H); 4.00 (m, 1H); 3.90 (m, 1H); 3.30 (m, 1H); 3.09 (m, 3H); 2.95 (m, 2H); 2.49 (m, 1H); 2.38 (s, 3H); 1.86 (m, 2H); 1.36–1.61 (m, 6H).

IR (KBr, cm$^{-1}$) 3400, 2960, 1720, 1535, 1430, 1350, 1200, 1160, 670, 590, 550.

MS ((+)ESI, m/z (%)) 605 (100[M+NH$_4$]$^+$).

Anal. Calc'd for C$_{28}$H$_{33}$N$_3$O$_9$S H$_2$O: C, 55.53; H, 5.65; N, 6.94.

Found: C, 55.23; H, 5.82; N, 6.59.

Example 244

Synthesis of N-(Toluene-4-sulfonyl)-L-prolyl-L-4-(N,N-bis-(2-hydroxyethyl)carbamyloxy)phenylalanine Isopropyl Ester The carbamate was prepared by treatment of Tos-Pro-Tyr-iPr ester with 4-nitrophenyl chloroformate, followed by addition of diethanol amine (triethylamine, methylene chloride, chilled to 0° C., stirred at room temperature overnight). The chloride product was purified by flash chromatography (silica, 98:2 EtOAc:EtOH) to afford a white foam. (0.180 g, 28%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.23 (D, 2H, J=8.56 Hz); 6.99 (d, 2H, J=8.56 Hz); 4.87 (m, 1H); 4.83 (t, 1H, J=5.49 Hz); 4.76 (t, 1H, J=5.49 Hz); 4.42 (m, 1H); 4.08 (m, 1H); 3.58 (m, 2H); 3.51 (m, 2H); 3.44 (m, 2H); 3.34 (m, 3H); 2.99–3.09 (m, 3H); 2.39 (s, 3H); 1.59 (m, 3H); 1.41 (m, 1H); 1.16 (d, 3H, J=6.15 Hz); 1.12 (d, 3H, J=6.15 Hz).

IR (KBr, cm$^{-1}$) 3420, 2940, 1725, 1535, 1670, 1520, 1460, 1410, 1350, 1220, 1160, 1110, 670, 600, 550.

MS ((+)ESI, m/z (%)) 606 (15[M+H]$^+$); 623 (100[M+NH$_2$]$^+$).

Anal. Calc'd for C$_{29}$H$_{39}$N$_3$O$_9$S H$_2$O: C, 56.66; H, 6.56; N, 6.84.

Found: C, 56.66; H, 6.41; N, 6.72.

Example 245

Synthesis of N-(Toluene-4-sulfonyl)-L-prolyl-L-4-[3-(hydroxymethyl)piperidin-1-ylcarbonyloxy]phenylalanine Isopropyl Ester The carbamate was prepared by treatment of Tos-Pro-Tyr-iPr ester with 4-nitrophenyl chloroformate, followed by addition of 3-piperidine methanol (triethylamine, methylene chloride, chilled to 0° C., stirred at room temperature overnight). The crude product was purified by flash chromatography (silica, 3:2 EtOAc:Hex) to afford a white foam (0.519 g, 67%).

NMR data was as follows:

$^1$H NMR (DMSO-d$_6$, 400 MHz): δ 8.26 (d, 1H, J=7.90 Hz); 7.69 (d, 2H, J=8.12 Hz); 7.40 (d, 2H, J=8.12 Hz); 7.22 (d, 2H, J=8.56 Hz); 6.98 (d, 2H, J=8.34 Hz); 4.85 (M, 1H); 4.57 (bs, 1H); 4.42 (m, 1H); 3.99–4.09 (m, 3H); 3.85 (m, 1H); 3.31 (m, 1H); 3.22 (m, 1H); 2.91–3.10 (m, 4H); 2.80 (m, 1H); 2.55 (m, 1H); 2.39 (s, 3H); 1.51–1.72 (m, 6H); 1.42 (m, 2H); 1.16 (d, 3H, J=6.15 Hz); 1.11 (d, 3H, J=6.15 Hz).

IR (KBr, cm$^{-1}$) 3400, 2990, 2940, 2880, 1725, 1520, 1430, 1350, 1220, 1165, 1100, 660, 600, 550.

MS ((–)ESI, m/z (%)) 614 (30[M–H]).

Anal. Calc'd for C$_{31}$H$_{41}$N$_3$O$_8$S: C, 60.47; H, 6.71; N, 6.82.

Found: C, 59.83; H, 6.61; N, 6.59.

Example 246

Synthesis of N-(Toluene-4-sulfonyl)-L-prolyl-L-4-(4-trifuoromethanesulfonylpiperazin-1-ylcarbonyloxy)phenylalanine tert-Butyl Ester The title compound was prepared following the procedure outlined for Example 128 and substitution of appropriate staring materials.

Physical data was as follows:

MS (+ESI):733 [M+H]$^+$.

Anal. Calc'd for C$_{31}$H$_{39}$F$_3$N$_4$O$_9$S$_2$.0.10 C4H8O2: C, 50.20; H, 5.40; 7.55.

Found: C, 50.25; H, 5.46; N, 7.07.

Example 247

Synthesis of N-(4-(N-Phenylurea)benzenesulfonyl)-L-prolyl-L-4-(N,N-dimethylcarbamyloxy)phenylalanine tert-Butyl Ester A mixture of Example 107 (250 mg, 0.51 mmol), phenyl isocyanate (62 mg, 0.56 mmol) and triethylamine (76 μL, 0.56 mmol) was heated to reflux under argon. Reflux was continued overnight. Solvent was removed under reduced pressure and the residue purified by flash chromatography. (silica, hexanes: EtOAc 1:1 then EtOAc) to give the title compound as an off-white foam (160 mg, 46%), mp 112–115° C.

Physical data was as follows:

MS (+ESI) [M+NH$_4$]$^+$ 697 (100%).

Example 248

Synthesis of N-(2-Trifluoroacetyl-1,2,3,4-tetrahydroisoquinolin-7-sulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

NMR data was as follows:

$^1$H NMR (CDCl$_3$): δ 7.70–7.66 (m, 2H), 7.35–7.30 (m, 1H), 7.27–7.21 (m, 1H), 7.14–7.10 (m, 2H), 7.01 (d, 2H), 5.09–4.95 (m, 1H), 4.89–4.75 (m, 2H), 4.14–4.07 (m, 1H), 3.93–3.85 (m, 2H), 3.35–3.20 (m, 2H), 3.13–2.97 (m, 9H), 2.05–2.01 (m, 1H), 1.63 (1.50 (m, 3H), 1.20 (d, 6H).

$^{13}$C NMR (CDCl$_3$): δ 170.7, 170.6, 170.5, 156.3, 155.8, 154.9, 150.6, 140.1, 139.2, 135.1, 135.1, 13.2, 133.0, 133.0, 132.9, 130.2, 130.1, 129.9, 126.9, 126.4, 126.3, 125.8, 121.7, 118.3, 114.5, 69.6, 62.1, 62.0, 53.2, 49.6, 46.6, 46.5, 45.1, 42.7, 40.9, 37.1, 36.6, 36.3, 30.1, 30.0, 29.2, 27.8, 24.2, 24.2, 21.6, 21.6.

Example 249

Synthesis of N-(1-Methylpyrazole-3-sulfonyl)-L-(5,5-dimethyl)thiaprolyl-L-4-(N,N-dimethylcarbamyloxy)phenylalanine Isopropyl Ester Substituting N-methylpyrazole-3-sulfonyl chloride (See European Patent Application, 095925) and following the method for the preparation of Example 56, gave the title compound.

NMR data was as follows:

$^1$H NMR (CDCl$_3$): δ 7.45 (d, 1H), 7.21 (d, 2H), 7.09 (d, 1H), 7.01 (d, 2H), 6.71 (d, 1H), 5.03–4.98 (m, 1H), 4.87–4.84 (m, 1H), 4.60–4.59 (m, 2H), 4.05 (s, 1H), 3.97 (s, 3H), 3.12–3.01 (m, 5H), 2.98 (s, 3H), 1.22–1.15 (m, 12H).

$^{13}$C NMR (CDCl$_3$): δ 170.3, 168.3, 154.9, 150.7, 146.7, 133.0, 131.9, 130.3, 121.7, 108.9, 73.5, 69.5, 54.7, 53.3, 50.7, 39.9, 37.7, 36.6, 36.3, 28.8, 24.1, 21.5, 21.5.

Example 250

Synthesis of N-(1-Methylpyrazole-3-sulfonyl)-L-(5,5-dimethyl)thiaprolyl-L-4-(N,N-dimethylcarbamyloxy)phenylalanine The title compound was prepared from the product of Example 249 using the procedure described in Method 7.

NMR data was as follows:

$^1$H NMR (CD$_3$OD): δ 8.25 (d, 1H), 7.76 (d, 1H), 7.32 (d, 2H), 7.01 (d, 2H), 6.70 (d, 1H), 4.74–4.71 (m, 1H), 4.68 (d, 1H), 4.56 (d, 1H), 4.12 (s, 1H), 3.97 (s, 3H), 3.24–3.07 (m, 5H), 2.97 (s, 3H), 1.14 (s, 3H), 1.13 (s, 3H).

$^{13}$C NMR (CD$_3$OD): δ 174.1, 171.4, 157.0, 151.9, 148.2, 135.7, 134.2, 131.8, 122.9, 109.6, 74.4, 55.6, 55.0, 51.5, 40.0, 37.6, 36.8, 36.7, 29.6, 24.8.

Example 251

Synthesis of N-(Pyridine-4-sulfonyl)-L-(5,5-dimethyl)thiaprolyl-L-4-(N,N-dimethylcarbamyloxy)phenylalanine Isopropyl Ester The title compound was prepared following the procedure outlined for the preparation of Example 56, where 4-pyridinesulfonyl chloride N-oxide was used in place of 3-pyridinesulfonyl chloride (see Marsais and coworkers, *J. Org. Chem.* 1987, 52, 1133–1136). Deoxygenation of the N-oxide was accomplished using the procedure of Aoyagi and coworkers, *Synthesis* 1997, 891.

NMR data was as follows:

$^1$H NMR (CDCl$_3$): δ 8.89–8.87 (m, 2H), 7.72–7.70 (m, 2H), 7.19 (d, 2H), 7.01 (d, 2H), 6.79 (d, 1H), 5.05–5.01 (m, 1H), 4.85–4.82 (m, 1H), 4.58 (d, 1H), 4.45 (d, 1H), 3.91 (s, 1H), 3.11–3.02 (m, 5H), 2.99 (s, 3H), 1.28–1.16 (m, 12H).

$^{13}$C NMR (CDCl$_3$): δ 170.3, 167.7, 154.9, 151.5, 150.7, 144.2, 132.7, 130.3, 121.8, 120.9, 73.6, 69.7, 54.6, 53.1, 50.4, 37.5, 36.6, 36.3, 29.1, 23.6, 21.6, 21.5.

Example 252

Synthesis of N-(Pyridine-4-sulfonyl)-L-(5,5-dimethyl)thiaprolyl-L-4-(N,N-dimethylcarbamyloxy)phenylalanine The title compound was prepared from the product of Example 251 using the procedure described in Method 7.

NMR data was as follows:

$^1$H NMR (CD$_3$OD): δ 8.78 (d, 2H), 7.42 (d, 1H), 7.69 (d, 2H), 7.35 (d, 2H), 7.06 (d, 2H), 4.69–4.61 (m, 3H), 4.16 (s, 1H), 3.25–3.19 (m, 1H), 3.13–3.05 (m, 4H), 2.97 (s, 3H), 1.25 (s, 6H).

$^{13}$C NMR (CD$_3$OD): δ 174.1, 170.5, 157.0, 152.2, 152.0, 147.2, 135.8, 131.8, 123.1, 122.7, 73.9, 55.6, 54.9, 54.4, 37.5, 36.8, 36.7, 30.1, 24.8.

Example 253

Synthesis of N-(Toluene-4-sulfonyl)-L-(5,5-dimethyl)thiaprolyl-L-4-(N-methyl-N-(2-dimethylaminoethyl)carbamyloxy)phenylalanine tert-Butyl Ester A solution of the starting acid (500 mg), (2S)-2-amino-3-{4-[(2-dimethylaminoethyl)-methylcarbamoyloxy]phenyl}propionic acid tert-butyl ester (730 mg), HOBt (235 mg), and 4-methylmorpholine (0.87 mL) in DMF (10 mL) was stirred in ice bath at 0° C. 1-[3-(Dimethylamino)propyl]-3-ethylcarbodiimide hydrochloride (360 mg) was added to the solution. The ice bath was removed after 10 minutes. The reaction was stirred at room temperature for 3 hours. Ethyl acetate (20 mg) was added. The solution was washed with saturated NaHCO$_3$ solution (30 mL) 2 times, then washed with brine. The solution was dried with MgSO$_4$. The solvent was evaporated in vacua, and the residue flash chromatographed on silica gel to give 385 mg of the title compound.

Physical data was as follows:

MS: [(+)ESI], [M+H]$^+$ 663.

Example 254

Synthesis of N-(Toluene-4-sulfonyl)-L-prolyl-L-4-(N-methyl-N-(2-dimethylaminoethyl)carbamyloxy)phenylalanine tert-Butyl Ester The title compound was prepared following the procedure described for the preparation of Example 253 and substitution of appropriate starting materials.

Physical data was as follows:

MS: [(+)ESI], [M+H]$^+$ 617.

Example 255

Synthesis of N-(Toluene-4-sulfonyl)-L-(5,5-dimethyl)thiapropyl-L-4-(N-methyl-N-(2-dimethylaminoethyl)carbamyloxy)phenylalanine The title compound was prepared from the product of Example 253 using the procedure described in Method 11.

Physical data was as follows:

MS: [(+)ESI], [M+H]$^+$ 607.

Example 256

Synthesis of N-(Toluene-4-sulfonyl)-L-prolyl-L-4-(N-methyl-N-(2-dimethylaminoethyl)carbamyloxy)phenylalanine The title compound was prepared from the product of Example 254 using the procedure described in Method 11.

Physical data was as follows:

MS: [(+)ESI], M+H]$^+$ 561.

Example 257

Synthesis of N-(4-Fluorobenzenesulfonyl)-L-(5,5-dimethyl)thiaprolyl-L-3-chloro-4-(4-methylpiperazin-1-ylcarbonyloxy)phenylalanine tert-Butyl Ester The title compound was prepared following the procedure described for the preparation of Example 4 and substitution of appropriate staring materials, mp: 64–67° C.

Physical data was as follows:

MS: [M+H]$^+$ 699.

Anal. Calcd. for C$_{31}$H$_{40}$ClFN$_4$O$_7$S$_2$.H$_2$O: C, 51.90; H, 5.9; N, 7.8.

Found: C, 51.53; H, 5.50; N, 7.62.

Example 259

Synthesis of N-(4-Fluorobenzenesulfonyl)-L-(5,5-dimethyl)thiaprolyl-L-3-chloro-4-(N,N-dimethylcarbamyloxy)phenylalanine The title compound was prepared for the product of Example 258 using the procedure described in Method 11.

Physical data was as follows:

MS: [M+1] 603.

Anal. Calcd. for C$_{24}$H$_{27}$FN$_3$O$_7$S$_2$: C, 49.02; H, 4.63; N, 7.15.

Found: C, 49.25; H, 4.89; N, 6.73.

Example 260

Synthesis of N-(4-Fluorobenzenesulfonyl)-L-(5,5-dimethyl)thiaprolyl-L-3-chloro-4-(thiomorpholin-4-ylcarbonyloxy)phenylalanine tert-Butyl Ester The title compound was prepared following the procedure described for the preparation of Example 82 and substitution of appropriate starting materials, mp.111–114° C.

Physical data was as follows:

MS: +ESI [M+NH4]+719.

Anal. Calcd. for C$_{30}$H$_{37}$ClFN$_3$O$_7$S: C, 50.02; H, 5.46; N, 5.8.

Found: C, 50.23; H, 5.10; N, 5.50.

Example 261

Synthesis of N-(4-Fluorobenzenesulfonyl)-L-(5,5-dimethyl)thiaprolyl-L-3-chloro-4-(thiomorpholin-4-ylcarbonyloxy)phenylalanine Isopropyl Ester The title compound was prepared following the procedure described for the preparation of Example 82 and substitution of appropriate starting materials, mp. 77–81° C.

Physical data was as follows:

MS: [M+NH$_4$]+705.

Anal. Calcd. for C$_{29}$H$_{35}$ClFN$_3$O$_7$S$_3$: C, 50.61; H, 5.13; N, 6.1.

Found: C, 50.33; H, 5.07; N, 5.94.

Example 262

Synthesis of N-(4-Fluorobenzenesulfonyl)-L-(5,5-dimethyl)thiaprolyl-L-3-chloro-4-(N,N-diethylcarbamyloxy)]phenylalanine Isopropyl Ester The title compound was prepared following the procedure described for the preparation of Example 2 and substitution of appropriate starting materials, mp. 65–69° C.

Physical data was as follows:

MS: [M+NH$_4$]$^+$ 647.

Anal. Calcd. for C$_{27}$H$_{33}$ClFN$_3$O$_7$S$_2$: C, 51.46; H, 5.28; N, 6.4.

Found: C, 51.29; H, 5.19; N, 6.50.

Example 263

Synthesis of N-(Toluene-4-sulfonyl)-L-(5,5-dimethyl)thiaprolyl-L-3-chloro-4-(N,N-dimethylcarbamyloxy)phenylalanine Isopropyl Ester The title compound was prepared following the procedure described for the preparation of Example 2 and substitution of appropriate starting materials, mp. 68–72° C.

Physical data was as follows:

MS: [M+H]$^+$ 626.

Anal. Calcd. for $C_{28}H_{36}ClN_3O_7S_2$: C, 53.77; H, 5.80; N, 6.71.

Found: C, 53.26; H, 5.8; N, 6.63.

Example 264

Synthesis of N-(4-Fluorobenzenesulfonyl)-L-(5,5-dimethyl)thiaprolyl-L-3-chloro(4-methylpiperazin-1-ylcarbonyloxy)phenylalanine Isopropyl Ester The title compound was prepared following the procedure described for the preparation of Example 4 and substitution of appropriate starting materials.

Physical data was as follows:

MS: [M+H]$^+$ 685.

Anal. Calcd. for $C_{30}H_{38}ClN_4O_7$: C, 52.59; H, 5.59; N, 8.18.

Found: C, 52.09; H, 5.48; N, 7.77.

Example 265

Synthesis of N-(Toluene-4-sulfonyl)-L-prolyl-L-3-chloro-4-(N,N-dimethylcarbamyloxy)]phenylalanine Isopropyl Ester The title compound was prepared following the procedure described for the preparation of Example 2 and substitution of appropriate stating materials.

Physical data was as follows:

MS: [M+H]$^+$ 580.

Anal. Calcd. for $C_{27}H_{34}ClN_3O_7S \cdot 0.5\ H_2O$: C, 55.04; H, 6.00; N, 7.13.

Found: C, 55.06; H, 5.71; N, 6.93.

Example 266

Synthesis of N-(4-Fluorobenzenesulfonyl)-L-(5,5-dimethyl)thiaprolyl-L-3-chloro-4-(4-(2'-pyridyl)-piperazin-1-ylcarbonyloxy)]phenylalanine Isopropyl Ester The title compound was prepared following the procedure described for the preparation of Example 4 and substitution of appropriate starting materials.

Physical data was as follows:

MS: [M+H]$^+$ 748.

Anal. Calcd. for $C_{34}H_{39}ClFN_5O_7S_2$: C, 54.57; H, 5.25; N, 9.3.

Found: C, 54.26; H, 5.10; N, 9.07.

Example 267

Synthesis of N-(4-Fluorobenzenesulfonyl)-L-(5,5-dimethyl)thiaprolyl-L-3-chloro-4-(4-(2'-pyridyl)-piperazin-1-ylcarbonyloxy)]phenylalanine tert-Butyl Ester The title compound was prepared following the procedure described for the preparation of Example 4 and substitution of appropriate starting materials, mp. 80–86° C.

Physical data was as follows:

MS: [M+H]$^+$ 762.

Anal. Calcd. for $C_{35}H_{41}ClFN_5O_7S_2$: C, 55.14; H, 5.42; N, 9.19.

Found: C, 54.67; H, 5.40; N, 8.69.

Example 268

Synthesis of N-(4-Nitrobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials.

Physical data was as follows:

Anal. Calcd. for $C_{26}H_{32}N_4O_9S$: C, 54.16; H, 5.59; N, 9.72.

Found: C, 53.69; H, 5.24; N, 9.52.

Example 269

Synthesis of N-(4-Aminobenzenesulfonyl)-L-prolyl-L-4-(N,N-dimethylcarbamyloxy)phenylalanine Isopropyl Ester The title compound was prepared from the product of Example 268 using the procedure described in Method 4.

Physical data was as follows:

Anal. Calcd. for $C_{26}H_{34}N_4O_7S$: C, 57.13; H, 6.27; N, 10.25.

Found: C, 56.30; H, 6.12; N, 10.05.

Example 270

Synthesis of N-(Toluene-4-sulfonyl)-L-prolyl-L-4-(thiomorpholin-4-ylcarbonyloxy)phenylalanine Isopropyl Ester The title compound was prepared following the procedure described for the preparation of Example 82 and substitution of appropriate starting materials.

Physical data was as follows:

Anal. Calcd. for $C_{29}H_{37}N_3O_7S_2$: C, 57.69; H, 6.18; N, 6.96.

Found: C, 57.36; H, 5.99; N, 6.76.

Example 271

Synthesis of N-(Toluene-4-sulfonyl)-L-prolyl-L-4-(4-phenylcarbamylpiperazin-1-ylcarbonyloxy)phenylalanine Isopropyl Ester The title compound was prepared following the procedure described for the preparation of Example 4 and substitution of appropriate starting materials.

NMR data was as follows:

$^1$H NMR (DMSO-d$_6$, 400 MHz): δ 8.62 (s, 1H); 8.11 (d, 1H); 7.73 (d, 2H); 7.45 (m, 4H); 7.26 (m, 3H); 7.04 (m, 2H); 6.95 (m, 1H); 6.25 (d, 1H); 4.90 (m, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H); 1.18 (d, 3H); 1.12 (d, 3H).

IR (KBr, cm$^{-1}$) 3400–3500(br), 2950, 2900, 1725, 1650, 1540, 1450, 1240, 1210, 1000, 760, 675, 580, 540.

MS ((+)ESI, m/z (%)) 706 (100 [M+H]$^+$).

Anal. Calcd. for $C_{36}H_{43}N_5O_8S \cdot 0.35$ EtOAc: C, 60.98; H, 6.27; N, 9.51.

Found: C, 50.31; H, 6.16; N, 9.33.

Example 272

Synthesis of N-(Toluene-4-sulfonyl)-L-prolyl-L-4-(4-phenylcarbamylpiperazin-1-ylcarbonyloxy)phenylalanine The title compound was prepared from the product of Example 271 using the procedure described in Method 7.

NMR data was as follows:

$^1$H NMR (DMSO-d$_6$, 400 MHz): δ 12.8 (s, 1H); 8.62 (s, 1H); 8.11 (d, 1H); 7.73 (d, 2H), 7.45 (m, 4H); 7.26 (m, 3H); 7.04 (m, 2H); 6.95 (m, 1H); 6.25 (d, 1H); 4.50 (m, 1H); 4.11 (m, 1H); 3.6 (br, 4H); 3.4 (br, 4H); 3.10 (m, 2H); 3.00 (m, 1H); 2.40 (s, 3H); 1.60 (m, 3H); 1.40 (m, 1H).

IR (KBr, cm$^{-1}$) 3400, 1725, 1650, 1540, 1450, 1240, 1210, 1000, 760, 675, 580, 540.

MS ((−)ESI, m/z (%)) 662 (100 [M−H]$^+$).

Example 273

Synthesis of N-(1-n-Butylpyrazole-4-sulfonyl)-L-(5,5-dimethyl)thiaprolyl-L-4-(N,N-dimethylcarbamyloxy)phenylalanine Isopropyl Ester The title compound was prepared following the procedure described for the preparation of Example 137 and substitution of appropriate starting materials.

NMR data was as follows:

$^1$H NMR (CDCl$_3$): δ 7.89 (s, 1H), 7.83 (s, 1H), 7.21 (d, 2H), 7.06 (d, 1H), 7.02 (d, 2H), 5.04 (sept, 1H), 4.89–4.82 (m, 1H), 4.57 (d, 1H), 4.41 (d, 1H), 4.16 (t, 2H), 3.78 (s, 1H), 3.14 (dd, 1H), 3.06 (dd, 1H), 3.09 (s, 3H), 3.00 (s, 3H), 1.85 (pent, 2H), 1.36–1.23 (m, 2H), 1.27 (s, 3H), 1.24 (d, 3H), 1.21 (d, 3H), 1.16 (s, 3H).

$^{13}$C NMR (CDCl$_3$): δ 170.4, 168.3, 154.9, 150.7, 139.2, 131.8, 130.3, 121.8, 117.0, 73.8, 69.6, 54.8, 53.2, 52.7, 50.6, 37.7, 36.6, 36.3, 31.8, 28.9, 24.0, 21.6, 21.5, 19.4, 13.3.

Example 274

Synthesis of N-(Toluene-4-sulfonyl)-L-prolyl-L-4-(pyridin-4-ylcarbonyl)piperazin-1-ylcarbonyloxy) phenylalanine Isopropyl Ester The title compound was prepared following the procedure described for the preparation of Example 4 and substitution of appropriate starting materials.

NMR data was as follows:

$^1$H NMR (DMSO-d$_6$, 400 MHz): δ 8.69 (dd, 2H), 8.28 (d, 1H); 7.71 (d, 2H); 7.43 (m, 4H); 7.26 (d, 2H); 7.04 (d, 2H); 4.86 (m, 1H); 4.42 (m, 1H); 4.05 (m, 1H); 3.4–3.8 (brm, 9H); 3.05 (m, 3H); 2.40 (s, 3H); 1.60 (m, 3H); 1.40 (m, 1H); 1.18 (d, 3H); 1.15 (d, 3H).

IR (KBr, cm$^{-1}$) 3400, 1725, 1650, 1510, 1200, 1160, 1100, 1010, 650, 600, 550.

MS ((+)ESI, m/z (%)) 692 (100 [M+H]$^+$).

Anal. Calcd. for C$_{35}$H$_{41}$N$_5$O$_9$S.0.75H$_2$O: C, 59.60; H, 6.07; N, 9.93

Found: C, 59.45; H, 5.86; N, 9.88.

Example 275

Synthesis of N-(Toluene-4-sulfonyl)-L-4-oxoprolyl-L-4-(N,N-dimethylcarbamyloxy)phenylalanine The title compound was prepared from the product of Example 164 using the procedure described in Method 11.

Physical data was as follows:

MS [(−)ESI] [M−H]) 516.

Example 276

Synthesis of N-(Toluene-4-sulfonyl)-L-trans-4-hydroxyprolyl-L-4-(N,N-dimethylcarbamyloxy) phenylalanine The title compound was prepared from the product of Example 165 using the procedure described in Method 11.

Physical data was as follows:

MS [(−)ESI] [M−H]) 518.

Example 277

Synthesis of N-(4-Cyanobenzenesulfonyl)-L-prolyl-L-4-(N,N-dimethylcarbamyloxy)phenylalanine Isopropyl Ester The title compound was prepared following the procedure described for the preparation of Example 2 and substitution of appropriate starting materials, mp. 166–167° C.

Example 278

Synthesis of N-(4-Aminobenzenesulfonyl)-L-prolyl-L-4-(N,N-dimethylcarbamyloxy)phenylalanine The title compound was prepared from the product of Example 107 using the procedure described in Method 11.

Physical data was as follows:

Anal. Calcd. For C$_{23}$H$_{28}$N$_4$O$_7$S: C, 47.34; H, 4.84; N, 9.60.

Found: C, 47.57; H, 5.20; N, 8.75.

Example 279

Synthesis of N-(Toluene-4-sulfonyl)-L-4-oxoprolyl-L-4-(4-methylpiperazin-1-ylcarbonyloxy) phenylalanine tert-Butyl Ester Acetonitrile (3 mL) was cooled to 40° C. (CH$_3$CN/dry ice). Oxalyl chloride (0.10 mL) was added. N-(Toluene-4-sulfonyl)-L-4-hydroxyprolyl-L-4-(4-methylpiperazin-1-ylcarbonyloxy)phenylalanine tert-butyl ester (300 mg) and dry DMSO (0.008 mL) were dissolved in acetonitrile (4 mL) and were added to the above solution. The reaction was stirred at −40° C. for half an hour under dry conditions. Triethylamine (0.33 mL) was added to the solution. The dry ice bath was removed after 5 minutes. The reaction was stirred at room temperature for 1 hour. The solvent was evaporated in vacuo, and ethyl acetate (15 mL) was added. The mixture was washed with water (3×), then washed with brine. The solution was dried over MgSO$_4$. The solvent was evaporated in vacuo, and the residue was flushed on a silica gel column to give 150 mg of the title compound, mp. 84–85° C.

Example 280

Synthesis of N-(Toluene-4-sulfonyl)-L-prolyl-L-4-[3-(hydroxymethyl)piperidin-1-ylcarbonyloxy] phenylalanine The title compound was prepared following the procedure described for the preparation of Example 4 and substitution of appropriate starting materials, mp. 84–85° C.

Example 281

Synthesis of N-(Toluene-4-sulfonyl)-L-(4,4-difluoro)prolyl-L-4-(N,N-dimethylcarbamyloxy) phenylalanine Isopropyl Ester The title compound was prepared following the procedure described for the preparation of Example 2 and substitution of appropriate starting materials.

Physical data was as follows:

MS: [(+)ESI], [M+NH$_4$]$^+$ 599.

Example 282

Synthesis of N-Toluene-4-sulfonyl)-L-(4,4-difluoro) prolyl-L-4-(N,N-dimethylcarbamyloxy) phenylalanine The title compound was prepared from the product of Example 281 using the procedure described in Method 7.
Physical data was as follows:
MS: [(+)ESI], [M+NH$_4$] 557.

Example 283

Synthesis of N-(Toluene-4-sulfonyl)-L-prolyl-L-(4-benzoylpiperazin-1-ylcarbonyloxy)phenylalanine Isopropyl Ester The title compound was prepared following the procedure described for the preparation of Example 4 and substitution of appropriate starting materials.
NMR data was as follows:
$^1$H NMR (DMSO-d$_6$, 400 MHz): δ 8.27 (d, 1H); 7.69 (d, 2H); 7.45 (m, 7H); 7.24 9d, 2H); 7.02 (d, 2H); 4.86 (m, 1H); 4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H); 1.18 (d, 3H); 1.11 (d, 3H).
IR (KBr, cm$^{-1}$) 3400, 1725, 1675, 1625, 1510, 1425, 1350, 1250, 1175, 1110, 1010, 700, 660, 590, 550.
MS ((+)ESI, m/z (%)) 708 (100[M+NH$_2$]$^+$).
Anal. Calcd. for C$_{36}$H$_{42}$N$_4$O$_8$S.0.5H$_2$O: C, 61.79; H, 6.19; N, 8.01.
Found: C, 61.64; H, 6.10; N, 7.72.

Example 284

Synthesis of N-(1-Methyl-1H-imidazole-4-sulfonyl)-L-prolyl-L-4-(N,N-dimethylcarbamyloxy) phenylalanine Isopropyl Ester The carbamate was prepared by treatment of 1-methylimidazole-4-sulfonyl-Pro-Try-iPr ester with 4-nitrophenyl chloroformate, followed by addition of dimethylamine (triethylamine, methylene chloride, 0° C., stirred at room temperature overnight.) The crude product was purified by flash chromatography (silica, 95:3:2 EtOAc:EtOH;Et$_3$N), followed by recrystallization from EtOAc. A white solid was obtained, mp 162–164° C. (8.7 g, 66%).
Physical data was as follows:
Anal. Calcd. for C$_{24}$H$_{33}$N$_5$O$_7$S: C, 53.82; H, 6.21; N, 13.08.
Found: C, 53.47; H, 6.13; N, 12.96.

Example 286

Synthesis of N-(Toluene-4-sulfonyl)-L-4-(thiomorpholin-4-ylcarbonyloxy)prolyl-L-4-(thiomorpholin-4-ylcarbonyloxy)phenylalanine The title compound was prepared from the product of Example 285 using the procedure described in Method 11, mp.116–118° C.

Example 287

Synthesis of N-(4-Cyanobenzenesulfonyl)-L-prolyl-L-4-(thiomorpholin-4-ylcarbonyloxy)phenylalanine Isopropyl Ester The title compound was prepared following the procedure described for the preparation of Example 4 and substitution of appropriate starting materials, mp. 70–71° C.

Example 288

Synthesis of N-(4-Amidinobenzenesulfonyl)-L-prolyl-L-4-(N,N-dimethylcarbamyloxy) phenylalanine Methyl Ester Methanol (dry) was cooled to 0° C. HCl was bubbled in the solution for 15 minutes to make a saturated solution. Example 277 was added and the reaction mixture was stirred at 0° C. for 30 minutes then at room temperature for 24 hours. The solvent was evaporated. NH$_3$ in methanol (2M, 5 mL) was added. The reaction was stirred at room temperature for 24 hours. The solvent was evaporated. The residue was purified by reverse phase HPLC in CH$_3$CN:H$_2$O (20:80). At a retention time of 12.45 minutes, the product was isolated and freeze-dried to provide the title compound.
NMR data was as follows:
$^1$H NMR (in DMSO) multiplet at 1.47–1.55 ppm (1H), 1.63–1.72 ppm (3H's), singlet at 2.87 ppm (3H's), singlet at 3.02 ppm (3H's), multiplet at 3.05–3.10 ppm (2H's), multiplet at 3.17–3.22 ppm (1H), multiplet at 3.37–3.42 ppm (1H), singlet at 3.62 ppm (3H's), multiplet at 4.21–4.23 ppm (1H), quartet at 4.48–4.56 ppm (1H), doublet at 7.00–7.03 ppm (2H's), doublet at 7.23–7.26 ppm (2H's), a broad peak at 7.20–7.50 ppm, doublet at 8.02–8.03 ppm (4H's), doublet at 8.48–8.52 ppm (1H).

Example 289

Synthesis of N-(Toluene-4-sulfonyl)-L-4-hydroxyprolyl-L-4-(thiomorpholin-4-ylcarbonyloxy) phenylalanine tert-Butyl Ester The title compound was prepared following the procedure described for the preparation of Example 4 and substitution of appropriate starting materials, mp. 80–82° C.

Example 290

Synthesis of N-(Toluene-4-sulfonyl)-L-4-hydroxyprolyl-L-4-(thiomorpholin-4-ylcarbonyloxy) phenylalanine N-(Toluene-4-sulfonyl)-L-4-hydroxyprolyl-L-4-(thiomorpholin-4-ylcarbonyloxy)phenylalanine tert-butyl ester (160 mg) was dissolved in formic acid (7 mL). The reaction was stirred at room temperature for 6 hours. The solvent was evaporated and the residue purified using reverse phase HPLC in 20:80 CH$_3$CN/water. At a retention time of 5.85 minutes, 50 mg of the title compound was obtained, mp. 170–172° C.

Example 291

Synthesis of N-(Toluene-4-sulfonyl)-L-prolyl-L-(4-benzoylpiperazin-1-ylcarbonyloxy)phenylalanine The title compound was prepared from the product of Example 283 using the procedure described in Method 11.
NMR data was as follows:
$^1$H NMR (DMSO-d$_6$, 400 MHz): δ 12.8 (s, 1H); 8.27 (d, 1H); 7.69 (d, 2H); 7.45 (m, 7H); 7.24 (d, 2H); 7.02 (d, 2H); 4.42 (m, 1H); 4.07 (m, 1H); 3.65 (br s, 4H); 3.45 (br s, 4H); 3.35 (m, 1H); 3.05 (m, 3H); 2.38 (s, 3H); 1.60 (m, 3H); 1.40 (m, 1H).
IR (KBr, cm$^{-1}$) 3400, 1725, 1675, 1625, 1510, 1425, 1350, 1260, 1175, 1110, 1010, 700, 660, 590, 550.
MS ((+)ESI, m/z (%)) 666 (100[M+NH$_4$]$^+$).
Anal. Calcd. for C$_{33}$H$_{36}$N$_4$O$_8$S.0.66H$_2$O: C, 60.00; H, 5.69; N, 8.48
Found: C, 60.36; H, 5.70; N, 7.81.

Example 292

Synthesis of N-(4-Amidinobenzenesulfonyl)-L-prolyl-L-4-(thiomorpholin-4-ylcarbonyloxy)phenylalanine Methyl Ester The title compound was prepared following the procedure described for the preparation of Examples 287 and 288.
Physical data was as follows:
MS: [(+)ESI] [M+H] 604.

Example 293

Synthesis of N-(3-Fluorobenzenesulfonyl)-L-prolyl-L-4-(N,N-dimethylcarbamyloxy)phenylalanine The title compound was prepared from the product of Example 166 using the procedure described in Method 11, mp. 82–83° C.

Example 294

Synthesis of N-(Toluene-4-sulfonyl)-L-prolyl-L-4-[N-methyl-N-(2-(N'-methyl-N'-toluenesulfonyl-amino)ethyl)carbamyloxy]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 8.27 (d, 1H); 7.71 (d, 2H); 7.69 (d, 2H); 7.40 (m, 4H); 7.24 (d, 2H); 6.99 (d, 2H); 4.86 (m, 1H); 4.43 (m, 1H); 4.06(m, 1H); 3.51 (m, 1H); 3.2–3.35 (m, 3H); 2.9–3.2 (overlapping m, 7H); 2.67 (d, 3H); 2.38 (s, 6H); 1.60 (m, 3H); 1.40 (m, 1H); 1.20 (d, 3H); 1.15 (d, 3H).
IR (KBr, cm$^{-1}$) 3400, 2975, 2950, 1725, 1680, 1510, 1450, 1400, 1280, 1225, 1150, 1110, 800, 730, 675, 575, 550.
MS ((+)ESI, m/z (%)) 760 (100 [M+NH$_4$]$^+$).
Anal. Calcd. for $C_{36}H_{46}N_4O_9S_2$: C, 58.20; H, 6.24; N, 7.54.
Found: C, 57.90; H, 6.30; N, 7.34.

Example 295

Synthesis of N-(Toluene-4-sulfonyl)-L-propyl-L-4-[N-(2-(N'-phenylaminocarbonyloxy)ethyl)carbamyloxy)]phenylalanine Isopropyl Ester The title compound was prepared following the procedure described for the preparation of Example 4 and substitution of appropriate starting materials.
NMR data was as follows:
$^1$H NMR (DMSO-$d_6$, 400 MHz): δ 9.67 (s, 1H); 8.27 (d, 1H); 7.72 (d, 2H); 7.47 (d, 2H); 7.42 (d, 2H); 7.24 (m, 4H); 6.98 (m, 3H); 4.87 (m, 1H); 4.45 (m, 1H); 4.18 (m, 2H); 4.05 (m, 1H); 3.4 (m, 3H); 3.05 (m, 3H); 2.40 (s, 3H); 1.6 (m, 3H); 1.40 (m, 1H); 1.2 (d, 3H); 1.15 (d, 3H).
IR (KBr, cm$^{-1}$) 3350, 2950, 1725, 1675, 1600, 1550, 1500, 1325, 1200, 1150, 1100, 650, 575, 525.
MS ((+)ESI, m/z (%)) 698 (100 [M+NH$_4$]$^+$).
Anal. Calcd. for $C_{34}H_{40}N_4O_9S.0.21$ EtOAc. $0.5H_2O$: C, 59.08; H, 6.07; N, 7.91.
Found: C, 59.08; H, 6.02; N, 7.80.

Example 296

Synthesis of N-(4-Fluorobenzenesulfonyl)-L-4-(trans-hydroxy)prolyl-L-4-(N,N-dimethylcarbamyloxy)phenylalanine Isopropyl Ester The title compound was prepared following the procedure described in Example 2 and substitution of appropriate starting materials.

Physical data was as follows:
MS: [(+)ESI], [M+NH$_4$] 583.

Example 297

Synthesis of N-(4-Fluorobenzenesulfonyl)-L-4-(trans-hydroxy)prolyl-L-4-(N,N-dimethylcarbamyloxy)phenylalanine tert-Butyl Ester The title compound was prepared following the procedure described in Example 2 and substitution of appropriate starting materials.
Physical data was as follows:
MS: [(+)ESI], [M+NH$_4$] 597.

Example 298

Synthesis of N-(4-Amidinobenzenesulfonyl)-L-prolyl-L-4-(N,N-dimethylcarbamyloxy)phenylalanine The title compound was prepared from the product of Example 288 using the procedure described in Method 5, mp. 130–132° C.

Example 299

Synthesis of Piperazine-1,4-dicarboxylic Acid Bis-{4-[(2S)-2-tert-butoxycarbonyl-2-((4R)-5,5-dimethyl-3-(toluene-4-sulfonyl)thiazolidine-4-carboxamido)ethyl]phenyl} Ester The title compound was prepared following the procedure described in Example 4, except that 0.5 equivalents of piperazine were used.

Physical data was as follows:

Anal. Calcd. for $C_{58}H_{74}N_6O_{14}S_4$: C, 57.69; H, 6.18; N, 6.96.

Found: C, 58.01; H, 6.07; N, 6.68.

Example 300

Synthesis of Piperazine-1,4-dicarboxylic Acid Bis-{4-[(2S)-2-carboxy-2-((4R)-5,5-dimethyl-3-(toluene-4-sulfonyl)thiazolidine-4-carboxamido)ethyl]phenyl} Ester The title compound was prepared by hydrolysis of the di-t-butyl ester from Example 299 with formic acid to give a white foam (300 mg, quantitative).

Physical data was as follows:

Anal. Calcd. for $C_{50}H_{58}N_6O_{14}S_4$: C, 54.83; H, 5.34; N, 7.67

Found: C, 55.10; H, 5.57; N, 7.37.

Other compounds prepared by the methods described above include those set forth in Examples 301–373 in Tables IIIA and IIIB below.

TABLE IIIA $$R^1-\overset{\overset{O}{\|}}{\underset{\underset{O}{\|}}{S}}-\underset{R^2}{N}-\underset{}{CH}(R^3)-\overset{O}{\overset{\|}{C}}-\underset{H}{N}-\underset{}{CH}(R^5)-\overset{O}{\overset{\|}{C}}-R^{6'}$$

| No. | $R^1$ | $R^2$ | $R^3$ | $R^5$ | $R^{6'}$ |
|---|---|---|---|---|---|
| 301 | p-CH$_3$-ϕ- | R$^2$R$^3$ = cyclic -CH$_2$CH$_2$—NH—CH$_2$— (L-piperizinyl) | | p-[(CH$_3$)$_2$NC(O)O-]benzyl- | —OC(CH$_3$)$_3$ |
| 302 | p-F-ϕ- | R$^2$R$^3$ = cyclic -CH$_2$S—C(CH$_3$)$_2$- (L-5,5-dimethylthiazolidin-4-yl) | | p[(2-hydroxymethyl)pyrrolidin-1-yl-C(O)O-]-benzyl- | —OC(CH$_3$)$_3$ |
| 303 | p-F-ϕ- | R$^2$R$^3$ = cyclic -CH$_2$S—C(CH$_3$)$_2$- (L-5,5-dimethylthiazolidin-4-yl) | | p[(2-hydroxymethyl)pyrrolidin-1-yl-C(O)O-]-benzyl- | —OH |
| 304 | p-CH$_3$ϕ- | R$^2$R$^3$ = cyclic 3 carbons atoms (L-pyrrolidinyl) | | p[(2-(CH$_3$OC(O)-)pyrrolidin-yl)-C(O)O-]benzyl- | —OC(CH$_3$)$_3$ |
| 305 | p-F-ϕ- | R$^2$R$^3$ = cyclic -CH$_2$S—C(CH$_3$)$_2$- (L-5,5-dimethylthiazolidin-4-yl) | | 3-chloro-4-[(thiomorpholin-4-yl)-C(O)O-]benzyl- | —OH |
| 306 | p-F-ϕ- | R$^2$R$^3$ = cyclic -CH$_2$S—C(CH$_3$)$_2$- (L-5,5-dimethylthiazolidin-4-yl) | | p-[(pyridin-2-yl)piperazine-1-yl)-C(O)O-]benzyl - | —OH |
| 307 | p-F-ϕ- | R$^2$R$^3$ = cyclic -CH$_2$S—C(CH$_3$)$_2$- (L-5,5-dimethylthiazolidin-4-yl) | | p-[(pyridin-2-yl)piperazine-1-yl)-C(O)O-]benzyl - | —OC(CH$_3$)$_3$ |
| 308 | p-CH$_3$-ϕ- | R$^2$R$^3$ = cyclic -CH$_2$CH(OH)CH$_2$- (L-4-hydroxypyrrolidinyl) | | p-[(thiomorpholin-4-yl)-C(O)O-]benzyl- | —OC(CH$_3$)$_3$ |
| 309 | p-CH$_3$ϕ- | R$^2$R$^3$ = cyclic 3 carbons atoms (L-pyrrolidinyl) | | p-[(CH$_3$)$_2$NC(O)O-]benzyl- | —O(CH$_2$CH$_2$O)$_2$CH$_3$ |
| 310 | p-F-ϕ- | R$^2$R$^3$ = cyclic -CH$_2$—S—C(CH$_3$)$_2$- (L-5,5-dimethylthiazolidin-4-yl) | | p-[(4-(pyrimidin-2-yl)piperazin-1-yl)-C(O)O-]benzyl- | —OC(CH$_3$)$_3$ |
| 311 | p-F-ϕ- | R$^2$R$^3$ = cyclic -CH$_2$—S—C(CH$_3$)$_2$- (l-5,5-dimethylthiazolidin-4-4yl) | | 3-flouro-4-[(CH$_3$)$_2$NC(O)O-]-benzyl- | —OCH(CH$_3$)$_2$ |
| 312 | p-CH$_3$-ϕ- | R$^2$R$^3$ = cyclic -CH$_2$CH$_2$N(SO$_2$CH$_3$)—CH$_2$- (L-4-methanesulfonyl-piperizinyl) | | p-[(CH$_3$)$_2$NC(O)O-]benzyl- | —OC(CH$_3$)$_2$ |
| 313 | R$^1$/R$^2$ = 1,1-dioxo-2,3-dihydro-3,3-dimethyl-1,2-benzisothiazol-2-yl- | | H | p-[(CH$_3$)$_2$NC(O)O-]benzyl- | —OH |
| 314 | R$^1$/R$^2$ = N-2,10-camphorsultamyl- | | H | p-[(CH$_3$)$_2$NC(O)O-]benzyl- | —OC(CH$_3$)$_3$ |
| 315 | R$^1$/R$^2$ = N-2,10-camphorsultamyl- | | H | p-[(CH$_3$)$_2$NC(O)O-]benzyl- | —OH |
| 316 | R$^1$/R$^2$ = N-2,10-camphorsultamyl- | | H | 3-chloro-4-[(CH$_3$)$_2$NC(O)O)-]-benzyl- | —OCH(CH$_3$)$_2$ |
| 317 | p-Br-ϕ- | R$^2$R$^3$ = cyclic -CH$_2$—S—C(CH$_3$)$_2$- (L-5,5-dimethylthiazolidin-4-yl) | | p[(CH$_3$)$_2$NC(O)O-]benzyl- | —OC(CH$_3$)$_3$ |
| 318 | p-Br-ϕ- | R$^2$R$^3$ = cyclic -CH$_2$—S—C(CH$_3$)$_2$- (L-5,5-dimethylthiazolidin-4-yl) | | p[(CH$_3$)$_2$NC(O)O-]benzyl- | —OH |
| 319 | p-CH$_3$-ϕ- | R$^2$R$^3$ = cyclic —CH$_2$CH(OH)—CH$_2$- (L-4-hydroxypyrrolidinyl) | | | |
| 320 | p-F-ϕ- | R$^2$R$^3$ = cyclic -CH$_2$—S—C(CH$_3$)$_2$- (L-5,5-dimethylthiazolidin-4-yl) | | p-[(4-pyrimidin-2-yl)piperazin-1-yl)-C(O)O-]benzyl- | —OH |
| 321 | p-F-ϕ- | R$^2$R$^3$ = cyclic -CH$_2$—S—C(CH$_3$)$_2$- (L-5,5-dimethylthiazolidin-4-yl) | | p-[(4-pyrimidin-2-yl)piperazin-1-yl)-C(O)O-]benzyl- | —OCH$_{(3)2}$ |
| 322 | p-F-ϕ- | R$^2$R$^3$ = cyclic -CH$_2$—CH$_2$—S- (thiazolidin-2-yl) | | p-[(CH$_3$)$_2$NC(O)O-]benzyl- | —OH |
| 323 | p-F-ϕ- | R$^2$R$^3$ = cyclic -CH$_2$—CH$_2$—S- (thiazolidin-2-yl) | | p-[(CH$_3$)$_2$NC(O)O-]benzyl- | —OC(CH$_3$)$_3$ |
| 324 | p-CH$_3$-ϕ- | R$^2$R$^3$ = cyclic -CH$_2$C(O)—CH$_2$- (L-4-oxopyrrolidinyl) | | p-[(thiomorpholin-4-yl)C(O)O-]benzyl- | —OH |

TABLE IIIA-continued $$R^1-\overset{O}{\underset{O}{\overset{\|}{S}}}-\underset{R^2}{N}-\overset{R^3}{\underset{|}{CH}}-\overset{O}{\overset{\|}{C}}-\underset{H}{N}-\overset{R^5}{\underset{|}{CH}}-\overset{O}{\overset{\|}{C}}-R^{6'}$$

| No. | R¹ | R² R³ | R⁵ | R⁶' |
|---|---|---|---|---|
| 325 | p-CH₃-φ- | R²R³ = cyclic -CH₂C(O)—CH₂- (L-4-oxopyrrolidinyl) | p-[(4-methylpiperazin-1-yl)-C(O)O-]benzyl- | —OH |
| 326 | p-Fφ- | R²R³ = cyclic -CH₂CH₂—S- (thiazolidin-2-yl) | p[(4-(pyridin-2-yl)piperazin-1-yl)-C(O)O-]benzyl- | —OH |
| 327 | p-NO₂-φ- | R²R³ = cyclic 3 carbon atoms (L-pyrrolidinyl) | p-[(4-(piridin-2-yl)piperazin-1-yl)-C(O)O-]benzyl- | —OC(CH₃)₃ |
| 328 | p-F-φ- | R²R³ = cyclic -CH₂—CH₂—S- (thiazolidin-2-yl) | p-[(4-(piridin-2-yl)piperazin-1-yl)-C(O)O-]benzyl- | —OC(CH₃)₃ |
| 329 | p-Br-φ- | R²R³ = cyclic -CH₂—S—C(CH₃)₂- (L-5,5-dimethylthiazolidin-4-yl) | p-[(4-(piridin-2-yl)piperazin-1-yl)-C(O)O-]benzyl- | —OH |
| 330 | p-CH₃-φ- | R²R³ = cyclic 3 carbon atoms (L-pyrrolidinyl) | p-[(4-(φNHC(S)-)piperazin-1-yl)-C(O)O-]benzyl- | —OCH(CH₃)₂ |
| 331 | p-F-φ- | R²R³ = cyclic -CH₂CH₂—S- (thiazolidin-2-yl) | p-[(4-CH₃-homopiperazin-1-yl)-C(O)O-]benzyl- | -OC(CH₃)₃ |
| 332 | p-CH₃-φ- | R²R³ = cyclic -CH₂CH(—OSO₂CH₃—CH₂- (L-4-methanesulfoxy-pyrrolidinyl) | p-[(CH₃)₂NC(O)O-]benzyl- | —OC(CH₃)₃ |
| 333 | p-H₂NC(O)-φ- | R²R³ = cyclic 3 carbon atoms (L-pyrrolidinyl) | p-[(CH₃)₂NC(O)O-]benzyl- | —OH |
| 334 | p-H₂NC(O)-φ- | R²R³ = cyclic 3 carbon atoms (L-pyrrolidinyl) | p-[(thiomorpholin-4-yl)C(O)O-)benzyl- | —OH |
| 335 | p-H₂NC(=N)-φ- | R²R³ = cyclic 3 carbon atoms (L-pyrrolidinyl) | p-[(thiomorpholin-4-yl)C(O)O-)benzyl- | —OH |
| 336 | p-NO₂-φ- | R²R³ = cyclic 3 carbon atoms (L-pyrrolidinyl) | p[(4-(pyridin-2-yl)piperazin-1-yl)-C(O)O-]benzyl- | —OH |
| 337 | p-F-φ- | R²R³ = cyclic -CH₂—S—C(CH₃)₂- (L-5,5-dimethylthiazolidin-4-yl) | 3-chloro-4-[4-(pyridin-2-yl)piperazin-1-yl(C(O)O-]-benzyl- | —OCH₂CH₃ |
| 338 | p-F-φ- | R²R³ = cyclic -CH₂—S—C(CH₃)₂- (L-5,5-dimethylthiazolidin-4-yl) | 3-chloro-4-[4-(pyridin-2-yl)piperazin-1-yl(C(O)O-]-benzyl- | —OH |
| 339 | p-F-φ- | R²R³ = cyclic -CH₂—CH₂—S- (thiazolidin-2-yl) | p-[(4-CH₃-homopiperizin-1-yl)C(O)O-]benzyl- | —OH |
| 340 | 1-methylpyrazol-4-yl- | R²R³ = cyclic -CH₂—S—C(CH₂)₂- (L-5,5-dimethylthiazolidin-4-yl) | 3-chloro-4-[(CH₃)₂NC(O)O-]benzyl- | —OCH(CH₃)₂ |
| 341 | 1-methylpyrazol-4-yl- | R²R³ = cyclic 3 carbon atoms (L-pyrrolidinyl) | p-[(4-(pyridin-2-yl)piperazin-1-yl)C(O)O-]benzyl- | —OCH(CH₃)₂ |
| 342 | 1-methylpyrazol-4-yl- | R²R³ = cyclic 3 carbon atoms (L-pyrrolidinyl) | p-[(4-(pyridin-2-yl)piperazin-1-yl)C(O)O-]benzyl- | —OCH(CH₃)₃ |
| 343 | p-CH₃-φ- | R²R³ = cyclic 3 carbon atoms (L-pyrrolidinyl) | p-[(4-(pyridin-2-yl)piperazin-1-yl)C(O)O-]benzyl- | —OH |
| 344 | p-CH₃-φ- | R²R³ = cyclic 3 carbon atoms (L-pyrrolidinyl) | p-[(4-(pyridin-2-yl)piperazin-1-yl)C(O)O-]benzyl- | —OC(CH₃)₃ |
| 345 | p-CH₃-φ- | R²R³ = cyclic 3 carbon atoms (L-pyrrolidinyl) | p-[(4-(pyridin-2-yl)piperazin-1-yl)C(O)O-]benzyl- | —OCH(CH₃)₂ |
| 346 | p-F-φ- | R²R³ = cyclic 3 carbon atoms (L-pyrrolidinyl) | p-[(4-(pyridin-2-yl)piperazin-1-yl)C(O)O-]benzyl- | —OCH(CH₃)₂ |
| 347 | p-F-φ- | R²R³ = cyclic 3 carbon atoms (L-pyrrolidinyl) | p-[(4-(pyridin-2-yl)piperazin-1-yl)C(O)O-]benzyl- | —OC(CH₃)₃ |
| 348 | p-CH₃-φ- | R²R³ = cyclic | p-[(CH₃)₂NC(O)O-]benzyl- | —OH |

TABLE IIIA-continued $$R^1-\underset{\underset{O}{\overset{O}{\|}}}{S}-\underset{R^2}{N}-\underset{R^3}{CH}-\overset{O}{\overset{\|}{C}}-\underset{H}{N}-\underset{R^5}{CH}-\overset{O}{\overset{\|}{C}}-R^{6'}$$

| No. | $R^1$ | $R^2$ | $R^3$ | $R^5$ | $R^{6'}$ |
|---|---|---|---|---|---|
| 349 | p-CH$_3$-φ- | -CH$_2$CH$_2$N(—SO$_2$—CH$_3$)CH$_2$-<br>(4-methanesulfonyl-piperizin-2-yl)<br>$R^2R^3$ = cyclic<br>-CH$_2$CH(—OSO$_2$—CH$_3$)CH$_2$-<br>(L-4-methanesulfoxy-pyrrolidinyl) | | p-[(CH$_3$)$_2$NC(O)O-]benzyl- | —OH |
| 350 | CH$_3$— | —CH$_2$φ | H | p-[(CH$_3$)$_2$NC(O)O-]benzyl- | —OC(CH$_3$)$_3$ |
| 351 | p-Br-φ- | $R^2R^3$ = cyclic<br>-CH$_2$—S—CH(CH$_3$)$_2$-<br>(L-5,5-dimethylthiazolidin-4-yl) | | p-[(4-(pyridin-2-yl)piperazin-1-yl)C(O)O-]benzyl- | —OC(CH$_3$)$_3$ |
| 352 | p-CF$_3$O-φ- | $R^2R^3$ = cyclic<br>-CH$_2$—S—CH(CH$_3$)$_2$-<br>(L-5,5-dimethylthiazolidin-4-yl) | | p-[(CH$_3$)$_2$NC(O)O-benzyl- | —OH |
| 353 | p-CF$_3$O-φ- | $R^2R^3$ = cyclic<br>-CH$_2$—S—CH(CH$_3$)$_2$-<br>(L-5,5-dimethylthiazolidin-4-yl) | | p-[(CH$_3$)$_2$NC(O)O-benzyl- | —OH |
| 354 | p-CF$_3$O-φ- | $R^2R^3$ = cyclic<br>-CH$_2$—S—CH(CH$_3$)$_2$-<br>(L-5,5-dimethylthiazolidin-4-yl) | | p-[(4-(pyridin-2-yl)piperazin-1-yl)C(O)O-]benzyl- | —OC(CH$_3$)$_3$ |
| 355 | p-F-φ- | $R^2R^3$ = cyclic<br>3 carbons atoms<br>(L-pyrrolidinyl) | | p-[(4-(pyridin-2-yl)piperazin-1-yl)C(O)O-]benzyl- | —OH |
| 356 | p-F-φ- | $R^2R^3$ = cyclic<br>-CH$_2$CH(OH)CH$_2$-<br>(L-4-hydroxypyrrolidinyl) | | p-[(4-(pyridin-2-yl)piperazin-1-yl)C(O)O-]benzyl- | —OH |
| 357 | p-CF$_3$O-φ- | $R^2R^3$ = cyclic<br>-CH$_2$—S—C(CH$_3$)$_2$-<br>(L-5,5-dimethylthiazolidin-4-yl) | | p-[(4-(pyridin-2-yl)piperazin-1-yl)C(O)O-]benzyl- | —OH |
| 358 | 1-methyllimidazol-4-yl- | $R^2R^3$ = cyclic<br>3 carbons atoms<br>(L-pyrrolidinyl) | | 3-chloro-4-[(CH$_3$)$_2$NC(O)O)-]benzyl- | —OH |
| 359 | 1-methyllimidazol-4-yl- | $R^2R^3$ = cyclic<br>3 carbons atoms<br>(L-pyrrolidinyl) | | 3-chloro-4-[(CH$_3$)$_2$NC(O)O)-]benzyl- | —OCH(CH$_3$)$_2$ |
| 360 | 1-methyllimidazol-4-yl- | $R^2R^3$ = cyclic<br>3 carbons atoms<br>(L-pyrrolidinyl) | | p-[(4-(pyridin-2-yl)piperazin-1-yl)C(O)O-]benzyl- | —OH |
| 361 | 1-methyllimidazol-4-yl- | $R^2R^3$ = cyclic<br>-CH$_2$—S—C(CH$_3$)$_2$-<br>(L-5,5-dimethylthiazolidin-4-yl) | | p-[(4-(pyridin-2-yl)piperazin-1-yl)C(O)O-]benzyl- | —OH |
| 362 | 1-methyllimidazol-4-yl- | $R^2R^3$ = cyclic<br>3 carbons atoms<br>(L-pyrrolidinyl) | | p-[(4-(pyridin-2-yl)piperazin-1-yl)C(O)O-]benzyl- | —OH |
| 363 | 1-methyllimidazol-4-yl- | $R^2R^3$ = cyclic<br>3 carbons atoms<br>(L-pyrrolidinyl) | | p-[(4-(pyridin-2-yl)piperazin-1-yl)C(O)O-]benzyl- | —OCH(CH$_3$)$_2$ |
| 364 | 1-methyllimidazol-4-yl- | $R^2R^3$ = cyclic<br>3 carbons atoms<br>(L-pyrrolidinyl) | | p-[(4-(pyridin-2-yl)piperazin-1-yl)C(O)O-]benzyl- | —OC(CH$_3$)$_3$ |
| 365 | 1-methyllimidazol-4-yl- | $R^2R^3$ = cyclic<br>-CH$_2$—S—C(CH$_3$)$_2$-<br>(L-5,5-dimethylthiazolidin-4-yl) | | p-[(4-(pyridin-2-yl)piperazin-1-yl)C(O)O-]benzyl- | —OC(CH$_3$)$_3$ |
| 366 | 1-methyllimidazol-4-yl- | $R^2R^3$ = cyclic<br>3 carbons atoms<br>(L-pyrrolidinyl) | | 3-chloro-4-[(4-(pyridin-2-yl)piperazin-1-yl)C(O)O]benzyl- | —OCH(CH$_3$)$_2$ |
| 367 | 1-methyllimidazol-4-yl- | $R^2R^3$ = cyclic<br>-CH$_2$—S—C(CH$_3$)$_2$-<br>(L-5,5-dimethylthiazolidin-4-yl) | | p-[(CH$_3$)$_2$NC(O)O-]benzyl- | —OCH$_2$CH$_2$Oφ |
| 368 | 1-methyllimidazol-4-yl- | $R^2R^3$ = cyclic<br>-CH$_2$—S—C(CH$_3$)$_2$-<br>(L-5,5-dimethylthiazolidin-4-yl) | | 3-chloro-4-[(4-(pyridin-2-yl)piperazin-1-yl)C(O)O-]-benzyl- | —OH |
| 369 | 1-methyllimidazol-4-yl- | $R^2R^3$ = cyclic<br>-CH$_2$—S—C(CH$_3$)$_2$-<br>(L-5,5-dimethylthiazolidin-4-yl) | | 3-chloro-4-[(4-(pyridin-2-yl)piperazin-1-yl)C(O)O-]-benzyl- | —OCH$_2$CH$_3$ |
| 370 | 1,5-dimethyl-3-chloropyrazol-4-yl | $R^2R^3$ = cyclic | | p-[4-]5-CF$_3$-pyridin-2-yl)piperazin-1-yl)-C(O)O-benzyl- | —OH |

TABLE IIIB

Structure: R¹-S(O)₂-N(R²)-CH(R³)-C(O)-NH-CH(-CH₂-C₆H₄-A-C₆H₄-CH₂-)-C(O)-R⁶' (symmetric dimer)

| No. | R¹ | R² | R³ | A | R⁶' |
|---|---|---|---|---|---|
| 371 | p-CH₃-100 - | R²/R³ cyclic 3 carbon atoms (L-pyrrolidinyl) | | —OC(O)-(piperazin-1,4-diyl)-C(O)O— | —OCH(CH₃)₂ |
| 372 | p-CH₃-100 - | R²/R³ cyclic 3 carbon atoms (L-pyrrolidinyl) | | —OC(O)-(piperazin-1,4-diyl)-C(O)O— | —OC(CH₃)₃ |
| 371 | p-CH₃-100 - | R²/R³ cyclic 3 carbon atoms (L-pyrrolidinyl) | | —OC(O)-(piperazin-1,4-diyl)-C(O)O— | —OH |

In addition, Examples 319, 324, 325, 332, 333, 334, 335 and 349 in Table IIIA are exemplified as follows:

Example 319

Synthesis of N-(Toluene-4-sulfonyl)-L-(4-hydroxy) prolyl-L-4-(4-methylpiperazin-1-ylcarbonyloxy) phenylalanine The starting N-(toluene-4-sulfonyl)-L-(4-hydroxy)prolyl-L-4-(4-methylpiperazin-1-ylcarbonyloxy)phenylalanine tert-butyl ester (300 mg) was dissolved in formic acid (15 mL). The reaction was stirred at room temperature for 72 hours. The solvent was evaporated and the residue was purified using HPLC, reverse phase, 20–80% CH₃CN/water. At a retention time of 10.75 minutes, 82 mg of the title compound was obtained, mp: 128–130° C.

Example 324

Synthesis of N-(Toluene-4-sulfonyl)-L-(4-oxo) prolyl-L-4-(thiomorpholin-4-ylcarbonyloxy) phenylalanine The starting N-(toluene-4-sulfonyl)-L-(4-oxo)prolyl-L-4-(thiomorpholin-4-ylcarbonyloxy)phenylalanine tert-butyl ester (130 mg) was dissolved in formic acid (7 mL). The reaction was stirred at room temperature for 6 hours. The solvent was evaporated in vacuo to give 150 mg of the desired product, mp: 111–112° C.

Example 325

Synthesis of N-(Toluene-4-sulfonyl)-L-(4-oxo) prolyl-L-4-(4-methylpiperazin-1-ylcarbonyloxy) phenylalanine The starting N-(toluene-4-sulfonyl)-L-(4-oxo)prolyl-L-4-(4-methylpiperazin-1-ylcarbonyloxy)phenylalanine tert-butyl ester (150 mg) was dissolved in formic acid (7 mL). The reaction was stirred at room temperature for 6 hours. The solvent was evaporated in vacuo, and the residue was purified using HPLC, reverse phase, 20–80% CH₃CH/water. The retention time was 10.34 minutes. The product was freeze dried to yield 82 mg of the title compound, mp: 99–101° C.

Example 332

Synthesis of N-(Toluene-4-sulfonyl)-L-(4-methanesulfonyloxy)prolyl-L-4-(N,N-dimethylcarbamyloxy)phenylalanine tert-Butyl Ester The starting N-(toluene-4-sulfonyl)-L-(4-hydroxy)prolyl-L-4-(N,N-dimethylcarbamyloxy)phenylalanine tert-butyl ester (300 mg) and methylsulfonyl chloride was dissolved in THF (7 mL) at 0° C. in an ice bath. Triethylamine (0.21 mL) was added. The ice bath was removed after 10 minutes. The reaction mixture was stirred at room temperature for 24 hours. Ethyl acetate (20 mL) as added. The mixture was washed with citric acid (5%, 20 mL, 2×), and washed with saturated NaHCO₃ solution (20 mL), then with brine. The solution was dried over MgSO₄. The solvent was evaporated, and the residue was flushed on a silica gel column. The solvent was evaporated in vacuo to give 300 mg of the desired product, mp: 73–74° C.

Example 333

Synthesis of N-(4-Aminobenzenesulfonyl)-L-prolyl-L-4-(N,N-dimethylcarbamyloxy)phenylalanine The starting N-(4-aminobenzenesulfonyl)-L-prolyl-L-4-(N,N-dimethylcarbamyloxy)phenylalanine methyl ester (300 mg) and LiOH solution (2M, 0.6 mL) were added to methanol (6 mL). The reaction was stirred at room temperature for 7 hours. The solvent was evaporated in vacuo, and the residue was purified using HPLC, reverse phase, 20–80% CH₃CN/water. At a retention time of 12.11 minutes, 27 mg of the desired product were obtained, mp: 130–132° C.

Example 334

Synthesis of N-(4-Aminocarbonylbenzenesulfonyl)-L-prolyl-L-4-(thiomorpholin-4-ylcarbonyloxy) phenylalanine The starting N-(4-aminocarbonylbenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 8 hours. The solvent was evaporated in vacuo, and the residue purified using HPLC, reverse phase, 20–80% CH₃CN/water. At a retention time of 12.69 minutes, 20 mg of the desired product was obtained, mp: 123–125° C.

Example 335

Synthesis of N-(4-Amidinobenzenesulfonyl)-L-prolyl-L-4-(thiomorpholin-4-ylcarbonyloxy) phenylalanine The starting N-(4-amidinobenzenesulfonyl)-L-prolyl-L-4-(thiomorpholin-4-ylcarbonyloxy)phenylalanine methyl ester (300 mg) and LiOH solution (2M, 0.5 mL) were added to methanol (6 mL). The reaction was stirred at room temperature for 8 hours. The solvent was evaporated in vacuo, and the residue was purified using HPLC, reverse phase, 20–80% $CH_3CN$/water. At a retention time of 11.78 minutes, 25 mg of the desired product were obtained, mp: 123–125° C.

Example 349

Synthesis of N-(Toluene-4-sulfonyl)-L-(4-methanesulfonyloxy)prolyl-L-4-(N,N-dimethylcarbamyloxy)phenylalanine The starting N-(toluene-4-sulfonyl)-L-(4-methanesulfonyloxy)prolyl-L-4-(N,N-dimethylcarbamyloxy)phenylalanine tert-butyl ester (200 mg) was dissolved in formic acid (5 mL). The reaction mixture was stirred at room temperature for 6 hours. The solvent was evaporated in vacuo to provide the desired product (195 mg), mp: 83–84° C.

Example A

In vitro Assay for Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive binding assays). This assay is sensitive to $IC_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ intergrin. VCAM-1 interacts with the cell surface in an $\alpha_4\beta_1$ intergrin-dependent fashion (Yednock, et al. J. Bio. Chem., 1995, 270:28740).

Recombinant soluble VCAM-1 was expressed as a chimeric fusion protein containing the seven extracellular domains of VCAM-1 on the N-terminus and the human $IgG_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM $MnCl_2$ and 5 µg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Bio. Chem. 271:11067) and may be used in this assay.

Cells were then incubated for 30 minutes at room temperature with candidate compounds, in various concentrations ranging from 66 µg/mL to 0.01 µg/mL using a standard 5-point serial dilution. 15 µL soluble recombinant VCAM-1 fusion protein was then added to Jurkat cells and incubated for 30 minutes on ice. (Yednock et al., supra.).

Cells were then washed two times and resuspended in PE-conjugated goat $F(ab')_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an $IC_{50}$ of less than about 15 µM possess binding affinity to $\alpha_4\beta_1$.

When tested in this assay, each of the compounds of Examples 1–373 (or the corresponding carboxylic acids of the ester compounds, i.e. the prodrugs) has an $IC_{50}$ of 15 µM or less.

Example B

In vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µg/mL to 0.01 µg/mL, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab') anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Bio. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmner et al, 1993, J. Cell Bio., 123:1289). Such binding is predictive of in vivo utility for inflammatory conditions mediated by $\alpha_4\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Bio. Chem., 269:26691), in place of the Jurkat cells, to measure the binding of the $\alpha_9\beta_1$ integrin. As a control, SW 480 cells which express other $\alpha$ and $\beta_1$ subunits may be used.

Using this assay, the plasma levels necessary to obtain efficacy in in vivo models for $\alpha_4\beta_1$ and $\alpha_9\beta_1$ have been established for compounds of formula I tested in this assay.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053–1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2–3 months old, 170–220 g) or Hartley guinea pigs (20 day old, 180–200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053–1059), which delays the onset of symptoms, was used as a positive control and was injected subcutaneously at 3 mg/kg on Day 8 and 11.

Body weight and motor impairment were measured daily. Motor impairment was rated with the following clinical score:

| 0 | no change |
|---|---|
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

When tested in this in vivo assay, the compounds of Examples 4, 9, 11, 12, 16, 51, 66, 73, 75, 82, 95, 101, 117, 137 and other Examples were active in this assay.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, *J. Clin. Invest*, 93:776–787 (1994) and Abraham et al, *Am J. Respir Crit Care Med*, 156:696–703 (1997), both of which are incorporated by reference in their entirety, compounds of this invention were formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen were used to study the airway effects of the candidate compounds. Following topical anesthesia of the nasal passages with 2% lidocaine, a balloon catheter was advanced through one nostril into the lower esophagus. The animals were then intubated with a cuffed endotracheal tube through the other nostril with a flexible fiberoptic bronchoscope as a guide.

Pleural pressure was estimated according to Abraham (1994). Aerosols (see formulation below) were generated using a disposable medical nebulizer that provides an aerosol with a mass median aerodynamic diameter of 3.2 µm as determined with an Andersen cascade impactor. The nebulizer was connected to a dosimeter system consisting of a solenoid valve and a source of compressed air (20 psi). The output of the nebulizer was directed into a plastic T-piece, one end of which was connected to the inspiratory port of a piston respirator. The solenoid valve was activated for 1 second at the beginning of the inspiratory cycle of the respirator. Aerosols were delivered at $V_T$ of 500 mL and a rate of 20 breaths/minute. A 0.5% sodium bicarbonate solution only was used as a control.

To assess bronchial responsiveness, cumulative concentration-response curves to carbachol were generated according to Abraham (1994). Bronchial biopsies were taken prior to and following the initiation of treatment and 24 hours after antigen challenge. Bronchial biopsies were preformed according to Abraham (1994).

An in vitro adhesion study of alveolar macrophages were also performed according to Abraham (1994), and a percentage of adherent cells was calculated.

Aerosol Formulation

A solution of the candidate compound in 0.5% sodium bicarbonate/saline (w/v) at a concentration of 30.0 mg/mL was prepared using the following procedure:

A. Preparation of 100 mL of 0.5% Sodium Bicarbonate/Saline Stock Solution:

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.

2. Add approximately 90.0 mL saline and sonicate until dissolved.

3. Q.S. to 100.0 mL with saline and mix thoroughly.

B. Preparation of 10.0 mL of 30.0 mg/mL Candidate Compound:

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.

2. Add approximately 9.7 mL of 0.5% sodium bicarbonate/saline stock solution.

3. Sonicate until the candidate compound is completely dissolved.

4. Q.S. to 10.0 mL with 0.5% sodium bicarbonate/saline stock solution and mix thoroughly.

Compounds of this invention were found to be active in this model. Additionally, using a conventional oral formula, a compound of this invention was active in this model.

What is claimed is:

1. A compound of formula I:

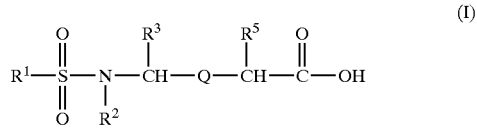

(I)

wherein $R^1$ is selected from the group consisting of alkyl, substituted alkyl, aryl, substituted aryl, cycloalkyl, substituted cycloalkyl, heterocyclic, substituted heterocylic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, and substituted heteroaryl;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, and substituted heterocyclic;

$R^5$ is —$(CH_2)_x$—Ar—$R^{5'}$ where $R^{5'}$ is selected from the group consisting of —O-Z-$NR^8$ $R^{8'}$ and —O-Z-$R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{12}$ is selected from the group consisting of heterocycle and substituted heterocycle, and Z is selected from the group consisting of —C(O)— and —$SO_2$—, Ar is aryl, heteroaryl, substituted aryl or substituted heteroaryl, x is an integer of from 1 to 4;

Q is —$C(X)NR^7$— wherein $R^7$ is selected from the group consisting of hydrogen and alkyl; and X is selected from the group consisting of oxygen and sulfur;

and pharmaceutically acceptable salts thereof.

2. A compound of formula IA:

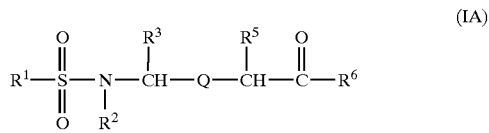

(IA)

wherein $R^1$ is selected from the group consisting of alkyl, substituted alkyl, aryl, substituted aryl, cycloalkyl, substituted cycloalkyl, heterocyclic, substituted heterocyclic, heteroaryl and substituted heteroaryl;

$R^2$ is selected from the group consisting of hydrogen, alkyl, cycloalkyl, substituted cycloalkyl, cycloalkenyl, substituted cycloalkenyl, heterocyclic, substituted heterocyclic, substituted alkyl, aryl, substituted aryl, heteroaryl, and substituted heteroaryl;

$R^3$ is selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic;

$R^5$ is —$(CH_2)_x$—Ar—$R^{5'}$ and $R^{5'}$ is selected from the group consisting of —O-Z-$NR^8$ $R^{8'}$ and —O-Z-$R^{12}$ wherein $R^8$ and $R^{8'}$ are independently selected from the group consisting of hydrogen, alkyl, substituted alkyl, cycloalkyl, substituted cycloalkyl, heterocyclic, substituted heterocyclic, and where $R^8$ and $R^{8'}$ are joined to form a heterocycle or a substituted heterocycle, $R^{12}$ is selected from the group consisting of heterocycle and substituted heterocycle, and Z is selected from the group consisting of —C(O)— and —$SO_2$—, Ar is aryl, heteroaryl, substituted aryl or substituted heteroaryl, x is an integer of from 1 to 4;

$R^6$ is selected from the group consisting of amino, alkoxy, substituted alkoxy, cycloalkoxy, substituted cycloalkoxy, —O—(N-succinimidyl), —NH-adamantyl, —O-cholest-5-en-3-β-yl, —NHOY where Y is hydrogen, alkyl, substituted alkyl, aryl, and substituted aryl, —$NH(CH_2)_p$COOY where p is an integer of from 1 to 8 and Y is as defined above, —$OCH_2NR^9R^{10}$ where $R^9$ is selected from the group consisting of —C(O)-aryl and —C(O)-substituted aryl and $R^{10}$ is selected from the group consisting of hydrogen and —$CH_2COOR^{11}$ where $R^{11}$ is alkyl, and —$NHSO_2Z'$ where $Z'$ is alkyl, substituted alkyl, cycloalkyl, substituted cycloalkyl, aryl, substituted aryl, heteroaryl, substituted heteroaryl, heterocyclic and substituted heterocyclic;

Q is —$C(X)NR^7$— wherein $R^7$ is selected from the group consisting of hydrogen and alkyl; and X is selected from the group consisting of oxygen and sulfur;

and pharmaceutically acceptable salts thereof.

3. A compound according to claim 1 or 2 wherein $R^1$ is selected from the group consisting of alkyl, substituted alkyl, aryl, substituted aryl, heterocyclic, substituted heterocyclic, heteroaryl and substituted heteroaryl.

4. A compound according to claim 1 or 2 wherein $R^1$ is selected from the group consisting of methyl, isopropyl, n-butyl, benzyl, phenethyl, phenyl, 4-methyiphenyl, 4-t-butylphenyl, 2,4,6-trimethylphenyl, 2-fluorophenyl, 3-fluorophenyl, 4-fluorophenyl, 2,4-difluorophenyl, 3,4-difluorophenyl, 3,5-difluorophenyl, 2-chlorophenyl, 3-chlorophenyl, 4-chlorophenyl, 3,4-dichlorophenyl, 3,5-dichlorophenyl, 3-chloro-4-fluorophenyl, 4-bromophenyl, 2-methoxyphenyl, 3-methoxyphenyl, 4-methoxyphenyl, 3,4-dimethoxyphenyl, 4-t-butoxyphenyl, 4-(3'-dimethylamino-n-propoxy)-phenyl, 2-carboxyphenyl, 2-(methoxycarbonyl)phenyl, 4-($H_2NC(O)$—)phenyl, 4-($H_2NC(S)$—)phenyl, 4-cyanophenyl, 4-trifluoromethyiphenyl, 4-trifluoromethoxyphenyl, 3,5-di-(trifluoromethyl)phenyl, 4-nitrophenyl, 4-aminophenyl, 4-($CH_3C(O)NH$-)phenyl, 4-(PhNHC(O)NH—)phenyl, 4-amidinophenyl, 4-methylamidinophenyl, 4-($CH_3SC(=NH)$—)phenyl, 4-chloro-3-($H_2NS(O)_2$—)phenyl, 1-naphthyl, 2-naphthyl, pyridin-2-yl, pyridin-3-yl, pyrimidin-2-yl, quinolin-8-yl, 2-(trifluoroacety 1)-1,2,3,4-tetrahydroisoquinolin-7-yl, morpholin-4-yl, 2-thienyl, 5-chloro-2-thienyl, 2,5-dichloro-4-thienyl, 1-N-methylimidazol-4-yl, 1-N-methylpyrazol-3-yl, 1-N-methylpyrazol-4-yl, 1-N-butylpyrazol-4-yl, 1-N-methyl-3-methyl-5-chloropyrazol-4-yl, 1-N-methyl-5-methyl-3-chloropyrazol-4-yl, 2-thiazolyl and 5-methyl-1,3,4-thiadiazol-2-yl.

5. A compound according to claim 1 or 2 wherein $R^2$ is selected from the group consisting of hydrogen, methyl, phenyl, benzyl, —$(CH_2)_2$-2-thienyl, and —$(CH_2)_2$-Φ.

6. A compound according to claim 1 or 2 wherein $R^3$ is selected from the group consisting of methyl, phenyl, benzyl, diphenylmethyl, —$CH_2CH_2$—COOH, —$CH_2$—COOH, 2-amidoethyl, iso-butyl, t-butyl, —$CH_2O$-benzyl and hydroxymethyl.

7. A compound according to claim 1 or 2 wherein Q is —C(O)NH— or —C(S)NH—.

8. A compound according to claim 1 or 2 wherein Ar is aryl or substituted aryl.

9. A compound according to claim 8 wherein Ar is phenyl or substituted phenyl and x is 1.

10. A compound according to claim 1 or 2 wherein $R^5$ is selected from the group consisting of 3-[$(CH_3)_2NC(O)O$—]benzyl,
4-[$(CH_3)_2NC(O)O$—]benzyl,
4-[$(CH_3)_2NS(O)_2O$—]benzyl,
4-[(piperidin-1'-yl)C(O)O—]benzyl,
4-[(piperidin-4'-yl)C(O)O—]benzyl,
4-[(1'-methylpiperidin-4'-yl)C(O)O—]benzyl,
4-[(4'-hydroxypiperidin-1'-yl)C(O)O—]benzyl,
4-[(4'-formyloxypiperidin-1'-yl)C(O)O—]benzyl,
4-[(4'-ethoxycarbonylpiperidin-1-yl)C(O)O—]benzyl,
4-[(4'-carboxylpiperidin-1'-yl)C(O)O—]benzyl,
4-[(3'-hydroxymethylpiperidin-1'-yl)C(O)O—]benzyl,
4-[(4'-hydroxymethylpiperidin-1'-yl)C(O)O—]benzyl,
4-[(4'-phenyl-1'-Boc-piperidin-4'-yl)—C(O)O—]benzyl,
4-[(4'-piperidon-1'-yl ethylene ketal)C(O)O—]benzyl,
4-[(piperazin-4'-yl)-C(O)O—]benzyl,
4-[(1'-Boc-piperazin-4'-yl )—C(O)O—]benzyl,
4-[(4'-methylpiperazin-1'-yl)C(O)O—]benzyl,
4-[(4'-methylhomopiperazin-1'-yl)C(O)O—]benzyl,
4-[(4'-(2-hydroxyethyl)piperazin-1'-yl)C(O)O—]benzyl,
4-[(4'-phenylpiperazin-1'-yl)C(O)O—]benzyl,
4-[(4'-(pyridin-2-yl)piperazin-1'-yl)C(O)O—]benzyl,
4-[(4'-(4-trifluoromethylpyridin-2-yl)piper-1'-yl)C(O)O—]benzyl,
4-[(4'-(pyrimidin-2-yl)piperazin-1'-yl)C(O)O—]benzyl,
4-[(4'-acetylpiperazin-1'-yl)C(O)O—]benzyl,
4-[(4'-(phenylC(O)—)piperazin-1'-yl)C(O)O—]benzyl,
4-[(4'-(pyridin-4-ylC(O)—)piperazin-1'-yl)C(O)O—]benzyl,
4-[(4'-(phenylNHC(O)—)piperazin-1'-yl)C(O)O—]benzyl,
4-[(4'-(phenylNHC(S)—)piperazin-1'-yl)C(O)O—]benzyl,
4-[(4'-methanesulfonylpiperazin-1'-yl-C(O)O—]benzyl,
4-[(4'-trifluoromethanesulfonylpiperazin-1'-yl-C(O)O—]benzyl,
4-[(morpholin-4'-yl)C(O)O—]benzyl,
3-nitro-4-[(morpholin-4'-yl)—C(O)O—]benzyl,
4-[(thiomorpholin-4'-yl)C(O)O—]benzyl,
4-[(thiomorpholin-4'-yl sulfone)—C(O)O—]benzyl,
4-[(pyrrolidin-1'-yl)C(O)O—]benzyl,
4-[(2'-methylpyrrolidin-1'-yl)C(O)O—]benzyl,
4-[(2'-(methoxycarbonyl)pyrrolidin-1'-yl)C(O)O—]benzyl,
4-[(2'-(hydroxymethyl)pyrrolidin-1'-yl)C(O)O—]benzyl,
4-[(2'-(N,N-dimethylamino)ethyl)($CH_3$)NC(O)O—]benzyl,
4-[(2'-(N-methyl-N-toluene-4-sulfonylamino)ethyl)($CH_3$)NC(O)O—]benzyl,
4-[(2-(morpholin-4'-yl)ethyl)($CH_3$)NC(O)O—]benzyl,
4-[(2'-(hydroxy)ethyl)($CH_3$)NC(O)O—]benzyl,
4-[bis(2'-(hydroxy)ethyl)NC(O)O—]benzyl,
4-[(2'-(formyloxy)ethyl)($CH_3$)NC(O)O—]benyl,
4-[($CH_3OC(O)CH_2$)HNC(O)O—]benzyl,
4-[2'-(phenylNHC(O)O—)ethyl-]HNC(O)O—]benzyl,
3-chloro-4-[$(CH_3)_2NC(O)O$—]benzyl,
3-chloro-4-[(4'-methylpiperazin-1'-yl)C(O)O—]benzyl,
3-chloro-4-[(4'-(pyridin-2-yl)piperazin-1'-yl)C(O)O—]benzyl,
3-chloro-4-[(thiomorpholin-4'-yl)C(O)O—]benzyl and
3-fluoro-4-[$(CH_3)_2NC(O)O$—]benzyl.

11. A compound according to claim 2 wherein $R^6$ is selected from the group consisting of 2,4-dioxo-tetrahydrofuran-3-yl (3,4-enol), methoxy, ethoxy, n-propoxy, isopropoxy, n-butoxy, t-butoxy, cyclopentoxy, cyclopropylmethoxy, neopentoxy, 2-α-isopropyl-4-β-methylcyclohexoxy, 2-β-isopropyl-4-β-methylcyclohexoxy, 2-methoxyphenoxy, 2-(morpholin-4-yl)ethoxy, —$O(CH_2CH_2O)_2CH_3$, 2-(phenoxy)ethoxy, —$OCH_2C(CH_3)_2$ NHBoc, —$NH_2$, benzyloxy, —$NHCH_2COOH$, —$NHCH_2CH_2COOH$, —NH-adamantyl, —$NHSO_2$-p-$CH_3$-Φ, —$NHCH_2CH_2COOCH_2CH_3$, —NHOY' where Y' is hydrogen, methyl, iso-propyl or benzyl, —O—(N-succinimidyl), —O-cholest-5-en-3-β-yl, —$OCH_2$—OC(O)C(CH_3)_3$, —$O(CH_2)_zNHC(O)W$ where z is 1 or 2 and W is selected from the group consisting of pyrid-3-yl, N-methylpyridyl, and N-methyl-1,4-dihydro-pyrid-3-yl, —NR"C(O)—R' where R' is aryl, heteroaryl or heterocyclic and R" is hydrogen or —CH$_2$C(O)OCH$_2$CH$_3$.

12. A compound selected from the group consisting of:

N-(toluene-4-sulfonyl)sarcosyl-L-4-(N,N-dimethylcarbaniyloxy)phenylalanine isopropyl ester N-(toluene-4-sulfonyl)sarcosyl-L-4-(N,N-dimethylcarbamyloxy)phenylalanine tert-butyl ester N-(toluene-4-sulfonyl)sarcosyl-L-4-(N,N-dimethylcarbamyloxy)phenylalanine N-(toluene-4-sulfonyl)sarcosyl-L-4-(morpholin-4-ylcarbonyloxy)phenylalanine tert-butyl ester N-(toluene-4-sulfonyl)sarcosyl-L-4-(isonipecotoyloxy) phenylalanine N-(toluene-4-sulfonyl)sarcosyl-L-4-(4-methylpiperazin-1-ylcarbonyloxy) phenylalanine tert-butyl ester N-(toluene-4-sulfonyl)-L-N-methylalanyl-L-4-(4-methylpiperazin-1-ylcarbonyloxy)phenylalanine tert-butyl ester N-(toluene-4-sulfonyl)sarcosyl-L-4-(thiomorpholin-4-ylcarbonyloxy)phenylalanine tert-butyl ester N-(toluene-4-sulfonyl)sarcosyl-L-4-(1,1-dioxothiomorpholin-4-ylcarbonyloxy)phenylalanine tert-butyl ester N-(toluene-4-sulfonyl)sarcosyl-L-4-(thiomorpholin-4-ylcarbonyloxy)phenylalanine N-(toluene-4-sulfonyl)-L-N-methylalanyl-L-4-(N,N-dimethylcarbaniyloxy)phenylalanine tert-butyl ester N-(toluene-4-sulfonyl)sarcosyl-L-4-(1,1-dioxothiomorpholin-4-ylcarbonyloxy)phenylalanine N-(toluene-4-sulfonyl)-L-N-methylalanyl-L-4-(N,N-dimethylcarbamyloxy)phenylalamine N-(toluene-4-sulfonyl)-L-N-methyl-2-(tert-butyl) glycinyl-L-4-(4-methylpiperazin-1-ylcarbonyloxy) phenylalanine tert-butyl ester 3-[N-(toluene-4-sulfonyl)-N-methylamino]-1-[1-carboxy-2-(N,N-dimethylcarbamyloxy)phenylethyl] azetidine N-(toluene-4-sulfonyl)-L-prolyl-L-4-(isonipecotoyloxy) phenylalanine tert-butyl ester N-(methanesulfonyl)-N-benylglycinyl-L-4-(N,N-dimethylcarbamyloxy)phenylalanine tert-butyl ester and pharmaceutically acceptable salts thereof as well as any of the ester compounds recited above wherein one ester is replaced with another ester selected from the group consisting of methyl ester, ethyl ester, n-propyl ester, isopropyl ester, n-butyl ester, isobutyl ester, sec-butyl ester, tert-butyl ester and neopentyl ester.

13. A method for binding VLA-4 in a biological sample which method comprises contacting the biological sample with a compound of claim 1 or 2 under conditions wherein said compound binds to VLA-4.

* * * * *

UNITED STATES PATENT AND TRADEMARK OFFICE
CERTIFICATE OF CORRECTION

PATENT NO. : 6,900,179 B2  
APPLICATION NO. : 09/987619  
DATED : May 31, 2005  
INVENTOR(S) : Eugene D. Thorsett et al.

Page 1 of 1

It is certified that error appears in the above-identified patent and that said Letters Patent is hereby corrected as shown below:

In Claim 10, Please replace: Col. 190 Line 42  
"4-[(2'-(formyloxy)ethyl)(CH$_3$)NC(O)O-]benyl,"  
With  
--4-[(2'-(formyloxy)ethyl)(CH$_3$)NC(O)O-]benzyl,--

In Claim 12, Please replace:

"N-(methanesulfonyl)-N-benyl-glycinyl-L-4-(N,N dimethylcarbayloxy)phenylalanine"  
With  
--N-(methanesulfonyl)-N-benzyl-glycinyl-L-4-(N,N dimethylcarbayloxy)phenylalanine--

In Claim 12 at two places: Col. 191 Line 5 and 28 Please replace:

"*N*-(toluene-4-sulfonyl)sarcosyl-L-4-(*N, N*- dimethylcarbaniyloxy)phenylalanine isopropyl ester"  
With  
--*N*-(toluene-4-sulfonyl)sarcosyl-L-4-(*N, N*-dimethylcarbamyloxy)phenylalanine isopropyl ester--

Please replace:  
"*N*-(toluene-4-sulfonyl)-L-N-methylalanyl-L-4-(*N,N*-dimethylcarbaniloxy) phenylalanine *tert*-butyl ester"  
With  
--*N*-(toluene-4-sulfonyl)-L-N-methylalanyl-L-4-(*N,N*-dimethylcarbamyloxy) phenylalanine *tert*-butyl ester--

Signed and Sealed this

Twenty-ninth Day of May, 2007

JON W. DUDAS  
*Director of the United States Patent and Trademark Office*